(12) United States Patent
Vosshall et al.

(10) Patent No.: US 7,241,881 B2
(45) Date of Patent: Jul. 10, 2007

(54) GENES ENCODING INSECT ODORANT RECEPTORS AND USES THEREOF

(75) Inventors: Leslie B. Vosshall, New York, NY (US); Hubert O. Amrein, Durham, NC (US); Richard Axel, New York, NY (US)

(73) Assignee: The Trustees of Columbia University in the city of New York, New York, NY (US)

( * ) Notice: Subject to any disclaimer, the term of this patent is extended or adjusted under 35 U.S.C. 154(b) by 221 days.

(21) Appl. No.: 10/183,708

(22) Filed: Jun. 25, 2002

(65) Prior Publication Data

US 2003/0143679 A1 Jul. 31, 2003

Related U.S. Application Data

(63) Continuation of application No. 09/932,227, filed on Aug. 17, 2001, now abandoned, which is a continuation of application No. PCT/US00/04995, filed on Feb. 25, 2000, which is a continuation-in-part of application No. 09/257,706, filed on Feb. 25, 1999, now abandoned.

(51) Int. Cl.
*C12N 15/12* (2006.01)
*C07K 14/705* (2006.01)
(52) U.S. Cl. .................... 536/23.5; 435/7.21; 435/69.1; 435/252.3; 435/320.1
(58) Field of Classification Search ............... 435/69.1, 435/252.3, 320.1; 530/350; 536/23.5
See application file for complete search history.

(56) References Cited

FOREIGN PATENT DOCUMENTS

| WO | WO 00/43410 | 6/2000 |
|----|-------------|--------|
| WO | 0043410     | 7/2000 |

OTHER PUBLICATIONS

Ben-Arie, N., Lancet, D., Taylor, C., Kehn, M., Walker, N., Ledbetter, D.H., Carrozzo, R., Patel, K., Sheer, D., Lehrach, H., and et al., (1994) Olfactory receptor gene cluster on human chromosome 17: possible duplication of an ancestral receptor repertoire. Hum. Mol. Genet. 3: 229-235.

Bowie, James U., Reidhaar-Olson, J.F. (1990) Deciphering the message in protein sequences: tolerance to amino acid substitutions. Science 247: 1306-1310.

Buck, L. and Axel, R. (1991) A novel multigene family may encode odorant receptors: a molecular basis for odor recognition. Cell. 65: 175-187.

Carlson, JR. (2001) Functional expression of a Drosophila odor receptor. Proc. Natl. Acad. Sci. 98(16): 8936-8937.

Doe, C. Q., and Skeath, J.B. (1996) Neurogenesis in the insect central nervous system. Curr.Opin. Neurobiol. 6:18-24.

Dulac, C., and Axel, R. (1995) A novel family of genes encoding putative pheromone receptors in mammals. Cell. 83: 195-206.

Faber, T., Joerges, J., and Menzel, R. (1998) Associative learning modifies neural representations of in the insect brain. Nature Neurosci. 2: 74-78.

Gao, Q. et al. (Jul. 1999) Identification of candidate olfactory receptors from genomic DNA sequence. Genomics 60: 31-39.

Gimelbrandt, A.A. et al. (Feb. 1999) Truncation releases olfactory receptors from endoplasmic reticulum of heterologous cells. J. Neurochem. 72(6): 2301-2311.

Grillenzoni, N., van Helden, J., Dambly-Chaudiere, C., and Ghysen, A. (1998) The iroquois complex controls the somatotopy of Drosophila notum mechanosensory projections. Development 125: 3563-3569.

Herrada, G., and Dulac, C. (1997) A novel family of putative pheromone receptors in mammals with a topographically organized and sexually dimorphic distribution. Cell 90:763-773.

Kim, M. S., Repp, A., and Smith, D.P. (1998) LUSH odorant-binding protein mediates chemosensory responses to alcohols in *Drosophila melanogaster*. Genetics 150: 711-721.

Levy, N.S., Bakalyar, H.A., and Reed, R.R. (1991) Signal transduction in olfactory neurons. J. Steroid Biochem. Mol. Biol. 39: 633-637.

Matsunami, H., and Buck, L.B. (1997) A multigene family encoding a diverse array of putative pheromone receptors in mammals. Cell 90: 775-784.

Mckenna, M.P., Hekmat-Scafe, D.S., Gaines, P., and Carlson, J.R. (1994) Putative *Drosophila* pheromone-binding proteins expressed in a subregion of the olfactory system. J. Biol. Chem. 269: 16340-16347.

Merrit, D. J., and Whitington, P.M. (1995) Central projections of sensory neurons in the *Drosophila* embryo correlate with sensory modality, soma position, and proneural gene function. J. Neurosci. 15:1755-1767.

Ngo, J.T., Marks, J., Karplus, M. (1994) Computational Complexity, Protein Structure Prediction, and the Levinthal Paradox. In: Merz, K. Jr. and Le Grand, S. (Eds) The Protein Folding Problem and Tertiary Structure, Chapter 14, pp. 492-495, Birkhäuser, Boston.

(Continued)

*Primary Examiner*—John Ulm
(74) *Attorney, Agent, or Firm*—John P. White; Cooper & Dunham LLP

(57) ABSTRACT

This invention provides an isolated nucleic acid molecule encoding an insect odorant receptor. This invention provides a nucleic acid molecule of at least 12 nucleotides capable of specifically hybridizing with the nucleic acid molecule encoding an insect odorant receptor. This invention also provides a purified, insect odorant receptor. This invention provides an antibody capable of specifically binding to an insect odorant receptor. This invention provides a method for identifying cDNA inserts encoding an insect odorant receptors. This invention provides a method of identifying a compound capable of specifically bind to an insect odorant receptor. This invention also provides a method of identifying a compound capable of activating the activity of an insect odorant receptor.

9 Claims, 24 Drawing Sheets

OTHER PUBLICATIONS

Parmentier, M., Libert, F., Schurmans, S., Schiffmann, S., Lefort, A., Eggericks, D., Ledent, C., Molleareau, C., Gerard, D., and et al. (1992) Expression of members of the putative olfactory receptor gene family in mammalian germ cells. Nature, 355:453-455.

Pelosi, P. (1994) Odorant-binding proteins. Crit. Rev. Biochem. Mol. Biol. 29: 199-228.

Pikielny, C.W., Hasan, G., Rouyer, F., and Rosbash, M. (1994) Members of a family of *Drosophila* putative odorant-binding proteins are expressed in different subsets of olfactory hairs. Neuron. 12: 35-49.

Robertson, H.M. (1998) Two large families of chemoreceptor genes in the nematodes *Caenorhabditis elegans* and *Caenorhabditis briggsae* reveal entensive gene duplication, diversification, movement, and intron loss. Genome Res. 8: 449-463.

Ryba, N.J., and Tirindelli, R. (1997) A new multigene family of putative pheromone receptors. Neuron 19: 371-379.

Stocker, R.F. (1994) The organization of the chemosensory system in *Drosophila melanogaster*: a review. Cell Tissue Res. 275: 3-26.

Störtkuhl, K.F. and Kettler, R. (2001) Functional analysis of an olfactory receptor in *Drosophila melanogaster*. Proc. Natl. Acad. Sci. 98(16):9381-9385.

Troemel, E.R., Chou, J. H., Dwyer, N.D., Colbert, H. A., and Bargmann, C.I. (1995) Divergent seven transmembrane receptors are candidate chemosensory receptors in *C. elegans*. Cell. 83: 207-218.

Vosshall, L.B. et al. (Mar. 5, 1999) A spatial map of olfactory receptor expression in the *Drosophilia antenna*. Cell 96: 725-737.

Wells, J.A. (1990) Additivity of mutational effects in proteins. Biochemistry 29:8509-8517.

Wetzel, C.H. et al. (2001) Functional expression and characterization of a *Drosophila* odorant receptor in a heterologous cell system. Proc. Natl. Acad. Sci. 98(16):9381-9385.

Supplementary Partial European Search Report Under Rule 46(1) EPC issued in connection with related European Patent Application No. 00915898.1, on behalf of The Trustees of Columbia University in the City of New York, regional stage of PCT International Application No. PCT/US00/04995, filed Feb. 25, 2000.

Carlson, J.R., "Olfaction in *Drosophila*: from odor to behavior," Trends in Genetics, vol. 12, No. 5, pp. 175-180 (May 1996).

Clyne, P.J., et al., "A novel family of divergent seven-transmembrane proteins: candidate odorant receptors in *Drosophila*," Neuron, vol. 22, No. 2, pp. 327-338 (Feb. 1999).

Supplementary Partial European Search Report Under Rule 45 EPC issued in connection with related European Patent Application No. 00915898.1, on behalf of The Trustees of Columbia University in the City of New York, regional stage of PCT International Application No. PCT/US00/04995, filed Feb. 25, 2000.

Database EMBL 'Online', Accession No. CNS00ZH7 (Jul. 26, 1999).

FIGURE 4A    FIGURE 4B    FIGURE 4C
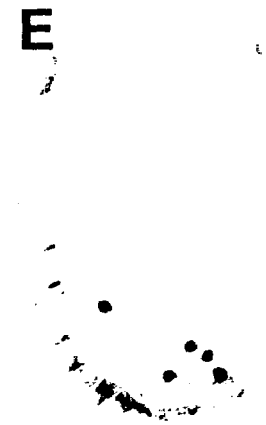
FIGURE 4D    FIGURE 4E    FIGURE 4F

*FIGURE 4G*  *FIGURE 4H*  *FIGURE 4I*

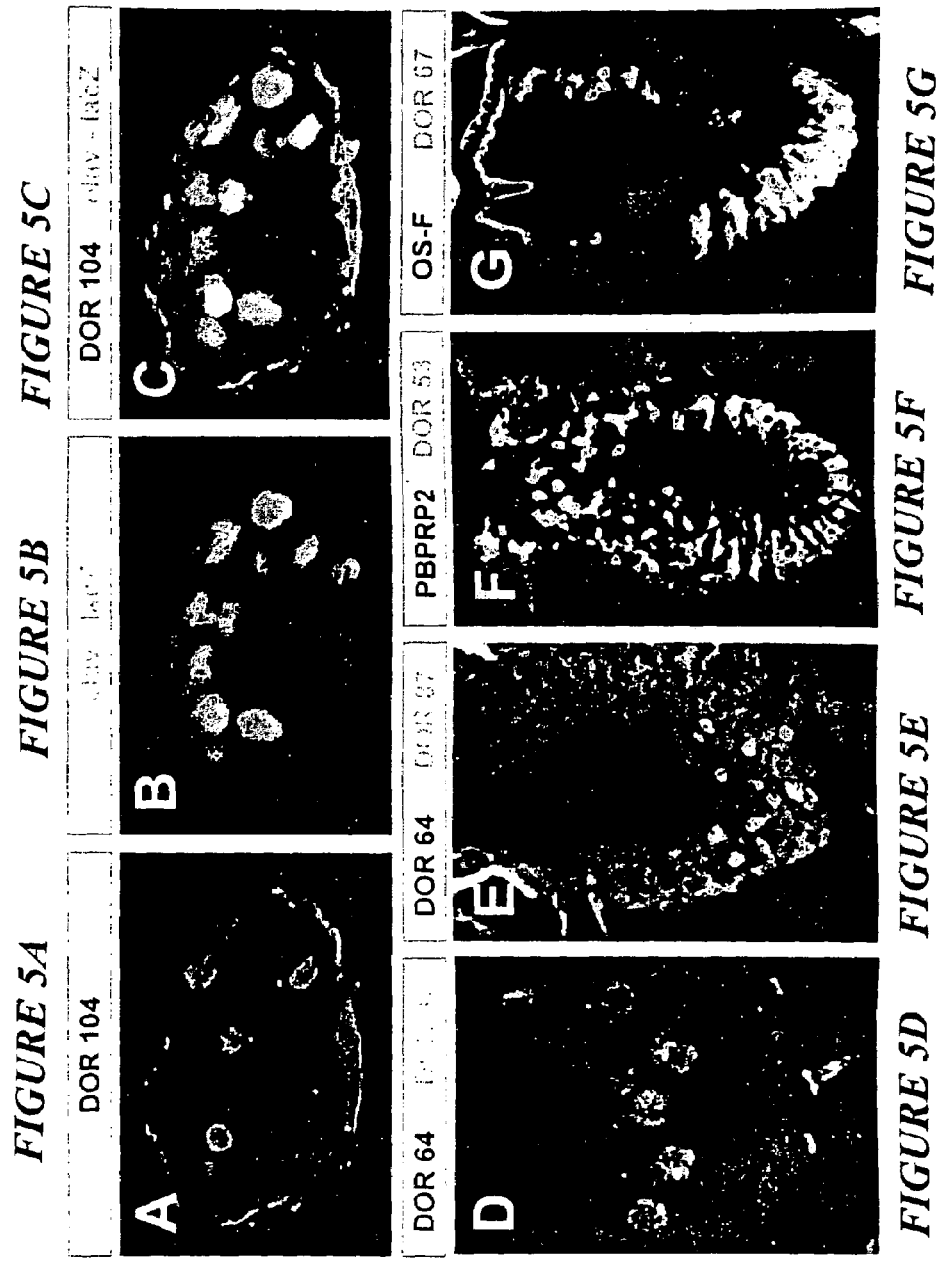

FIGURE 6A  FIGURE 6B  FIGURE 6C
FIGURE 6D  FIGURE 6E  FIGURE 6F

| | | 410 | | 420 | | 430 |
|---|---|---|---|---|---|---|
| DOR119 | A K F A F S | I | T | I | V R Q M N L A E Q F Q | |
| DOR118 | A K F A F S | V | I | T | I T K Q M N I A D K F K T D | |
| DOR110 | A K L A F S | V | V | T | F V N Q L N I A D R L T K N | |
| DOR120 | A K F A F T | I | I | T | I V N Q M N L G E K F F S D R S N G D I N P |
| DOR53 | V K L A F S | V | V | T | V T I K Q F N L A E R F Q | |
| DOR67 | V K L A F T | V | V | T | I V K Q F N L A E K F Q | |
| DOR117 | S R C A L | | | | | |
| DOR31 | A K F A F S | V | V | T | I V N E M D L A E K L R R E | |
| DOR81 | A K F A F T | V | Y | A | I A S G M N L D Q K L S I | |
| DOR30 | A K F S F S | L | Y | T | L I K G M N L G E R F N R T N | |

GENES ENCODING INSECT ODORANT RECEPTORS AND USES THEREOF

This application is a continuation of U.S. Ser. No. 09/932,227, filed Aug. 17, 2001 now abandoned, which is a continuation of PCT International Application No. PCT/US00/04995, filed Feb. 25, 2000, which was a continuation-in-part of, and claimed priority of, U.S. Ser. No. 09/257,706, filed Feb. 25, 1999, now abandoned, the contents of all of which are hereby incorporated by reference into the subject application.

The invention disclosed herein was made with Government support under NIH:NIMH, 5P50, MH50733-05 and NINDS, NS29832-07 from the Department of Health and Human Services. Accordingly, the U.S. Government has certain rights in this invention.

Throughout this application, various publications are referred to by arabic numeral within parentheses. Full citations for these publications are presented immediately before the claims. Disclosures of these publications in their entireties are hereby incorporated by reference into this application in order to more fully describe the state of the art to which this invention pertains.

BACKGROUND OF THE INVENTION

All animals possess a "nose," an olfactory sense organ that allows for the recognition and discrimination of chemosensory information in the environment. Humans, for example, are thought to recognize over 10,000 discrete odors with exquisite discriminatory power such that subtle differences in chemical structure can often lead to profound differences in perceived odor quality. What mechanisms have evolved to allow the recognition and discrimination of complex olfactory information and how is olfactory perception ultimately translated into appropriate behavioral responses? The recognition of odors is accomplished by odorant receptors that reside on olfactory cilia, a specialization of the dendrite of the olfactory sensory neuron. The odorant receptor genes encode novel serpentine receptors that traverse the membrane seven times. In several vertebrate species, and in the invertebrate *Caenorhabditis elegans*, as many as 1000 genes encode odorant receptors, suggesting that 1–5% of the coding potential of the genome in these organisms is devoted to the recognition of olfactory sensory stimuli (Buck and Axel, 1991; Levy et al., 1991; Parmentier et al., 1992; Ben-Arie et al., 1994; Troemel et al., 1995; Sengupta et al., 1996; Robertson, 1998). Thus, unlike color vision in which three photoreceptors can absorb light across the entire visible spectrum, these data suggest that a small number of odorant receptors are insufficient to recognize the full spectrum of distinct molecular structures perceived by the olfactory system. Rather, the olfactory sensory system employs an extremely large number of receptors, each capable of recognizing a small number of odorous ligands.

The discrimination of olfactory information requires that the brain discern which of the numerous receptors have been activated by an odorant. In mammals, individual olfactory sensory neurons express only one of a thousand receptor genes such that the neurons are functionally distinct (Ngai et al., 1993; Ressler et al., 1993; Vassar et al., 1993; Chess et al., 1994). The axons from olfactory neurons expressing a specific receptor converge upon two spatially invariant glomeruli among the 1800 glomeruli within the olfactory bulb (Ressler et al., 1994; Vassar et al., 1994; Mombaerts et al., 1996; Wang et al., 1998). The bulb therefore provides a spatial map that identifies which of the numerous receptors has been activated within the sensory epithelium. The quality of an olfactory stimulus would therefore be encoded by specific combinations of glomeruli activated by a given odorant.

The logic of olfactory discrimination is quite different in the nematode, *C. elegans*. Despite the large size of the odorant receptor gene family, volatile odorants are recognized by only three pairs of chemosensory cells each likely to express a large number of receptor genes (Bargmann and Horvitz, 1991; Colbert and Bargmann, 1995; Troemel et al., 1995). Activation of any one of the multiple receptors in one cell will lead to chemoattraction, whereas activation of receptors in a second cell will result in chemorepulsion (Troemel et al., 1997). The specific neural circuit activated by a given sensory neuron is therefore the determinant of the behavioral response. Thus, this invertebrate olfactory sensory system retains the ability to recognize a vast array of odorants but has only limited discriminatory power.

Vertebrates create an internal representation of the external olfactory world that must translate stimulus features into neural information. Despite the elucidation of a precise spatial map, it has been difficult in vertebrates to discern how this information is decoded to relate the recognition of odors to specific behavioral responses. Genetic analysis of olfactory-driven behavior in invertebrates may ultimately afford a system to understand the mechanistic link between odor recognition and behavior. Insects provide an attractive model system for studying the peripheral and central events in olfaction because they exhibit sophisticated olfactory-driven behaviors under control of an olfactory sensory system that is significantly simpler anatomically than that of vertebrates (Siddiqi, 1987; Carlson, 1996). Olfactory-based associative learning, for example, is robust in insects and results in discernible modifications in the neural representation of odors in the brain (Faber et al., 1998). It may therefore be possible to associate modifications in defined olfactory connections with in vivo paradigms for learning and memory.

Olfactory recognition in the fruit fly *Drosophila* is accomplished by sensory hairs distributed over the surface of the third antennal segment and the maxillary palp. Olfactory neurons within sensory hairs send projections to one of 43 glomeruli within the antennal lobe of the brain (Stocker, 1994; Laissue et al., 1999). The glomeruli are innervated by dendrites of the projection neurons, the insect equivalent of the mitral cells in the vertebrate olfactory bulb, whose cell bodies surround the glomeruli. These antennal lobe neurons in turn project to the mushroom body and lateral horn of the protocerebrum (reviewed in Stocker, 1994). 2-deoxyglucose mapping in the fruit fly (Rodrigues, 1988) and calcium imaging in the honeybee (Joerges et al., 1997; Faber et al., 1998) demonstrate that different odorants elicit defined patterns of glomerular activity, suggesting that in insects as in vertebrates, a topographic map of odor quality is represented in the antennal lobe. However, in the absence of the genes encoding the receptor molecules, it has not been possible to define a physical basis for this spatial map.

The present application discloses a large family of genes that are likely to encode the odorant receptors of *Drosophila melanogaster*. Difference cloning, along with analysis of *Drosophila* genomic sequences, has led to the identification of a novel family of putative seven transmembrane domain receptors likely to be encoded by 100 to 200 genes within the *Drosophila* genome. Each receptor is expressed in a small subset of sensory cells (0.5–1.5%) that is spatially defined within the antenna and maxillary palp. Moreover, different neurons express distinct complements of receptor genes such that individual neurons are functionally distinct. Identification of a large family of putative odorant receptors in insects indicates that, as in other species, the diversity and specificity of odor recognition is accommodated by a large family of receptor genes. The identification of the family of putative odorant receptor genes may afford insight into the logic of olfactory perception in *Drosophila*.

Insects provide an attractive system for the study of olfactory sensory perception. The present application identifies a novel family of seven transmembrane domain proteins, encoded by 100 to 200 genes, that is likely to represent the family of *Drosophila* odorant receptors. Members of this gene family are expressed in topographically defined subpopulations of olfactory sensory neurons in either the antenna or the maxillary palp. Sensory neurons express different complements of receptor genes, such that individual neurons are functionally distinct. The isolation of candidate odorant receptor genes along with a genetic analysis of olfactory-driven behavior in insects may ultimately afford a system to understand the mechanistic link between odor recognition and behavior.

SUMMARY OF THE INVENTION

This invention provides an isolated nucleic acid encoding an insect odorant receptor.

The invention provides an isolated nucleic acid encoding a polypeptide present in an insect odorant receptor which polypeptide comprises seven transmembrane domains and a C-terminal domain, wherein one of the seven transmembrane domains is located within the polypeptide at a position adjoining the C-terminal domain and wherein this seventh transmembrane domain and the adjoining C-terminal domain together comprise consecutive amino acids the sequence of which is as follows:

```
                                            (SEQ ID NO: 107)
-(F, Y, L, A, T, S or C)-(P, I, M, V, T, L, Q, S
or H)-(F, Y, I, S, L, C, N or V)-(C, Y, T, S, L or
A)-(Y, N, F, M, I, L, K, S, H or T)-(X)20-W-;
``` wherein each X in $(X)_{20}$ represents an amino acid and the identity of each X is independent of the identity of any other X.

The invention provides an isolated nucleic acid encoding a polypeptide present in an insect odorant receptor, wherein the polypeptide is selected from the group consisting of polypeptides comprising consecutive amino acids the sequence of which is one of the following:
(a) SEQ ID NO: 2, (b) SEQ ID NO: 4, (c) SEQ ID NO: 6, (d) SEQ ID NO: 8, (e) SEQ ID NO: 10, (f) SEQ ID NO: 12, (g) SEQ ID NO: 14, (h) SEQ ID NO: 16, (i) SEQ ID NO: 18, (j) SEQ ID NO: 20, (k) SEQ ID NO: 22, (l) SEQ ID NO: 24, (m) SEQ ID NO: 26, (n) SEQ ID NO: 28, (o) SEQ ID NO: 30, (p) SEQ ID NO: 32, (q) SEQ ID NO: 34, (r) SEQ ID NO: 36, (s) SEQ ID NO: 38, (t) SEQ ID NO: 40, (u) SEQ ID NO: 42, (v) SEQ ID NO: 44, (w) SEQ ID NO: 46, (x) SEQ ID NO: 48, (y) SEQ ID NO: 50, (z) SEQ ID NO: 52, (aa) SEQ ID NO: 54, (bb) SEQ ID NO: 56, (cc) SEQ ID NO: 58, (dd) SEQ ID NO: 60, (ee) SEQ ID NO: 62, (ff) SEQ ID NO: 64, (gg) SEQ ID NO: 66, (hh) SEQ ID NO: 68, (ii) SEQ ID NO: 70, (jj) SEQ ID NO: 72, (kk) SEQ ID NO: 74, (ll) SEQ ID NO: 76, (mm) SEQ ID NO: 78, (nn) SEQ ID NO: 80, (oo) SEQ ID NO: 82, (pp) SEQ ID NO: 84, (qq) SEQ ID NO: 86, (rr) SEQ ID NO: 88, (ss) SEQ ID NO: 90, (tt) SEQ ID NO: 92, (uu) SEQ ID NO: 94, (vv) SEQ ID NO: 96, (ww) SEQ ID NO: 98, (xx) SEQ ID NO: 100, (yy) SEQ ID NO: 102, (zz) SEQ ID NO: 104, (aaa) SEQ ID NO: 106, or
(bbb) a polypeptide which shares greater than 25% amino acid identity with any one of the polypeptides of (a)–(aaa), and comprises a transmembrane domain and an adjoining C-terminal domain which together comprise consecutive amino acids the sequence of which is as follows:

```
                                            (SEQ ID NO: 107)
-(F, Y, L, A, T, S or C)-(P, I, M, V, T, L, Q, S
or H)-(F, Y, I, S, L, C, M or V)-(C, Y, T, S, L or
A)-(Y, N, F, M, I, L, K, S, H or T)-(X)20-W-;
``` wherein each X in $(X)_{20}$ represents an amino acid and the identity of each X is independent of the identity of any other X.

The invention provides an isolated nucleic acid encoding an odorant receptor protein from an insect, wherein the receptor protein comprises consecutive amino acids having a sequence identical to that set forth for DORA45 in SEQ ID NO: 104.

The invention provides an isolated nucleic acid encoding an odorant receptor protein from an insect, wherein the nucleic acid comprises:
(a) a nucleic acid sequence given in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, or 105; or
(b) a nucleic acid sequence degenerate to a sequence of (a) as a result of the genetic code.

This invention provides a nucleic acid of at least 12 nucleotides capable of specifically hybridizing with the sequence of any of the herein described nucleic acids. This invention provides a nucleic acid comprising at least 12 nucleotides which specifically hybridize with nucleic acid having any of the sequences described herein. This invention provides a vector which comprises any of the herein described isolated nucleic acids. In another embodiment, the vector is a plasmid.

This invention also provides a host vector system for the production of a polypeptide having the biological activity of an insect odorant receptor which comprises the above described vector and a suitable host.

This invention provides a method of producing a polypeptide having the biological activity of an insect odorant receptor which comprising growing the above described host vector system under conditions permitting production of the polypeptide and recovering the polypeptide so produced.

This invention also provides a purified, insect odorant receptor. This invention further provides a polypeptide encoded by the herein described isolated nucleic acids.

This invention provides an antibody which specifically binds to an insect odorant receptor. This invention also provides an antibody which competitively inhibits the binding of the antibody capable of specifically binding to an insect odorant receptor.

This invention provides a method for identifying cDNA inserts encoding an insect odorant receptors comprising: (a) generating a cDNA library which contains clones carrying cDNA inserts from antennal or maxillary palp sensory neurons; (b) hybridizing nucleic acid molecules of the clones from the cDNA libraries generated in step (a) with probes prepared from the antenna or maxillary palp neurons and probes from heads lacking antenna or maxillary palp neurons or from virgin female body tissue; (c) selecting clones which hybridized with probes from the antenna or maxillary palp neurons but not from head lacking antenna or maxillary palp neurons or virgin female body tissue; and (d) isolating clones which carry the hybridized inserts, thereby identifying the inserts encoding odorant receptors.

This invention also provides cDNA inserts identified by the above method.

This invention further provides a method for identifying DNA inserts encoding an insect odorant receptors comprising: (a) generating DNA libraries which contain clones carrying inserts from a sample which contains at least one antennal or maxillary palp neuron; (b) contacting clones from the cDNA libraries generated in step (a) with nucleic acid molecule capable of specifically hybridizing with the sequence which encodes an insect odorant receptor in appropriate conditions permitting the hybridization of the nucleic acid molecules of the clones and the nucleic acid molecule; (c) selecting clones which hybridized with the nucleic acid molecule; and (d) isolating the clones which carry the hybridized inserts, thereby identifying the inserts encoding the odorant receptors.

This invention also provides a method to identify DNA inserts encoding an insect odorant receptors comprising: (a) generating DNA libraries which contain clones with inserts from a sample which contains at least one antenna or maxillary palp sensory neuron; (b) contacting the clones from the DNA libraries generated in step (a) with appropriate polymerase chain reaction primers which specifically bind to nucleic acid molecules encoding odorant receptors in appropriate conditions permitting the amplification of the hybridized inserts by polymerase chain reaction; (c) selecting the amplified inserts; and (d) isolating the amplified inserts, thereby identifying the inserts encoding the odorant receptors.

This invention also provides a method to isolate DNA molecules encoding insect odorant receptors comprising:(a) contacting a biological sample known to contain nucleic acids with appropriate polymerase chain reaction primers which specifically bind to nucleic acid molecules encoding insect odorant receptors in appropriate conditions permitting the amplification of the hybridized molecules by polymerase chain reaction; (b) isolating the amplified molecules, thereby identifying the DNA molecules encoding the insect odorant receptors.

This invention also provides a method for obtaining a nucleic acid encoding an insect odorant receptor which comprises:
(a) contacting a sample containing nucleic acids of insect origin with primers which comprise a nucleic acid corresponding to a nucleic acid which encodes consecutive amino acids having the sequence set forth in SEQ ID NO: 107 and are capable of specifically binding to a nucleic acid encoding an insect odorant receptor under appropriate conditions permitting hybridization of the primers to such nucleic acid to produce a hybridization product;
(b) amplifying the resulting hybridization product using a polymerase chain reaction; and
(c) isolating the amplified molecules, thereby identifying the DNA molecules encoding the insect odorant receptors.

This invention also provides a method of transforming cells which comprises transfecting a host cell with a suitable vector described above. This invention also provides transformed cells produced by the above method.

This invention provides a method of identifying a compound which specifically binds to an insect odorant receptor which comprises contacting a transfected cell or membrane fraction of the above described transfected cell with an appropriate amount of the compound under conditions permitting binding of the compound to such receptor, detecting the presence of any such compound specifically bound to the receptor, and thereby identifying the compound as a compound which specifically binds to the receptor.

This invention provides a method of identifying a compound which specifically binds to an insect odorant receptor which comprises contacting an appropriate amount of the purified insect odorant receptor with an appropriate amount of the compound under conditions permitting binding of the compound to such purified receptor, detecting the presence of any such compound specifically bound to the receptor, and thereby determining identifying the compound as a compound which specifically binds to the receptor.

This invention also provides a method of identifying a compound which activates an insect odorant receptor which comprises contacting the transfected cells or membrane fractions of the above-described transfected cells with the compound under conditions permitting the activation of a functional odorant receptor response, the activation of the receptor indicating that the compound is a compound which activates an insect odorant receptor.

This invention also provides a method of identifying a compound which activates an odorant receptor which comprises contacting a purified insect odorant receptor with the compound under conditions permitting the activation of a functional odorant receptor response, the activation of the receptor indicating that the compound is a compound which activates an insect odorant receptor. In an embodiment, the purified receptor is embedded in a lipid bilayer.

This invention also provides a method of identifying a compound which inhibits the activity of an insect odorant receptor which comprises contacting the transfected cells or membrane fractions of the above-described transfected cells with an appropriate amount of the compound under conditions permitting the inhibition of a functional odorant receptor response, the inhibition of the receptor response indicating that the compound is a compound which inhibits the activity of an insect odorant receptor.

This invention provides a method of identifying a compound which inhibits the activity of an insect odorant receptor which comprises contacting an appropriate amount of the purified insect odorant receptor with an appropriate amount of the compound under conditions permitting the inhibition of a functional odorant receptor response, the inhibition of the receptor response indicating that the compound is a compound which inhibits the activity of a odorant receptor. In an embodiment, the purified receptor is embedded in a lipid bilayer.

This invention also provides the compound identified by any of the above-described methods.

This invention provides a method of controlling pest populations which comprises identifying odorant ligands by the above-described method which are alarm odorant ligands and spraying the desired area with the identified odorant ligands.

This invention provides a method of controlling a pest population which comprises identifying odorant ligands by the above-described method which interfere with the interaction between the odorant ligands and the odorant receptors which are associated with fertility.

Candidate antennal/maxillary palp-specific phage were subjected to in vivo excision, digestion of resulting pBLUESCRIPT plasmid DNAs with BamHI/Asp718, and electrophoresis on 1.5% agarose gels. Southern blots were hybridized with $^{32}$P-labeled cDNA probes generated from antennal/maxillary palp mRNA (Panel A), head minus antennal/maxillary palp mRNA (Panel B), or virgin female body mRNA (Panel C). The ethidium bromide stained gel is shown in Panel D. Of the thirteen clones displayed in this figure, four appear to be antennal/maxillary palp specific (lanes 5, 7, 9, and 11). However, only two are selectively expressed in subsets of cells in chemosensory organs of the adult fly. DOR104, a putative maxillary palp odorant receptor, is in Lane 9. The clone in Lane 11 (RN106) is homologous to lipoprotein and triglyceride lipases and is expressed in a restricted domain in the antenna (data not shown).

Figure 2A:
Figure 2B:
Figure 2C:

FIGS. 2A–2C Expression of DOR104 in a Subset of Maxillary Palp Neurons (A) A frontal section of an adult maxillary palp was hybridized with a digoxigenin-labeled antisense RNA probe and visualized with anti-digoxigenin conjugated to alkaline phosphatase. Seven cells expressing DOR104 are visible in this 15 µm section, which represents about one third of the diameter of the maxillary palp. Serial sections of multiple maxillary palps were scored for DOR104 expression and on average 20 cells per maxillary palp are positive for this receptor.

(B) Transgenic flies carrying a DOR104-lacZ reporter transgene were stained with X-GAL in a whole mount preparation. Maxillary palps were dissected from the head and viewed in a flattened cover slipped preparation under Nomarski optics, which allows the visualization of all 20 cells expressing DOR104-lacZ.

(C) Dendrites and axons of neurons expressing DOR104-lacZ are visible in this horizontal section of a maxillary palp. LacZ expression was visualized with a polyclonal anti-β-galactosidase primary antibody and a CY3-conjugated secondary antibody. Sections were viewed under epifluorescence and photographed on black and white film.

Figure 3A:
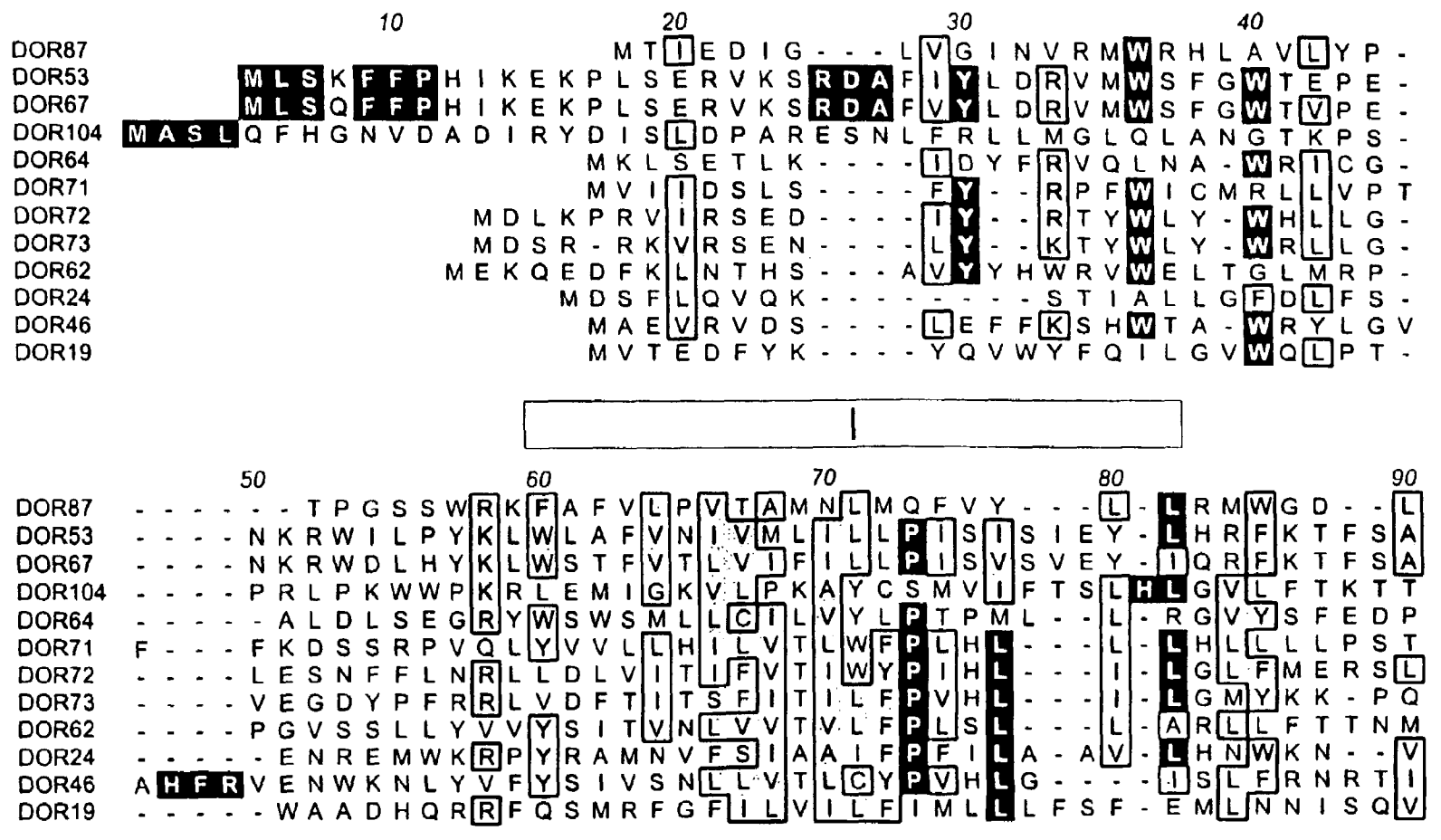
Figure 3B:
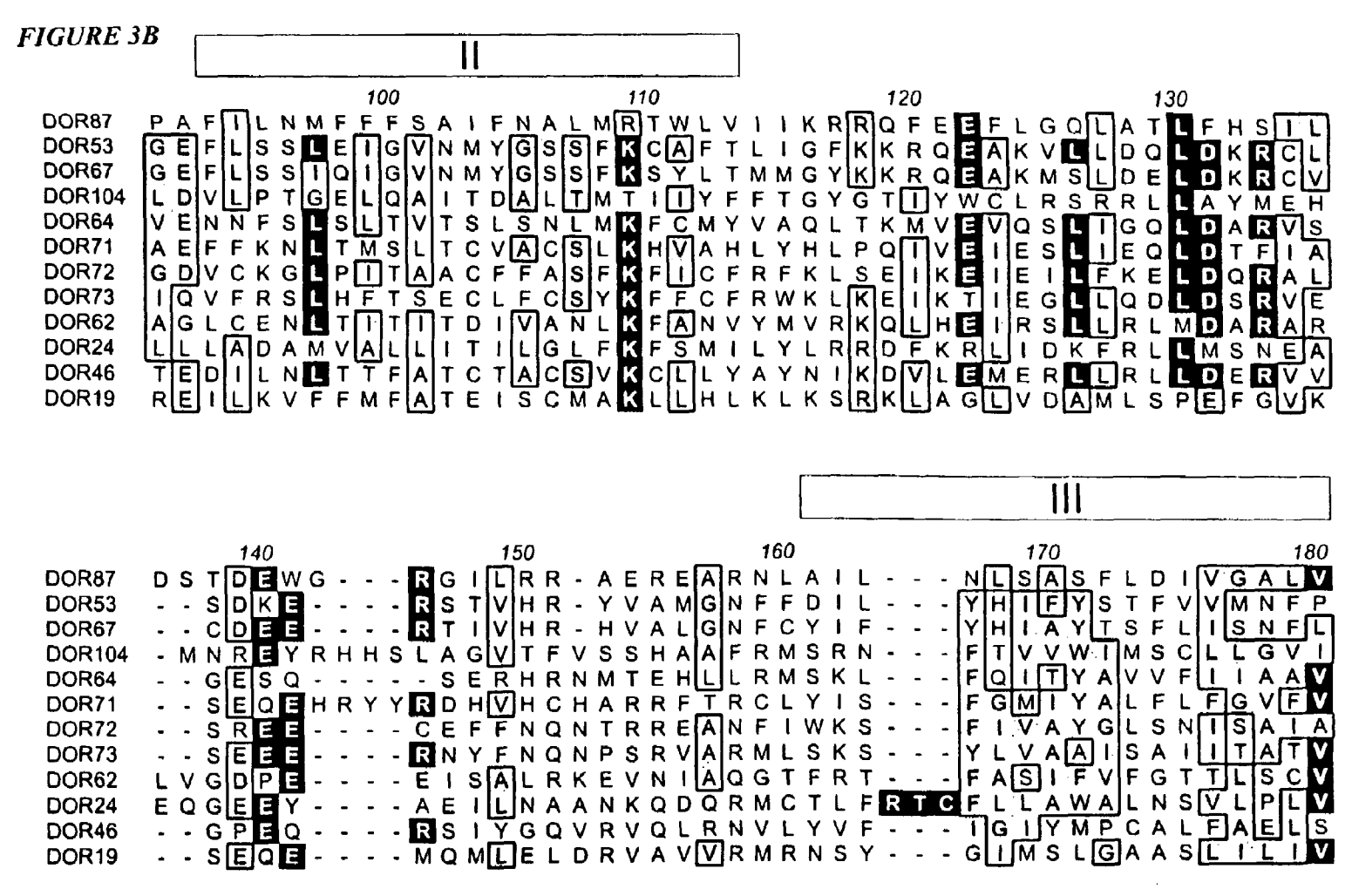
Figure 3C:
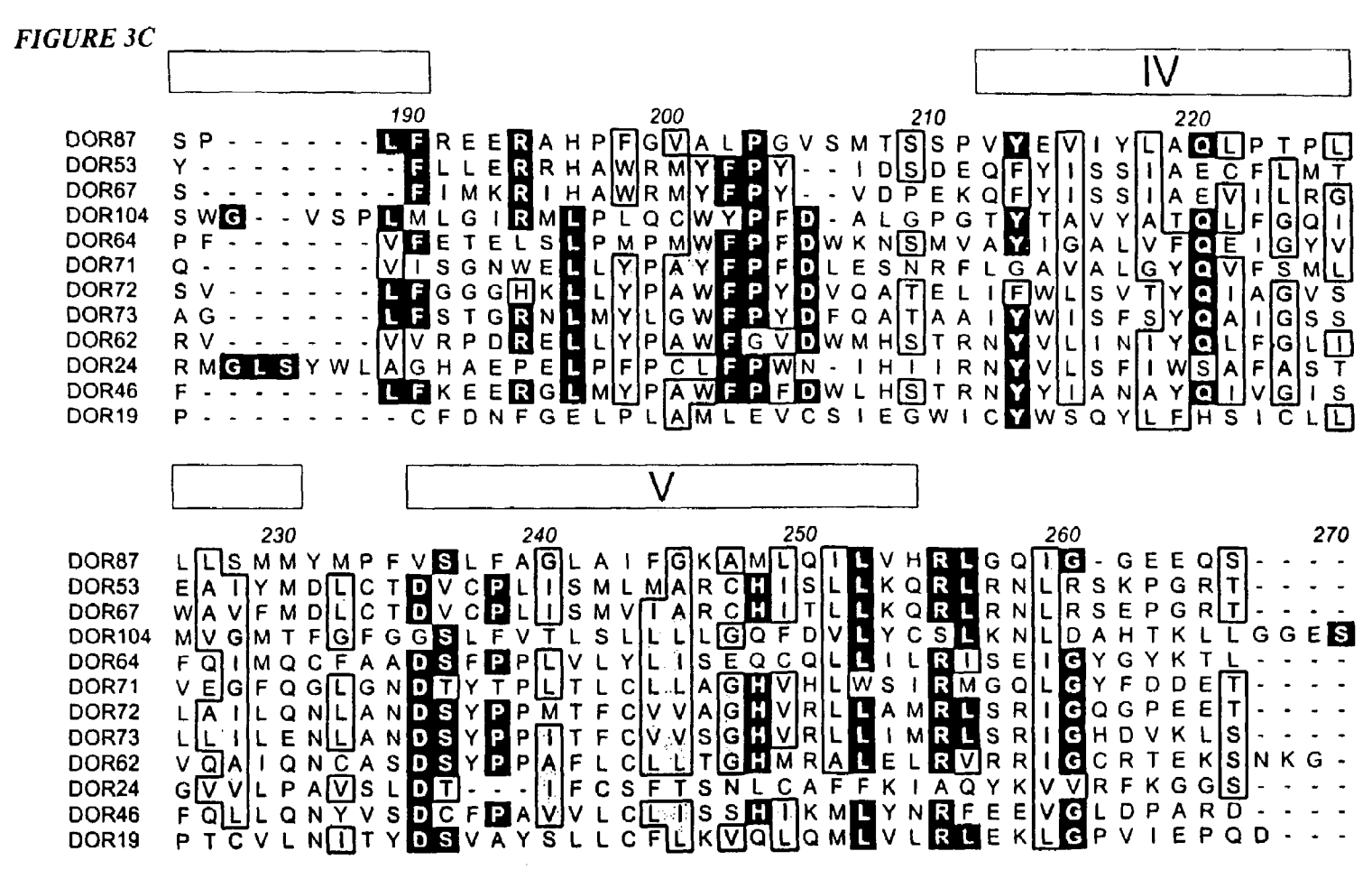
Figure 3D:
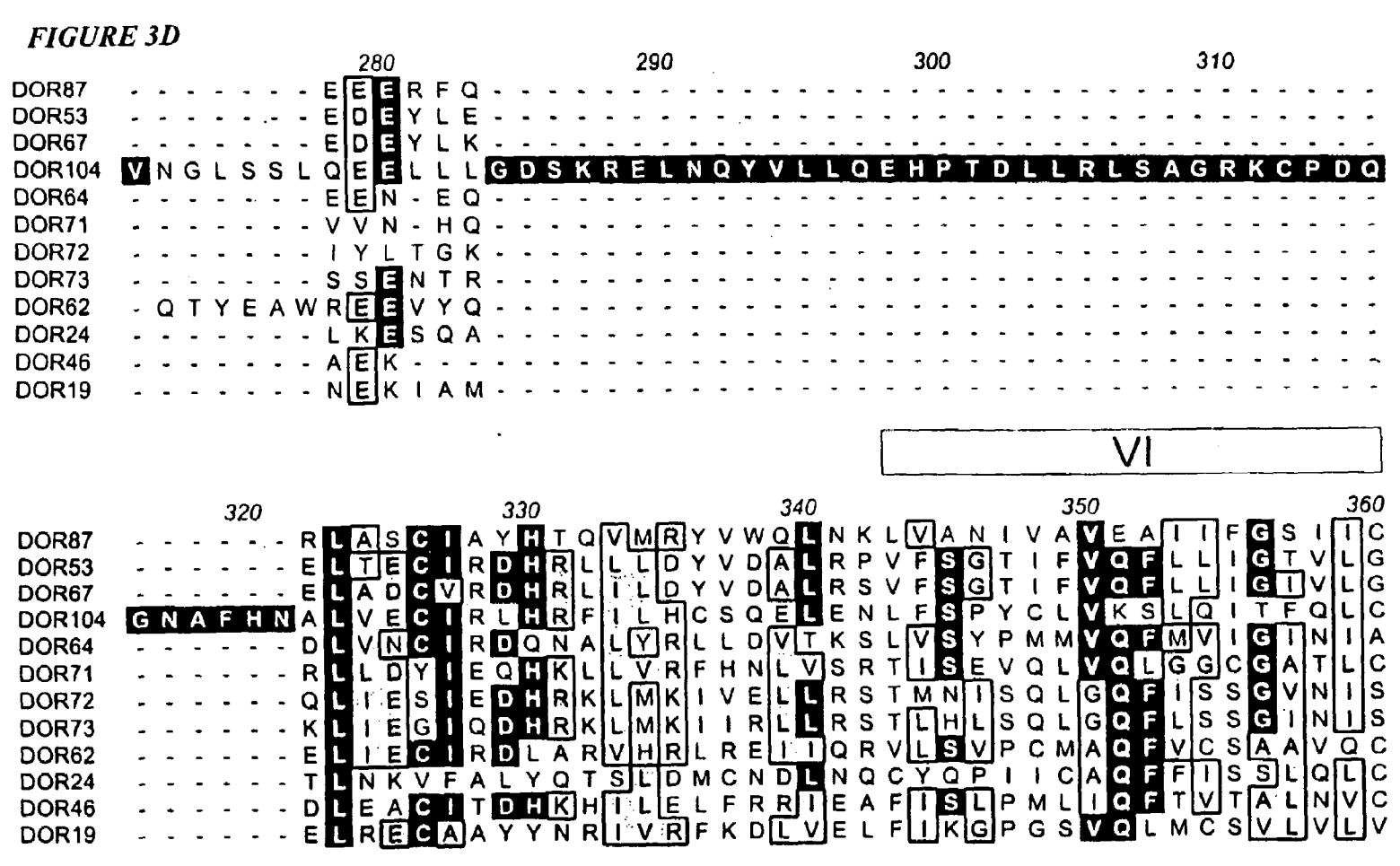
Figure 3E:
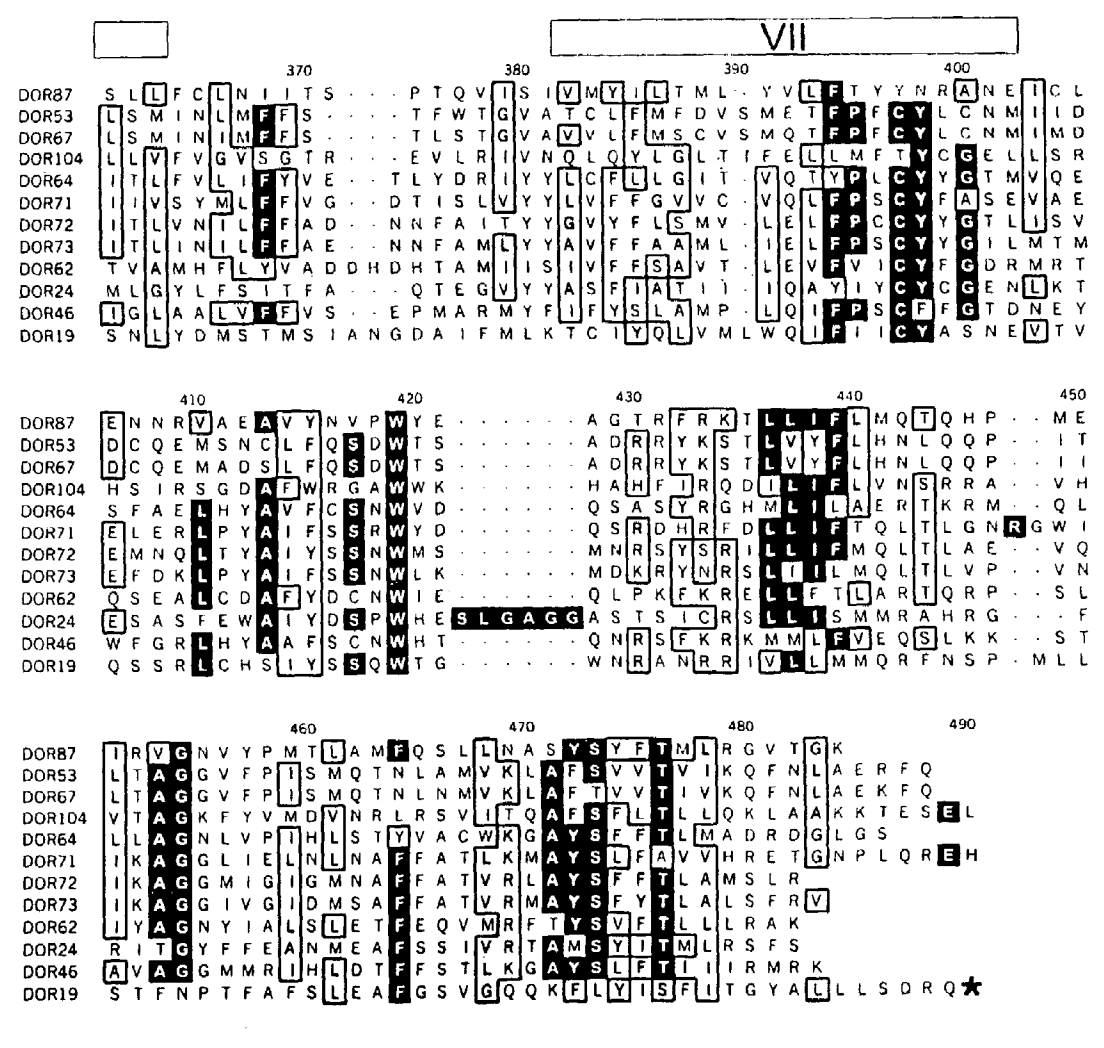

FIGS. 3A–3E Predicted Amino Acid Sequences of *Drosophila* Odorant Receptor Genes Deduced amino acid sequences of 12 DOR genes are aligned using ClustalW (MacVector, Oxford Molecular). Predicted positions of transmembrane regions (I–VII) are indicated by rectangular boxes above the alignment. Amino acids identities are marked with black shading and similarities are indicated with light shading. Protein sequences of DOR87 (SEQ ID NO: 6), DOR53 (SEQ ID NO: 8), DOR67 (SEQ ID NO: 10), DOR104 (SEQ ID NO: 4), and DOR64 (SEQ ID NO: 12) were derived from cDNA clones. All others were derived from GENSCAN predictions of intron-exon arrangements in genomic DNA, as indicated by the letter "g" after the gene name.

FIGS. 4A–4I Receptor Gene Expression in Spatially Restricted Regions of the Antenna Digoxigenin-labeled antisense RNA probes against 8 DOR genes each hybridize to a small number of cells distributed in distinct regions in the antenna. The total number of cells per antenna expressing a given receptor was obtained by counting positive cells in serial sections of multiple antennae. There are approximately 20 positive cells per antenna for DOR67 (A), DOR53 (B), and DOR24 (data not shown); 15 positive cells for DOR62 (C) and DOR87 (D); and 10 positive cells for DOR64 (E). The actual number of cells staining in these sections is a subset of this total number. With the exception of DOR53 and DOR67, which strongly cross-hybridize, the receptor genes likely identify different olfactory neurons, such that the number of cells staining with a mixed probe (F) is equal to the sum of those staining with the individual probes (A–E). The mixture of DOR53, 67, 62, 87 and 64 labels a total of about 60 cells per antenna. A total of 34 cells stain with the mixed probe in this 15 µm section. Expression of the linked genes DOR71g, DOR72g, and DOR73g is shown in panels (G), (H), and (I), respectively. DOR71g is expressed in approximately 10 cells in the maxillary palp. Five positive cells are seen in the horizontal section in panel (G). The expression of the other members of this linkage group was also examined. DOR72g was found in approximately 15 cells (of which 3 label in this section) (H) and DOR73g in 1 to 2 cells per antenna (I).

FIGS. 5A–5G Odorant Receptors are Restricted to Distinct Populations of Olfactory Neurons (A–C) Flies of the C155 elav-GAL4; UAS-lacZ genotype express cytoplasmic lacZ in all neuronal cells. Panels (A–C) show confocal images of a horizontal maxillary palp section from such a fly incubated with an antisense RNA probe against DOR104 (red) and anti-β-galactosidase antibody (green). DOR104 recognizes five cells in this maxillary palp section (A), all of which also express elav-lacZ (B), as demonstrated by the yellow cells in the merged image in panel (C).

(D, E) DOR64 and DOR87 are expressed in non-overlapping neurons at the tip of the antenna. Antisense RNA probes for DOR64 (digoxigenin-RNA; red) and DOR87 (FITC-RNA; green) were annealed to the same antennal sections and viewed by confocal microscopy. Panel (D) is a digital superimposition of confocal images taken at 0.5 µm intervals through a 10 µm section of the antenna. Cells at different focal planes express both receptors, but no double labeled cells are found.

(F, G) Two color RNA in situ hybridization with odorant receptors and odorant binding proteins demonstrates that these proteins are expressed in different populations of cells. DOR53 (FITC-RNA; green) labels a few cells internal to the cuticle at the proximal-medial edge, while PBPRP2 (digoxigenin-RNA; red) labels a large number of cells apposed to the cuticle throughout the antenna (F). The more restricted odorant binding protein OS-F (digoxigenin-RNA; red) also stains cells distinct from those expressing DOR67 (FITC-RNA; green)(G).

FIGS. 6A–6F Receptor Expression is Conserved Between Individuals

Frontal sections of antennae from six different individuals were hybridized with digoxigenin-labeled antisense RNA probes against DOR53 (A–C) or DOR87 (D–F). DOR53 labels approximately 20 cells on the proximal-medial edge of the antenna, of which approximately 5 are shown labeling in these sections. DOR87 is expressed in about the same number of cells at the distal tip. Both the position and number of staining cells is conserved between different individuals and is not sexually dimorphic.

FIGS. 7A–7E *Drosophila* Odorant Receptors are Highly Divergent

Oregon R genomic DNA isolated from whole flies was digested with BamHI (B), EcoRI (E), or HindIII (H), electrophoresed on 0.8% agarose gels, and blotted to nitrocellulose membranes. Blots were annealed with $^{32}$P-labeled probes derived from DOR53 cDNA (A), DOR67 cDNA (B), or DNA fragments generated by RT-PCR from antennal mRNA for DOR24 (C), DOR62 (D), and DOR72g (E). Strong crosshybridization of DOR53 and DOR67 is seen at both high and low stringency (A, B), while DOR24, 62, and 72 reveal only a single hybridizing band in each lane at both low stringency (C–E) and high stringency (data not shown).

Figure 8:
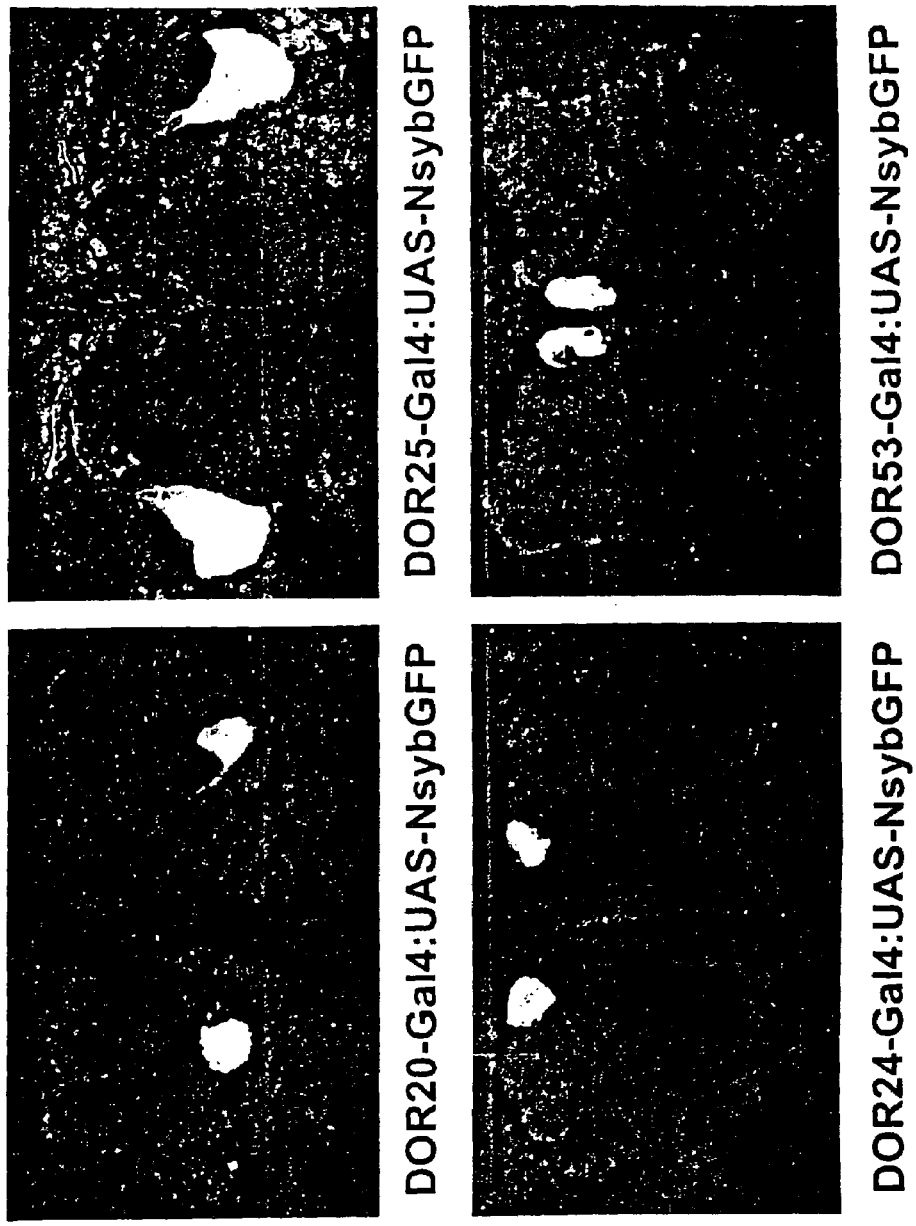

FIG. 8 Analysis of axonal projections of olfactory receptor neurons expressing a given *Drosophila* odorant receptor. Result: all neurons expressing a given receptor send their axons to a single glomerulus, or discrete synaptic structure, in the olfactory processing center of the fly brain. This result is identical to that obtained with mouse odorant receptors: each glomerulus is dedicated to receiving axonal input from neurons expressing a given odorant receptor. Therefore, this result strengthens the argument that these genes indeed function as odorant receptors in *Drosophila*.

Figure 9A-1:
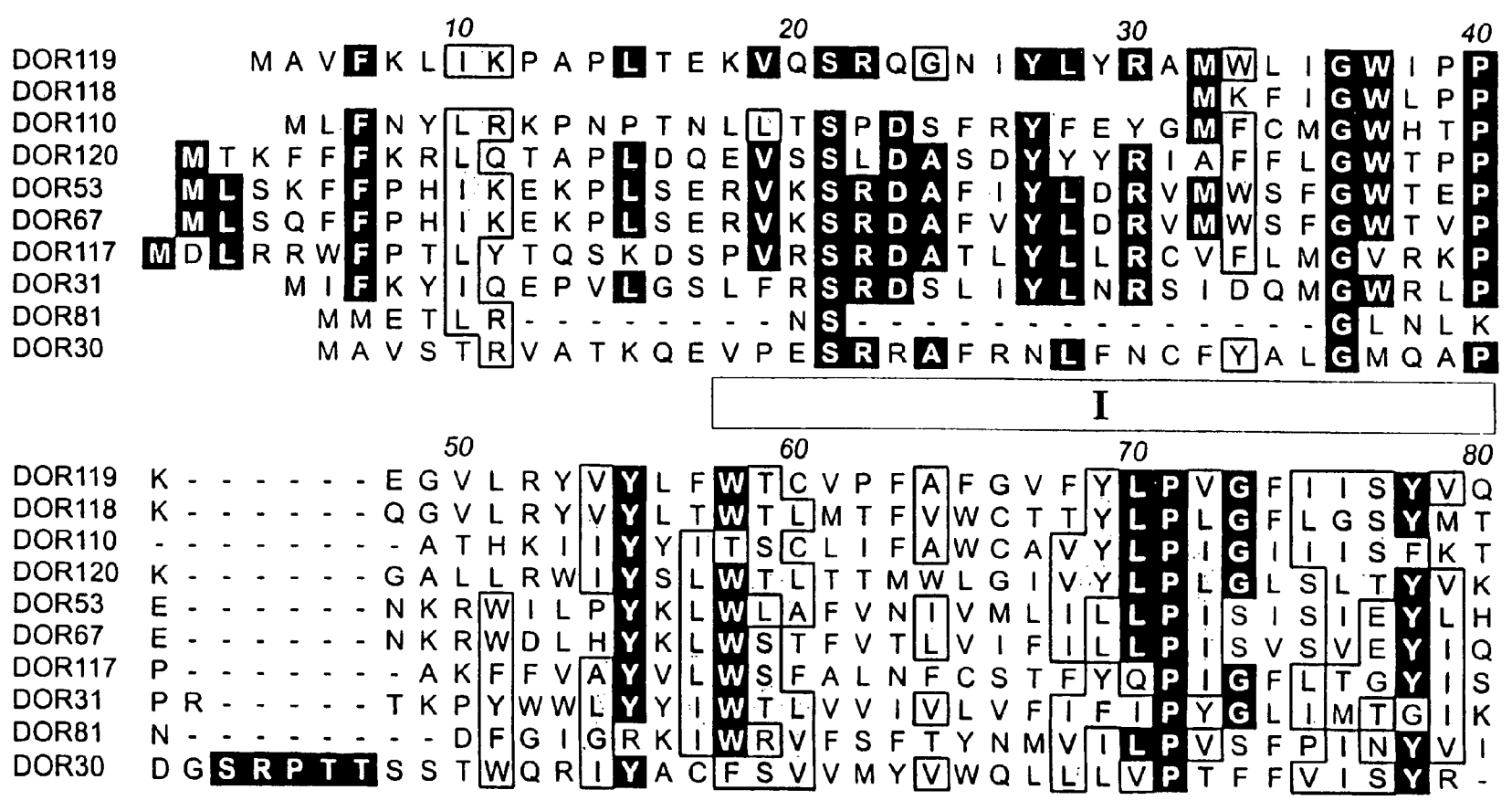
Figure 9A-2:
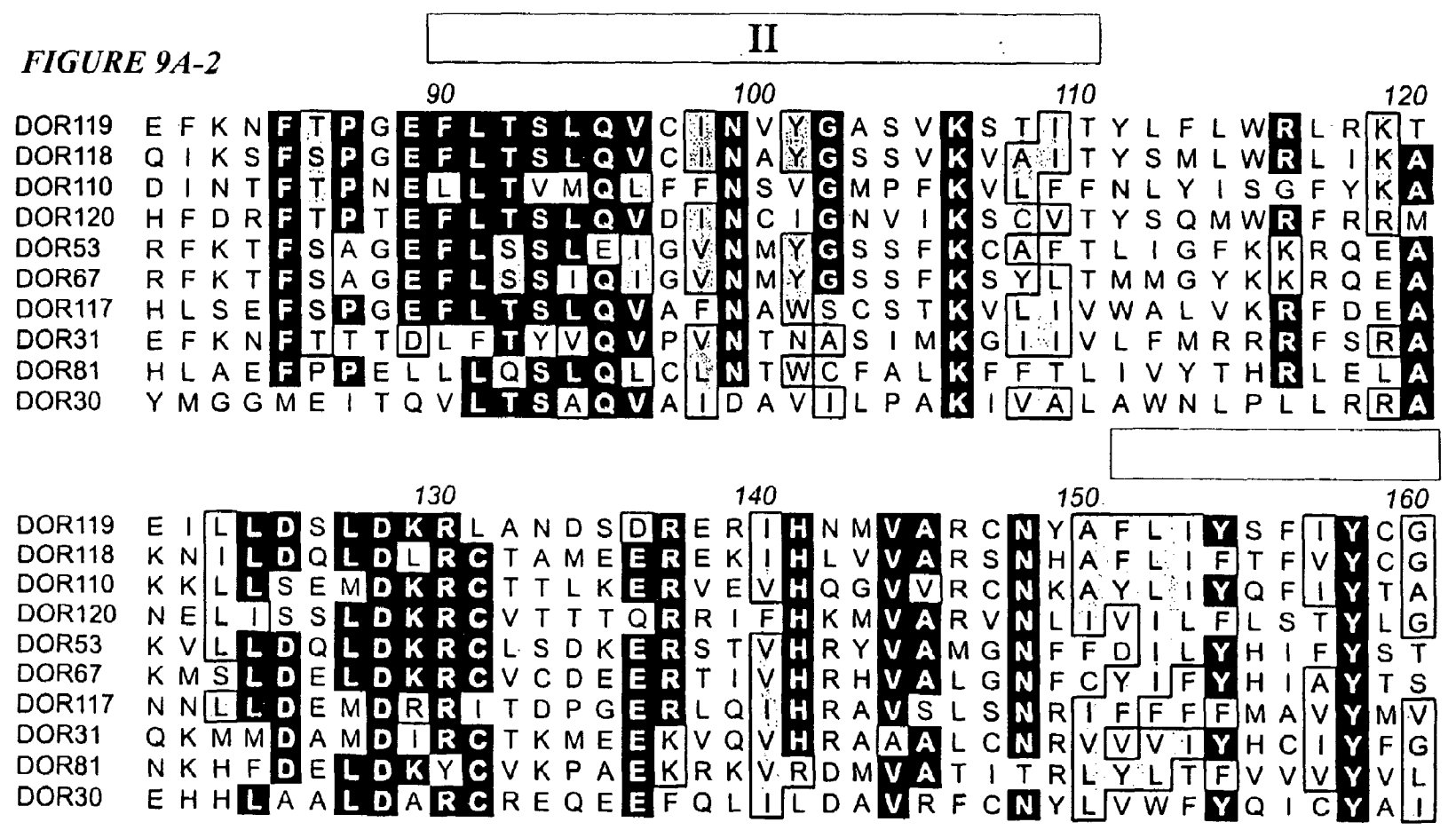
Figure 9A-3:
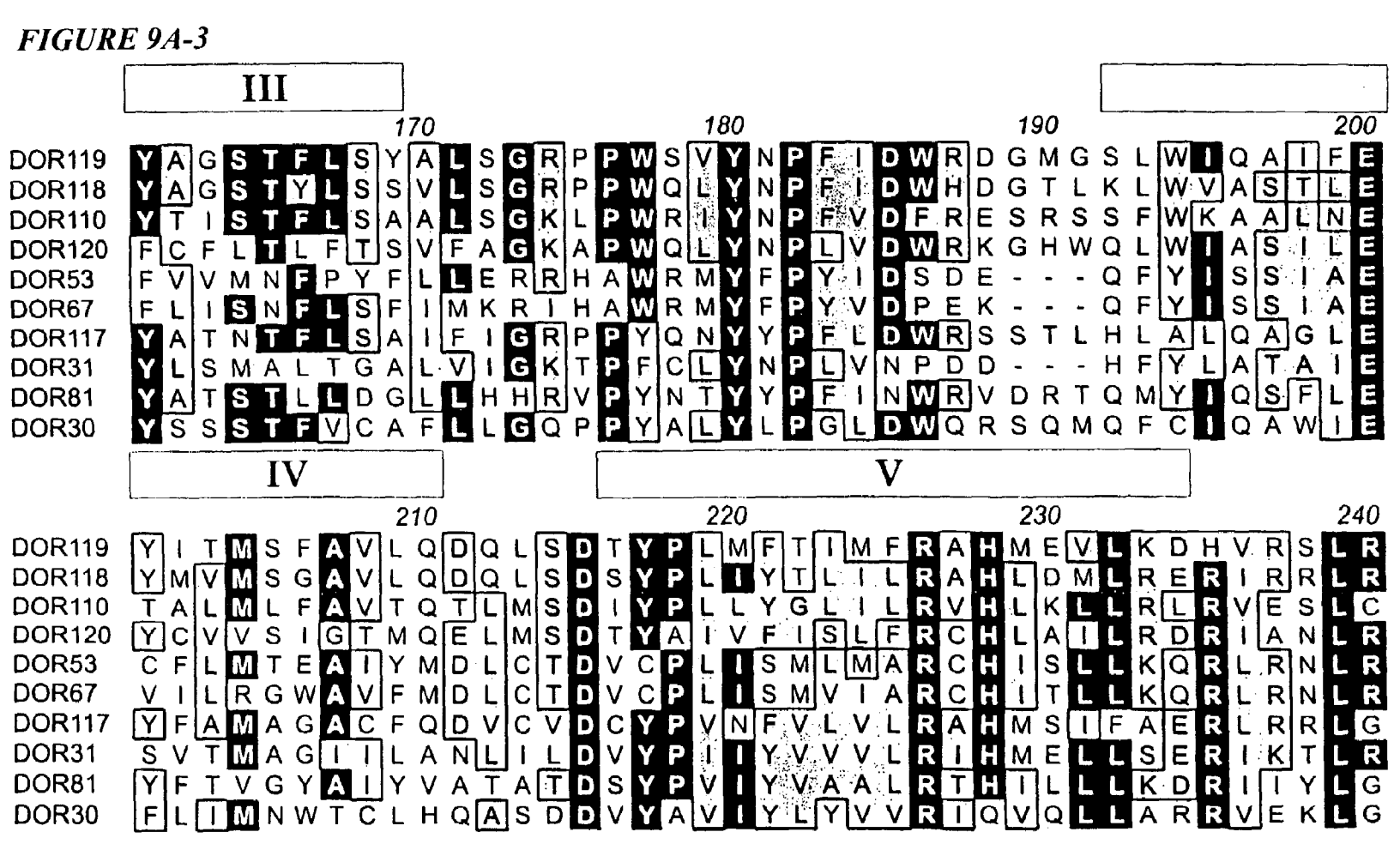
Figure 9A-4:
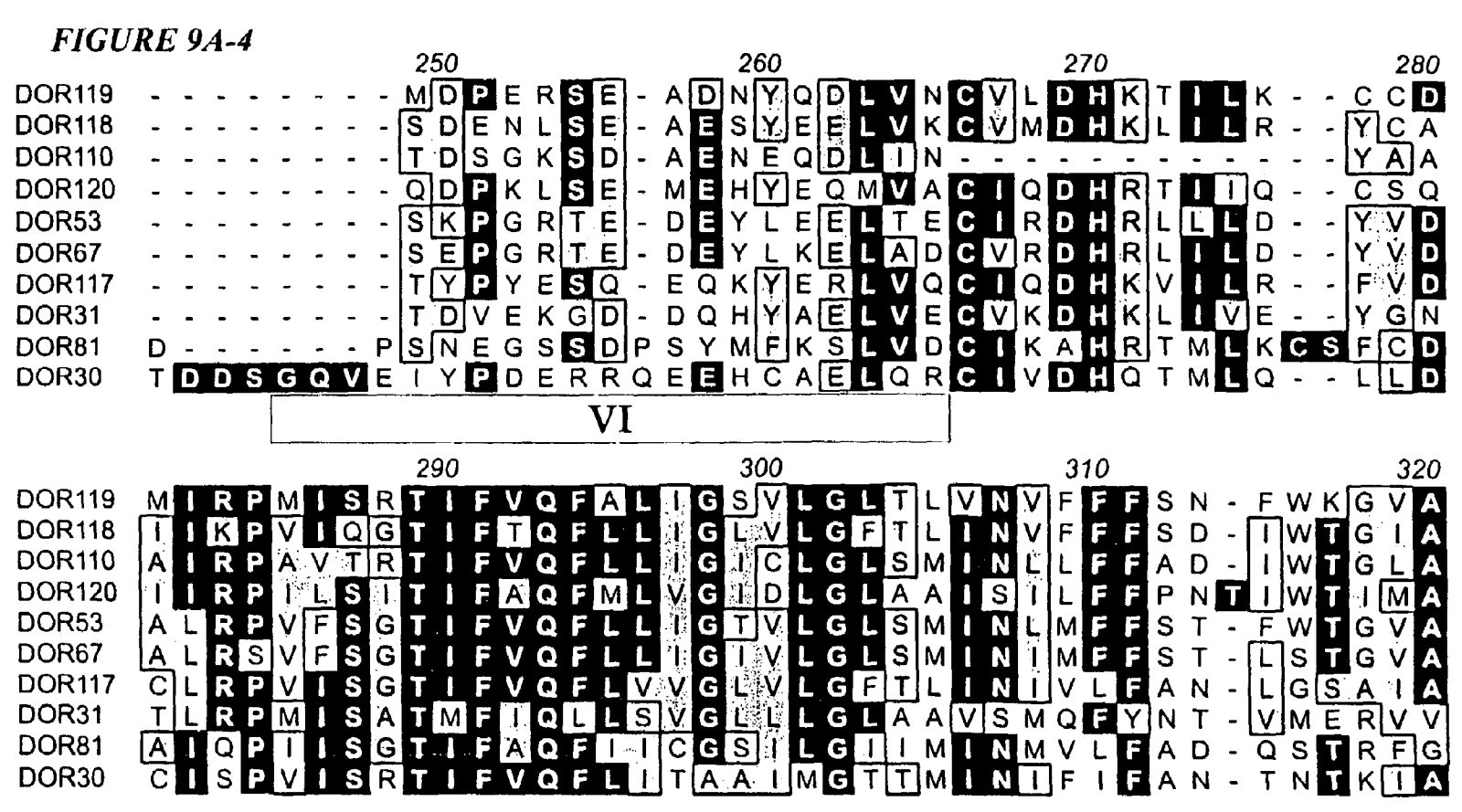
Figure 9A-5:
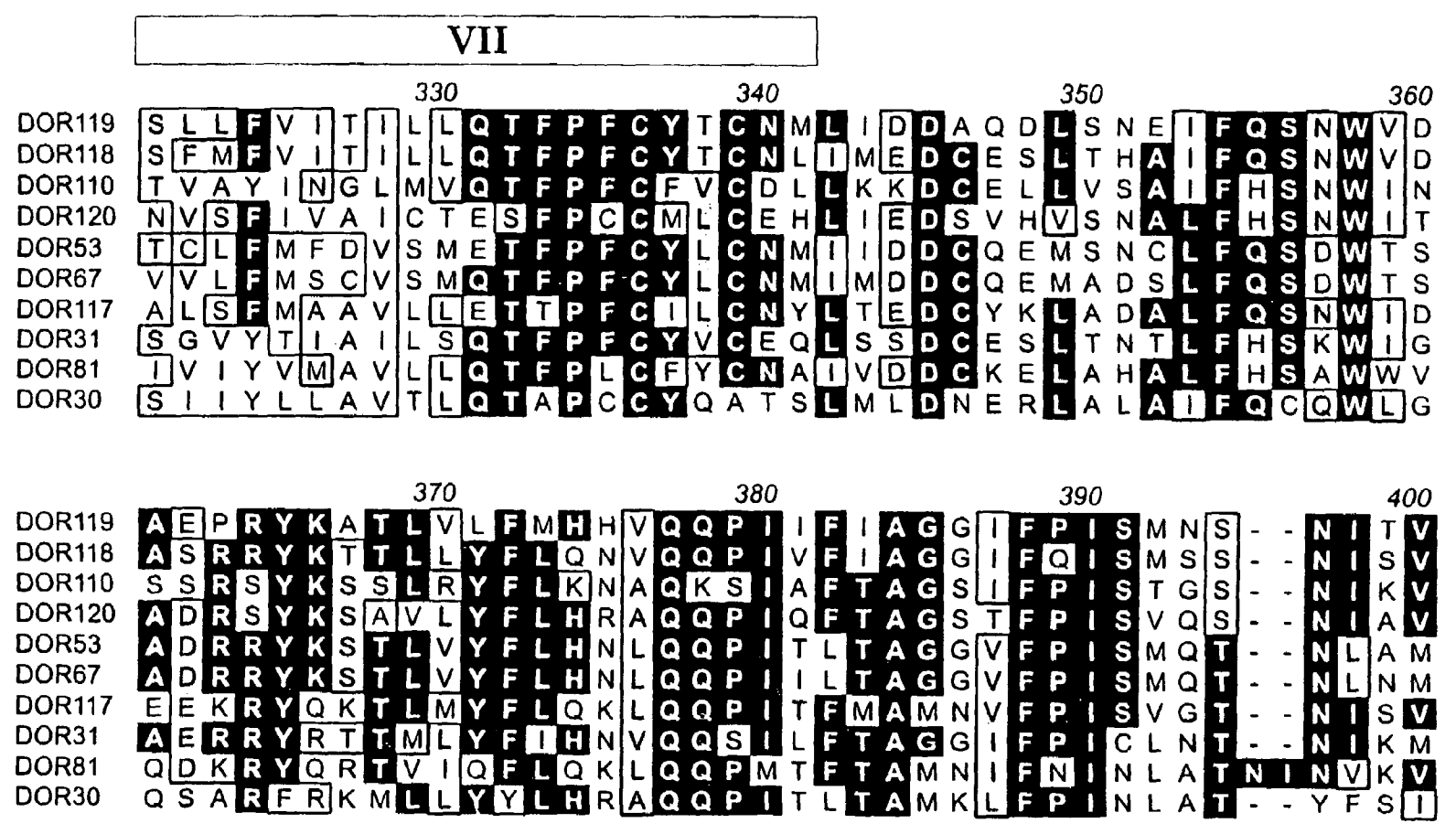
Figure 9B-1:
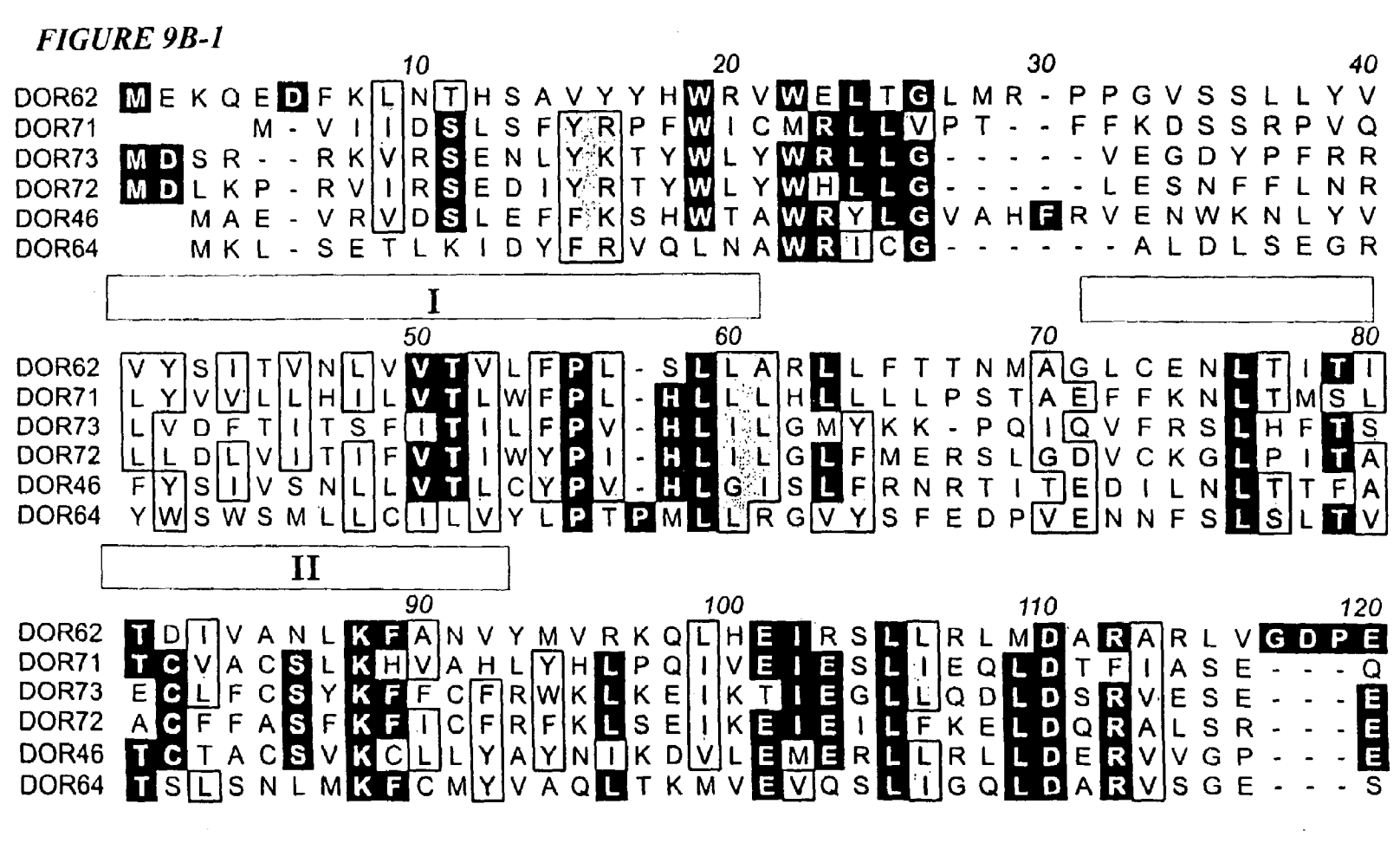
Figure 9B-2:
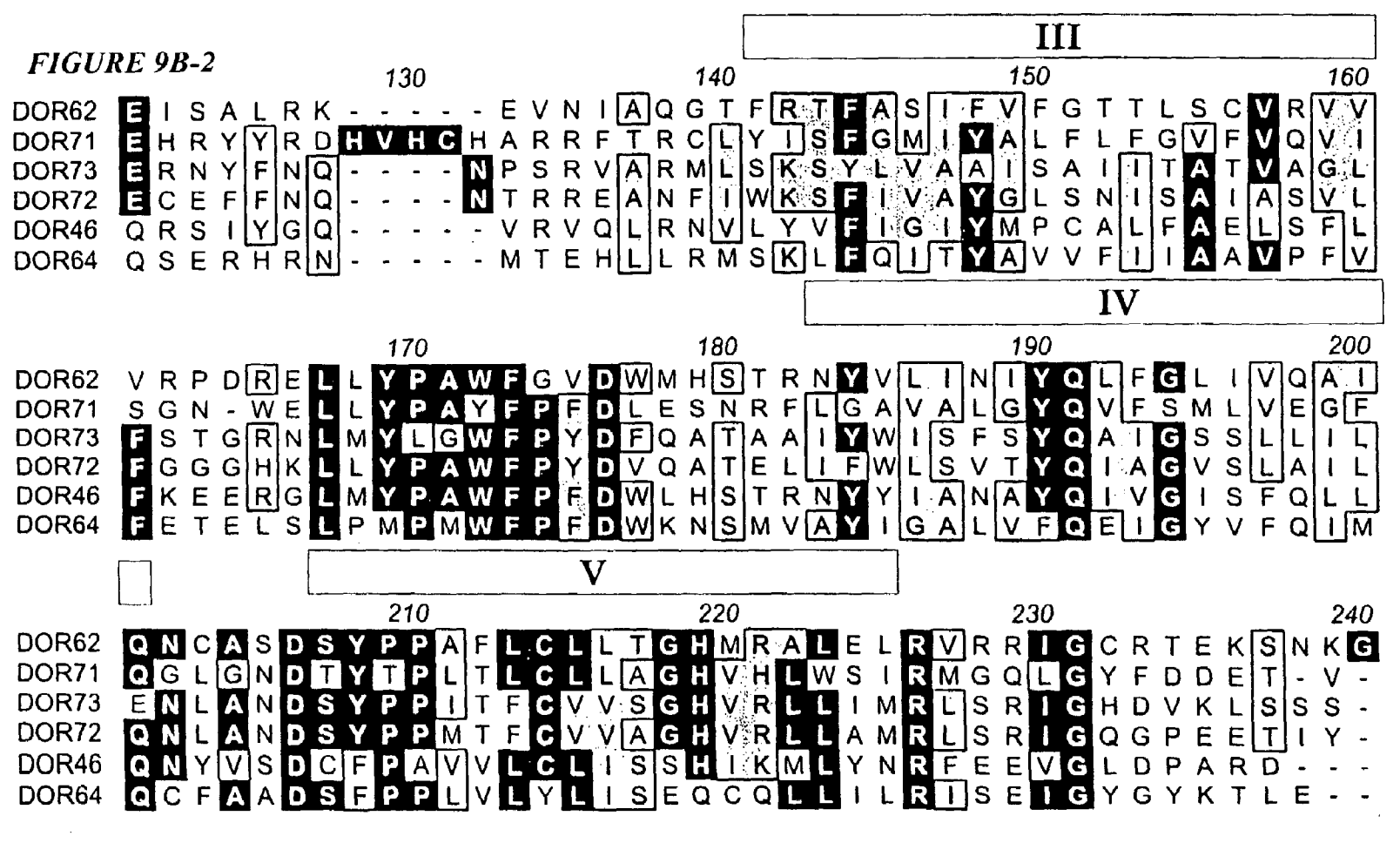
Figure 9B-3:
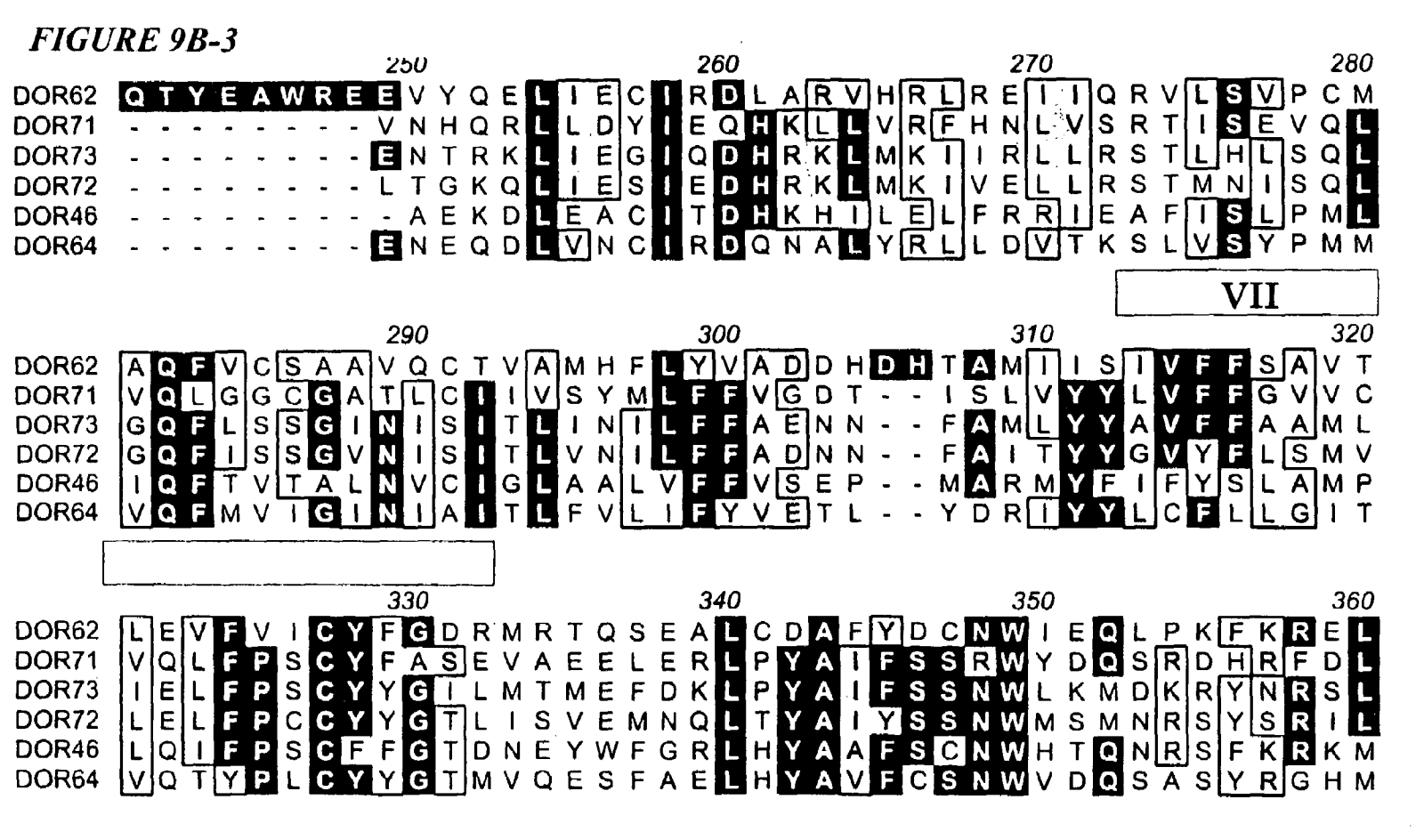
Figure 9B-4:
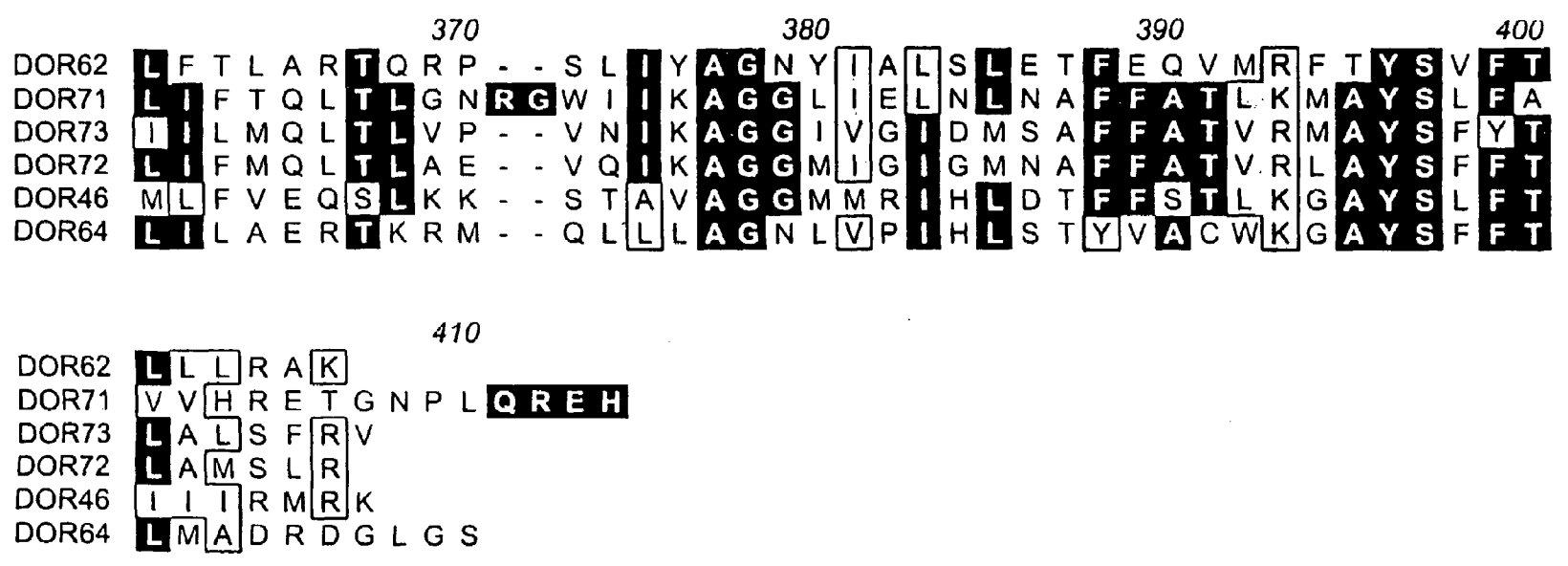

FIGS. 9A1–9A6 and 9B1–9B4 ClustalW alignments of two subfamilies of the *Drosophila* odorant receptors, the DOR53 (A1-A6) and DOR64 (B1-B4) families.

These figures highlight sequence similarities between DOR genes, that are diagnostic hallmarks of the proteins. Residues that are identical in different DOR genes are highlighted in black shading, while residues that are similar are highlighted in light shading.

DETAILED DESCRIPTION OF THE INVENTION

In order to facilitate an understanding of the Experimental Procedures section which follow, certain frequently occurring methods and/or terms are described in Sambrook, et al. (1989).

Throughout this application, the following standard abbreviations are used throughout the specification to indicate specific nucleotides:

| | |
|---|---|
| C = cytosine | A = adenosine |
| T = thymidine | G = guanosine. |

This invention provides an isolated nucleic acid molecule encoding an insect odorant receptor. The nucleic acid includes but is not limited to DNA, cDNA, genomic DNA, synthetic DNA or RNA. In an embodiment, the nucleic acid molecule encodes a *Drosophila* odorant receptor.

The invention provides an isolated nucleic acid encoding a polypeptide present in an insect odorant receptor which polypeptide comprises seven transmembrane domains and a C-terminal domain, wherein one of the seven transmembrane domains is located within the polypeptide at a position adjoining the C-terminal domain and wherein this seventh transmembrane domain and the adjoining C-terminal domain together comprise consecutive amino acids the sequence of which is as follows:

(SEQ ID NO: 107)
-(F, Y, L, A, T, S or C)-(P, I, M, V, T, L, Q, S or H)-(F, Y, I, S, L, C, M or V)-(C, Y, T, S, L or A)-(Y, N, F, M, I, L, K, S, H or T)-(X)$_{20}$-W-;

wherein each X in (X)$_{20}$ represents an amino acid and the identity of each X is independent of the identity of any other X.

In one embodiment, the seventh transmembrane domain and the adjoining C-terminal domain together comprise consecutive amino acids the sequence of which is as follows:

(SEQ ID NO: 111)
-(F, Y, L, A or T)-(P, I, M, V or T)-(F, Y, I, S, L or C)-(C, Y or T)-(Y, N, F, M or I)-(X)$_{20}$-W-.

In one embodiment, the seventh transmembrane domain and the adjoining C-terminal domain together comprise consecutive amino acids the sequence of which is as follows:

(SEQ ID NO: 109)
-(F, Y or L)-(P, I, M, V or T)-(F, Y, I, S, L or C)-(C, Y or T)-(Y, N or F)-(X)$_{20}$-W-.

In one embodiment, the seventh transmembrane domain and the adjoining C-terminal domain together comprise consecutive amino acids the sequence of which is as follows:

—F—P—X—C—Y—(X)$_{20}$—W— (SEQ ID NO: 112).

The invention provides an isolated nucleic acid encoding a polypeptide present in an insect odorant receptor, wherein the polypeptide is selected from the group consisting of polypeptides comprising consecutive amino acids the sequence of which is one of the following:

(a) SEQ ID NO: 2, (b) SEQ ID NO: 4, (c) SEQ ID NO: 6, (d) SEQ ID NO: 8, (e) SEQ ID NO: 10, (f) SEQ ID NO: 12, (g) SEQ ID NO: 14, (h) SEQ ID NO: 16, (i) SEQ ID NO: 18, (j) SEQ ID NO: 20, (k) SEQ ID NO: 22, (l) SEQ ID NO: 24, (m) SEQ ID NO: 26, (n) SEQ ID NO: 28, (o) SEQ ID NO: 30, (p) SEQ ID NO: 32, (q) SEQ ID NO: 34, (r) SEQ ID NO: 36, (s) SEQ ID NO: 38, (t) SEQ ID NO: 40, (u) SEQ ID NO: 42, (v) SEQ ID NO: 44, (w) SEQ ID NO: 46, (x) SEQ ID NO: 48, (y) SEQ ID NO: 50, (z) SEQ ID NO: 52, (aa) SEQ ID NO: 54, (bb) SEQ ID NO: 56, (cc) SEQ ID NO: 58, (dd) SEQ ID NO: 60, (ee) SEQ ID NO: 62, (ff) SEQ ID NO: 64, (gg) SEQ ID NO: 66, (hh) SEQ ID NO: 68, (ii) SEQ ID NO: 70, (jj) SEQ ID NO: 72, (kk) SEQ ID NO: 74, (ll) SEQ ID NO: 76, (mm) SEQ ID NO: 78, (nn) SEQ ID NO: 80, (oo) SEQ ID NO: 82, (pp) SEQ ID NO: 84, (qq) SEQ ID NO: 86, (rr) SEQ ID NO: 88, (ss) SEQ ID NO: 90, (tt) SEQ ID NO: 92, (uu) SEQ ID NO: 94, (vv) SEQ ID NO: 96, (ww) SEQ ID NO: 98, (xx) SEQ ID NO: 100, (yy) SEQ ID NO: 102, (zz) SEQ ID NO: 104, (aaa) SEQ ID NO: 106, or (bbb) a polypeptide which shares greater than 25% amino acid identity with any one of the polypeptides of (a)–(aaa), and comprises a transmembrane domain and an adjoining C-terminal domain which together comprise consecutive amino acids the sequence of which is as follows:

```
                                              (SEQ ID NO: 107)
-(F, Y, L, A, T, S or C)-(P, I, M, V, T, L, Q, S
or H)-(F, Y, I, S, L, C, M or V)-(C, Y, T, S, L or
A)-(Y, N, F, M, I, L, K, S, H or T)-(X)<sub>20</sub>-W-;
``` wherein each X in $(X)_{20}$ represents an amino acid and the identity of each X is independent of the identity of any other X.

In one embodiment, the nucleic acid encodes a polypeptide which shares greater than 35% amino acid identity with any one of the polypeptides of (a)–(aaa). In one embodiment, the nucleic acid encodes a polypeptide which shares greater than 45% amino acid identity with any one of the polypeptides of (a)–(aaa). In one embodiment, the nucleic acid encodes a polypeptide which shares greater than 55% amino acid identity with any one of the polypeptides of (a)–(aaa). In one embodiment, the nucleic acid encodes a polypeptide which shares greater than 65% amino acid identity with any one of the polypeptides of (a)–(aaa). In one embodiment, the nucleic acid encodes a polypeptide which shares greater than 75% amino acid identity with any one of the polypeptides of (a)–(aaa).

The invention provides an isolated nucleic acid encoding a polypeptide present in an insect odorant receptor, wherein the nucleic acid hybridizes under high stringency to a complement of any of the nucleic acids disclosed herein. The invention also provides an isolated nucleic acid encoding a polypeptide present in an insect odorant receptor, wherein the nucleic acid hybridizes under high stringency to any of the nucleic acids disclosed herein.

The invention provides an isolated nucleic acid encoding a polypeptide present in an insect odorant receptor, wherein the polypeptide comprises consecutive amino acids having a sequence identical to that set forth for DORA45 in SEQ ID NO: 104.

The invention provides an isolated nucleic acid encoding a polypeptide present in an insect odorant receptor, wherein the nucleic acid comprises:

(a) a nucleic acid sequence given in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, or 105; or (b) a nucleic acid sequence degenerate to a sequence of (a) as a result of the genetic code.

In one embodiment, the insect odorant receptor comprises seven transmembrane domains.

In different embodiments of any of the isolated nucleic acids described herein, the nucleic acid is DNA or RNA. In different embodiments, the DNA is cDNA, genomic DNA, or synthetic DNA. In different embodiments, the RNA is synthetic RNA.

In one embodiment of any of the isolated nucleic acids described herein, the nucleic acid molecule encodes a *Drosophila* odorant receptor.

The nucleic acids encoding an insect odorant receptor includes molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms.

These molecules include but not limited to: the incorporation of codons "preferred" for expression by selected non-mammalian hosts; the provision of sites for cleavage by restriction endonuclease enzymes; and the provision of additional initial, terminal or intermediate sequences that facilitate construction of readily expressed vectors. Accordingly, these changes may result in a modified insect odorant receptor. It is the intent of this invention to include nucleic acid molecules which encode modified insect odorant receptors. Also, to facilitate the expression of receptors in different host cells, it may be necessary to modify the molecule such that the expressed receptors may reach the surface of the host cells. The modified insect odorant receptor should have biological activities similar to the unmodified insect odorant receptor. The molecules may also be modified to increase the biological activity of the expressed receptor.

The invention provides a nucleic acid comprising at least 12 nucleotides which specifically hybridizes with any of the isolated nucleic acids described herein. In one embodiment, the nucleic acid hybridizes with a unique sequence within the sequence of any of the nucleic acid molecules described herein. In different embodiments, the nucleic acid is DNA, cDNA, genomic DNA, synthetic DNA or RNA.

This invention provides a nucleic acid probe which comprises:

(a) a nucleic acid sequence given in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, or 105; or (b) a nucleic acid sequence degenerate to a sequence of (a) as a result of the genetic code; or (c) a portion of a nucleic acid sequence of (a) or (b) which encodes consecutive amino acids having the sequence set forth in SEQ ID NO: 107.

In an embodiment, the probes are cDNA probes.

This invention provides a vector which comprises any of the isolated nucleic acids described herein. In one embodiment, the vector is a plasmid.

In one embodiment of the vector, the isolated nucleic acids described herein is operatively linked to a regulatory element. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described herein for constructing vectors in general.

The invention provides a host vector system for production of a polypeptide having the biological activity of an insect odorant receptor, which comprises any of the vectors described herein and a suitable host. In different embodiments, the suitable host is a bacterial cell, a yeast cell, an insect cell, or an animal cell.

The host cell of the expression system described herein may be selected from the group consisting of the cells where the protein of interest is normally expressed, or foreign cells such as bacterial cells (such as *E. coli*), yeast cells, fungal cells, insect cells, nematode cells, plant or animal cells, where the protein of interest is not normally expressed. Suitable animal cells include, but are not limited to Vero cells, HeLa cells, Cos cells, CV1 cells and various primary mammalian cells.

The invention provides a method of producing a polypeptide having the biological activity of an insect odorant receptor which comprising growing any of the host vector systems described herein under conditions permitting production of the polypeptide and recovering the polypeptide so produced.

The invention provides a purified insect odorant receptor protein encoded by any of the isolated nucleic acids described herein. This invention further provides a polypeptide encoded by any of the isolated nucleic acids described herein.

The invention provides an antibody which specifically binds to an insect odorant receptor protein encoded by any of the isolated nucleic acids described herein. In one embodiment, the antibody is a monoclonal antibody. In another embodiment, the antibody is polyclonal. The invention provides an antibody which competitively inhibits the binding of any of the antibodies described herein capable of specifically binding to an insect odorant receptor. In one embodiment, the antibody is a monoclonal antibody. In another embodiment, the antibody is polyclonal.

Monoclonal antibody directed to an insect odorant receptor may comprise, for example, a monoclonal antibody directed to an epitope of an insect odorant receptor present on the surface of a cell. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment.

Antibodies directed to an insect odorant receptor may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or 293 cells which express the receptor may be used as immunogens to raise such an antibody. Alternatively, synthetic peptides may be prepared using commercially available machines.

As a still further alternative, DNA, such as a cDNA or a fragment thereof, encoding the receptor or a portion of the receptor may be cloned and expressed. The expressed polypeptide may be recovered and used as an immunogen.

The resulting antibodies are useful to detect the presence of insect odorant receptors or to inhibit the function of the receptor in living animals, in humans, or in biological tissues or fluids isolated from animals or humans.

This antibodies may also be useful for identifying or isolating other insect odorant receptors. For example, antibodies against the *Drosophila* odorant receptor may be used to screen an cockroach expression library for a cockroach odorant receptor. Such antibodies may be monoclonal or monospecific polyclonal antibody against a selected insect odorant receptor. Different insect expression libraries are readily available and may be made using technologies well-known in the art.

One means of isolating a nucleic acid molecule which encodes an insect odorant receptor is to probe a libraries with a natural or artificially designed probes, using methods well known in the art. The probes may be DNA or RNA. The library may be cDNA or genomic DNA.

The invention provides a method for identifying cDNA inserts encoding insect an odorant receptor which comprises:
(a) generating a cDNA library which contains clones carrying cDNA inserts from antennal or maxillary palp sensory neurons;
(b) hybridizing nucleic acid molecules of the clones from the cDNA libraries generated in step (a) with probes prepared from the antenna or maxillary palp neurons and probes from heads lacking antenna or maxillary palp neurons or from virgin female body tissue;
(c) selecting clones which hybridized with probes from the antenna or maxillary palp neurons but not from head lacking antenna or maxillary palp neurons or virgin female body tissue; and
(d) isolating clones which carry the hybridized inserts, thereby identifying inserts encoding an odorant receptor.

In one embodiment, the method described herein, after step (c), further comprises:
(a) amplifying the inserts from the selected clones by polymerase chain reaction;
(b) hybridizing the amplified inserts with probes from the antennal or maxillary palp neurons; and
(c) isolating the clones which carry the hybridized inserts, thereby identifying inserts encoding the odorant receptor.

The invention provides a method for identifying a cDNA insert encoding an insect odorant receptor which comprises:
(a) generating a cDNA library comprising clones carrying cDNA inserts from antennal or maxillary palp sensory neurons from an insect;
(b) hybridizing nucleic acids of the clones from the cDNA libraries generated in step (a) with a probe which comprises (i) a nucleic acid sequence given in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, or 105; or (ii) a nucleic acid sequence degenerate to a sequence of (i) as a result of the genetic code; or (iii) a portion of a nucleic acid sequence of (i) or (ii) which encodes consecutive amino acids having the sequence set forth in SEQ ID NO: 107; and
(c) isolating the resulting hybridized nucleic acids so as to thereby identify the cDNA insert encoding the insect odorant receptor.

This invention provides a method for identifying a cDNA insert encoding an insect odorant receptor which comprises:
(a) generating a cDNA library comprising clones carrying cDNA inserts from antennal or maxillary palp sensory neurons from an insect;
(b) hybridizing nucleic acids of the clones from the cDNA libraries generated in step (a) with a probe which comprises (i) a nucleic acid sequence given in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, or 105; or (ii) a nucleic acid sequence degenerate to a sequence of (i) as a result of the genetic code; or (iii) a portion of a nucleic acid sequence of (i) or (ii) which encodes consecutive amino acids having the sequence set forth in SEQ ID NO: 107; and
  (c) isolating the hybridized inserts, thereby identifying a cDNA insert encoding an insect odorant receptor.

The appropriate polymerase chain reaction primers may be chosen from the conserved regions of the known insect odorant receptor sequences. Alternatively, the primers may be chosen from the regions which are the active sites for the binding of ligands.

In one embodiment of any of the methods described herein, the insect odorant receptor is encoded by any of the isolated nucleic acid molecules described herein.

The invention provides the cDNA inserts identified by any of the methods described herein.

The invention provides a method for identifying a cDNA insert encoding an insect odorant receptor which comprises:
  (a) generating cDNA libraries which contain clones carrying inserts from a sample which contains at least one antennal or maxillary palp neuron;
  (b) contacting clones from the cDNA libraries generated in step (a) with any of the nucleic acid molecules described herein which specifically hybridize with any of the isolated nucleic acid molecules described herein which encode an insect odorant receptor protein, in conditions permitting hybridization of the nucleic acid molecules of the clones and the nucleic acid molecule;
  (c) selecting clones which hybridized with the nucleic acid molecule; and
  (d) isolating the clones which carry the hybridized inserts, thereby identifying inserts encoding the odorant receptor.

The invention provides a method for identifying cDNA inserts encoding an insect odorant receptor which comprises:
  (a) generating cDNA libraries which contain clones with inserts from a sample which contains at least one antenna or maxillary palp sensory neuron;
  (b) contacting the clones from the cDNA libraries generated in step (a) with appropriate polymerase chain reaction primers capable of specifically binding to nucleic acid molecules encoding odorant receptors in appropriate conditions permitting the amplification of the hybridized inserts by polymerase chain reaction;
  (c) selecting the amplified inserts; and
  (d) isolating the amplified inserts, thereby identifying the inserts encoding the odorant receptor.

In one embodiment, the insect odorant receptor is encoded by any of the isolated nucleic acids described herein.

The invention provides the cDNA inserts identified by any of the methods described herein.

This invention provides a method for identifying a cDNA insert encoding an odorant receptor from an insect which comprises:
  (a) generating cDNA libraries which contain clones carrying CDNA inserts from the insect;
  (b) contacting the CDNA libraries containing the clones generated in step (a) with any of the nucleic acid molecules described herein which specifically hybridize with any of the isolated nucleic acid molecules described herein which encode an insect odorant receptor protein under conditions permitting hybridization of the clones and the nucleic acid;
  (c) selecting clones which hybridized with the nucleic acid; and
  (d) isolating the hybridized clones which contain the cDNA inserts so as to thereby identify inserts encoding the odorant receptor from the insect.

The invention provides a method for obtaining a nucleic acid encoding an odorant receptor from an insect which comprises:
  (a) contacting a sample containing nucleic acid of insect origin with primers which comprise nucleic acid corresponding to a nucleic acid which encodes an amino acid sequence set forth in SEQ ID NO: 107 under appropriate conditions permitting hybridization of the primers to the nucleic acid of insect origin to produce a hybridization product;
  (b) amplifying the resulting hybridization product using a polymerase chain reaction; and
  (c) isolating the amplified molecules, thereby obtaining a nucleic acid encoding an odorant receptors from an insect.

This invention provides a method for obtaining a nucleic acid encoding an odorant receptor from an insect which comprises:
  (a) contacting a sample containing nucleic acid of insect origin with polymerase chain reaction primers which specifically hybridize with nucleic acid which encodes an amino acid sequence set forth in SEQ ID NO: 107 under appropriate conditions permitting hybridization of the primers to the nucleic acid to produce a hybridization product;
  (b) amplifying the resulting hybridization product using a polymerase chain reaction; and
  (c) isolating the amplified molecules, thereby obtaining a nucleic acid encoding an odorant receptor from an insect.

In one embodiment, the insect odorant receptor is encoded by any of the isolated nucleic acids described herein.

This invention also provides a method to isolate DNA molecules encoding insect odorant receptors comprising: (a) contacting a biological sample known to contain nucleic acids with appropriate polymerase chain reaction primers capable of specifically binding to nucleic acid molecules encoding insect odorant receptors in appropriate conditions permitting the amplification of the hybridized molecules by polymerase chain reaction; (b) isolating the amplified molecules, thereby identifying the DNA molecules encoding the insect odorant receptors.

This invention provides a cDNA insert encoding an insect odorant receptor obtainable by the following method:
  (a) generating cDNA libraries which contain clones carrying cDNA inserts from the insect;
  (b) contacting the cDNA libraries containing the clones generated in step (a) with any of the nucleic acid molecules described herein which specifically hybridize with any of the isolated nucleic acid molecules described herein which encode an insect odorant receptor protein under conditions permitting hybridization of the clones and the nucleic acid;
  (c) selecting clones which hybridized with the nucleic acid; and
  (d) isolating the hybridized clones which contain the cDNA inserts so as to thereby identify inserts encoding the odorant receptor from the insect.

The invention provides a method of transforming a cell which comprises transfecting a host cell with any of the vectors described herein.

The invention provides a transformed cell produced by any of the methods described herein. In one embodiment, prior to being transfected with the vector the host cell does not express an insect odorant receptor. In one embodiment, prior to being transfected with the vector the host cell does express an insect odorant receptor.

The invention provides a method of identifying a compound which specifically binds to an insect odorant receptor which comprises contacting any of the transformed cells described herein, or a membrane fraction from said cells, with the compound under conditions permitting binding of the compound to the odorant receptor, detecting the presence of any such compound specifically bound to the receptor, and thereby identifying the compound as a compound which specifically binds to an insect odorant receptor.

The invention provides a method of identifying a compound which specifically binds to an insect odorant receptor which comprises contacting any of the purified insect odorant receptor proteins described herein with the compound under conditions permitting binding of the compound to the purified odorant receptor protein, detecting the presence of any such compound specifically bound to the receptor, and thereby identifying the compound as a compound which specifically binds to an insect odorant receptor. In one embodiment, the purified insect odorant receptor protein is embedded in a lipid bilayer. The purified receptor may be embedded in the liposomes with proper orientation to carry out normal functions. Liposome technology is well-known in the art.

The invention provides a method of identifying a compound which activates an insect odorant receptor which comprises contacting any of the transformed cells described herein, or a membrane fraction from said cells, with the compound under conditions permitting activation of the odorant receptor, detecting activation of the receptor, and thereby identifying the compound as a compound which activates an insect odorant receptor.

The invention provides a method of identifying a compound which activates an insect odorant receptor which comprises contacting any of the purified insect odorant receptor proteins described herein with the compound under conditions permitting activation of the odorant receptor, detecting activation of the receptor, and thereby identify the compound as a compound which activates an insect odorant receptor. In one embodiment, the purified insect odorant receptor protein is embedded in a lipid bilayer. The purified receptor may be embedded in the liposomes with proper orientation to carry out normal functions. Liposome technology is well-known in the art.

The invention provides a method of identifying a compound which inhibits the activity of an insect odorant receptor which comprises contacting any of the transformed cells described herein, or a membrane fraction from said cells, with the compound under conditions permitting inhibition of the activity of the odorant receptor, detecting inhibition of the activity of the receptor, and thereby identifying the compound as a compound which inhibits the activity of an insect odorant receptor.

The invention provides a method of identifying a compound which inhibits the activity of an insect odorant receptor which comprises contacting any of the purified insect odorant receptor proteins described herein with the compound under conditions permitting inhibition of the activity of the odorant receptor, detecting inhibition of the activity of the receptor, and thereby identifying the compound as a compound which inhibits the activity of an insect odorant receptor. In one embodiment, the purified insect odorant receptor protein is embedded in a lipid bilayer. The purified receptor may be embedded in the liposomes with proper orientation to carry out normal functions. Liposome technology is well-known in the art.

In one embodiment of any of the methods described herein, the compound is not previously known to specifically bind to an insect odorant receptor. In one embodiment, the compound is not previously known to activate an insect odorant receptor. In one embodiment, the compound is not previously known to inhibit the activity of an insect odorant receptor.

The invention provides a compound identified by any of the methods described herein.

In one embodiment, the compound is an alarm odorant ligand. In one embodiment, the compound is an odorant ligand associated with fertility of the insect.

The invention provides a method of controlling a population of an insect in an area which comprises identifying a compound using any of the methods described herein and spraying the area with the compound. In one embodiment, the compound is an alarm odorant ligand or a ligand associated with fertility of the insect.

The invention provides a method of controlling a population of an insect which comprises using a compound identified by any of the methods described herein, wherein the compound interferes with an interaction between an odorant ligand and an odorant receptor, which interaction is associated with fertility of the insect.

This invention provides a method of preparing a composition which comprises identifying a compound using any of the methods described herein, recovering the compound free of any insect odorant receptor, and admixing a carrier.

This invention will be better understood from the Experimental Procedures which follow. However, one skilled in the art will readily appreciate that the specific methods and results discussed are merely illustrative of the invention as described more fully in the claims which follow thereafter.

Experimental Procedures

Experimental Animals

Oregon R flies (*Drosophila melanogaster*) were raised on standard cornmeal-agar-molasses medium at 25° C. Transgenic constructs were injected into yw embryos. C155 elav-GAL4 flies were obtained from Corey Goodman (Lin and Goodman, 1994) and Gary Struhl provided the UAS-(cytoplasmic) lacZ stock.

Preparation and Differential Screening of a *Drosophila* Antennal/maxillary Palp cDNA Library

*Drosophila* antennae and maxillary palps were obtained by manually decapitating and freezing 5000 adult flies and shaking antennae and maxillary palps through a fine metal sieve. mRNA was prepared using a polyA+ RNA Purification Kit (Stratagene). An antennal/maxillary palp cDNA library was made from 0.5 µg mRNA using the LambdaZA-PIIXR kit from Stratagene.

Briefly, phage were plated at low density (500–1000 pfu/150 mm plate) and UV-crosslinked after lifting in triplicate to Hybond-N+ (Amersham). Complex probes were generated by random primed labeling (PrimeItII, Stratagene) of reverse transcribed mRNA (RT-PCR kit, Stratagene) from virgin adult female body mRNA and duplicate lifts hybridized at high stringency for 36 hours (65° C. in 0.5M Sodium Phosphate buffer (pH7.3) containing 1% bovine serum albumin, 4% SDS, and 0.5 mg/ml herring sperm DNA). The third lift was prescreened with a mix of all previously cloned OBPs/PBPs (McKenna et al., 1994; Pikielny et al., 1994; Kim et al., 1998) remove a source of abundant but undesired olfactory-specific clones. Approximately 5000 individual OBP/PBP and virgin female body negative phage clones were isolated, their inserts amplified by PCR with T3 and T7 primers, and approximately 3 µg of DNA were electrophoresed on 1.5% agarose gels. Gels were blotted in duplicate to Hybond-N+ (Amersham), filters were UV-crosslinked, and the resulting Southern blots were subjected to reverse Northern analysis using complex probes generated from virgin female body mRNA. Approximately 500 clones not hybridizing with virgin female body probes were identified and consolidated onto secondary Southern blots in triplicate. These blots were probed with complex probes derived from antennal/maxillary palp, head-minus-antenna/maxillary palp, and virgin female body mRNA. A total of 210 clones negative with head-minus-antenna/maxillary palp and virgin female body probes and strongly positive, weakly positive, or negative with antennal/maxillary palp probes were further analyzed by sequencing and in situ hybridization.

Analysis of *Drosophila* Genome Project Sequences for Transmembrane Proteins

All *Drosophila* genomic sequences were batch downloaded in April 1998 from the Berkeley *Drosophila* Genome Project (Berkeley *Drosophila* Genome Project, unpublished). Genomic P1 sequences were first analyzed with the GENSCAN program (Burge and Karlin, 1997) which predicts intron-exon structures and generates hypothetical coding sequences (CDS) and open reading frames. GENSCAN predicted proteins shorter than 50 amino acids were discarded. The remaining open reading frames were used to search for putative transmembrane regions greater than 15 amino acids with two programs that were obtained from the authors and used in stand-alone mode locally (see Persson and Argos, 1994; Cserzo et al., 1997). The Dense Surface Alignment (DAS) program is available from M. Cserzo (miklos@pugh.bip.bham.ac.uk). TMAP is available by contacting the author, Bengt Persson (bpn@mbb.ki.se).

Scripts were written to apply the DAS and TMAP programs repeatedly to genome scale sequence sets. Genes showing significant sequence similarity to the NCBI non-redundant protein database using BLAST analysis (Altschul et al., 1990; Altschul et al., 1997) were eliminated. All scripts required for these computations were written in standard ANSI C and run on a SUN Enterprise 3000.

Of 229 novel *Drosophila* proteins with three or more predicted transmembrane spanning regions, 35 showed no clear sequence similarity to any known protein and were selected for further analysis by in situ hybridization. Probes for in situ hybridization were generated by RT-PCR using antennal/maxillary palp MRNA as a template.

Map Positions of DOR Genes

The chromosome position of DOR104 was determined by in situ hybridization of a biotin-labeled probe to salivary gland polytene chromosome squashes as described (Amrein et al., 1988).

Chromosomal positions of all other DOR genes were based on chromosome assignments of the P1 clones to which they map, as determined by the Berkeley *Drosophila* Genome Project (see also Hartl et al., 1994; Kimmerly et al., 1996). DOR62 maps to a cosmid sequenced by the European *Drosophila* Genome Project (Siden-Kiamos et al., 1990).

| RECEPTOR | MAP POSITION | P1 CLONE ACCESSION NUMBER |
|---|---|---|
| DOR62 | (X) 2F | 62D9 (EDGP cosmid) |
| DOR67 | (2L) 22A3 | DS00676 |

-continued

| RECEPTOR | MAP POSITION | P1 CLONE ACCESSION NUMBER |
|---|---|---|
| DOR53 | (2L) 22A2-3 | DS05342 |
| DOR64 | (2L) 23A1-2 | DS06400 |
| DOR71g | (2L) 33B1-2 | DS07071 |
| DOR72g | (2L) 33B1-2 | DS07071 |
| DOR73g | (2L) 33B1-2 | DS07071 |
| DOR87 | (2R) 43B1-2 | DS08779 |
| DOR19g | (2R) 46F5-6 | DS01913 |
| DOR24 | (2R) 47D6-E2 | DS00724 |
| DOR46 | (2R) 59D5-7 | DS07462 |
| DOR104 | (3L) 85B | not applicable |

The Isolation of DOR cDNA Clones and Southern Blotting $3\times10^6$ clones of the antennal/maxillary palp library described above were screened with PCR probes for the genes DOR87, DOR53, DOR67, DOR64, and DOR62. cDNAs were present at a frequency ranging from 1:200,000 (DOR67) to 1:1,000,000 (DOR62) in the library and their sequences were remarkably similar to the hypothetical CDS predicted by the GENSCAN program. The frequency of these genes is similar to that of DOR104, which is present at 1:125,000 in the antennal/maxillary palp library. All sequencing was with ABI cycle sequencing kits and reactions were run on an ABI 310 or 377 sequencing system.

Five µg of Oregon R genomic DNA isolated from whole flies were digested with BamHI, EcoRI, or HindIII, electrophoresed on 0.8% agarose gels, and blotted to Nitropure nitrocellulose membranes (Micron Separations Inc.). Blots were baked and annealed with $^{32}$P-labeled probes derived from cDNA probes of DOR53 and DOR67, or PCR fragments from DOR24, DOR62, and DOR72g. Hybridization was at 42° C. for 36 hours in 5×SSCP, 10× Denhardts, 500 µg/ml herring sperm DNA, and either 50% (high stringency) or 25% (low stringency) formamide (Sambrook et al., 1989). Blots were washed for 1 hour in 0.2×SSC, 0.5% SDS at 65° C. (high stringency) or 1×SSC, 0.5% SDS at 42° C. (low stringency)

In Situ Hybridization

RNA in situ hybridization was carried out essentially as described (Schaeren-Wiemers and Gerfin-Moser, 1993). This protocol was modified to include detergents in most steps to increase sensitivity and reduce background. The hybridization buffer contained 50% formamide, 5×SSC, 5× Denhardts, 250 µg/ml yeast tRNA, 500 µg/ml herring sperm DNA, 50 µg/ml Heparin, 2.5 mM EDTA, 0.1% Tween-20, 0.25% CHAPS. All antibody steps were in the presence of 0.1% Triton X-100, and the reaction was developed in buffer containing 0.1% Tween-20. Slides were mounted in Glycergel (DAKO) and viewed with Nomarski optics.

Fluorescent in situ hybridization was carried out as above with either digoxigenin or FITC labeled RNA probes. The digoxigenin probe was visualized with sheep anti-digoxigenin (Boehringer) followed by donkey anti-sheep CY3 (Jackson). FITC probes were visualized with mouse anti-FITC (Boehringer) and goat anti-mouse Alexa 488 (Molecular Probes) following preincubation with normal goat serum. Sections were mounted in Vectashield reagent (Vector Labs) and viewed on a Biorad 1024 Confocal Microscope.

For double labeling with a neural marker, animals of the genotype C155 elav-Gal4; UAS-lacZ were sectioned and first hybridized with a digoxigenin labeled antisense DOR104 RNA probe and developed as described above. Neuron-specific expression of lacZ driven by the elav-Gal4 enhancer trap was visualized with a polyclonal rabbit anti- β-galactosidase antibody (Organon-Technika/Cappel), visualized by a goat anti-rabbit Alexa488 conjugated secondary antibody (Molecular Probes) following preincubation with normal goat serum.

The proportion of neurons in the third antennal segment was calculated by comparing the number of nuclei staining with the 44C11 ELAV monoclonal (kindly provided by Lily Jan) and those staining with TOTO-3 (Molecular Probes), a nucleic acid counterstain, in several confocal sections of multiple antennae. On average, 36% of the nuclei in the antenna were ELAV positive.

DOR104-lacZ Transgene Construction and Histochemical Staining

A genomic clone containing the DOR104 coding region and several kb of upstream sequence was isolated from a genomic library prepared from flies isogenic for the third chromosome (a gift of Kevin Moses and Gerry Rubin). Approximately 3 kb of DNA immediately upstream of the putative translation start site of DOR104 were isolated by PCR and subcloned into the pCasperAUGβGal vector (Thummel et al., 1988). β-galactosidase activity staining was carried out with whole mount head preparations essentially as described in Wang et al. (1998). Frozen sections of DOR104-lacZ maxillary palps were incubated with a polyclonal rabbit anti-β-galactosidase antibody and as described above.

Experimental Results

Cloning Candidate Odorant Receptors

In initial experiments, a cDNA encoding a putative odorant receptor was isolated by a difference cloning strategy designed to detect cDNA copies of MRNA present at extremely low frequencies in an mRNA population. In the antenna and maxillary palp, about 30% of the cells are olfactory neurons. If each neuron expressed only one of a possible 100 different odorant receptor genes at a level of 0.1% of the mRNA in a sensory neuron, then a given receptor mRNA would be encountered at a frequency of one in 300,000 in antennal mRNA. If 100 different receptor genes were expressed, then the entire family of receptor genes would be represented at a frequency of one in 3,000 mRNAs. Experimental modifications were therefore introduced into standard difference cloning to allow for the identification of extremely rare mRNAs whose expression is restricted to either the antenna or the maxillary palp.

Figures 1A, 1B:
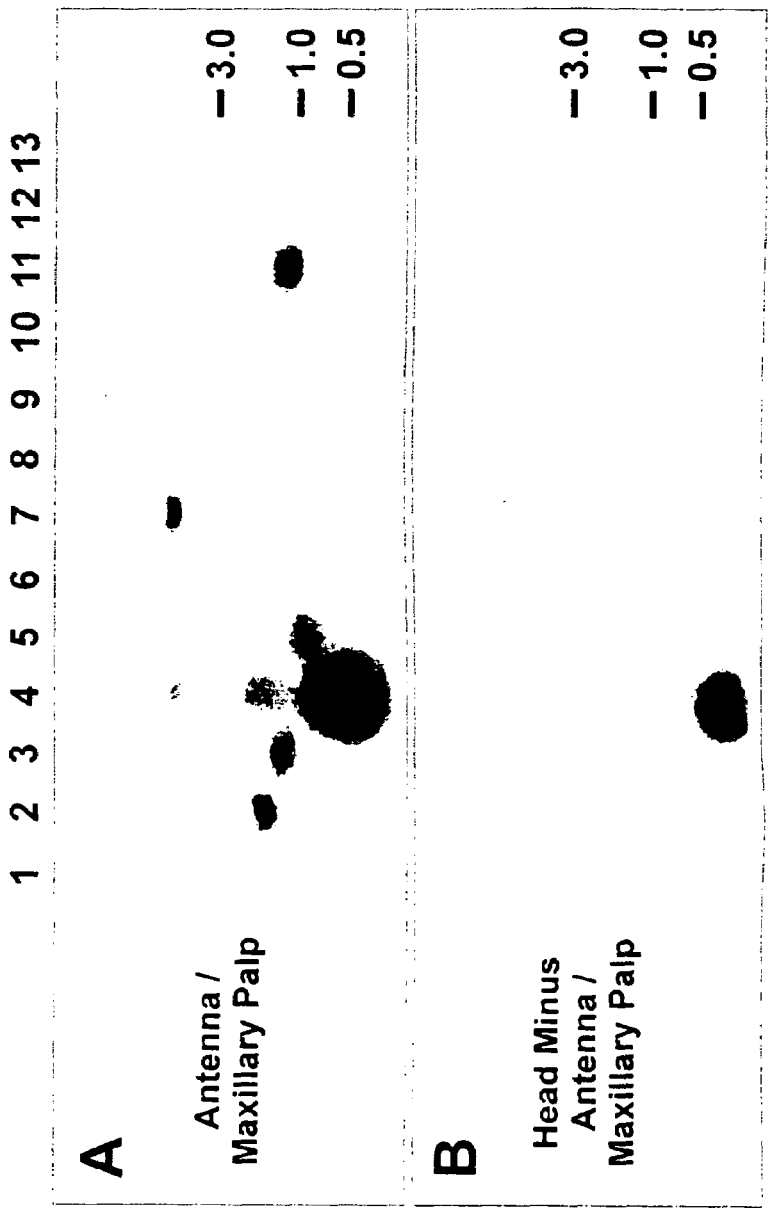
FIGS. 1A–1D Identification of Rare Antennal- and Maxillary Palp-Specific Genes
Figures 1C, 1D:
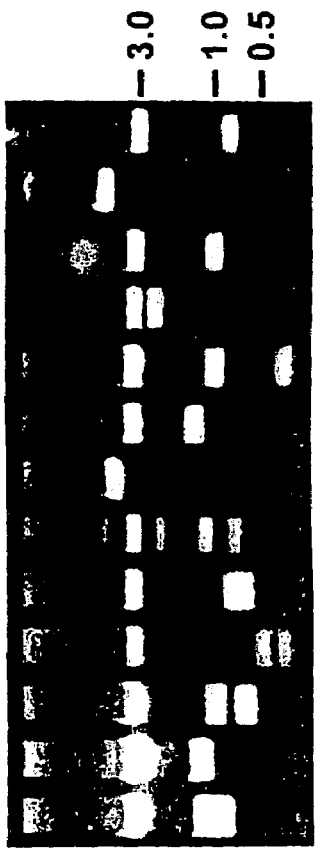

Briefly, 5000 insets from an antennal/maxillary palp cDNA library were prescreened (see Experimental Procedures) and then subjected to Southern blot hybridization with cDNA probes from antennal/maxillary palp, head minus antenna/maxillary palp, or virgin female body mRNA (see FIG. 1). This Southern blot hybridization (or reverse Northern) to candidate cDNAs allows for the detection of sequences present at a frequency of 1 in 100,000 in the probe, a sensitivity about one hundred-fold greater than that of plaque screening (see Experimental Procedures). This procedure led to the identification of multiple antennal/maxillary palp-specific cDNAs that were analyzed by DNA sequencing and in situ hybridization. One cDNA, DOR104 (for *Drosophila* Odorant Receptor) (SEQ ID NO: 3) (FIG. 1, Lane 9), encodes a putative seven-transmembrane domain protein (SEQ ID NO: 4) with no obvious sequence similarity to known serpentine receptors (FIG. 3). In situ hybridization revealed that this cDNA anneals to about 15% of the 120 sensory neurons within the maxillary palp but does not anneal with neurons in either the brain or antenna. Seven cells expressing DOR104 are shown in the frontal maxillary palp section in FIG. 2A.

These observations suggested that DOR104 might be one member of a larger family of odorant receptor genes within the *Drosophila* genome. However, additional genes homologous to DOR104 could not be identified by low stringency hybridization to genomic DNA and cDNA libraries or upon analysis of linked genes in a genomic walk. Therefore, the *Drosophila* genome database was analyzed for families of multiple transmembrane domain proteins that share sequence similarity with DOR104. Sequences representing about 10% of the *Drosophila* genome were downloaded (Berkeley *Drosophila* Genome Project) and subjected to GENSCAN analysis (Burge and Karlin, 1997) to predict the intron-exon structure of all sequences within the database. Open reading frames greater than 50 amino acids were searched for proteins with three or more predicted transmembrane-spanning regions using the dense alignment surface (DAS) and TMAP algorithms (Persson and Argos, 1994; Cserzo et al., 1997; also see Experimental Procedures). Of 229 candidate genes identified in this manner, 11 encode proteins that define a novel divergent family of presumed seven transmembrane domain proteins with sequence similarity to the DOR104 sequence. This family of candidate odorant receptors does not share any conserved sequence motifs with previously identified families of seven transmembrane domain receptors. cDNA clones containing the coding regions for 5 of the 11 genes identified by GENSCAN analysis have been isolated from an antennal/maxillary palp cDNA library and their sequences are provided in FIG. 3. The remaining 6 protein sequences derive from GENSCAN predictions for intron-exon arrangement. Their organization conforms well to the actual structure determined from the cDNA sequences of other members of the gene family (FIG. 3).

The receptors consist of a short extracellular N-terminal domain (usually less than 50 amino acids) and seven presumed membrane-spanning domains. Analysis of presumed transmembrane domains (Kyte and Doolittle, 1982; Persson and Argos, 1994; Cserzo et al., 1997) reveals multiple hydrophobic segments, but it is not possible from this analysis to unequivocally determine either the number or placement of the membrane spanning domains. At present, the assignment of transmembrane domains is therefore tentative.

The individual family members are divergent and most exhibit from 17–26% amino acid identity. Two linked clusters of receptor genes constitute small subfamilies of genes with significantly greater sequence conservation. Two linked genes when expressed, DOR53 (SEQ ID NOs: 7 and 8) and DOR67 (SEQ ID NOs: 9 and 10), exhibit 76% amino acid identity; whereas the three linked genes when expressed, DOR71g (SEQ ID NOs: 13 and 14), DOR72g (SEQ ID NOs: 15 and 16)and DOR73g (SEQ ID Nos: 17 and 18), reveal 30–55% identity (FIG. 3; see below). Despite the divergence, each of the genes shares short, common motifs in fixed positions within the putative seven transmembrane domain structure that define these sequences as highly divergent members of a novel family of putative receptor molecules.

Expression of the DOR Gene Family in Olfactory Neurons

If this gene family encodes putative odorant receptors in the fly, one might expect that other members of the family in addition to DOR104 would also be expressed in olfactory sensory neurons. Therefore, in situ hybridization was performed to examine the pattern of receptor expression of each of the 11 additional members of the gene family in adult and developing organisms. In *Drosophila*, olfactory sensory neurons are restricted to the maxillary palp and third antennal segment. The third antennal segment is covered with approximately 500 fine sensory bristles or sensilla (Stocker, 1994), each containing from one to four neurons (Venkatesh and Singh, 1984). The maxillary palp is covered with approximately 60 sensilla, each of which is innervated by two or three neurons (Singh and Nayak, 1985). Thus, the third antennal segment and maxillary palp contain about 1500 and 120 sensory neurons, respectively.

RNA in situ hybridization experiments were performed with digoxigenin-labeled RNA antisense probes to each of the 11 new members of the gene family under conditions of high stringency. One linked pair of homologous genes, DOR53 and DOR67, crosshybridizes, whereas the remaining 10 genes exhibit no crosshybridization under these conditions (see below). Eight of the 11 genes hybridize to a small subpopulation (0.5–1.5%) of the 1500 olfactory sensory neurons in the third antennal segment (FIG. 4). One gene, DOR71g, is expressed in about 10% of the sensory neurons in the maxillary palp but not in the antenna (FIG. 4G). Expression of DOR46 or DOR19g has not been detected in the antenna or the maxillary palp. Expression of this gene family is only observed in cells within the antenna and maxillary palp. No hybridization was observed in neurons of the brain, nor was hybridization observed in any sections elsewhere in the adult fly or in any tissue at any stage during embryonic development. However, hybridization was observed to a small number of cells in the developing antennae in the late pupal stage. We have not yet determined whether this family of receptors is expressed in the larval olfactory apparatus.

Only about one third of the cells in the third antennal segment and the maxillary palp are neurons (data not shown), which are interspersed with non-neuronal sensillar support cells and glia. Two experiments were performed to demonstrate that the family of seven transmembrane domain receptor genes is expressed in sensory neurons rather than support cells or glia within the antenna and maxillary palp. First, two-color fluorescent antibody detection schemes were developed to co-localize receptor expression in cells that express the neuron-specific RNA binding protein, ELAV (Robinow and White, 1988). An enhancer trap line carrying an insertion of GAL4 at the elav locus expresses high levels of lacZ in neurons when crossed to a transgenic UAS-lacZ responder line (Lin and Goodman, 1994). Fluorescent antibody detection of lacZ identifies the sensory neurons in a horizontal section of the maxillary palp (FIG. 5B). Hybridization with the receptor probe DOR104 reveals expression in 5 of the 12 lacZ positive cells in a horizontal section of the maxillary palp (FIG. 5A). All cells that express DOR104 are also positive for lacZ (FIG. 5C), indicating that this receptor is expressed only in neurons.

In a second experiment, it was demonstrated that the receptor genes are not expressed in non-neuronal cells. The support cells of the antenna express different members of a family of odorant binding proteins (McKenna et al., 1994; Pikielny et al., 1994; Kim et al., 1998). These genes encode abundant low molecular weight proteins thought to transport odorants through the sensillar lymph (reviewed in Pelosi, 1994). Two-color in situ experiments with a probe for the odorant binding protein, PBPRP2 (Pikielny et al., 1994), reveal hybridization to a large number of cells broadly distributed throughout the antenna (FIG. 5F). In the same section, however, the probe DOR53 anneals to a non-overlapping subpopulation of neurons restricted to the medial-proximal domain of the antenna. In a similar experiment, in situ hybridization with the odorant binding protein, OS-F (McKenna et al., 1994), identifies a spatially restricted subpopulation of support cells in the antenna, whereas the DOR67 probe identifies a distinct subpopulation of neurons in a medial-proximal domain (FIG. 5G). Thus, the putative odorant receptor genes are expressed in a subpopulation of sensory neurons distinct from the support cells that express the odorant binding proteins. Taken together, these data demonstrate that 10 of the 12 family members disclosed herein are expressed in small subpopulations of olfactory sensory neurons in the antenna and maxillary palp.

Spatially Defined Patterns of Receptor Expression

The in situ hybridization experiments reveal that each receptor is expressed in a spatially restricted subpopulation of neurons in the antenna or maxillary palp (FIG. 4). The total number of cells expressing each receptor per antenna was obtained by counting the positive cells in serial sections of antennae from multiple flies. These numbers are presented in the legend of FIG. 4. DOR67 and 53 probes, for example, anneal to about 20 neurons on the medial proximal edge of the antenna (FIGS. 4A and B), whereas DOR62 and 87 probes anneal to subpopulations of 20 cells at the distal edge of the antenna (FIGS. 4C–D). Approximately 10 cells in the distal domain express DOR64 (FIG. 4E). Each of the three linked genes DOR71g, DOR72g, and DOR73g is expressed in different neurons. DOR72g is expressed in approximately 15 antennal cells (FIG. 4H), while DOR73g is expressed in 1 to 2 cells at the distal edge of the antenna (FIG. 4I). In contrast, DOR71g is expressed in approximately 10 maxillary palp neurons but is not detected in the antenna (FIG. 4G). The three sensillar types are represented in a coarse topographic map across the third antennal segment. The proximal-medial region, for example, contains largely basiconic sensilla. Receptors expressed in this region (DOR53 and 67) are therefore likely to be restricted to the large basiconic sensilla. More distal regions contain a mixture of all three sensilla types and it is therefore not possible from these data to assign specific receptors to specific sensillar types.

The spatial pattern of neurons expressing a given receptor is conserved between individuals. In situ hybridization with two receptor probes to three individual flies reveals that both the frequency and spatial distributions of the hybridizing neurons is conserved in different individuals (FIG. 6). At present, the precision of this topographic map cannot be determined and one can only argue that given receptors are expressed in localized domains.

In preliminary experiments, the spatial pattern of expression of one receptor, DOR104, was recapitulated in transgenic flies with a promoter fragment flanking the DOR104 gene. The fusion of the presumed DOR104 promoter (consisting of 3 kb of 5' DNA immediately adjacent to the coding region) to the lacZ reporter gene has allowed us to visualize a subpopulation of neurons expressing DOR104 within the maxillary palp. Whole mount preparations of the heads of transgenic flies reveal a small subpopulation of sensory neurons within the maxillary palp whose cell bodies exhibit blue color after staining with X-gal (FIG. 2B). The number of positive cells, approximately 20 per maxillary palp, corresponds well with that seen for DOR104 RNA expression. Immunofluorescent staining of sections with antibodies directed against β-galactosidase more clearly reveals the dendrites and axons of these bipolar neurons in the maxillary palp (FIG. 2C). Levels of lacZ expression in these transgenic lines are low and further amplification will be necessary to allow us to trace the axons to glomeruli in the antennal lobe. Nonetheless, the data suggest that the information governing the spatial pattern of DOR104 expression in a restricted subpopulation of maxillary palp neurons resides within 3 kb of DNA 5' to the DOR104 gene.

Individual Neurons Express Different Complements of Receptors

An understanding of the logic of olfactory discrimination in Drosophila will require a determination of the diversity and specificity of receptor expression in individual neurons. In the vertebrate olfactory epithelium, a given neuron is likely to express only one receptor from the family of 1,000 genes (Ngai et al., 1993; Ressler et al., 1993; Vassar et al., 1993; Chess et al., 1994). In the nematode C. elegans, however, individual chemosensory neurons are thought to express multiple receptor genes (Troemel et al., 1995). Our observations with the putative Drosophila odorant receptors indicate that a given receptor probe anneals with 0.5–1.5% of antennal neurons, suggesting that each cell expresses only a subset of receptor genes. If we demonstrate that each of the different receptor probes hybridizes with distinct, nonoverlapping subpopulations of neurons, this would provide evidence that neurons differ with respect to the receptors they express.

In situ hybridization was therefore performed with either a mix of five receptor probes (FIG. 4F) or individually with each of the five probes (FIGS. 4A–E). The number of olfactory neurons identified with the mixed probe (about 60 per antenna) approximates the sum of the positive neurons detected with the five individual probes. These results demonstrate that individual receptors are expressed in distinct nonoverlapping populations of olfactory neurons.

An additional experiment was performed using two-color RNA in situ hybridization to ask whether two receptor genes, DOR64 and DOR87, expressed in interspersed cells in the distal antenna are expressed in different neurons. Antisense RNA probes for the two genes were labeled with either digoxigenin- or FITC-UTP and were used in pairwise combinations in in situ hybridization to sections through the Drosophila antenna. Although these two genes are expressed in overlapping lateral-distal domains, two-color in situ hybridization reveals that neurons expressing DOR64 do not express DOR87, rather each gene is expressed in distinct cell populations (FIGS. 5D and E). Taken together, these data suggest that olfactory sensory neurons within the antenna are functionally distinct and express different complements of odorant receptors. At the extreme, the experiments are consistent with a model in which individual neurons express only a single receptor gene.

Our differential cloning procedure identified one additional gene, DORA45 (SEQ ID NOs: 103 and 104), which shares weak identity (24%) with the DOR gene family over a short region (93 amino acids). This gene, however, does not appear to be a classical member of the DOR family: it is far more divergent and significantly larger than the other family members (486 amino acids). This gene is expressed in all olfactory sensory neurons. If DORA45 does encode a divergent odorant receptor, then it would be present in all sensory neurons along with different complements of the more classical members of the DOR gene family.

The Size and Organization of the Odorant Receptor Gene Family

Figure 7A:
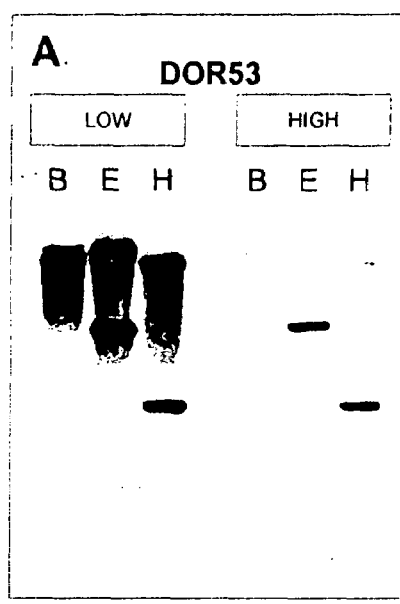
Figure 7B:
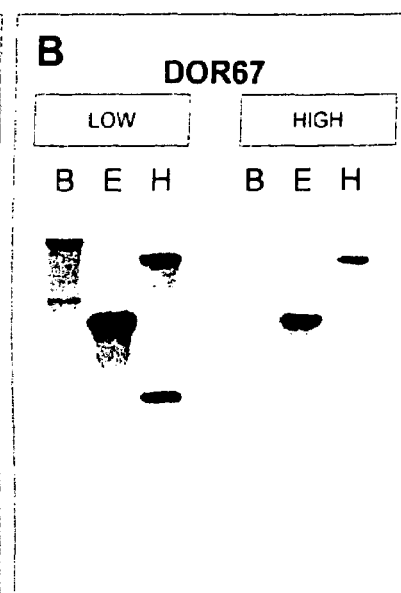
Figure 7C:
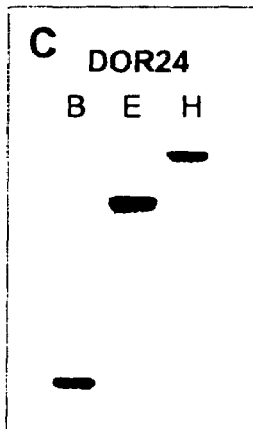
Figure 7D:
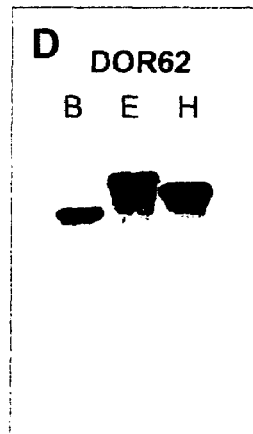
Figure 7E:
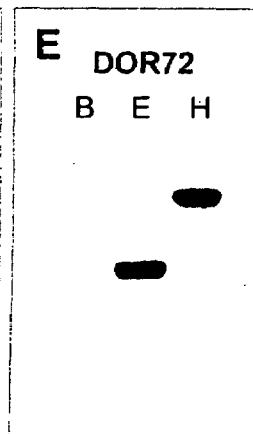

How large is the family of odorant receptor genes in Drosophila? Unlike vertebrate odorant receptors, which share 40–98% sequence identity at the amino acid level, the fly receptors are extremely divergent. The extent of sequence similarity between receptor subfamilies ranges from 20–30%. The maxillary palp receptor DOR104 is the most distantly related member of the family with about 17% identity to the other receptor genes. Inspection of the receptor sequences suggests that Southern blot hybridizations, even those performed at low stringency, are unlikely to reveal multiple additional members of a gene family. In accord with this, Southern blot hybridization with receptor probes for DOR24, DOR62, and DOR72g, performed at either high or low stringency, reveals only a single hybridizing band following cleavage of genomic DNA with three different restriction endonucleases (FIGS. 7C–E). The two linked clusters of receptors contain genes with a greater degree of sequence conservation and define small subfamilies of receptor genes. A cluster of three receptors, DOR71g, DOR72g, and DOR73g, is located at map position 33B1-2. The antennal receptors DOR72g and DOR73g are 55% identical and both exhibit about 30% identity to the third gene at the locus, DOR71g, which is expressed in the maxillary palp. DOR67 and DOR53, members of a second subfamily, reside within 1 kb of each other at map position 22A2-3 and exhibit 76% sequence identity. Not surprisingly, these two linked genes crosshybridize at low stringency. Southern blots with either DOR67 or DOR53 probes reveal two hybridizing bands corresponding to the two genes within the subfamily but fail to detect additional subfamily members in the chromosome (FIGS. 7A and B).

The members of the receptor gene family described here are present on all but the small fourth chromosome. No bias is observed toward telomeric or centromeric regions. The map positions, as determined from P1 and cosmid clones (Berkeley Drosophila Genome Project; European Drosophila Genome Project) are provided in Experimental Procedures. A comparatively large number of receptor genes map to chromosome 2 because the Berkeley Drosophila Genome Project has concentrated its efforts on this chromosome. Unlike the distribution of odorant receptors in nematodes and mammals (Ben-Arie et al., 1994; Troemel et al., 1995; Robertson, 1998), only small linked arrays have been identified and the majority of the family members are isolated at multiple, scattered loci in the Drosophila genome.

The high degree of divergence among members of the Drosophila odorant receptor gene family is more reminiscent of the family of chemoreceptors in C. elegans than the more highly conserved odorant receptors of vertebrates. Estimates of the size of the Drosophila receptor gene family, therefore, cannot be obtained by either Southern blot hybridization or PCR analysis of genomic DNA. Rather, estimates of the gene family derive from the statistics of small numbers. Twelve members of the odorant receptor gene family were detected from a Drosophila genome database that includes roughly 10% of the genome. Recognizing a possible bias in this estimate, it seems reasonable at present to estimate that the odorant receptor family is likely to include 100 to 200 genes. This is in accord with independent estimates from in situ hybridization experiments that demonstrate that a given receptor probe hybridizes with 0.5–1.5% of the neurons. If one assumes that a given neuron expresses only a single receptor gene, these observations suggest that the gene family would include 100 to 200 members.

Experimental Discussion

The Size and Divergence of the Gene Family

The present application discloses a novel family of seven transmembrane domain proteins that is likely to encode the Drosophila odorant receptors. The number of different receptor genes expressed in the neurons of the antenna and maxillary palp will reflect the diversity and specificity of odor recognition in the fruit fly. How large is the Drosophila odorant receptor gene family? We have identified 11 members of this divergent gene family in the Drosophila DNA database. The potential for bias notwithstanding, it seems reasonable to assume then that since only 10% of genomic sequence has been deposited, this gene family is likely to contain from 100 to 200 genes. However, significant errors in these estimates could result from bias in the nature of the sequences represented in the 10% of the *Drosophila* genome analyzed to date. In situ hybridization experiments demonstrating that each of the receptor genes labels from 0.5–1.5% of the olfactory sensory neurons are in accord with the estimate of 100 to 200 receptor genes.

Several divergent odorant receptor gene families, each encoding seven transmembrane proteins, have been identified in vertebrate and invertebrate species. In mammals, volatile odorants are detected by a family of as many as 1,000 receptors each expressed in the main olfactory epithelium (Buck and Axel, 1991; Levy et al., 1991; Parmentier et al., 1992; Ben-Arie et al., 1994). This gene family shares features with the serpentine neurotransmitter receptors and is conserved in all vertebrates examined. Terrestrial vertebrates have a second anatomically and functionally distinct olfactory system, the vomeronasal organ, dedicated to the detection of pheromones. Vomeronasal sensory neurons express two distinct families of receptors each thought to contain from 100 to 200 genes: one novel family of serpentine receptors (Dulac and Axel, 1995), and a second related to the metabotropic neurotransmitter receptors (Herrada and Dulac, 1997; Matsunami and Buck, 1997; Ryba and Tirindelli, 1997).

In the invertebrate *C. elegans*, chemosensory receptors are organized into four gene families that share 20–40% sequence similarity within a family and essentially no sequence similarity between families (Troemel et al., 1995; Sengupta et al., 1996; Robertson, 1998). The four gene families in *C. elegans* together contain about 1,000 genes engaged in the detection of odors. The nematode receptors exhibit no sequence conservation with the three distinct families of vertebrate odorant receptor genes. Our studies reveal that *Drosophila* has evolved an additional divergent gene family of serpentine receptors comprised of from 100 to 200 genes.

The observation that a similar function, chemosensory detection, is accomplished by at least eight highly divergent gene families, sharing little or no sequence similarity, is quite unusual.

Why is the evolutionary requirement for odorant receptors so often met by recruitment of novel gene families rather than exploiting pre-existing odorant receptor families in ancestral genomes? The character of natural odorants along with their physical properties (e.g. aqueous or volatile) represent important selectors governing the evolution of receptor gene families. The use of common "anthropomorphic" odorant sets in the experimental analysis of olfactory specificity has led to the prevailing view that significant overlap exists in the repertoire of perceived odors between different species. Studies of odorant specificity in different species often employ odors at artificially high concentrations and may present an inaccurate image of the natural repertoire of odorants. We simply do not know the nature of the odors that initially led to the ancestral choice of receptor genes during the evolution of the nematode, insect, or vertebrate species. Clearly, vastly different properties in salient odors could dictate the recruitment of new gene families to effect an old function, olfaction. The character of the odor is not the only evolutionary selector. Odorant receptors must interact with other components in the signal transduction pathway [G proteins (for review see Buck, 1996; Bargmann and Kaplan, 1998) and perhaps even RAMPs (McLatchie et al, 1998) and rho (Mitchell et al., 1998)] that may govern the choice of one family of serpentine receptors over another. Moreover, mammalian receptors not only recognize odorants in the environment but are likely to recognize guidance cues governing formation of a sensory map in the brain (Wang et al., 1998). Thus, the multiple properties required of the odorant receptors might change vastly over evolutionary time and this might underlie the independent origins of the multiple chemosensory receptor gene families.

Establishing a Topographic Map in the Antenna and the Brain

Individual receptor genes in the fly are expressed in topographically conserved domains within the antenna. This highly ordered spatial distribution of receptor expression differs from that observed in the mammalian olfactory epithelium. In mammals, a given receptor can be expressed in one of four broad but circumscribed zones in the main olfactory epithelium (Ressler et al., 1993; Vassar et al., 1993). A given zone can express up to 250 different receptors and neurons expressing a given receptor within a zone appear to be randomly dispersed (Ressler et al., 1993; Vassar et al., 1993). The highly ordered pattern of expression observed in the *Drosophila* antenna might have important implications for patterning the projections to the antennal lobe. In visual, somatosensory, and auditory systems the peripheral receptor sheet is highly ordered and neighbor relations in the periphery are maintained in the projections to the brain. These observations suggest that the relative position of the sensory neuron in the periphery will determine the pattern of projections to the brain.

Our data on the spatial conservation of receptor expression in the antenna suggest that superimposed upon coarse spatial patterning of olfactory sensilla (Venkatesh and Singh, 1984; Ray and Rodrigues, 1995; Reddy et al., 1997) must be more precise positional information governing the choice of receptor expression. This spatial information might dictate the fixed topographic pattern of receptor expression in the peripheral receptor sheet and at the same time govern the ordered sensory projections to the brain. This relationship between positional identity and the pattern of neuronal projections has been suggested for both peripheral sensory neurons (Merritt and Whitington, 1995; Grillenzoni et al., 1998) and neurons in the embryonic central nervous system of *Drosophila* (Doe and Skeath, 1996).

Implications for Sensory Processing

In mammals, olfactory neurons express only one of the thousand odorant receptor genes. Neurons expressing a given receptor project with precision to 2 of the 1800 glomeruli in the mouse olfactory bulb. Odorants will therefore elicit spatially defined patterns of glomerular activity such that the quality of an olfactory stimulus is encoded by the activation of a specific combination of glomeruli (Stewart et al., 1979; Lancet et al., 1982; Kauer et al., 1987; Imamura et al., 1992; Mori et al., 1992; Katoh et al., 1993; Friedrich and Korsching, 1997). Moreover, the ability of an odorant to activate a combination of glomeruli allows for the discrimination of a diverse array of odors far exceeding the number of receptors and their associated glomeruli. In the nematode, an equally large family of receptor genes is expressed in 16 pairs of chemosensory cells, only three of which respond to volatile odorants (Bargmann and Horvitz, 1991; Bargmann et al., 1993). This immediately implies that a given chemosensory neuron will express multiple receptors and that the diversity of odors recognized by the nematode might approach that of mammals, but the discriminatory power is necessarily dramatically reduced.

What does the character of the gene family identified herein in *Drosophila* tell us about the logic of olfactory processing in this organism? We estimate that the *Drosophila* odorant receptors comprise a family of from 100 to 200 genes. Moreover, the pattern of expression of these genes in the third antennal segment suggests that individual sensory neurons express a different complement of receptors and, at the extreme, the data presented herein are consistent with the suggestion that individual neurons express one or a small number of receptors. As in the case of mammals, the problem of odor discrimination therefore reduces to a problem of the brain discerning which receptors have been activated by a given odorant. If the number of different types of neurons exceeds the number of glomeruli (43) (Stocker, 1994; Laissue et al., 1999), it immediately follows that a given glomerulus must receive input from more than one kind of sensory neuron. This implies that a single glomerulus will integrate multiple olfactory stimuli. One possible consequence of this model would be a loss of discriminatory power while maintaining the ability to recognize a vast array of odors. Alternatively, significant processing of sensory input may occur in the fly antennal lobe to afford discrimination commensurate with the large number of receptors.

This model of olfactory coding is in sharp contrast with the main olfactory system of vertebrates in which sensory neurons express only a single receptor and converge on only a single pair of spatially fixed glomeruli in the olfactory bulb. Moreover, each projection neuron in the mammalian bulb extends its dendrite to only a single glomerulus. Thus the integration and decoding of spatial patterns of glomerular activity, in vertebrates, must occur largely in the olfactory cortex. In the fruit fly, the observation that the number of receptors may exceed the number of glomeruli suggests that individual glomeruli will receive input from more than one type of sensory neuron. A second level of integration in the antennal lobe is afforded by subsets of projection neurons that elaborate extensive dendritic arbors that synapse with multiple glomeruli. Thus, the *Drosophila* olfactory system reveals levels of processing and integration of sensory input in the antennal lobe that is likely to be restricted to higher cortical centers in the main olfactory system of vertebrates.

Protein and Nucleic Acid (nt) Sequences of 55 *Drosophila* Odorant Receptor Genes The following includes those genes first identified in 1998–1999. Protein sequences used single letter amino acid codes.

```
DOR10
MEKLRSYEDFIFMANMMFKTLGYDLFHTPKPWWRYLLVRGYFVLCTISNFYEASMVTT     (SEQ ID NO: 26)
RIIEWESLAGSPSKIMRQGLHFFYMLSSQLKFITFMINRKRLLQLSHRLKELYPHKEQ
NQRKYEVNKYYLSCSTRNVLYVYYFVMVVMALEPLVQSQFIVNVSLGTDLWMMCVSSQ
ISMHLGYLANMLASIRPSPETEQQDCDFLASIIKRHQLMIRLQKDVNYVFGLLLASNL
FTTSCLLCCMAYYTVVEGFNWEGISYMMLFASVAAQFYVVSSHGQMLIDLLMTITYRF
FAVIRQTVEK

DOR10nt
ATGGAAAAACTACGTTCCTATGAGGATTTCATCTTCATGGCCAACATGATGTTCAAGA     (SEQ ID NO: 25)
CCCTTGGCTACGATCTATTCCATACACCCAAACCCTGGTGGCGCTATCTGCTTGTGCG
AGGATACTTCGTTTTGTGCACGATCAGCAACTTTTACGAGGCTTCCATGGTGACGACA
AGGATAATTGAGTGGGAATCCTTGGCCGGAAGTCCCTCCAAAATAATGCGACAGGGTC
TGCACTTCTTTTACATGTTGAGTAGCCAATTGAAATTTATCACATTCATGATAAATCG
CAAACGCCTACTGCAGCTGAGCCATCGTTTGAAAGAGTTGTATCCTCATAAAGAGCAA
AATCAAAGGAAGTACGAGGTGAATAAATACTACCTATCCTGTTCCACGCGCAATGTTT
TGTACGTGTACTACTTTGTAATGGTCGTCATGGCACTGGAACCCCTCGTTCAGTCCCA
GTTCATAGTGAATGTGAGCCTGGGCACAGATCTGTGGATGATGTGCGTCTCAAGCCAA
ATATCGATGCACTTGGGCTATCTGGCCAATATGTTGGCCTCCATTCGACCAAGTCCAG
AAACGGAACAACAAGACTGTGACTTCTTGGCCAGCATTATAAAGAGACATCAACTAAT
GATCAGGCTTCAAAAGGACGTGAACTATGTTTTTGGACTCTTATTGGCATCTAATCTG
TTTACCACATCCTGTTTACTTTGCTGCATGGCGTACTATACCGTCGTCGAAGGTTTCA
ATTGGGAGGGCATTTCCTATATGATGCTCTTTGCTAGTGTAGCTGCCCAGTTCTACGT
TGTCAGCTCACACGGACAAATGTTAATAGATTTGTTGATGACCATCACATACAGATTT
TTCGCGGTTATACGACAAACTGTAGAAAAG

DOR104
MASLQFHGNVDADIRYDISLDPARESNLFRLLMGLQLANGTKPSPRLPKWWPKRLEMI     (SEQ ID NO: 4)
GKVLPKAYCSMVIFTSLHLGVLFTKTTLDVLPTGELQAITDALTMTIIYFFTGYGTIY
WCLRSRRLLAYMEHMNREYRHHSLAGVTFVSSHAAFRMSRNFTVVWIMSCLLGVISWG
VSPLMLGIRMLPLQCWYPFDALGPGTYTAVYATQLFGQIMVGMTFGFGGSLFVTLSLL
LLGQFDVLYCSLKNLDAHTKLLGGESVNGLSSLQEELLLGDSKRELNQYVLLQEHPTD
LLRLSAGRKCPDQGNAFHNALVECIRLHRFILHCSQELENLFSPYCLVKSLQITFQLC
LLVFVGVSGTREVLRIVNQLQYLGLTIFELLMFTYCGELLSRHSIRSGDAFWRGAWWK
HAHFIRQDILIFLVNSRRAVHVTAGKFYVMDVNRLRSVITQAFSFLTLLQKLAAKKTE
SEL

DOR104nt
GAATTCGGCACGAGCAGTCGATGGCCAGTCTTCAGTTCCACGGCAACGTCGATGCGGA     (SEQ ID NO: 3)
CATCAGGTATGATATTAGCCTGGATCCGGCTAGGGAATCGAATCTCTTCCGTCTGCTA
ATGGGACTCCAGTTGGCGAATGGCACGAAGCCATCGCCGCGGTTACCCAAATGGTGGC
CAAAGCGGCTGGAAATGATTGGTAAAGTGCTGCCCAAAGCCTATTGTTCCATGGTGAT
TTTCACCTCCCTGCATTTGGGTGTCCTGTTCACGAAAACCACACTGGATGTCCTGCCG
ACGGGGGAGCTGCAGGCCATAACGGATGCCCTCACCATGACCATAATATACTTTTTCA
CGGGCTACGGCACCATCTACTGGTGCCTGCGCTCCCGGCGCCTCTTGGCCTACATGGA
GCACATGAACCGGGAGTATCGCCATCATTCGCTGGCCGGGGTGACCTTTGTGAGTAGC
CATGCGGCCTTTAGGATGTCCAGAAACTTCACGGTGGTGTGGATAATGTCCTGCCTGC
TGGGCGTGATTTCCTGGGGCGTTTCGCCACTGATGCTGGGCATCCGGATGCTGCCGCT
CCAATGTTGGTATCCCTTCGACGCCCTGGGTCCCGGCACATATACGGCGGTCTATGCT
ACACAACTTTTCGGTCAGATCATGGTGGGCATGACCTTTGGATTCGGGGGATCACTGT
TTGTCACCCTGAGCCTGCTACTCCTGGGACAATTCGATGTGCTCTACTGCAGCCTGAA
GAACCTGGATGCCCATACCAAGTGGCTGGGCGGGAGTCTGTAAATGGCCTGAGTTCG
CTGCAAGAGGAGTTGCTGCTGGGGGACTCGAAGAGGGAATTAAATCAGTACGTTTTGC
TCCAGGAGCATCCGACGGATCTGCTGAGATTGTCGGCAGGACGAAAATGTCCTGACCA
AGGAAATGCGTTTCACAACGCCTTGGTGGAATGCATTCGCTTGCATCGCTTCATTCTG
```

-continued

CACTGCTCACAGGAGTTGGAGAATCTATTCAGTCCATATTGTCTGGTCAAGTCACTGC
AGATCACCTTTCAGCTTTGCCTGCTGGTCTTTGTGGGCGTTTCGGGTACTCGAGAGGT
CCTGCGGATTGTCAACCAGCTACAGTACTTGGGACTGACCATCTTCGAGCTCCTAATG
TTCACCTATTGTGGCGAACTCCTCAGTCGGCATAGTATTCGATCTGGCGACGCCTTTT
GGAGGGGTGCGTGGTGGAAGCACGCCCATTTCATCCGCCAGGACATCCTCATCTTTCT
GGTCAATAGTAGACGTGCAGTTCACGTGACTGCCGGCAAGTTTTATGTGATGGATGTG
AATCGTCTAAGATCGGTTATAACGCAGGCGTTCAGCTTCTTGACTTTGCTGCAAAAGT
TGGCTGCCAAGAAGACGGAATCGGAGCTCTAAACTGGTACCACGCATCGATATTTATT
TAGCGCATTAAAAAAAAGTCGAGTAAAAGCAAAAAAAAAAAAAAAAAAA

DOR105
MFEDIQLIYMNIKILRFWALLYDKNLRRYVCIGLASFHIFTQIVYMMSTNEGLTGIIR (SEQ ID NO: 28)
NSYMLVLWINTVLRAYLLLADHDRYLALIQKLTEAYYDLLNLNDSYISEILDQVNKVG
KLMARGNLFFGMLTSMGFGLYPLSSSERVLPFGSKIPGLNEYESPYYEMWYIFWMLIT
PMGCCMYIPYTSLIVGLIMFGIVRCKALQHRLRQVALKHPYGDRDPRELREEIIACIR
YQQSIIEYMDHINELTTMMFLFELMAFSALLCALLFMLIIVSGTSQLIIVCMYINMIL
AQILALYWYANELREQNLAVATAAYETEWFTFDVPLRKNILFMMMRAQRPAAILLGNI
RPITLELFQNLLNTTYTFFTVLKRVYG

DOR105nt
ATGTTTGAAGACATTCAGCTAATCTACATGAATATCAAGATATTGCGATTCTGGGCCC (SEQ ID NO: 27)
TGCTCTATGACAAAAACTTGAGGCGTTATGTGTGCATTGGACTGGCCTCATTCCACAT
CTTCACCCAAATCGTCTACATGATGAGTACCAATGAAGGACTAACCGGGATAATTCGT
AACTCATATATGCTCGTCCTTTGGATTAATACGGTGCTGCGAGCTTATCTCTTGCTGG
CGGATCACGACAGATATTTGGCTTTGATCCAAAAACTAACTGAGGCCTATTACGATTT
ACTGAATCTGAACGATTCGTATATATCGGAAATATTGGACCAGGTGAACAAGGTGGGA
AAGTTGATGGCTAGGGGCAATCTGGTCTTTGGCATGCTCACATCCATGGGATTCGGTC
TGTACCCATTGTCCTCCAGCGAAAGAGTCCTGCCATTTGGCAGCAAAATTCCTGGTCT
AAATGAGTACGAGAGTCCGTACTATGAGATGTGGTACATCTTTCAGATGCTCATCACC
CCGATGGGCTGTTGCATGTACATTCCGTACACCAGTCTGATTGTGGGCTTGATAATGT
TCGGCATTCTGAGGTGCAAGGCTTTGCAGCATCGCCTCCGCCAGGTGGCGCTTAAGCA
TCCGTACGGAGATCGCGATCCCCGTGAACTGAGGGAGGAGATCATAGCCTGCATACGT
TACCAGCAGAGCATTATCGAGTACATGGATCACATAAACGAGCTGACCACCATGATGT
TCCTATTCGAACTGATGGCCTTTTCGGCGCTGCTCTGTGCGTGCTCTTTATGCTGAT
TATCGTCAGCGGCACCAGTCAGCTGATAATTGTTTGCATGTACATTAACATGATTCTG
GCCCAAATACTGGCCCTCTATTGGTATGCAAATGAGTTAAGGGAACAGAATCTGGCGG
TGGCCACCGCAGCCTACGAAACGGAGTGGTTCACCTTCGACGTTCCACTGCGCAAAAA
CATCCTGTTCATGATGATGAGGGCACAGCGGCCAGCTGCAATACTACTGGGCAATATA
CGCCCCATCACTTTGGAACTGTTCCAAAACCTACTGAACACAACCTATACATTTTTTA
CGGTTCTCAAGCGAGTCTACGGA

DOR107
MYPRFLSRNYPLAKHLFFVTRYSFGLLGLRFGKEQSWLHLLWLVFNFVNLAHCCQAEF (SEQ ID NO: 30)
VFGWSHLRTSPVDAMDAFCPLACSFTTLFKLGWMWWRRQEVADLMDRIRLLIGEQEKR
EDSRRKVAQRSYYLMVTRDGMLVFTLGSITTGAFVLRSLWEMWVRRHQEFKFDMPFRM
LFHDFAHRMPWFPVFYLYSTWSGQVTVYAFAGTDGFFFGFTYLMAFLLQALRYDIQRA
LKPIRDPSLRESKICCQRLADIVDRHNEIEKIVKEFSGIMAAPTFVHFVSASLVIATS
VIDILLYSGYNIRRYVVYTFTVSSAIFLYCYGGTEMSTESLSLGEAAYSSAWYTWDRE
TRRRVFLIILRAQRPITVRVPFFAPSLPVFTSVIKFTGSIVALAKTIL

DOR107nt
ATGTATCCGCGATTCCTCAGCCGTAACTATCCGCTGGCCAAGCATTTGTTCTTCGTCA (SEQ ID NO: 29)
CCAGATACTCCTTTGGCCTGCTGGGCCTGAGATTTGGCAAAGAGCAATCGTGGCTTCA
CCTCTTGTGGCTGGTGTTCAATTTCGTTAACCTGGCGCACTGCTGCCAGGCGGAGTTC
GTCTTCGGCTGGAGTCACTTGCGCACCAGTCCCGTGGATGCCATGGACGCCTTTTGTC
CTCTGGCCTGCAGTTTCACCACGCTCTTCAAGCTGGGATGGATGTGGTGGCGTCGCCA
GGAAGTAGCTGATCTAATGGACCGCATCCGCTTGCTCATCGGGGAGCAGGAGAAGAAG
GAGGACTCCCGGAGAAAGGTGGCTCAAAGGAGCTACTATCTCATGGTCACCAGGTGCG
GTATGCTGGTCTTCACCCTGGGCAGCATTACCACTGGAGCCTTCGTTCTGCGTTCCCT
TTGGGAAATGTGGGTGCGTCGTCATCAGGAGTTCAAATTCGATATGCCCTTTCGCATG
CTGTTCCACGACTTTGCGCATCGCATGCCCTGGTTTCCAGTTTTCTATCTCTACTCCA
CATGGAGTGGCCAGGTCACTGTGTACGCCTTTGCTGGTACAGATGGTTTCTTCTTTGG
CTTTACCCTCTACATGGCCTTCTTGCTGCAGGCCTTAAGATACGATATCCAGGATGCC
CTCAAGCCAATAAGAGATCCCTCGCTTAGGGAATCCAAAATCTGCTGTCAGCGATTGG
CGGACATCGTGGATCGCCACAATGAGATAGAGAAGATAGTCAAGGAATTTTCTGGAAT
TATGGCTGCTCCAACTTTTGTTCACTTCGTATCAGCCAGCTTAGTGATAGCCACCAGC
GTCATTGATATACTATTGTATTCCGGCTATAACATCATCCGTTACGTGGTGTACACCT
TCACGGTTTCCTCGGCCATCTTCCTCTATTGCTACGGAGGCACAGAAATGTCAACTGA
GAGCCTTTCCTTGGGAGAAGCAGCCTACAGCAGTGCCTGGTATACTTGGGATCGAGAG
ACCCGCAGGCGGGTCTTTCTCATTATCCTGCGTGCTCAACGACCCATTACGGTGAGGG
TGCCCTTTTTTGCACCATCGTTACCAGTCTTCACATCGGTCATCAAGTTTACAGGTTC
GATTGTGGCACTGGCTAAGACGATACTG

DOR108
MDKHKDRIESMRLILQVMQLFGLWPWSLKSEEEWTFTGFVKRNYRFLLHLPITFTFIG (SEQ ID NO: 32)
LMWLEAFISSNLEQAGQVLYMSITEMALVVKILSIWHYRTEAWRLMYELQHAPDYQLH
NQEEVDFWRREQRFFKWFFYIYILISLGVVYSGCTGVLFLEGYELPFAYYVPFEWQNE
RRYWFAYGYDMAGMTLTCISNITLDTLGCYFLFHISLLYRLLGLRLRETKNMKNDTIF
GQQLRAIFIMHQRIRSLTLTCQRIVSPYILSQIILSALIICFSGYRLQHVGIRDNPGQ

-continued
FISMLQFVSVMILQIYLPCYYGNEITVYANQLTNEVYHTNWLECRPPIRKLLNAYMEH
LKKPVTIRAGNSFAVGLPIFVKTINNAYSFLALLLNVSN DOR108nt
ATGGATAAACACAAGGATCGCATTGAATCCATGCGCCTAATTCTTCAGGTCATGCAAC    (SEQ ID NO: 31)
TATTTGGCCTCTGGCCGTGGTCCTTGAAATCGGAAGAGGAGTGGACTTTCACCGGTTT
TGTAAAGCGCAACTATCGCTTCCTGCTCCATCTGCCCATTACCTTCACCTTTATTGGA
CTCATGTGGCTGGAGGCCTTCATCTCGAGCAATCTGGAGCAGGCTGGCCAGGTTCTGT
ACATGTCCATCACCGAGATGGCTTTGGTGGTGAAAATCCTGAGCATTTGGCACTATCG
CACCGAAGCTTGGCGGCTGATGTACGAACTCCAACATGCTCCGGACTACCAACTCCAC
AACCAGGAGGAGGTAGACTTTTGGCGCCGGGAGCAACGATTCTTCAAGTGGTTCTTCT
ACATCTACATTCTGATTAGCTTGGGCGTGGTATATAGTGGCTGCACTGGAGTACTTTT
TCTGGAGGGCTACGAACTGCCCTTTGCCTACTACGTGCCCTTCGAATGGCAGAACGAG
AGAAGGTACTGGTTCGCCTATGGTTACGATATGGCGGGCATGACGTCGACCTGCATCT
CAAACATTACCCTGGACACCCTGGGTTGCTATTTCCTGTTCCATATCTCTCTTTTGTA
CCGACTGCTTGGTCTGCGATTGAGGGAAACGAAGAATATGAAGAATGATACCATTTTT
GGCCAGCAGTTGCGTGCCATCTTCATTATGCATCAGAGGATTAGAAGCCTAACCCTGA
CCTGCCAGAGAATCGTATCTCCCTATATCCTATCTCAGATCATTTTGAGTGCCCTGAT
CATCTGCTTTAGTGGATACCGCTTGCAGCATGTGGGAATTCGCGATAATCCCGGCCAG
TTTATATCCATGTTGCAGTTTGTCAGTGTGATGATCCTGCAGATTTACTTGCCCTGAT
ACTATGGAAACGAGATAACCGTGTATGCCAATCAGCTGACCAACGAGGTTTACCATAC
CAATTGGCTGGAATGTCGGCCACCGATTCGAAAGTTACTCAATGCCTACATGGAGCAC
CTGAAGAAACCGGTGACCATCCGGGCTGGCAACTCCTTCGCCGTGGGACTACCAATTT
TTGTTAAGACCATCAACAACGCCTACAGTTTCTTGGCTTTATTACTAAATGTATCGAA
T DOR109
MESTNRLSAIQTLLVIQRWIGLLKWENEGEDGVLTWLKRIYPFVLHLPLTFTYIALMW    (SEQ ID NO: 34)
YEAITSSDFEEAGQVLYMSITELALVTKLLNIWRRHEASSLIEHELQHDPAFNLRNSE
EIKFWQQNQRNFKRIFYWYIWGSLFVAVMGYISVFFQEDYELPFGYYVPFEWRTRERY
FYAWGYNVVAMTLCCLSNILLDTLGCYFMFHIASLFRLLGMRLEALKNAAEEKARPEL
RRIFQLHTKVRRLTRECEVLVSPYVLSQVVFSAFIICFSAYRLVHMGFKQRPGLFVTT
VQFVAVMIVQIFLPCYYGNELTFHANALTNSVFGTNWLEYSVGTRKLLNCYMEFLKRP
VKVRAGVFFEIGLPIFVKTINNAYSFFALLLKISK DOR109nt
ATGGAGTCTACAAATCGCCTAAGTGCCATCCAAACACTTTTAGTAATCCAACGTTGGA    (SEQ ID NO: 33)
TAGGACTTCTTAAATGGGAAAACGAGGGCGAGGATGGAGTATTAACCTGGCTAAAACG
AATATATCCTTTTGTACTGCACCTTCCACTGACCTTCACGTATATTGCCTTAATGTGG
TATGAAGCTATTACATCGTCAGATTTTGAGGAAGCTGGTCAAGTTCTGTACATGTCCA
TCACCGAACTGGCATTGGTCACTAAACTGCTGAATATTTGGTATCGTCGTCATGAAGC
TGCTAGTCTAATCCACGAATTGCAACACGATCCCGCATTTAATCTGCGCAATTCGGAG
GAAATCAAATTCTGGCAGCAAAATCAGAGGAACTTTAAGAGAATATTTTACTGGTACA
TCTGGGGCAGCCTTTTCGTGGCTGTAATGGGTTATATAAGCGTGTTTTTCCAGGAGGA
TTACGAGCTGCCCTTTGGCTACTACGTGCCATTCGAGTGGCGCACCAGGGAACGATAC
TTCTACGCTTGGGGCTATAATGTGGTGGCCATGACCCTGTGCTGTCTATCCAACATCC
TACTGGACACACTAGGCTGTTATTTCATGTTCCACATCGCCTCGCTTTTCAGGCTTTT
GGGAATGCGACTGGAGGCCTTGAAAAATGCAGCCGAAGAGAAAGCCAGACCGGAGTTG
CGCCGCATTTTCCAACTGCACACTAAAGTCCGCCGATTGACGAGGGAATGCGAAGTGT
TAGTTTCACCCTATGTTCTATCCCAAGTGGTCTTCAGTGCCTTCATCATCTGCTTCAG
TGCCTATCGACTGGTGCACATGGGCTTCAAGCAGCGACCTGGACTCTTCGTGACCACC
GTGCAATTCGTGGCCGTCATGATCGTCCAGATTTTCTTGCCCTGTTACTACGGCAATG
AGTTGACCTTTCATGCCAATGCACTCACTAATAGTGTCTTCGGTACCAATTGGCTGGA
GTACTCCGTGGGCACTCGCAAGCTGCTTAACTGCTACATGGAGTTCCTCAAGCGACCG
GTTAAAGTGCGAGCTGGGGTGTTCTTTGAAATAGGACTACCCATCTTTGTGAAGACCA
TCAACAATGCCTACAGTTTCTTCGCCCTGCTGCTAAAGATATCCAAG DOR110
MLFNYLRKPNPTNLLTSPDSFRYFEYGMFCMGWHTPATHKIIYYITSCLIFAWCAVYL    (SEQ ID NO: 36)
PIGIIISFKTDINTFTPNELLTVMQLFFNSVGMPFKVLFFNLYISGFYKAKKLLSEMD
KRCCTLKERVEVHQGVVRCHKAYLIYQFIYTAYTISTFLSAALSGKLPWRIYNPFVDF
RESRSSFWKALLNETALMLFAVTQTLMSDIYPLLYGLILRVHLKLLRLRVESLCTDSG
KSDAENEQDLINYAAAIRPAVTRTIFVQFLLIGICLGLSMINLLFFADIWTGLAYVAY
INGLMVQTFPFCFVCDLLKKDCELLVSAIFHSNWINSSRSYKSSLRYFLKNAQKSIAF
TAGSIFPISTGSNIKVAKAFSVVTFVNQLNIADRLTKN DOR110nt
ATGTTGTTCAACTATCTGCGAAAGCCGAATCCCACAAACCTTTTGACTTCTCCGGACT    (SEQ ID NO: 35)
CATTTAGATACTTTGAGTATGGAATGTTTTGCATGGGATGGCACACACCAGCAACGCA
TAAGATAATCTACTATATAACATCCTGTTTGATTTTTGCTTGGTGTGCCGTATACTTG
CCAATCGGAATCATCATTAGTTTCAAAACGGATATTAACACATTCACACCGAATGAAC
TGTTGACAGTTATGCAATTATTTTTCAATTCAGTGGGAATGCCATTCAAGGTTCTGTT
CTTCAATTTGTATATTTCTGGATTTTACAAGGCCAAAAAGCTCCTTAGCGAAATGGAC
AAACGTTGCACCACTTTGAAGGAGCGAGTGGAAGTGCACCAAGGTGTGGTCCGTTGCA
ACAAGGCCTACCTCATTTACCAGTTCATTTATACCGCGTACACTATTTCAACATTTCT
ATCGGCGGCTCTTAGTGGAAAATTGCCATGGCGCATCTATAATCCTTTTGTGGATTTT
CGAGAAAGTAGATCCAGTTTTTGGAAAGCTGCCCTCAACGAGACAGCACTTATGCTAT
TTGCTGTGACTCAAACCCTAATGAGTGATATATATCCACTGCTTTATGGTTTGATCCT
GAGAGTTCACCTCAAACTTTTGCGACTAAGAGTGGAGAGCCTGTGCACAGATTCTGGA
AAAAGCGATGCTGAAAACGAGCAAGATTTGATTAACTATGCTGCAGCAATACGACCAG -continued

```
CGGTTACCCGCACAATTTTCGTTCAATTCCTCTTGATCGGAATTTGCCTTGGCCTTTC
AATGATCAATCTACTCTTCTTTGCCGACATCTGGACAGGATTGGCCACAGTGGCTTAC
ATCAATGGTCTAATGGTGCAGACATTTCCATTTTGCTTCGTTTGTGATCTACTCAAAA
AGGATTGTGAACTTCTTGTGTCGGCCATATTTCATTCCAACTGGATTAATTCAAGCCG
CAGTTACAAGTCATCTTTGAGATATTTTCTGAAGAACGCCCAGAAATCAATTGCTTTT
ACAGCCGGCTCTATTTTTCCCATTTCTACTGGCTCGAATATTAAGGTGGCTAAGCTGG
CATTTTCGGTGGTTACTTTTGTCAATCAACTTAACATAGCTGACAGATTGACAAAGAA
C
```

DOR111

```
MLFRKRKPKSDDEVITFDELTRFPMTFYKTIGEDLYSDRDPNVIRRYLLRFYLVLGFL    (SEQ ID NO: 38)
NFNAYVVGEIAYFIVHIMSTTTLLEATAVAPCIGFSFMADFKQFGLTVNRKRLVRLLD
DLKEIFPLDLEAQRKYNVSFYRKHMNRVMTLFTILCMTYTSSFSFYPAIKSTIKYYLM
GSEIFERNYGFNILFPYDAETDLTVYWFSYWGLAHCAYVAGVSYVCVDLLLIATITQL
TMHFNFIANDLEAYEFFDHTDEENIKYLHNLVVYHARALDINKKCTFQSSRIGHSAFN
QNWLPCSTKYKRILQFIIARSQKPASIRPPTFPPISFNTFMKVISMSYQFFALLRTTY
YG
```

DOR111nt

```
ATGCTGTTCCGCAAACGTAAGCCAAAAAGTGACGATGAAGTCATCACCTTCGACGAAC    (SEQ ID NO: 37)
TTACCCGGTTTCCGATGACTTTCTACAAGACCATCGGCGAGGATCTGTACTCCGATAG
GGATCCGAATGTGATAAGGCGTTACCTGCTACGTTTTTATCTGGTACTCGGTTTTCTC
AACTTCAATGCCTATGTGGTGGGCGAAATCGCGTACTTTATAGTCCATATAATGTCGA
CGACTACTCTTTTGGAGGCCACTGCAGTGGCACCGTGCATTGGCTTCAGCTTCATGGC
CGACTTTAAGCAGTTCGGTCTCACAGTGAATAGAAAGCGATTGGTCAGATTGCTGGAT
GATCTCAAGGAGATATTTCCTTTAGATTTAGAAGCGCAGCGGAAGTATAACGTATCGT
TTTACCGGAAACACATGAACAGGGTCATGACCCTATTCACCATCCTCTGCATGACCTA
CACCTCGTCATTTAGCTTTTATCCAGCCATCAAGTCGACCATAAAGTATTACCTTATG
GGATCGGAAATCTTTGAGCGCAACTACGGATTTCACATTTTGTTTCCCTACGACGCAG
AAACGGATCTGACGGTCTACTGGTTTTCCTACTGGGGATTGGCTCATTGTGCCTATGT
GGCCGGAGTTTCCTACGTCTGCGTGGATCTCCTGCTGATCGCGACCATAACCCAGCTG
ACCATGCACTTCAACTTTATAGCGAATGATTTGGAGGCCTACGAAGGAGGTGATCATA
CGGATGAAGAAAATATCAAATACCTGCACAACTTGGTCGTCTATCATGCCAGGGCGCT
GGATATTAACAAGAAATGTACATTTCAGAGCTCTCGGATTGGCCATTCGGCATTTAAT
CAGAACTGGTTGCCATGCAGCACCAAATACAAACGCATCCTGCAATTTATTATCGCGC
GCAGCCAGAAGCCCGCCTCTATAAGACCGCCTACCTTTCCACCCATATCTTTTAATAC
CTTTATGAAGGTAATCAGCATGTCGTATCAGTTTTTTGCACTGCTCCGCACCACATAT
TATGGT
```

DOR114

```
MLTKKDTQSAKEQEKLKAIPLHSFLKYANVFYLSIGMMAYDHKYSQKWKEVLLHWTFI    (SEQ ID NO: 40)
AQMVNLNTVLISELIYVFLAIGKGSNFLEATMNLSFIGFVIVGDFKIWNISRQRKLT
QVVSRLEELHPQGLAQQEPYNIGHHLSGYSRYSKFYFGMHMVLIWTYNLYWAVYYLVC
DFWLGMRQFERMLPYYCWVPWDWSTGYSYYFMYISQNIGGQACLSGQLAADMLMCALV
TLVVMHFIRLSAHIESHVAGIGSFQHDLEFLQATVAYHQSLIHLCQDINEIFGVSLLS
NFVSSSFIICFVGFQMTIGSKIDNLVMLVLFLFCAMBQVFMIATHAQRLVDASEQIGQ
AVYNHDWFRADLRYRKMLILIIKRAQQPSRLKATMFLNISLVTVSDLLQLSYKFFALL
RTMYVN
```

DOR114nt

```
ATGTTGACTAAGAAGGATACTCAAAGTGCCAAGGAGCAGGAAAAGTTGAAGGCCATTC    (SEQ ID NO: 39)
CATTGCACAGCTTTCTGAAATATGCCAACGTGTTCTATTTATCGATTGGAATGATGGC
CTACGATCACAAGTACAGTCAAAAGTGGAAGGAGGTCCTGCTGCACTGGACATTCATT
GCCCAGATGGTCAATCTGAATACAGTGCTCATCTCGGAACTCGATTTACGTATTCCTGG
CGATCGGCAAAGGTAGCAATTTTCTGGAGGCCACCATGAATCTGTCTTTCATTGGATT
TGTCATCGTTGGTGACTTCAAAATCTGGAACATTTCGCGGCAGAGAAAGAGACTCACC
CAAGTGGTCAGCCGATTGGAAGAACTGCATCCGCAAGGCTTGGCTCAACAAGAACCCT
ATAATATAGGGCATCATCTGAGCGGCTATAGCCGATATAGCAAATTTTACTTCGGCAT
GCACATGGTGCTGATATGGACTACAACCTGTATTGGGCCGTTTACTATCTGGTCTGT
GATTTCTGGCTGGGAATGCGTCAATTTGAGAGGATGCTGCCCTACTACTGCTGGGTTC
CCTGGGATTGGAGTACCGGATATAGCTACTATTTCATGTATATCTCACAGAATATCGG
CGGTCAGGCTTGTCTGTCCGGTCAGCTAGCAGCTGACATGTTAATGTGCGCCCTGGTC
ACTTTGGTGGTGATGCACTTCATCCGGCTTTCCGCTCACATCGAGAGTCATGTTGCGG
GCATTGGCTCATTCCAGCACGATTTGGAGTTCCTCCAAGCGACGGTGGCGTATCACCA
GAGCTTGATCCACCTCTGCCAGGATATCAATGAGATATTCGGTGTTTCACTGTTGTCC
AACTTTGTATCCTCGTCGTTTATCATCTGCTTCGTGGGTTTCCAGATGACCATCGGCA
GCAAGATCGACAACCTGGTAATGCTTGTGCTTTTCCTGTTTTGTGCCATGGTTCAGGT
CTTCATGATTGCCACCCATGCTCAGAGGCTCGTTGATGCGAGTGAACAGATTGGTCAA
GCGGTCTATAATCACGACTGGTTCCGTGCTAGATCTGCGGTATCGTAAATGCTGATCC
TGATTATTAAGAGGGCCCAACAGCCGAGTCGACTCAAGGCCACAATGTTCCTGAACAT
CTCACTGGTCACCGTGTCGGATCTCTTGCAACTCTCGTACAAATTCTTTGCCCTTCTG
CGCACAATGTACGTGAAT
```

DOR115

```
MEKLMKYASFFYTAVGIRPYTNGEESKMNKLIFHIVSWSNVINLSFVGLFESIYVYSA    (SEQ ID NO: 42)
FMDNKFLEAVTALSYIGFVTVGMSKMFFIRWKKTAITELINELKEIYPNGLIREERYN
LPMYLGTCSRISLIYSLLYSVLIWTFNLFCVMEYWVYDKWLNIRVVGKQLPYLMYIPW
KWQDNWSYYPLLFSQNFAGYTSAAGQISTDVLLCAVATQLVMHFDFLSNSMERHELSG
DWKKDSRFLVDIVRYHERILRLSDAVNDIFGIPLLLNFMVSSFVICFVGFQMTVGVPP
```

-continued

DIVVKLFLFLVSSMSQVYLICHYGQLVADASYGFSVATYNQKWYKADVRYKRALVIII
ARSQKVTFLKATIFLDITRSTMTDVRNCVLSV

DOR115nt
ATGGAGAAGCTAATGAAGTACGCTAGCTTCTTCTACACAGCAGTGGGCATACGGCCAT (SEQ ID NO: 41)
ATACCAATGGTGAAGAATCCAAAATGAACAAACTTATATTTCACATAGTTTTTTGGTC
CAATGTGATTAACCTCAGCTTCGTTGGATTATTTGAGAGCATTTACGTTTACAGTGCC
TTCATGGATAATAAGTTCCTGGAAGCAGTCACTGCGTTGTCCTACATTGGCTTCGTAA
CCGTAGGCATGAGCAAGATGTTCTTCATCCGGTGGAAGAAAACGGCTATAACTGAACT
GATTAATGAATTGAAGGAGATCTATCCGAATGGTTTGATCCGAGAGGAAAGATACAAT
CTGCCGATGTATCTGGGCACCTGCTCCAGAATCAGCCTTATATATTCCTTGCTCTACT
CTGTTCTCATCTGGACATTCAACTTGTTTTGTGTAATGGAGTATTGGGTCTATGACAA
GTGGCTCAACATTCGAGTGGTGGGCAAACAGTTGCCGTACCTCATGTACATTCCTTGG
AAATGGCAGGATAACTGGTCGTACTATCCACTGTTATTCTCCCAGAATTTTGCAGGAT
ACACATCTGCAGCTGGTCAAATTTCAACCGATGTCTTGCTCTGCGCGGTGGCCACTCA
GTTGGTAATGCACTTCGACTTTCTCTCAAATAGTATGGAACGCCACGAATTGAGTGGA
GATTGGAAGAAGGACTCCCGATTTCTGGTGGACATTGTTAGGTATCGCAACGTATAC
TCCGCCTTTCAGATGCAGTGAACGATATATTTGGAATTCCACTACTACTCAACTTCAT
GGTATCCTCGTTCGTCATCTGCTTCGTGGGATTCCAGATGACTGTTGGAGTTCCGCCG
GATATAGTTGTGAAGCTCTTCCTCTTCCTTGTCTCTTCGATGAGTCAGGTCTATTTGA
TTTGTCACTATGGTCAACTGGTGGCCGATGCTAGCTACGGATTTTCGGTTGCCACCTA
CATTCAGAAGTGGTATAAAGCCGATGTGCGCTATAAACGAGCCTTGGTTATTATTATA
GCTAGATCGCAGAAGGTAACTTTTCTAAAGGCCACTATATTCTTGGATATTACCAGGT
CCACTATGACAGATGTACGCAACTGTGTATTGTCAGTG

DOR116
MELLPLAMLMYDGTRVTAMQYLIPGLPLENNYCYVVTYMIQTVTMLVQGVGFYSGDLF (SEQ ID NO: 44)
VFLGLTQILTFADMLQVKVKELNDALEQKAEYRALVRVGASIDGAENRQRLLLDVIRW
HQLFTDYCRAINALYYELIATQVLSMALAMMLSFCINLSSFHMPSAIFFVVSAYSMSI
YCILGTILEFAYDQVYESICNVTWYELSGEQRKLFGFLLRESQYPHNIQILGVMSLSV
RTALQIVKLIYSVSMMMMNRA

DOR116nt
ATGGAACTCCTGCCATTGGCCATGCTAATGTACGATGGAACCCGGGTTACTGCGATGC (SEQ ID NO: 43)
AGTATTTAATTCCGGGTCTACCGCTTGAGAACAATTATTGCTACGTAGTCACGTACAT
GATTCAGACGGTGACAATGCTCGTGCAAGGAGTCGGATTCTACTCCGGTGATTTGTTC
GTATTTCTCGGCTTAACGCAGATCCTAACTTTCGCCGATATGCTGCAGGTGAAGGTGA
AAGAGCTAAACGATGCCCTGGAACAAAAAGCGGAATACAGAGCTCTAGTCCGAGTTGG
AGCTTCTATTGATGGAGCGGAAAATCGTCAACGCCTTCTCTTGGATGTTATAAGATGG
CATCAATTATTCACGGACTACTGTCGCGCCATAAATGCCCTCTACTACGAATTGATCG
CCACTCAGGTTCTTTCGATGGCTTTGGCCATGATGCTCAGCTTCTGCATTAATTTGAG
CAGCTTTCACATGCCTTCGGCTATCTTTTTCGTGGTTTCTGCCTACAGCATGTCCATC
TATTGCATTCTGGGCACCATTCTTGAGTTTGCATATGACCAGGTGTACGAGAGCATCT
GTAATGTGACCTGGTATGAGTTGAGTGGCGAACAGCGAAAGCTTTTTGGTTTTTTGTT
GCGGGAATCCCAGTATCCGCACAATATTCAGACTTGGAGTTATGTCGCTTTCCGTG
AGAACGGCTCTGCAGATTGTTAAACTAATTTATAGCGTATCCATGATGATGATGAATC
GGGCG

DOR117
MDLRRWFPTLYTQSKDSPVRSRDATLYLLRCVFLMGVRKPPAKFFVAYVLWSFALNFC (SEQ ID NO: 46)
STFYQPIGFLTGYISHLSEFSPGEFLTSLQVAFNAWSCSTKVLIVWALVKRFDEANNL
LDEMDRRITDPGERLQIHRAVSLSNRIFFFFMAVYMVYATNTFLSAIFIGRPPYQNYY
PFLDWRSSTLHLALQAGLEYFAMAGACFQDVCVDCYPVNFVLVLRAHMSIFAERLRRL
GTYPYESQEQKYERLVQCIQDHKVILRFVDCLRPVISGTIFVQFLVVGLVLGFTLINI
VLFANLGSAIAALSFMAAVLLETTPFCILCNYLTEDCYKLADALFQSNWIDEEKRYQK
TLMYFLQKLQQPITFMAMNVFPISVGTNISVSRCAL

DOR117nt
ATGGATCTGCGAAGGTGGTTTCCGACCTTGTACACCCAGTCGAAGAATTCGCCAGTTC (SEQ ID NO: 45)
GCTCCCGAGACGCGACCCTGTACCTCCTACGCTGCGTCTTCTTAATGGGCGTCCGCAA
GCCACCTGCCAAGTTTTTCGTGGCCTACGTGCTCTGGTCCTTCGCACTGAATTTCTGC
TCAACATTTTATCAGCCAATTGGCTTTCTCACAGGCTATATAAGCCATTTATCAGAGT
TCTCCCCGGAGAGTTTCTAACTTCGCTGCAGGTGGCCTTTAATGCTTGGTCCTGCTC
TACAAAAGTCCTGATAGTGTGGGCACTAGTTAAGCGCTTTGACGAGGCTAATAACCTT
CTCGACGAGATGGATAGGCGTATCACAGACCCCGGAGAGCGTCTTCAGATTCATCGCG
CTGTCTCCCTCAGTAACCGTATATTCTTCTTTTTCATGGCAGTCTACATGGTTTATGC
CACTAATACGTTTCTGTCGGCGATCTTCATTGGAAGGCCACCGTACCAAAATTACTAC
CCTTTTCTGGACTGGCGATCTAGCACTCTGCATCTAGCTCTGCAGGCCGGTCTGGAAT
ACTTCGCCATGGCTGGCGCCTGCTTCCAGGACGTTTGCGTTGATTGCTACCCAGTCAA
TTTCGTTTTGGTCCTGCGTGCCCACATGTCGATCTTCGCGGAGCGCCTTCGACGTTTG
GGAACTTATCCTTATGAAAGCCAGGAGCAGAAATATGAACGATTGGTCAGTGCATAC
AAGATCACAAAGTAATTTTGCGATTTGTTGACTGCCTGCGTCCTGTTATTTCTGGTAC
CATCTTCGTGCAATTCTTGGTTGTGGGGTTGGTGCTGGGCTTTACCCTAATTAACATT
GTCCTGTTCGCCAACTTGGGATCGGCCATCGCAGCGCTCTCGTTTATGGCCGCAGTGC
TTCTAGAGACGACTCCCTTCTGCATATTGTGCAATTATCTCACAGAAGACTGCTACAA
GCTGGCCGATGCCCTGTTTCAGTCAAACTGGATTGATGAGGAGAAACGATACCAAAAG
ACACTCATGTACTTCCTACAGAAACTGCAGCAGCCTATAACCTTCATGGCTATGAACG
TGTTTCCAATATCTGTGGGAACTAACATCAGTGTAAGCAGATGTGCCCTT

-continued

DOR118
MKFIGWLPPKQGVLRYVYLTWTLMTFVWCTTYLPLGFLGSYMTQIKSFSPGEFLTSLQ  (SEQ ID NO: 48)
VCINAYGSSVKVAITYSMLWRLIKAKNILDQLDLRCTAMEEREKIHLVVARSNHAFLI
FTFVYCGYAGSTYLSSVLSGRPPWQLYNFFIDWHDGTLKLWVASTLEYMVMSGAVLQD
QLSDSYPLIYTLILRAHLDMLRERIRRLRSDENLSEAESYEELVKCVMDHKLILRYCA
IIKPVIQGTIFTQFLLIGLVLGFTLINVFFFSDIWTGIASFMFVITILLQTFPFCYTC
NLIMEDCESLTHAIFQSNWVDASRRYKTTLLYFLQNVQQPIVFIAGGIFQISMSSNIS
VAKFAFSVITITKQMNIADKFKTD

DOR118nt
ATGAAGTTTATTGGATGGCTGCCCCCCAAGCAGGGTGTGCTCCGGTATGTGTACCTCA  (SEQ ID NO: 47)
CCTGGACGCTAATGACGTTCGTGTGGTGTACAACGTACCTGCCGCTTGGCTTCCTTGG
TAGCTACATGACGCAGATCAAGTCCTTCTCCCTGGAGAGTTTCTCACTTCACTGCCAG
GTGTGCATTAATGCCTACGGCTCATCGGTAAAAGTTGCAATCACATACTCCATGCTCT
GGCGCCTTATCAAGGCCAAGAACATTTTGGACCAGCTGGACCTGCGCTGCACCGCCAT
GGAGGAGCGCGAAAAGATCCACCTAGTGGTGGCCCGCAGCAACCATGCCTTTCTCATC
TTCACCTTTGTCTACTGCGGATATGCCGGCTCCACCTACCTGAGTTCGGTTCTCAGCG
GGCGTCCGCCCTGGCAGCTGTACAATCCCTTTATTGATTGGCATGACGGCACACTCAA
GCTCTGGGTGGCCTCCACGTTGGAGTACATGGTGATGTCAGGCGCCGTTCTGCAGGAT
CAACTCTCGGACTCTTACCCATTGATCTATACCCTCATCCTTCGTGCTCACTTGGACA
TGCTAAGGGAGCGCATCCGACGCCTCCGTTCCGATGAGAACCTGAGCGAGGCCGAGAG
CTATGAAGAGCTGGTCAAATGTGTGATGGACCACAAGCTCATTCTAAGATACTGCGCG
ATTATTAAACCAGTAATCCAGGGGACCATCTTCACACAGTTTCTGCTGATCGGCCTGG
TTCTGGGCTTCACGCTGATCAACGTGTTTTTCTTCTCAGACATCTGGACGGGCATCGC
ATCATTTATGTTTGTTATAACCATTTTGCTGCAGACCTTCCCCTTCTGCTACACATGC
AACCTCATCATGGAGGACTGCGAGTCCTTGACCCATGCTATTTTCCAGTCCAACTGGG
TGGATGCCAGTCGTCGCTACAAAACAACACTACTGTATTTTCTCCAAAACGTGCAGCA
GCCTATCGTTTTCATTGCAGGCGGTATCTTTCAGATATCCATGAGCAGCAACATAAGT
GTGGCAAAGTTTGCTTTCTCCGTGATAACCATTACAAAGCAAATGAATATAGCTGACA
AATTTAAGACGGAC

DOR119
MAVFKLIKPAPLTEKVQSRQGNIYLYRAMWLIGWIPPKEGVLRYVYLFWTCVPFAFGV  (SEQ ID NO: 50)
FYLPVGFIISYVQEFKNFTPGEFLTSLQVCINVYGASVKSTITYLFWRLRKTEILLD
SLDKRLANDSDREFIHNMVARCNYAFLIYSFIYCGYAGSTFLSYALSGRPPWSVYNPF
IDWRDGMGSLWIQAIFEYITMSFAVLQDQLSDTYPLMFTIMFRAHMEVLKDHVRSLRM
DPERSEADNYQDLVNCVLDHKTILKCCDMIRPMISRTIFVQFALIGSVLGLTLVNVFF
FSNFWKGVASLLFVITILLQTFPFCYTCNMLIDDAQDLSNEIFQSNWVDAEPRYKATL
VLFMHHVQQPIIFIAGGIFPISMNSNITVAKFAFSIITIVRQMNLAEQFQ

DOR119nt
ATGGCGGTGTTCAAGCTAATCAAACCGGCTCCGTTGACCGAGAAGGTGCAGTCCCGCC  (SEQ ID NO: 49)
AGGGGAATATATATCTGTACCGTGCCATGTGGCTCATCGGATGGATTCCGCCGAAGAA
GGGAGTCCTGCGCTACGTGTATCTCTTCTGGACCTGCGTGCCCTTCGCCTTCGGGGTG
TTTTACCTGCCCGTGGGCTTCATCATCAGCTACGTGCAGGAGTTCAAGAACTTCACGC
CGGGCGAGTTCCTTACCTCGCTGCAGGTGTGCATCAATGTGTATGGCGCCTCGGTGAA
GTCCACCATCACCTACCTCTTCCTCTGGCGACTGCGCAAGACGGAGATCCTTCTGGAC
TCCCTGGACAAGAGGCTGGCGAACGACAGCGATCGCGAGAGGATCCACAATATGGTGG
CGCGCTGCAACTACGCCTTTCTCATCTACAGCTTCATCTACTGCGGATACGCGGGTTC
ATCGATTGGCGCGATGGCATGGGCAGCCTGTGGATCCAGGCCATATTCGAGTACATCA
CCATGTCCTTCGCCGTGCTGCAGGACCAGCTATCCGACACGTATCCCCTGATGTTCAC
CATTATGTTCCGGGCCCACATGGAGGTCCTCAAGGATCACGTGCGGAGCCTGCGCATG
CATTATGTTCCGGGCCCACATGGAGGTCCTCAAGGATCACGTGCGGAGCCTGCGCATG
GATCCCGAGCGCAGTGAGGCAGACAACTATCAGGATCTGGTGAACTGCGTGCTGGACC
ACAAGACTATACTGAAATGCTGTGACATGATTCGCCCCATGATATCCCGCACCATCTT
CGTGCAATTCGCGCTGATTGGTTCCGTTTTGGGCCTGACCCTGGTGAACGTGTTCTTC
TTCTCGAACTTCTGGAAGGGCGTGGCCTCGCTCCTGTTCGTCATCACCATCCTGCTGC
AGACCTTCCCGTTCTGCTACACCTGCAACATGCTGATCGACGATGCCCAGGATCTGTC
CAACGAGATTTTCCAGTCCAACTGGGTGGACGCGGAGCCGCGCTACAAGGCGACGCTG
GTGCTCTTCATGCACCATGTTCAGCAGCCCATAATCTTCATTGCCGGAGGCATCTTTC
CCATCTCTATGAACAGCAACATAACCGTGGCCAAGTTCGCCTTCAGCATCATTACAAT
AGTGCGACAAATGAATCTGGCCGAGCAGTTCCAG

DOR120
MTKFFFKRLQTAPLDQEVSSLDASDYYYRIAFFLGWTPPKGALLRWIYSLWTLTTMWL  (SEQ ID NO: 52)
GIVYLPLGLSLTYVKHFDRFTPTEFLTSLQVDINCIGNVIKSCVTYSQMWRFRRMNEL
ISSSLDKRCVTTTQRRIFHKMVARVNLIVILFLSTYLGFCFLTLFTSVFAGKAPWQLYN
PLVDWRKGHWQLWIASILEYCVVSIGTMQELMSDTYAIVFISLFRCHLAILRDRIANL
RQDPKLSEMEHYEQMVACIQDHRTIIQCSQIIRPILSITIFAQFMLVGIDLGLAAISI
LFFPNTIWTIMANVSFIVAICTESFPCCMLCEHLIEDSVHVSNALFHSNWITADRSYK
SAVLYFLHRAQQPIQFTAGSTFPISVQSNIAVAKFAFTIITIVNQMNLGEKFFSDRSN
GDINP

DOR120nt
ATGACCAAGTTCTTCTTCAAGCGCCTGCAAACTGCTCCACTTGATCAGGAGGTGAGTT  (SEQ ID NO: 51)
CCCTTGATGCCAGCGACTACTACTACCGCATCGCATTTTTCCTGGGCTGGACCCCGCC
CAAGGGGGCTCTGCTCCGATGGATCTACTCCCTGTGGACTCTGACCACGATGTGGCTG
GGTATCGTGTACCTGCCGCTCGGACTGAGCCTCACCTATGTGAAGCACTTCGATAGAT
TCACGCCGACGGAGTTCCTGACCTCCCTGCAGGTGGATATCAACTGCATCGGGAACGT
GATCAAGTCATGCGTAACTTATTCCCAGATGTGGCGTTTTCGCCGGATGAATGAGCTT

-continued

```
ATCTCGTCCCTGGACAAGAGATGTGTGACTACGACACAGCGTCGAATTTTCCATAAGA
TGGTGGCACGGGTTAATCTCATCGTGATTCTGTTCTTGTCCACGTACTTGGGCTTCTG
CTTTCTAACTCTGTTCACTTCGGTTTTCGCTGGCAAAGCTCCTTGGCAGCTGTACAAC
CCACTGGTGGACTGGCGGAAAGGCCATTGGCAGCTATGGATTGCCTCCATCCTGGAGT
ACTGTGTGGTCTCCATTGGCACCATGCAGGAGTTGATGTCCGACACCTACGCCATAGT
GTTCATCTCCTTGTTCCGCTGCCACCTGGCTATTCTCAGAGATCGCATAGCTAATCTG
CGGCAGGATCCGAAACTCAGTGAGATGGAACACTATGAGCAGATGGTGGCCTGCATTC
AGGATCATCGAACCATCATACAGTGCTCCCAGATTATTCGACCCATCCTGTCGATCAC
TATCTTTGCCCAGTTCATGCTGGTTGGCATTGACTTGGGTCTGGCCGCCATCAGCATC
CTCTTCTTTCCGAACACCATTTGGACGATCATGGCAAACGTGTCGTTCATCGTGGCCA
TCTGTACAGAGTCCTTTCCATGCTGCATGCTCTGCGAGCATCTGATCGAGGACTCCGT
CCATGTGAGCAACGCCCTGTTCCACTCAAACTGGATAACGCGGACAGGAGCTACAAG
TCGGCGGTTCTGTATTTCCTGCACCGGGCTCAGCAACCCATTCAATTCACGGCCGGCT
CCATATTTCCCATTTCGGTGCAGAGCAACATAGCCGTGGCCAAGTTCGCGTTCACAAT
CATCACAATCGTGAACCAAATGAATCTGGGCGAGAAGTTCTTCAGTGACAGGAGCAAT
GGCGATATAAATCCT
```

DOR121
```
MLTDKFLRLQSALFRLLGLELLHEQDVGHRYPWRSICCILSVASFMPLTIAFGLQNVQ          (SEQ ID NO: 54)
NVEQLTDSLCSVLVDLLALCKIGLFLWLYKDFKFLIGQFYCVLQTETHTAVAEMIVTR
ESRRDQFISAMYAYCFITAGLSACLMSPLSMLISYHEQVNCSRNFHFPVCKKKYCLIS
RILRYSFCRYPWDNMKLSNYIISYFWNVCAALGVALPTVCVDTLFCSLSHNLCALFQI
ARHKMMHFEGRNTKETHENLKHVFQLYALCLNLGHFLNEYFRPLICQFVASSLHLCVL
CYQLSANILQPALLFYAAFTAAVVGQCSIYCFCGSSIHSECQLFGQAIYESSWPHLLQ
ENLQLVSSLKIAMMRSSLGCPIDGYFFEANRETLITVSKAFIKVSKKTPQVND
```

DOR121
```
ATGCTGACGGACAAGTTCCTCCGACTGCAGTCCGCTTTATTTCGCCTTCTCGGACTCG          (SEQ ID NO: 53)
AATTGTTGCACGAGCAGGATGTTGGCCATCGATATCCTTGGCGCAGCATCTGCTGCAT
TCTCTCGGTGGCCAGTTTCATGCCCCTGACCATTGCGTTTGGCCTGCAAAACGTCCAA
AATGTGGAGCAATTAACCGACTGCACTCTGCTCGGTTCTCGTGGATTTGCTGGCCCTGT
GCAAAATCGGGCTTTTCCTTTGGCTTTACAAGGACTTCAAGTTCCTAATAGGGCAGTT
CTATTGTGTTTTGCAAACGGAAACCCACACCGCTGTCGCTGAAATGATAGTGACCAGG
GAAAGTCGTCGGGATCAGTTCATCAGTGCTATGTATGCCTACTGTTTCATTACGGCTG
GCCTTTCGGCCTGCCTGATGTCCCCTCTATCCATGCTGATTAGCTACCACGAACAGGT
GAATTGCAGCCGAAATTTCCATTTCCCAGTGTGAAGAAAAAGTACTGCTTAATATCC
AGAATATTAAGATACAGTTTCTGCAGATATCCCTGGGACAATATGAAGCTGTCCAACT
ACATCATTTCCTATTTCTGGAATGTGTGCTGCATTGGGCGTGGCACTGCCCACCGT
TTGTGTGGACACACTGTTCTGTTCTCTGAGCCATAATCTCTGTGCCCTATTCCAGATT
GCCAGGCACAAAATGATGCACTTTGAGGGCAGAAATACCAAAGAGACTCATGAGAACT
TAAAGCACGTGTTTCAACTATATGCGTTGTGTTTGAACCTGGGCATTTCTTAAACGA
ATATTTCAGACCGCTCATCTGCCAGTTTGTGGCAGCCTCACTGCACTTGTGTGTCCTG
TGCTACCAACTGTCTGCCAATATCCTGCAGCCAGCGTTACTCTTCTATGCCGCATTTA
CGGCAGCAGTTGTTGGCCAGGTGTCTATATACTGCTTCTGCGGATCGAGCATCCATTC
GGAGTGTCAGCTATTTGGCCAGGCCATCTACGAGTCCAGCTGGCCCCATCTGCTGCAG
GAAAACCTGCAGCTTGTAAGCTCCTTAAAAATTGCCATGATGCGATCGAGTTTGGGAT
GTCCCATCGATGGTTACTTCTTCGAGGCCAATCGGGAGACGCTCATCACGGTGAGTAA
AGCGTTTATAAAAGTGTCCAAAAAGACACCTCAAGTGAATGAT
```

DOR14
```
MDYDRIRPVRFLTGVLKWWRLWPRKESVSTPDWTNWQAYALHVPFTFLFVLLLWLEAI          (SEQ ID NO: 56)
KSRDIQHTADVLLICLTTTALGGKVINIWKYAHVAQGILSEWSTWDLFELRSKQEVDM
WRFEHRRFNRVFMFYCLCSAGVIPFIVIQPLFDIPNRLPFWMWTPFDWQQPVLFWYAF
IYQATTIPIACACNVTMDAVNWYLMLHLSLCLRMLGQRLSKLQHDDKDLREKFLELIH
LHQRLKQQALSIEIFISKSTFTQILVSSLIICFTIYSMQMDLPGFAAMMQYLVAMIMQ
VMLPTIYGNAVIDSANMLTDSMYNSDWPDMNCRMRRLVLMFMVYLNRPVTLKAGGFFH
IGLPLFTKVVFSTLENPCISYLYFRP
```

DOR14nt
```
ATGGACTACGATCGAATTCGACCGGTGCGATTTTTGACGGGAGTGCTGAAATGGTGGC          (SEQ ID NO: 55)
GTCTCTGGCCGAGGAAGGAATCGGTGTCCACACCGGACTGGACTAACTGGCAGGCATA
TGCCTTGCACGTTCCATTTACATTCTTGTTTGTGTTGCTTTTGTGGTTGGAGGCAATC
AAGAGCAGGGATATACAGCATACCGCCGATGTCCTTTTGATTTGCCTAACCACACTG
CCTTGGGAGGTAAAGTTATCAATATCTGGAAGTATGCCCATGTGGCCCAAGGCATTTT
GTCCGAGTGGAGCACGTGGGATCTTTTCGAGCTGAGGAGCAAACAGGAAGTGGATATG
TGGCGATTCGAGCATCGACGTTTCAATCGTTTTTTTATGTTTTACTGTTTGTGCAGTG
CTGGTGTAATCCCATTTATTGTGATTCAACCGTTGTTTGATATCCCAAATCGATTGCC
CTTCTGGATGTGGACACCATTCGATTGGCAGCAGCCTGTTCTCTTCTGGTATGCATTC
ATCTATCAGGCCACAACCATTCCTATTGCCTGTGCTTGCAACGTAACCATGGACGCTG
TTAATTGGTACTTGATGCTGCATCTGTCCTTGTGTTTGCGTATGTTGGGCCAGCGATT
GAGTAAGCTTCAGCATGATGACAAGGATCTGAGGGAGAAGTTCCTGGAACTGATCCAT
CTGCACCAGCGACTCAAGCAACAGGCCTTGAGCATTGAAATCTTTATTTCGAAGAGCA
CGTTCACCCAAATTCTGGTCAGTTCCCTTATCATTTGCTTCACCATTTACAGCATGCA
GATGGACTTGCCAGGATTTGCCGCCATGATGCAGTACCTAGTGGCCATGATCATGCAG
GTCATGCTGCCCACCATATATGGTAACGCCGTCATCGATTCTGCAAATATGTTGACCG
ATTCCATGTACAATTCGGATTGGCCGGATATGAATTGCCGAATGCGTCGCCTAGTTTT
AATGTTTATGGTGTACTTAAATCGACCGGTGACCTTAAAAGCCGGTGGCTTTTTTCAT
ATTGGTTTACCTCTGTTTACCAAGGTTGTATTTTCTACTCTGGAAATCCTTGTATAA
GTTATCTTTATTTCAGACCA
```

-continued

DOR16
MTDSGQPAIADHFYRIPRISGLIVGLWPQRIRGGGGRPWHAHLLFVFAFAMVVVGAVG (SEQ ID NO: 58)
EVSYGCVHLDNLVVALEAFCPGTTKAVCVLKLWVFFRSNRRWAILVQRLRAILWESRR
QEAQRMLVGLATTANRLSLLLLSSGTATNAAFTLQPLIMGLYRWIVQLPGQTELPFNI
ILPSFAVQPGVFPLTYVLLTASGACTVFAFSFVDGFFICSCLYICGAFRLVQQDIRRI
FADLHGDSVDVFTEEMNAEVRHRLAQVVERHNAIIDFCTDLTRQFTVIVLMHFLSAAF
VLCSTILDIMLVSPFSEAFLWGGYPWVCRATGFSHRLHSAAVLKVFPCFHCLLFFPGF
SSRSVLIRFSRFCLLCGCGCGSLRWQFISA

DOR16nt
ATGACTGACAGCGGGCAGCCTGCCATTGCCGACCACTTTTATCGGATTCCCCGCATCT (SEQ ID NO: 57)
CCCGGCCTCATTGTCGGCCTCTGGCCGCAAAGGATAAGGGGCGGGGGCGGTCGTCCTTG
GCACGCCCATCTGCTCTTCGTGTTCGCCTTCGCCATGGTGGTGGGTGCGGTGGGC
GAGGTGTCGTACGGCTGTGTCCACCTGGACAACCTGGTGGTGGCGCTGGAGGCCTTCT
GCCCCGGAACCACCAAGGCGGTCTGCGTTTTGAGGCTGTGGGTCTTCTTCCGCTCCAA
TCGCCGGTGGGCGGAGTTGGTCCAGCGCCTGCGGGCTATTTTGTGGGAATCGCGGCGG
CAGGAGGCCCAGAGGATGCTGGTCGGACTGGCCACCACGGCCAACAGGCTCAGCCTGT
TGTTGCTCAGCTCTGGCACGGCGACAAATGCCGCCTTCACCTTGCAACCGCTGATTAT
GGGTCTCTACCGCTGGATTGTGCAGCTGCCAGGTCAAACCGAGCTGCCCTTTAATATC
ATACTGCCCTCGTTTGCCGTGCAGCCAGGAGTCTTTCCGCTCACCTACGTGCTGCTGA
CCGCTTCCGGTGCCTGCACCGTTTTCGCCTTCAGCTTCGTGGACGGATTCTTCATTTG
CTCGTGCCTCTACATCTGCGGCGCTTTCCGGCTGGTGCAGCAGGACATTCGCAGGATA
TTTGCCGATTTGCATGGCGACTCAGTGGATGTGTTCACCGAGGAGATGAACGCGGAGG
TGCGGCACAGACTGGCCCAAGTTGTCGAGCGGCACAATGCGATTATCGATTTCTGCAC
GGACCTAACACGCCAGTTCACCGTTATCGTTTTAATGCATTTCCTGTCCGCCGCCTTC
GTCCTCTGCTCGACCATCCTGGACATCATGTTGGTGAGCCCCTTTTCAGAGGCCTTCC
TTTGGGGCGGGTATCCTTGGGTTTGTCGCGCCACTGGCTTTTCGCATCGCCTGCATTC
GGCGGCTGTTTTAAAAGTTTTTCCCTGTTTTCACTGTTTGCTGTTTTTCCCTGGCTTT
TCCAGCCGCTCCGTTCTGATTCGGTTTTCCCGATTTGTTTGTTTGCTTTGTGGCTGCG
GCTGCGGCTCTCTCCGGTGGCAATTTATAAGCGCATGA

DOR19g
MVTEDFYKYQVWYFQILGVWQLPTWAADHQRRFQSMRFGFILVILFIMLLLFSFEMLN (SEQ ID NO: 22)
NISQVREILKVFFMFATEISCMAKLLHLKLKSRKLAGLVDAMLSPEFGVKSEQEMQML
ELDRVAVVRMRNSYGIMSLGAASLILIVPCFDNFGELPLAMLEVCSIEGWICYWSQYL
FHSICLLPTCVLNITYDSVAYSLLCFLKVQLQMLVLRLEKLGPVIEPQDNEKIAMELR
ECAAYYNRIVRFKDLVELFIKGPGSVQLMCSVLVLVSNLYDMSTMSIANGDAIFMLKT
CIYQLVMLWQIFIICYASNEVTVQSSRLCHSIYSSQWTGWNRANRRIVLLMMQRFNSP
MLLSTFNPTFAFSLEAFGSVGQQKFLYISFITGYALLLSDRQLLLQLLRTAEARQQLN
FETPQHLKIFKPIFKSTQNVMHVH

DOR19gnt
ATGGTTACGGAGGACTTTTATAAGTACCAGGTGTGGTACTTCCAAATCCTTGGTGTTT (SEQ ID NO: 21)
GGCAGCTCCCCACTTGGGCCGCAGACCACCAGCGTCGTTTTCAGTCCATGAGGTTTGG
CTTCATCCTGGTCATCCTGTTCATCATGCTGCTGCTTTTCTCCTTCGAAATGTTGAAC
AACATTTCCCAAGTTAGGGAGATCCTAAAGGTATTCTTCATGTTCGCCACGGAAATAT
CCTGCATGGCCAAATTATTGCATTTGAAGTTAAGAGCCGCAAACTCGCTGGCTTGGT
TGATGCGATGTTGTCCCCAGAGTTCGGCGTTAAAAGTGAACAGGAAATGCAGATGCTG
GAATTGGATAGAGTGGCGGTTGTCCGCATGAGGAACTCCTACGGCATCATGTCCCTGG
GCGCGGCTTCCCTGATCCTTATAGTTCCCTGTTTCGACAACTTTGGCGAGCTACCACT
GGCCATGTTGGAGGTATGCAGCATCGAGGGATGGATCTGCTATTGGTCGCAGTACCTT
TTCCACTCGATTTGCCTGCTGCCCACTTGTGTGCTGAATATAACCTACGACTCGGTGG
CCTACTCGTTGCTCTGTTTCTTGAAGGTTCAGCTACAAATGCTGGTCCTGCGATTAGA
AAAGTTGGGTCCTGTGATCGAACCCCAGGATAATGAGAAAATCGCAATGGAACTGCGT
GAGTGTGCCGCCTACTACAACAGGATTGTTCGTTTCAAGGACCTGGTGGAGCTGTTCA
TAAAGGGGCCAGGATCTGTGCAGCTCATGTGTTCTGTTCTGGTGCTGGTGTCCAACCT
GTACGACATGTCCACCATGTCCATTGCAAACGGCGATGCCATCTTTATGCTCAAGACC
TGTATCTATCAGCTGGTGATGCTCTGGCAGATCTTCATCATTTGCTACGCCTCCAACG
AGGTAACTGTCCAGAGCTCTAGGTTGTGTCACAGCATCTACAGCTCCCAATGGACGGG
ATGGAACAGGGCAAACCGCCGGATTGTCCTTCTCATGATGCAGCGCTTTAATTCCCCG
ATGCTCCTGAGCACCTTTAACCCCACCTTTGCTTTCAGCTTGGAGGCCTTTGGTTCTG
TAGGGCAGCAGAAATTCCTTTATATATCATTTATTACTGGTTATGCTCTTCTCCTTTC
AGATCGTCAACTGCTCCTACAGCTACTTCGCACTGCTGAAGCGCGTCAACAGTTAAAT
TTCGAAACACCGCAGCACCTAAAGATTTTCAAGCCGATTTTTAAAAGCACTCAAAACG
TTATGCACGTACAT DOR20
MSKGVEIFYKGQKAFLNILSLWPQIERRWRIIHQVNYVHVIVFWVLLFDLLLVLHVMA (SEQ ID NO: 60)
NLSYMSEVVKAIFILATSAGNTTKLLSIKANNVQMEELFRRLDNEEFRPRGANEELIF
AAACERSRKLRDFYGALSFALLSMILIPQFALDWSHLPLKTYNPLGENTGSPAYWLLY
CYQCLALSVSCITNIGFDSLCSSLFIFLKCQLDILAVRLDKIGRLITTSGGTVEQQLK
ENIRYHMTIVELSKTVERLLCKPISVQIFCSVLVLTANFYAIAVVSCEFATRRLSVCD
LSGVHVDSDFYIVLLCRVGIPYPKCLPRPVMNFIVSEVTQRSLDLPHELYKTSWVDWD
YRSRRIALLFMQRLHSTLRIRTLNPSLGFDLMLFSSVSSFRVLTFLCTVANFHNEAH DOR20nt
ATGAGCAAAGGAGTAGAAATCTTTTACAAGGGCCAGAAGGCATTCTTGAACATCCTCT (SEQ ID NO: 59)
CGTTGTGGCCTCAGATAGAACGCCGGTGGAGAATCATCCACCAGGTGAACTATGTCCA
CGTAATTGTGTTTTGGGTGCTGCTCTTTGATCTCCTCTTGGTGCTCCATGTGATGGCT
AATTTGAGCTACATGTCCGAGGTTGTGAAAGCCATCTTTATCCTGGCCACCAGTGCAG -continued
```
GGCACACCACCAAGCTGCTGTCCATAAAGGCGAACAATGTGCAGATGGAGGAGCTCTT
TAGGAGATTGGATAACGAAGAGTTCCGTCCTAGAGGCGCCAACGAAGAGTTGATCTTT
GCAGCAGCCTGTGAAAGAAGTAGGAAGCTTCGGGACTTCTATGGAGCGCTTTCGTTTG
CCGCCTTGAGCATGATTCTCATACCCCAGTTCGCCTTGGACTGGTCCCACCTTCCGCT
CAAAACATACAATCCGCTTGGCGAGAATACCGGCTCACCTGCTTATTGGCTCCTCTAC
TGCTATCAGTGTCTGGCCTTGTCCGTATCCTGCATCACCAACATAGGATTCGACTCAC
TCTGCTCCTCACTGTTCATCTTCCTCAAGTGCCAGCTGGACATTCTGGCCGTGCGACT
GGACAAGATCGGTCGGTTAATCACTACTTCTGGTGGCACTGTGGAACAGCAACTTAAG
GAAAAATATCCGCTATCACATGACCATCGTTGAACTGTCGAAAACCGTGGAGCGTCTA
TTTGCAAGCCGATTTCGGTGCAGATCTTCTGCTCGGTTTTGGTGCTGACTGCCAATTT
CTATGCCATTGCTGTGGTGAGCTGTGAATTCGCAACAAGAAGACTATCAGTATGTGAC
CTATCAGGCGTGCATGTTGATTCAGATTTTTATATTGTGCTACTATGCCGGGTGGGTA
TTCCATATCCGAAATGCCTCCCCAGGCCAGTAATGAATTTCATCGTCAGTGAGGTAAC
CCAGCGCAGCCTGGACCTTCCGCACGAGCTGTACAAGACCTCCTGGGTGGACTGGGAC
TACAGGAGCCGAAGGATTGCGCTCCTCTTTATGCAACGCCTTCACTCGACCTTGAGGA
TTAGGACACTTAATCCAAGTCTTGGTTTTGACTTAATGCTCTTCAGCTCGGTGAGTTC
TTTCCGTGTTTTGACTTTTTTGTGCACTGTAGCCAATTTCCATAATGAGGCTCAT DOR24
MDSFLQVQKSTIALLGFDLFSENREMWKRPYRAMNVFSIAAIFPFILAAVLHNWKNVL    (SEQ ID NO: 24)
LLADAMVALLITILGLFKFSMILYLRRDFKRLIDKFRLLMSNEAEQGEEYAEILNAAN
KQDQRMCTLFRTCFLLAWALNSVLPLVRMGLSYWLAGHAEPELPFPCLFPWNIHIIRN
YVLSFIWSAFASTGVVLPAVSLDTIFCSFTSNLCAFFKIAQYKVVRFKGGSLKESQAT
LNKVFALYQTSLDMCNDLNQCYQPIICAQFFISSLQLCMLGYLFSITFAQTEGVYYAS
FIATIIIQAYIYCYCGENLKTESASFEWAIYDSPWHELSGAGGASTSICRSLLISMMR
AHRGFRITGYFFEANMEAFSSIVRTAMSYITMLRSFS DOR24nt
GGCACGAGCCTTGTCGACATGGACAGTTTTCTGCAAGTACAGAAGAGCACCATTGCTC    (SEQ ID NO: 23)
TTCTGGGCTTTGATCTCTTTAGTGAAAATCGAGAAATGTGGAAACGCCCCTATAGAGC
AATGAATGTGTTTAGCATAGCTGCCATTTTTCCCTTTATCCTGGCAGCTGTGCTCCAT
AATTGGAAGAATGTATTGCTGCTGGCCGATGCCATGGTGGCCCTACTAATAACCATTC
TGGGGCCTATTCAAGTTTAGCATGATACTTTACTTACGTCGCGATTTCAAGCGACTGAT
TGACAAATTTCGTTTGCTCATGTCGAATGAGGCGGAACAGGGCGAGGAATACGCCGAG
ATTCTCAACGCAGCAAACAAGCAGGATCAACGAATGTGCACTCTGTTTAGGACTTGTT
TCCTCCTCGCCTGGGCCTTGAATAGTGTTCTGCCCCTCGTGAGAATGGGTCTCAGCTA
TTGGTTAGCAGGTCATGCAGAGCCCGAGTTGCCTTTTCCCTGTCTTTTTCCCTGGAAT
ATCCACATCATTCGCAATTATGTTTTGAGCTTCATCTGGAGCGCTTTCGCCTCGACAG
GTGTGGTTTTACCTGCTGTCAGCTTGGATACCATATTCTGTTCCTTCACCAGCAACCT
GTGCGCCTTCTTCAAAATTGCGCAGTACAAGGTGGTTAGATTTAAGGGCGGATCCCTT
AAAGAATCACAGGCCACATTGAACAAAGTCTTTGCCCTGTACCAGACCAGCTTGGATA
TGTGCAACGATCTGAATCAGTGCTACCAACCGATTATCTGCGCCCAGTTCTTCATTTC
ATCTCTGCAACTCTGCATGCTGGGATATCTGTTCTCCATTACTTTTGCCCAGACAGAG
GGCGTGTACTATGCCTCTTTCATAGCCACCATCATTATACAAGCCTATATCTACTGCT
ACTGCGGGGAGAACCTGAAGACGGAGAGTGCCAGCTTCGAGTGGGCCATCTACGACAG
TCCGTGGCACGAGAGTTTGGGTGCTGGTGGAGCCTCTACCTCGATCTGCCGATCCTTG
CTGATCAGCATGATGCGGGCTCATCGGGGATTCCGCATTACGGGATACTTCTTCGAGG
GAGATCATTCTCCTAAATGTGGTTTGACCACAAGGCTTTGGATTGATTTTTGTGCAAT
TTTTGTTTTATTGCTGAGCATGCGTTGCCGTACGACATTTAACAATCGATCTTACGTA
ATTTACATATGATAATCTCACATATTGTTCGTTAAGCACTAAGTAGAATGTAGAATGT
GAATTGGCTGTAGAAATGCACAGATGAAGCACGAAAAAAAAAAAAAAAAAAAAAAAA DOR25
MNDSGYQSNLSLLRVFLDEFRSVLRQESPGLIPRLAFYYVRAFLSLPLYRWINLFIMC    (SEQ ID NO: 62)
NVMTIFWTMFVALPESKNVIEMGDDLVWISGMALVFTKIFYMHLRCDEIDELISDFEY
YNRELRPHNIDEEVLGWQRLCYVIESGLYINCFCLVNFFSAAIFLQPLLGEGKLPFHS
VYPFQWHRLDLHPYTFWFLYIWQSLTSQHNLMSILMVDMVGISTFLQTALNLKLLCIE
IRKLGDMEVSDKRFHEEFCRVVRFHQHIIKLVGKANRAFNGAFNAQLMASFSLISIST
FETMAAAAVDPKMAAKFVLLMLVAFIQLSLWCVSGTLVYTQSVEVAQAAFDINDWHTK
SPGIQRDISFVILRAQKPLMYVAEPFLPFTLGTYMLVLKNCYRLLALMQESM DOR25nt
ATGAACGACTCGGGTTATCAATCAAATCTCAGCCTTCTGCGGGTTTTTCTCGACGAGT    (SEQ ID NO: 61)
TCCGATCGGTTCTGCGGCAGGAAAGTCCCGGTCTCATCCCACGCCTGGCTTTTTACTA
TGTTCGCGCCTTTCTGAGCTTGCCCCTGTACCGATGGATCAACTTGTTCATCATGTGC
AATGTGATGACCATTTTCTGGACCATGTTCGTGGCCCTGCCCGAGTCGAAGAACGTGA
TCGAAATGGGCGACGACTTGGTTTGGATTTCGGGGATGGCACTGGTGTTCACCAAGAT
CTTTTACATGCATTTGCGTTGCGACGAGATCGATGAACTTATTTCGGATTTTGAATAC
TACAACCGGGAGCTGAGACCCCATAATATCGATGAGGAGGTGTTGGGTTGGCAGAGAC
TGTGCTACGTGATAGAATCGGGTCTATATATCAACTGCTTTTGCCTGGTCAACTTCTT
CAGTGCCGCTATTTTCCTGCAACCTCTGTTGGGCGAGGGAAAGCTGCCCTTCCACGCC
GTCTATCCGTTTCAATGGCATCGCTTGGATCTGCATCCCTACACGTTCTGGTTCCTCT
ACATCTGGCAGAGTCTGACCTCGCAGCACAACCTAATGAGCATTCTAATGGTGGATAT
GGTAGGCATTTCCACGTTCCTCCAGACGGCGCTCAATCTCAAGTTGCTTTGCATCGAG
ATAAGGAAACTGGGGGACATGGAGGTCAGTGATAAGAGGTTCCACGAGGAGTTTTGTC
GTGTGGTTCGTTTCCACCAGCACATTATCAAGTTGGTGGGGAAAGCCAATAGAGCTTT
CAATGGCGCCTTCAATGCACAATTAATGGCCAGTTTCTCCCTGATTTCCATATCCACT
TTCGAGACCATGGCTGCAGCGGCTGTGGATCCCAAAATGGCCGCCAAGTTCGTGCTTC
TCATGCTGGTGGCATTCATTCAACTGTCGCTTTGGTGCGTCTCTGGAACTTTGGTTTA
TACTCAGTCAGTGGAGGTGGCTCAGGCTGCTTTTGATATCAACGATTGGCACACCAAA
```

-continued
```
TCGCCAGGCATCCAGAGGGATATATCCTTTGTGATACTACGAGCCCAGAAACCCCTGA
TGTATGTGGCCGAACCATTTCTGCCCTTCACCCTGGGAACCTATATGCTTGTACTGAA
GAACTGCTATCGTTTGCTGGCCCTGATGCAAGAATCGATGTAG
```

```
DOR28
MYSPEEAAELKRRNYRSIREMIRLSYTVGFNLLDPSRCGQVLRIWTIVLSVSSLASLY    (SEQ ID NO: 64)
GHWQMLARYIHDIPRIGETAGTALQFLTSIAKMWYFLFAHRQIYELLRKARCHELLQK
CELFERMSDLPVIKEIRQQVESTMNRYWASTRRQILIYLYSCICITTNYFINSFVINL
YRYFTKPKGSYDIMLPLPSLYPAWEHKGLEFPYYHIQMYLETCSLYICGMCAVSGDGV
FIVLCLHSVGLMRSLNQMVEQATSELVPPDRRVEYLRCCIYQYQRVANFATEVNNCFR
HITFTQFLLSLFNWGLALFQMSVGLGNNSSITMIRMTMYLVAAGYQIVVYCYNGQRFA
TASEEIANAFYQVRWYGESREFRHLIRMMLMRTNRGFRLDVSWFMQMSLPTLMAVSSG
AEQSRGPAGPAGPAGPPPRVPSYSQFHLIDSQMVRTSGQYFLLLLQNVNQK
```

```
DOR28nt
ATGTACTCACCGGAAGAGGCGGCCGAACTGAAGAGGCGCAACTATCGCAGCATCAGGG    (SEQ ID NO: 63)
AGATGATCCGACTCTCCTATACGGTGGGCTTCAACCTGTTGGATCCTTCCCGATGCGG
ACAGGTGCTCAGAATCTGGACAATTGTCCTTAGCGTGAGTAGCTTGGCATCGCTTTAT
GGGCACTGGCAAATGTTAGCCAGGTACATTCATGATATTCCACGCATTGGAGAGACCG
CTGGAACTGCCCTGCAGTTCCTAACATCGATAGCAAAGATGTGGTACTTTCTGTTTGC
CCATAGACAGATATACGAATTGCTACGAAAGGCGCGCTGCCATGAATTACTCCAAAAG
TGTGAGCTCTTTGAAAGGATGTCAGATCTACCTGTTATCAAAGAGATTCGCCAGCAGG
TTGAGTCCACGATGAATCGGTACTGGGCCAGCACTCGTCGGCAAATTCTTATCTATTT
GTACAGCTGTATTTGTATTACTACAAACTACTTTATCAACTCCTTCGTAATCAACCTC
TATCGCTATTTCACTAAACCGAAAGGATCCTACGACATAATGTTACCTCTGCCATCTC
TGTATCCCGCCTGGGAGCACAAGGGATTAGAGTTTCCCTACTATCATATACAGATGTA
CCTGGAAACCTGTTCTCTGTATATCTGCGGCATGTGTGCCGTTAGCTTTGATGGAGTC
TTTATTGTCCTGTGCCTTCATAGCGTGGGACTTATGAGGTCACTTAACCAAATGGTGG
AACAAGCCACATCTGAGTTGGTTCCTCCAGATCGCAGGGTTGAATACTTGCGATGCTG
TATTTATCAGTACCAACGAGTGGCGAACTTTGCAACCGAGGTTAACAACTGCTTTCGG
CACATCACTTTCACGCAGTTCCTGCTTAGCCTTTTCAACTGGGGCCTGGCCTTGTTCC
AAATGAGCGTCGGATTGGGCAACAACAGCAGCATCACCATGATCCGGATGACCATGTA
CCTGGTGGCAGCCGGCTATCAGATAGTTGTGTACTGCTACAATGGCCAGCGATTTGCG
ACTGCTAGCGAGGAGATTGCCAACGCCTTTTACCAGGTGCGATGGTACGGAGAGTCCA
GGGAGTTCCGCCACCTCATCCGCATGATGCTGATGCGCACGAACCGGGGATTCAGGCT
GGACGTGTCCTGGTTCATGCAAATGTCCTTGCCCACACTCATGGCGGTGAGTAGCGGA
GCAGAGCAGAGCAGGGGTCCTGCAGGTCCTGCAGGTCCTGCAGGTCCACCCCCAAGGG
TCCCCTCCTACAGCCAGTTCCACTTGATTGATTCGCAGATGGTCCGGACAAGTGGACA
GTACTTCCTGCTGCTGCAGAACGTCAACCAGAAA
```

```
DOR30
MAVSTRVATKQEVPESRRAFRNLFNCFYALGMQAPDGSRPTTSSTWQRIYACFSVVMY    (SEQ ID NO: 66)
VWQLLLVPTFFVISYRYMGGMEITQVLTSAQVAIDAVILPAKIVALAWNLPLLRRAEH
HLAALDARCREQEEFQLILDAVRFCNYLVWFYQICYAIYSSSTFVCAFLLGQPPYALY
LPGLDWQRSQMQFCIQAWIEFLIMNWTCLHQASDDVYAVIYLYVVRIQVQLLARRVEK
LGTDDSGQVEIYPDERRQEEHCAELQRCIVDHQTMLQLLDCISPVISRTIFVQFLITA
AIMGTTMINIFIFANTNTKIASIIYLLAVTLQTAPCCYQATSLMLDNERLALAIFQCQ
WLGQSARFRKMLLYYLHRAQQPITLTAMKLFPINLATYFSIAKFSFSLYTLIKGMNLG
ERFNRTN
```

```
DOR30nt
ATGGCGGTGAGCACTCGTGTGGCCACAAAGCAGGAAGTGCCCGAATCCCGGCGAGCGT    (SEQ ID NO: 65)
TTAGGAATCTCTTCAATTGCTTCTATGCCCTTGGCATGCAGGCACCGGATGGCAGTCG
ACCGACCACGAGCAGCACATGGCAACGCATCTACGCCTGCTTCTCGGTGGTCATGTAC
GTGTGGCAACTGCTGCTGGTGCCCACATTCTTTGTGATCAGCTATCGGTACATGGGCG
GCATGGAGATTACCCAGGTGCTGACCTCCGCCCAGGTGGCCATCGATGCGGTCATTCT
GCCGGCCAAGATTGTGGCACTGGCGTGGAATTTGCCATTGCTGCGCAGAGCAGAGCAT
CATCTGGCCGCCTTGGATGCGCGGTGCAGGGAACAGGAGGAGTTCCAATTGATCCTCG
ATGCGGTGAGGTTTTGCAACTATCTGGTATGGTTCTACCAGATCTGCTATGCCATCTA
CTCCTCGTCGACATTTGTGTGCGCCTTCCTGCTGGGCCAACCGCCATATGCCCTCTAT
TTGCCTGGCCTCGATTGGCAGCGTTCCCAGATGCAGTTCTGCATCCAGGCCTGGATTG
AGTTCCTTATCATGAACTGGACGTGCCTGCACCAAGCTAGCGATGATGTGTACGCCGT
TATCTATCTGTATGTGGTCCGGATTCAAGTGCAATTGCTGGCCAGGCGGGTGGAGAAG
CTGGGCACGGATGATAGTGGCCAGGTGGAGATCTATCCCGATGAGCGGCGGCAGGAGG
AGCATTGCGCGGAACTGCAGCGCTGCATTGTAGATCACCAGACGATGCTGCAGCTGCT
CGACTGCATTAGTCCCGTCATCTCGCGTACCATATTCGTTCAGTTCCTGATCACCGCC
GCCATCATGGGCACCACCATGATCAACATTTTCATTTTCGCCAATACGAACACGAAGA
TCGCATCGATCATTTACCTGCTGGCGGTGACCCTGCAGACGGCTCCATGTTGCTATCA
GGCCACCTCGCTGATGTTGGACAACGAGAGGCTGGCCCTGGCCATCTTCCAGTGCCAG
TGGCTGGGCCAGAGTGCCCGGTTCCGTAAGATGCTGCTCTACTATCTTCATCGCGCCC
AGCAGCCCATCACGCTGACCGCCATGAAGCTGTTTCCCATCAATCTGGCCACGTACTT
CAGTATAGCCAAGTTCTCGTTTTCGCTCTACACGCTCATCAAGGGGATGAATCTCGGC
GAGCGATTCAACAGGACAAAT
```

```
DOR31
MIFKYIQEPVLGSLFRSRDSLIYLNRSIDQMGWRLPPRTKPYWWLYYIWTLVVIVLVF    (SEQ ID NO: 68)
IFIPIPYGLIMTGIKEFKNFTTTDLFTYVQVPVNTNASIMKGIIVLFMRRRFSRAQKMMD
AMDIRCTKMEEKVQVHRAAALCNRVVVIYHCIYFGYLSMALTGALVIGKTPFCLYNPL
VNPDDHFYLATAIESVTMAGIILANLILDVYPIIYVVVLRIHMELLSERIKTLRTDVE
KGDDQHYAELVECVKDHKLIVEYGNTLRPMISATMFIQLLSVGLLLGLAAVSMQFYNT
```

-continued

VMERVVSGVYTIAILSQTFPFCYVCEQLSSDCESLTNTLFHSKWIGAERRYRTTMLYF
IHNVQQSILFTAGGIFPICLNTNIKMAKFAGSVVTIVNEMDLAEKLRRE

DOR31nt
ATGATTTTTAAGTACATTCAAGAGCCAGTCCTTGGATCCTTATTTCGATCCCGGGATT (SEQ ID NO: 67)
CGCTGATCTACTTAAACAGATCCATAGATCAAATGGGATGGAGACTGCCGCCACGAAC
TAAGCCGTACTGGTGGCTCTATTACATTTGGACATTGGTGGTCATAGTACTCGTCTTT
ATCTTTATACCCTATGGACTGATAATGACTGGAATAAAGGAGTTCAAGAACTTCACGA
CCACGGATCTGTTTACGTATGTCCAGGTGCCGGTTAACACCAATGCTTCGATCATGAA
GGGCATTATAGTGTTGTTTATGCGGCGGCGATTTTCAAGGGCTCAGAAGATGATGGAC
GCCATGGACATTCGATGCACCAAGATGGAGGAGAAAGTCCAGGTGCACCGAGCAGCAG
CCTTATGCAATCGTGTTGTTGTGATTTACCATTGCATATACTTCGGCTATCTATCCAT
GGCCTTAACCGGAGCTCTGGTGATTGGGAAGACTCCATTCTGTTTGTACAATCCACTG
GTTAACCCCGACGATCATTTCTATCTGGCCACTGCCATTGAATCGGTCACCATGGCTG
GCATTATTCTGGCCAATCTCATTTTGGACGTATATCCCATCATATATGTGGTCGTTCT
GCGGATCCACATGGAGCTCTTGAGTGAGCGAATCAAGACGCTGCGTACTGATGTGGAA
AAAGGCGACGATCAACATTATGCCGAGCTGGTGGAGTGTGTAAAGGATCACAAGCTAA
TTGTCGAATATGGAAACACTCTGCGTCCCATGATATCCGCCACGATGTTCATCCAACT
ACTATCCGTTGGCTTACTTTTGGGTCTGGCAGCGGTGTCCATGCAGTTCTATAACACC
GTAATGGAGCGTGTTGTCTCCGGGGTCTACACCATAGCCATTCTATCCCAGACCTTTC
CATTTTGCTATGTCTGTGAGCAGCTGAGCAGCGATTGCGAATCCCTGACCAACACACT
GTTCCATTCCAAGTGGATTGGAGCTGAGCGACGATACAGAACCACGATGTTGTACTTC
ATTCACAATGTTCAGCAGTCGATTTTGTTCACTGCGGGCGGAATTTTCCCCATATGTC
TAAACACCAATATAAAGATGGCCAAGTTCGCTTTCTCAGTGGTGACCATTGTAAATGA
GATGGACTTGGCCGAGAAATTGAGAAGGGAG

DOR32
MEPVQYSYEDFARLPTTVFWIMGYDMLGVPKTRSRRILYWIYRFLCLASHGVCVGVMV (SEQ ID NO: 68)
FRMVEAKTIDNVSLIMRYATLVTYIINSDTKFATVLQRSAIQSLNSKLAELYPKTTLD
RIYHRVNDHYWTKSFVYLVIIYIGSSIMVVIGPIITSIIAYFTHNVFTYMHCYPYFLY
DPEKDPVWIYISIYALEWLHSTQMVISNIGADIWLLYFQVQINLHFRGIIRSLADHKP
SVKHDQEDRKFIAKIVDKQVHLVSLQNDLNGIFGKSLLLSLLTTAAVICTVAVYTLIQ
GPTLEGFTYVIFIGTSVMQVYLVCYYGQQVLDLSGEVAHAVYNHDFHDASIAYKRYLL
IIIIRAQQPVELNAMGYLSISLDTFKQLMSVSYRVITMLMQMIQ

DOR32nt
ATGGAACCTGTGCAGTACAGCTACGAGGATTTCGCTCGATTGCCCACGACGGTGTTCT (SEQ ID NO: 61)
GGATCATGGGCTACGACATGCTGGGCGTTCCGAAGACCCGCTCTCGCAGGATACTATA
CTGGATATATCGTTTCCTCTGTCTCGCCAGCCATGGGGTCTGTGTAGGAGTCATGGTA
TTTCGTATGGTGGAGGCAAAGACCATTGACAATGTTTCGCTGATCATGCGGTATGCCA
CTCTGGTCACCTATATCATCAACTCGGATACGAAATTCGCAACTGTCTTACAAAGGAG
TGCAATTCAAAGTCTAAACTCAAAACTGGCCGAACTATATCCGAAGACCACGCTGGAC
AGGATCTATACCGGGTGAATGATCACTATTGGACCAAGTCATTTGTATATTTGGTTA
TTATCTACATTGGTTCGTCGATTATGGTTGTTATTGGACCGATTATTACGTCGATTAT
AGCTTACTTCACGCACAACGTTTTCACCTACATGCACTGCTATCCGTACTTTTTGTAT
GATCCTGAGAAGGATCCGGTTTGGATCTACATCAGCATCTATGCTCTGGAATGGTTGC
ACAGCACACAGATGGTCATTTCGAACATTGGCGCGGATATCTGGCTGCTGTACTTTCA
GGTGCAGATAAATCTCCACTTCAGGGGCATTATACGATCACTGGCGGATCACAAGCCC
AGTGTGAAGCACGACCAGGAGGACAGGAAATTCATTGCGAAAATTGTCGACAAGCAGG
TGCACCTGGTCAGTTTGCAAAACGATCTGAATGGTATCTTTGGAAAATCGCTGCTTCT
AAGCCTGCTGACCACCGCAGCGGTTATCTGCACGGTGGCGGTGTACACTCTGATTCAG
GGTCCCACCTTGGAGGGCTTCACCTATGTGATCTTCATCGGGACTTCTGTGATGCAGG
TCTACCTGGTGTGCTATTACGGTCAGCAAGTTCTCGACTTGAGCGGCGAGGTGGCCCA
CGCCGTGTACAATCATGATTTTCACGATGCTTCTATAGCGTACAAGAGGTACCTGCTC
ATAATCATTATCAGGGCGCAGCAGCCCGTGGAACTTAATGCCATGGGCTACCTGTCCA
TTTCGCTGGACACCTTTAAACAGCTGATGAGCGTCTCCTACCGGGTTATAACCATGCT
CATGCAGATGATTCAG

DOR37
(protein sequence is incomplete)
KVDSTRALVNHWRIFRIMGIHPPGKRTFWGRHYTAYSMVWNVTFHICIWVSFSVNLLQ (SEQ ID NO: 110)
SNSLETFCELSCVTMPHTLYMLKLINVRRMRGQMISSHWLLRLLDKRLGCDDERQIIM
AGIERAEFIFRTIFRGLACTVVLGIIYISASSEPTLMYPTWIPWNWRDSTSAYLATAM
LHTTALMANATLVLNLSSYPGTYLILVSVHTKALALRVSKLGYGAPLPAVRMQAILVG
YIHDHQIILR*VSGNLISQCKNF*SISGVLTFIERRMYTHFGVPNIFIVIEDYYILFL
NYSLFKSLERSLSMTCFLQFFSTACAQCTICYFLLFGNVGIMRFMNMLFLLVILTTET
LLLCYTAELPCKEGESLLTAVYSCNWLSQSVNFRRLLLLMLARCQIPMILVSGVIVPI
SMKTF DOR38
MRLIKISYSALNEVCVWLKLNGSWPLTESSRPWRSQSLLATAYIVWAWYVIASVGITI (SEQ ID NO: 72)
SYQTAFLLNNLSDIIITTENCCTTFMGVLNFVRLIHLRLNQRKFRQLIENFSYEIWIP
NSSKNNVAAECRRRMVTFSIMTSLLACLIIMYCVLPLVEIFFGPAFDAQNKPFPYKMI
FPYDAQSSWIRYVMTYIFTSYAGICVVTTLFAEDTILGFFITYTCGQFHLLHQRIAGL
FAGSNAELAESIQLERLKRIVEKHNNIISANSV DOR38nt
ATGCGTTTGATCAAAATTTCATATTCGGCACTTAATGAGGTGTGCGTTTGGCTGAAAC
TGAATGGTTCTTGGCCATTAACCGAATCATCGAGGCCATGGAGGAGCCAATCCTTATT
GGCCACCGCCTACATCGTGTGGGCGTGGTACGTCATTGCATCTGTGGGCATAACAATC -continued

```
AGCTATCAGACGGCCTTTTTGCTGAACAACCTTTCGGACATTATTATCACCACGGAAA
ATTGTTGCACCACCTTTATGGGTGTCCTGAACTTTGTCCGACTCATCCATCTTCGCCT
CAATCAGAGGAAATTCCGCCAGCTTATTGAGAACTTTTCCTACGAAATTTGGATACCT
AATTCTTCCAAAAACAATGTTGCCGCCGAGTGTCGCAGACGCATGGTTACCTTCAGCA
TAATGACATCCTTGCTAGCGTGCCTGATCATAATGTATTGTGTCCTGCCGCTGGTGGA
GATCTTCTTTGGACCCGCCTTCGATGCACAGAACAAGCCGTTTCCCTACAAGATGATC
TTTCCGTACGATGCCCAGAGCAGTTGGATCCGATATGTGATGACCTACATCTTCACCT
CCTACGCGGGAATCTGTGTGGTCACCACCTTGTTTGCAGAGGACACCATTCTTGGCTT
CTTCATAACCTACACTTGTGGCCAATTTCATTTGCTACACCAACGAATCGCAGGTTTA
TTTGCGGGTTCCAATGCGGAATTGGCCGAGAGCATTCAGCTGGAGCGACTCAAACGTA
TTGTGGAAAAACACAACAATATTATCAGCGCAAATTCTGTA
```

DOR44

```
MKSTFKEERIKDDSKRRDLFVFVRQTMCIAAMYPFGYYVNGSGVLAVLVRFCDLTYEL    (SEQ ID NO: 106)
FNYFVSVHIAGLYICTIYINYGQGDLDFFVNCLIQTIIYLWTIAMKLYFRRFRPGLLN
TILSNINDEYETRSAVGFSFVTMAGSYRMSKLWIKTYVYCCYIGTIFWLALPIAYRDR
SLPLACWYPFDYTQPGVYEVVFLLQAMGQIQVAASFASSSGLHMVLCVLISGQYDVLF
CSLKNVLASSYVLMGANMTELNQLQAEQSAADVEPGQYAYSVEEETPLQELLKVGSSM
DFSSAFRLSFVRCIQHHRYIVAALKKIESFYSPIWFVKIGEVTFLMCLVAFVSTKSTA
ANSFMRMVSLGQYLLLVLYELFIICYFADIVFQNSQRCGEALWRSPWQRHLKDVRSDY
MFFMLNSRRQFQLTAGKISNLNVDRFRGVGILT
```

DOR44nt

```
ATGAAGAGCACATTCAAGGAAGAAAGGATTAAGGACGACTCCAAGCGTCGCGACCTGT    (SEQ ID NO: 105)
TTGTATTCGTGAGGCAAACCATGTGTATAGCGGCCATGTATCCCTTCGGTTACTACGT
GAATGGATCTGGAGTCCTGGCCGTTCTGGTGCGATTCTGTGACTTGACCTACGAGCTC
TTTAACTACTTCGTTTCGGTACACATAGCTGGCCTGTACATCTGCACCATCTACATCA
ACTATGGGCAAGGCGATTTGGACTTCTTCGTGAACTGTTTGATACAAACCATTATTTA
TCTGTGGACAATAGCGATGAAACTCTACTTTCGGAGGTTCAGACCTGGTTTGTTGAAT
ACCATTCTGTCCAACATCAATGATGAGTACGAGACACGTTCGGCTGTGGGATTCAGTT
TCGTCACAATGGCGGGATCCTATCGGATGTCCAAGCTATGGATCAAAACCTATGTGTA
TTGCTGCTACATAGGCACCATTTTCTGGCTGGCTCTTCCCATTGCCTACCGGGATAGG
AGTCTTCCTCTTGCCTGCTGGTATCCCTTTGACTATACAACCCGGTGTCTATGAGG
TAGTGTTCCTTCTCCAGGCGATGGGACAGATCCAAGTGGCCGCATCCTTTGCCTCCTC
CAGTGGCCTGCATATGGTGCTTTGTGTGCTGATATCAGGGCAGTACGATGTCCTCTTT
TGCAGTCTCAAGAATGTATTAGCCAGCAGCTATGTCCTTATGGGAGCCAATATGACGG
AACTGAATCAATTGCAGGCTGAGCAATCTGCGGCCGATGTCGAGCCAGGTCAGTATGC
TTACTCCGTGGAGGAGGAGACACCTTTGCAAGAACTTCTAAAAGTTGGGAGCTCAATG
GACTTCTCCTCCGCATTCAGGCTGTCTTTTGTGCGGTGCATTCAGCACCATCGATACA
TAGTGGCGGCACTGAAGAAAATTGAGAGTTTCTACAGTCCCATATGGTTCGTGAAGAT
TGGCGAAGTCACCTTTCTTATGTGCCTGGTAGCCTTCGTCTCCACGAAGAGCACCGCG
GCCAACTCATTCATGCGAATGGTCTCCTTGGGCCAGTACCTGCTCTTAGTTCTCTACG
AGCTGTTCATCATCTGCTACTTCGCGGACATCGTTTTTCAGAACAGCCAGCGGTGCGG
TGAAGCCCTCTGGCGAAGTCCTTGGCAGCGACATTTGAAGGATGTTCGCAGTGATTAC
ATGTTCTTTATGCTGAATTCCCGCAGGCAGTTCCAACTTACGGCCGGAAAAATAAGCA
ATCTAAACGTGGATCGTTTCAGAGGGGTGGGTATCCTTACT
```

DOR46

```
MAEVRVDSLEFFKSHWTAWRYLGVAHFRVENWKNLYVFYSIVSNLLVTLCYPVHLGIS    (SEQ ID NO: 20)
LFRNRTITEDILNLTTFATCTACSVKCLLYAYNIKDVLEMERLLRLLDERVVGPEQRS
IYGQVRVQLRNVLYVFIGIYMPCALFAELSFLFKEERGLMYPAWFPFDWLHSTRNYYI
ANAYQIVGISFQLLQNYVSDCFPAVVLCLISSHIKMLYNRFEEVGLDPARDAEKDLEA
CITDHKHILELFRRIEAFISLPMLIQFTVTALNVCIGLAALVFFVSEPMARMYFIFYS
LAMPLQIFPSCFFGTDNEYWFGRLHYAAFSCNWHTQNRSFKRKMMLFVEQSLKKSTAV
AGGMMRIHLDTFFSTLKGAYSLFTIIIRMRK
```

DOR46nt

```
ATGGCAGAGGTCAGAGTGGACAGTCTGGAGTTTTTCAAGAGCCATTGGACCGCCTGGC    (SEQ ID NO: 19)
GGTACTTGGGAGTGGCTCATTTTCGGGTCGAGAACTGGAAGAACCTTTACGTGTTTTA
CAGCATTGTGTCGAATCTTCTCGTGACCCTGTGCTACCCCGTTCACCTGGGAATATCC
CTCTTTCGCAACCGCACCATCACCGAGGACATCCTCAACCTGACCACCTTTGCGACCT
GCACAGCCTGTTCGGTGAAGTGCCTGCTCTACGCCTACAACATCAAGGATGTGCTGGA
GATGGAGCGGCTGTTGAGGCTTTTGGATGAACGCGTCGTGGGTCCGGAGCAACGCAGC
ATCTACGGACAAGTGAGGGTCCAGCTGCGAAATGTGTATATCGTGTTCATCGGCATCT
ACATGCCGTGTGCCCTGTTCGCCGAGCTATCCTTTCTGTTCAAGGAGGAGCGCGGTCT
GATGTATCCCGCCTGGTTTCCCTTCGACTGGCTGCACTCCACCAGGAACTATTACATA
GCGAACGCCTATCAGATAGTGGGCATCTCGTTTCAGCTGCTGCAAAACTATGTTAGCG
ACTGCTTTCCGGCGGTGGTGCTGTGCCTGATCTCATCCCACATCAAAATGTTGTACAA
CAGATTCGAGGAGGTGGGCCTGGATCCAGCCAGAGATGCGGAGAAGAACCTGGAGGCC
TGCATCACCGATCACAAGCATATTCTAGAGTGGCAGGCGGCTCATTGGTTCGTGTTC
TATTCACTTTCCAACTTTTTTCCAGACTATTCCGACGCATCGAGGCCTTCATTTCCCT
GCCCATGCTAATTCAGTTCACAGTGACCGCCTTGAATGTGTGCATCGGTTTAGCAGCC
CTGGTGTTTTTCGTCAGCGAGCCCATGGCACGGATGTACTTCATCTTCTACTCCCTGG
CCATGCCGCTGCAGATCTTTCCGTCCTGCTTTTTCGGCACCGACAACGAGTACTGGTT
CGGACGCCTCCACTACGCGGCCTTCAGTTGCAATTGGCACACACAGAACAGGAGCTTT
AAGCGGAAAATGATGCTGTTCGTTGAGCAATCGTTGAAGAAGAGCACCGCTGTGGCTG
GCGGAATGATGCGTATCCACCTGGACACGTTCTTTTCCACCCTAAAGGGGGCCTACTC
CCTCTTTACCATCATTATTCGGATGAGAAAG
```

-continued

DOR48
MERHYFMVPKFALSLIGFYPEQKRTVLVKLWSFFNFFILTYGCYAEAYYGIHYIPINI  (SEQ ID NO: 26)
ATALDALCPVASSILSLVKMVAIWWYQDELRSLIERRFYTLATQLTFLLLCCGFCTST
SYSVRHLIDNILRRTHGKDWIEYTPFKMMFPDLLLRLPLYPITYILVHWHGYITVVCF
VGADGFFLGFCLYFTVLLLCLQDDVCDLLEVENIEKSPSEAEEARIVREMEKLVDRHN
EVAELTERLSGVMVEITLAHFVTSSLIIGTSVVDILLFSGLGIIVYVVYTCAVGVEIF
LYCLGGSHIMEACSNLARSTFSSHWYGHSVRVQKMTLLMVARAQRVLTIKIPFFSPSL
ETLTSILRFTGSLIALAKSVI

DOR48nt
ATGGAGCGCCATTATTTCATGGTGCCAAAGTTTGCATTATCGCTGATTGGTTTTTATC  (SEQ ID NO: 25)
CCGAACAGAAGCGAACGGTTTTGGTGAAACTTTGGAGTTTCTTCAACTTTTTCATCCT
CACCTACGGCTGTTATGCAGAGGCTTACTATGGCATACACTATATACCGATTAACATA
GCCACTGCATTGGATGCCCTTTGTCCTGTGGCCTCCAGCATTTTGTCGCTGGTGAAAA
TGGTCGCCATTTGGTGGTATCAAGATGAATTAAGGAGTTTGATAGAGCGGGTAAGATT
TTTAACAGAGCAACAGAAGTCCAAGAGGAAACTGGGCTATAAGAAGAGGTTCTATACA
CTGGCAACGCAACTAACATTCCTGCTACTATGCTGTGGATTTTGCACCAGTACTTCCT
ATTCCGTCAGACATTTGATTGATAATATCCTGAGACGCACCCATGGCAAGGACTGGAT
CTACGAGACTCCGTTCAAGATGATGTAAGGAAAGGGAAGAATGGTTTATATATACTTT
TGGAACGAAATAATGATGTGATCTAAACAAGATGCACTTTTTTTAGGTTCCCCGATC
TTCTCCTGCGTTTGCCACTCTATCCCATCACCTATATACTCGTGCATTGGCATGGCTA
CATTACTGTGGTTTGTTTTGTCGGCGCGGATGGTTTCTTCCTGGGGTTCTGTTTGTAC
TTCACTGTTTTGCTGCTCTGTCTGCAGGACGATGTTTGTGATTTACTAGAGGTTGAAA
ACATCGAGAAGAGTCCCTCCGAAGCGGAGGAAGCTCGCATAGTTCGGGAAATGGAAAA
ACTGGTGGACCGGCATAACGAGGTGGCCGAGCTGACAGAAAGATTGTCGGGTGTTATG
GTGGAAATAACACTGGCCCACTTTGTTACTTCGAGTTTGATAATCGGAACCAGCGTGG
TGGATATTTTATTAGTGGGTATTTACATTTGATTAGATCCTTTCGATATATGTTCTTA
AATTCTAGTTTTCCGGCCTGGGAATCATTGTGTATGTGGTCTACACTTGTGCCGTAGG
TGTGGAAATATTTCTATACTGTTTAGGAGGATCTCATATTATGGAAGCGGTATATTCA
TAAGAAACTACTATAAAGTTACTTTTAAATTCATTGCATTTCTTAGTGTTCCAATCTA
GCGCGCTCCACATTTTCCAGCCACTGGTATGGCCACAGTGTTCGGGTCCAAAAGATGA
CCCTTTTGATGGTAGCTCGTGCTCAACGAGTTCTCACAATTAAAATTCCTTTCTTTTC
CCCATCATTAGAGACTCTAACTTCGGTAAGCTTATGCGAAAATGTTATGGTACACACA
AGTCTACATTTCTATGAGGTCTTGTAGATTTTGCGCTTCACTGGATCTCTGATTGCCC
TGCCAAAGTCGGTTATA

DOR53
MLSKFFPHIKEKPLSERVKSRDAFIYLDRVMWSFGWTEPENKRWILPYKLWLAFVNIV  (SEQ ID NO: 8)
MLILLPISISIEYLHRFKTFSAGEFLSSLEIGVNMYGSSFKCAFTLIGFKKRQEAKVL
LDQLDKRCLSDKERSTVHRYVAMGNFFDILYHIFYSTFVVMNFPYFLLERRHAWRMYF
PYIDSDEQFYISSIAECFLMTEAIYMDLCTDVCPLISMLARCHISLLKQRLRNLRSK
PGRTEDEYLEELTECIRDHRLLLDYVDALRPVFSGTIFVQFLLIGTVLGLSMINLMFF
STFWTGVATCLFMFDVSMETFPFCYLCNMIIDDCQEMSNCLFQSDWTSADRRYKSTLV
YFLHNLQQPITLTAGGVFPISMQTNLAMVKLAFSVVTVIKQFNLAERFQ

DOR53nt
TCAAACAAAGCCACGGACAAGATGTTAAGCAAGTTTTTTCCCCACATAAAAGAAAAGC  (SEQ ID NO: 7)
CATTGAGCGAGCGGGTAAGTCCCGAGATGCCTTCATTTACTTGGATCGGGTGATGTG
GTCCTTTGGCTGGACAGAGCCTGAAAACAAAAGGTGGATCCTTCCTTATAAACTGTGG
TTAGCGTTCGTGAACATAGTAATGCTCATCCTTCTGCCGATCTCGATAAGCATCGAGT
ACCTCCACCGATTTAAAACCTTCTCGGCGGGGAGTTCCTTAGTTCCCTCGAGATTGG
AGTCAACATGTACGGAAGCTCTTTTAAGTGCGCCTTCACCTTGATTGGATTCAAGAAA
AGACAGGAAGCTAAGGTTTTACTGGATCAGCTGGACAAGAGATGCCTTAGCGATAAGG
AGAGGTCCACTGTTCATCGCTATGTCGCCATGGGAAACTTTTTCGATATTTTGTATCA
CATTTTTTACTCCACCTTCGTGGTAATGAACTTCCCGTATTTTCTGCTTGAGAGACGC
CATGCTTGGCGCATGTACTTTCCATATATCGATTCCGACGAACAGTTTTACATCTCCA
GCATCGCCGAGTGTTTTCTGATGACGGAGGCCATCTACATGGATCTCTGTACGGAGT
GTGTCCCTTGATCTCCATGCTTATGGCTCGATGCCACATCAGCCTCCTGAAACAGCGA
CTGAGAAATCTCCGATCGAAGCCAGGAAGGACCGAAGATGAGTACTTGGAGGAGCTCA
CCGAGTGCATTCGGGATCATCGATTGCTATTGGACTATGTTGACGCATTGCGACCCGT
CTTTTCGGGAACCATTTTTGTGCAGTTCCTCCTGATCGGTACTGTACTGGGTCTCTCA
ATGATAAATCTAATGTTCTTCTCGACATTTTGGACTGGTGTCGCCACTTGCCTTTTA
TGTTCGACGTGTCCATGGAGACGTTCCCCTTTTGCTATTTGTGCAACATGATTATCGA
TGACTGCCAGGAAATGTCCAATTGCCTCTTTCAATCGGACTGGACCTCTGCCGATCGT
CGCTACAAATCCACTTTGGTATACTTTCTTCACAATCTTCAGCAACCCATTACTCTCA
CGGCTGGTGGAGTGTTTCCTATTTCCATGCAAACAAATTTGGCTATGGTGAAGCTGGC
ATTTTCTGTGGTTACGGTAATTAAGCAATTTAACTTGGCCGAAAGGTTTCAATAAGTT
GAGAGGGACGAGCTCTGCTACTATTATATTATATATTATATTATATTATATATATATT
ATTTTATATTATATATTGCTGTACCCTAATAAATATTTAGTAATAAAAAAAAAAAAAA
AAAA

DOR56
MDPVEMPIFGSTLKLMKFWSYLFVHNWRRYVAMTPYIINCTQYVDIYLSTESLDFII  (SEQ ID NO: 76)
RNVYLAVLFTNTVVRGFLLCVQRFSYERFINILKSFYIELLVSTERLSQKCILHKWAV
LPYGMYLPTIDEYKYASPYYEIFFVIQAIMAPMGCCMYIPYTNMVVTFTLFAILMCRV
LQHKLRSLEKLKNEQVRGEIAQTIAQTVIVIAYMVMIFANSVVLYYVANELYFQSFDI
AIAAYESNWMDFDVDTQKTLKFLIMRSQKPLASLVGGTYPMNLKMLQSLLNAIYSFFT
LLRRVYG

-continued

DOR56nt
ATGGATCCGGTGGAGATGCCCATTTTTGGTAGCACTCTGAAGCTAATGAAGTTCTGGT (SEQ ID NO: 75)
CATATCTGTTTGTTCACAACTGGCGCCGCTATGTCGCAATGACTCCGTACATCATTAT
CAACTGTACTCAGTATGTGGATATATATCTGAGCACCGAATCCTTGGACTTTATCATC
AGAAATGTATACCTGGCTGTATTGTTTACCAACACGGTGGTCAGAGGTGTATTGTTAT
GCGTACAGCGGTTTAGCTACGAGCGTTTCATTAATATTTTGAAAAGCTTTTACATTGA
GTTGTTGGTGAGTACCGAAAGATTATCTCAAAAATGCATATTGCATAAATGGGCAGTT
CTGCCATATGGCATGTATTTGCCCACTATTGATGAATACAAATACGCATCACCTTACT
ACGAGATTTTCTTTGTGATTCAAGCCATTATGGCTCCAATGGGGTGTTGCATGTACAT
ACCATACACAAACATGGTAGTGACATTTACCCTTTTCGCCATTCTCATGTGTCGAGTG
TTGCAACATAAGTTGAGAAGCCTAGAAAAGCTGAAAAATGAACAAGTACGTGGTGAAA
TCGCTCAAACAATTGCTCAGACCGTCATAGTCATCGCATACATGGTAATGATATTTGC
CAACAGTGTAGTCCTTTACTACGTGGCCAATGAGCTATACTTTCAAAGCTTTGATATT
GCCATTGCTGCCTATGAGAGCAATTGGATGGACTTTGATGTGGACACACAAAAGACTT
TGAAGTTCCTCATCATGCGCTCGCAAAAGCCCTTGGCGAGTCTGGTGGGTGGCACATA
TCCCATGAACTTGAAAATGCTTCAGTCACTACTAAATGCCATTTACTCCTTCTTCACC
CTTCTGCGTCGCGTTTACGGC

DOR58
MDASYFAVQRRALEIVGFDPSTPQLSLKHPIWAGILILSLISHNWPMVVYALQDLSDL (SEQ ID NO: 78)
TRLTDNFAVFMQGSQSTFKFLVMMAKRRRIGSLIHRLHKLNQAASATPNHLEKIEREN
QLDRYVARSFRNAAYGVICASAIAPMLLGLWGYVETFVFTPTTPMEFNFWLDERKPHF
YWPIYVWGVLGVAAAAWLAIATDTLFSWLTHNVVIQFQLLELVLEEKDLNGGDSRLTG
FVSRHRIALDLAKELSSIFGEIVFVKYMLSYLQLCMLAFRFSRSGWSAQVPFRATFLV
AIIIQLSSYCYGGEYIKQQSLAIAQAVYGQINWPEMTPKKRRLWQMVIMRAQRPAKIF
GFMFVVDLPLLLWVIRTAGSFLAMLRTFER

DOR58nt
ATGGACGCCAGCTACTTTGCCGTCCAGAGAAGAGCTCTGGAAATAGTTGGATTCGATC (SEQ ID NO: 77)
CCAGTACTCCGCAACTGAGTCTGAAACATCCCATCTGGGCCGGGATTCTCATCCTGTC
CTTGATCTCTCACAACTGGCCCATGGTAGTCTATGCCCTGCAGGATCTCTCCGACTTG
ACCCGTCTGACGGACAACTTTGCGGTGTTTATGCAAGGATCACAGAGCACCTTCAAGT
TCCTGGTCATGATGGCGAAACGAAGGCGCATTGGATCGTTGATTCACCGTTTGCATAA
GCTAAACCAGGCGGCCAGTGCCACGCCCAATCACCTGGAGAAGATCGAGAGGGAAAAC
CAACTGGATAGGTATGTCGCCAGGTCCTTTAGAAATGCCGCCTACGGAGTGATTTGTG
CCTCGGCCATAGCGCCCATGTTGCTTGGCCTGTGGGGATATGTGGAGACGGGTGTATT
TACCCCCCACCACACCCATGGAGTTCAACTTCTGGCTGGACGAGCGAAAGCCTCACTTT
TATTGGCCCATCTACGTTTGGGGCGTACTGGGCGTGGCAGCTGCCGCCTGGTTGGCCA
TTGCAACGGACACCCTGTTCTCCTGGCTGACTCACAATGTGGTGATTCAGTTCCAACT
ACTGGAGCTTGTTCTCGAAGAGAAGGATCTGAATGGCGGAGACTCTCGCCTGACCGGG
TTTGTTAGTCGTCATCGTATAGCTCTGGATTTGGCCAAGGAACTAAGTTCGATTTTCG
GGGAGATCGTCTTTGTGAAATACATGCTCAGTTACCTGCAACTCTGCATGTTGGCCTT
TCGCTTCAGCCGCAGTGGCTGGAGTGCCCAGGTGCCATTTAGAGCCACCTTCCTAGTG
GCCATCATCATCCAACTGAGTTCGTATTGCTATGGAGGCGAGTATATAAAGCAGCAAA
GTTTGGCCATCGCACAAGCCGTTTATGGTCAAATCAATTGGCCAGAAATGACGCCAAA
GAAAAGAAGACTCTGGCAAATGGTGATCATGAGGGCGCAGCGACCGGCTAAGATTTTT
GGATTCATGTTCGTTGTGGACTTGCCACTGCTGCTTTGGGTCATCAGAACTGCGGGCT
CATTTCTGGCCATGCTTAGGACTTTCGAGCGT

DOR59
MHEADNREMELLVATQAYTRTITLLIWIPSVIAGLMAYSDCIYRSLFLPKSVFNVPAV (SEQ ID NO: 80)
RRGEEHPILLFQLFPFGELCDNFVVGYLGPWYALGLGITAIPLWHTFITCLMKYVNLK
LQILNKRVEEMDITRLNSKLVIGRLTASELTFWQMQLFKEFVKEQLRIRKFVQELQYL
ICVPVMADFIIFSVLICFLFFALTVGHDELSLAYFSCGWYNFEMPLQKMLVFMMMHAQ
RPMKMRALLVDLNLRTFIDIGRGAYSYFNLLRSSHLY

DOR59nt
ATGCACGAAGCAGATAATCGGGAGATGGAACTTTTGGTCGCCACTCAGGCTTATACAC (SEQ ID NO: 79)
GAACCATTACCCTGTTGATCTGGATACCATCGGTTATTGCTGGCCTAATGGCCTATTC
AGACTGCATCTACAGGAGTCTGTTTCTGCCGAAATCGGTTTTCAATGTGCCAGCTGTG
CGACGTGGTGAGGAGCATCCCATTCTGCTATTTCAGCTGTTTCCCTTCGGAGAACTTT
GCGATAACTTCGTTGTTGGATACTTGGGACCTTGGTATGCTCTGGGCCTGGGAATCAC
GGCTATCCCATTGTGGCACACCTTTATCACTTGCCTCATGAAGTACGTAAATCTCAAG
CTGCAAATACTCAACAAGCGAGTGGAGGAGATGGATATTACCCGACTTAATTCCAAAT
TGGTAATTGGTCGCCTAACTGCCAGTGAGTTAACCTTCTGGCAAATGCAACTCTTCAA
GGAATTTGTAAAGGAACAGCTGAGGATTCGAAAATTTGTCCAGGAACTACAGTATCTG
ATTTGCGTGCCTGTGATGGCAGATTTCATTATCTTCTCGGTTCTCATTTGCTTTCTCT
TTTTTGCCTTGACAGTTGGCCACGATGAACTGAGCCTTGCTTACTTTTCTTGCGGATG
GTACAACTTCGAAATGCCTTTGCAGAAAATGCTGGTTTTTATGATGATGCATGCCCAA
AGGCCGATGAAGATGCGCGCCCTGCTGGTCGATTTGAATCTGAGGACCTTCATAGACA
TTGGCCGTGGAGCCTACAGCTACTTCAATTTGCTGCGTAGCTCCCACTTGTAT

DOR61
MGHKDDMDSTDSTALSLKHISSLIFVISAQYPLISYVAYNRNDMEKVTACLSVVFTNM (SEQ ID NO: 108)
LTVIKISTFLANRKDFWEMIHRFRKMHEQCKYREGLDYVAEANKLASFLGRAYCVSCG
LTGLYFMLGPIVKIGVCRWHGTTCDKELPMPMKFPFNDLESPGYEVCFLYTVLVTVVV
VAYASAVDGLFISFAINLRAHFQTLQRQIENWEFPSSEPDTQIRLKSIVEYHVLLLSL
SRKLRSIYTPTVMGQFVITSLQVGVIIYQLVTNMDSVMDLLLYASFFGSIMLQLFIYC
YGGEIIKAESLQVDTAVRLSNWHLASPKTRTSLSLIILQSQKEVLIRAFGGVASLANF
PYRLITLIKSIDSIC

-continued

DOR62
MEKQEDFKLNTHSAVYYHWRVWELTGLMRPPGVSSLLYVVYSITVNLVVTVLFPLSLL  (SEQ ID NO: 2)
ARLLFTTNMAGLCENLTITITDIVANLKFANVYMVRKQLHEIRSLLRLMDARARLVGD
PEEISALRKEVNIAQGTFRTFASIFVFGTTLSCVRVVVRPDRELLYPAWFGVDWMHST
RNYVLINIYQLFGLIVQAIQNCASDSYPPAFLCLLTGHMRALELRVRRIGCRTEKSNK
GQTYEAWREEVYQELIECIRDLARVHRLREIIQRVLSVPCMAQFVCSAAVQCTVAMHG
LYVADDHDHTAMIISIVFFSAVTLEVFVICYFGDRMRTQSEALCDAFYDCNWIEQLPK
FKRELLFTLARTQRPSLIYAGNYIALSLETFEQVMRFTYSVFTLLLRAK

DOR62nt
ATGGAGAAGCAAGAGGATTTCAAACTGAACACCCACAGTGCTGTGTACTACCACTGGC  (SEQ ID NO: 1)
GCGTTTGGGAGCTCACTGGCCTGATGCGTCCTCCGGGCGTTTCAAGCCTGCTTTACGT
GGTATACTCCATTACGGTCAACTTGGTGGTCACCGTGCTGTTTCCCTTGAGCTTGCTG
GCCAGGCTGCTGTTCACCACCAACATGGCCGGATTGTGCGAGAACCTGACCATAACTA
TTACCGATATTGTGGCCAATTTGAAGTTTGCGAATGTGTACATGGTGAGGAAGCAGCT
CCATGAGATTCGCTCTCTCCTAAGGCTCATGGACGCTAGAGCCCGGCTGGTGGGCGAT
CCCGAGGAGATTTCTGCCTTGAGGAAGGAAGTGAATATCGCACAGGGCACTTTCCGCA
CCTTTGCCAGTATTTTCGTATTTGGCACTACTTTGAGTTGCGTCCGCGTGGTCGTTCG
CCCGGATCGAGAGCTCCTGTATCCGGCCTGGTTCGGCGTTGACTGGATGCACTCCACC
AGAAACTATGTGCTCATCAATATCTACCAGCTCTTCGGCTTGATAGTGCAGGCTATAC
AGAACTGCGCTAGTGACTCCTATCCGCCTGCGTTTCTCTGCCTGCTCACGGGTCATAT
GCGTGCTTTGGAGCTGAGGGTGCGGCGGATTGGCTGCAGGACGGAAAAGTCCAATAAA
GGGCAGACATATGAAGCCTGGCGGGAGGAGGTGTACCAGGAACTCATCGAGTGCATCC
GCGATCTGGCGCGGGTCCATCGGCTGAGGGAGATCATTCAGCGGGTCCTTTCAGTGCC
CTGCATGGCCCAGTTCGTCTGCTCCGCGCCGTCCAGTGTACCGTCGCCATGCACTTC
CTGTACGTAGCGGATGACCACGACCACACCGCCATGATCATCTCGATTGTATTTTTCT
CGGCCGTCACCTTGGAGGTGTTTGTAATCTGCTATTTTGGGGACAGGATGCGGACACA
GAGCGAGGCGCTGTGCGATGCCTTCTACGATTGCAACTGGATAGAACAGCTGCCCAAG
TTCAAGCGCGAACTGCTCTTCACCCTGGCCAGGACGCAGCGGCCTTCTCTTATTTACG
CAGGCAACTACATCGCACTCTCGCTGGAGACCTTCGAGCAGGTCATGAGGTTCACATA
CTCTGTTTTCACACTCTTGCTGAGGGCCAAGTAAGAACTTTATAATCTCTTTTTGGGG
AGAAAAATTTTAAAGCACAATAGCAGAAAAATATATCAGATAATATAACAAAAAAAAA
AAAAAAAAA

DOR64
MKLESTLKIDYFRVQLNAWRICGALDLSEGRYWSWSMLLCILVYLPTPMLLRGVYSFE  (SEQ ID NO: 12)
DVPENNFSLSLTVTSLSNLMKFCMYVAQLTKMVEVQSLIGQLDARVSGESQSERHRNM
TEHLLRMSKLFQITYAVVFIIAAVPFVFETELSLPMPMWFPFDWKNSMVAYIGALVFQ
EIGYVFQIMQCFAADSFPPLVLYLISEQCQLLILRISEIGYGYKTLEENEQDLVNCIR
DQNALYRLLDVTKSLVSYPMMVQFMVIGINIAITLFVLIFYVETLYDRIYYLCFLLGI
TVQTYPLCYYGTMVQESFAELHYAVFCSNWVDQSASYRGHMLILAERTKRMQLLLAGN
LVPIHLSTYVACWKGAYSFFTLMADRDGLGS

DOR64nt
GGCACGAGCCAAGAATTCAAAATGAAACTCAGCGAAACCCTAAAAATCGACTATTTTC  (SEQ ID NO: 11)
GAGTCCAGTTGAATGCCTGGCGAATTTGTGGTGCCTTGGATCTCAGCGAGGGTAGGTA
CTGGAGTTGGTCGATGCTATTGTGCATCTTGGTGTACCTGCCGACACCCATGCTACTG
AGAGGAGTATACAGTTTCGAGGATCCGGTGGAAAATAATTTCGACTTGAGCCTGACGG
TCACATCGCTGTCCAATCTCATGAAGTTCTGCATGTACGTGGCCCAACTAACAAAGAT
GGTCGAGGTCCAGAGTCTTATTGGTCAGCTGGATGCCCGGGTTTCTGGCGAGAGCCAG
TCTGAGCGTCATAGAAATATGACCGAGCACCTGCTAAGGATGTCCAAGCTGTTCCAGA
TCACCTACGCTGTAGTCTTCATCATTGCTGCAGTTCCCTTCGTTTTCGAAACTGAGCT
AAGCTTACCCATGCCCATGTGGTTTCCCTTCGACTGGAAGAACTCGATGGTGGCCTAC
ATCGGAGCTCTGGTTTTCCAGGAGATTGGCTATGTCTTTCAAATTATGCAATGCTTTG
CAGCTGACTCGTTTCCCCCGCTCGTACTGTACCTGATCTCCGAGCAATGTCAATTGCT
GATCCTGAGAATCTCTGAAATCGGATATGGTTACAAGACTCTGGAGGAGAACGAACAG
GATCTGGTCAACTGCATCAGGGATCAAAACGCGCTGTATAGATTACTCGATGTGACCA
AGAGTCTCGTTTCGTATCCCATGATGGTGCAGTTTATGGTTATTGGCATCAACATCGC
CATCACCCTATTTGTCCTGATATTTTACGTGGAGACCTTGTACGATCGCATCTATTAT
CTTTGCTTTCTCTTGGGCATCACCGTGCAGACATATCCATTGTGCTACTATGGAACCA
TGGTGCAGGAGAGTTTTGCTGAGCTTCACTATGCGGTATTCTGCAGCAACTGGGTGGA
TCAAAGTGCCAGCTATCGTGGGCACATGCTCATCCTGGCGGAGCGCACTAAGCGGATG
CAGCTTCTCCTCGCCGGCAACCTGGTGCCCATCCACCTGAGCACCTACGTGGCCTGTT
GGAAGGGAGCCTACTCCTTCTTCACCCTGATGGCCGATCGAGATGGCCTGGGTTCTTA
GTAGCCCAGTCATTTCACTCACATTCTACATCAAGTAGTACTACCACTGAACACGAAC
ACGAATATTTCAAAAGTAAACACATAATATTCACAATAGTGTATCACTTTAATAAAAT
TTTTGGTTACCATGAAAAAAAAAAAAAAAAAA

DOR67
MLSQFFPHIKEKPLSERVKSRDAFVYLDRVMWSFGWTVPENKRWDLHYKLWSTFVTLV  (SEQ ID NO: 10)
IFILLLPISVSVEYIQRFKTFSAGEFLSSIQIGVNMYGSSFKSYLTMMGYKKRQEAKMS
LDELDKRCVCDEERTIVHRHVALGNFCYIFYHIAYTSFLISNFLSFIMKRIHAWRMYF
PYVDPEKQFYISSIAEVILRGWAVFMDLCTDVCPLISMVIARCHITLLKQRLRNLRSE
PGRTEDEYLKELADCVRDHRLILDYVDALRSVFSGTIFVQFLLIGIVLGLSMINIMFF
STLSTGVAVVLFMSCVSMQTFPFCYLCNMIMDDCQEMADSLFQSDWTSADRRYKSTLV
YFLHNLQQPIILTAGGVFPISMQTNLNMVKLAFTVVTIVKQFNLAEKFQ

-continued

DOR67nt
GGCACGAGGAAATGTTAAGCCAGTTCTTTCCCCACATTAAAGAAAAGCCATTGAGCGA (SEQ ID NO: 9)
GCGGGTTAAGTCCCGAGATGCCTTCGTTTACTTAGATCGGGTGATGTGGTCCTTTGGC
TGGACAGTGCCTGAAAACAAAAGGTGGGATCTACATTACAAACTGTGGTCAACTTTCG
TGACATTGGTGATATTTATCCTTCTGCCGATATCGGTAAGCGTTGAGTATATTCAGCG
GTTCAAGACCTTCTCGGCGGGTGAGTTTCTTAGCTCAATCCAGATTGGCGTTAACATG
TACGGAAGCAGCTTTAAAAGTTATTTGACCATGATGGGATATAAGAAGAGACAGGAGG
CTAAGATGTCACTGGATGAGCTGGACAAGAGATGCGTTTGTGATGAGGAGAGGACCAT
TGTACATCGACATGTCGCCCTGGGAAACTTTTGCTATATTTTCTATCACATTGCGTAC
ACTAGCTTTTTGATTTCAAACTTTTTGTCATTTATAATGAAGAGAATCCATGCCTGGC
GCATGTACTTTCCCTACGTCGACCCCGAAAAGCAATTTTACATCTCTAGCATCGCCGA
AGTCATTCTTAGGGGGTGGGCCGTCTTCATGGATCTCTGCACGGATGTGTGTCCTTTG
ATCTCCATGGTAATAGCACGATGCCACATCACCCTTCTGAAACAGCGCCTGCGAAATC
TACGATCGGAACCAGGAAGGACGGAAGATGAGTACTTGAAGGAGCTCGCCGACTGCGT
TCGAGATCACCGCTTGATATTGGACTATGTCGACGCATTGCGATCCGTCTTTTCGGGG
ACAATTTTTGTGCAGTTCCTCTTGATCGGTATTGTACTGGGTCTGTCAATGATAAATA
TAATGTTTTTCTCAACACTTTCGACTGGTGTCGCCGTTGTCCTTTTTATGTCCTGCGT
ATCTATGCAGACGTTCCCCTTTTGCTATTTGTGTAACATGATTATGGATGACTGCCAA
GAGATGGCCGACTCCCTTTTTCAATCGGACTGGACATCTGCCGATCGTCGCTACAAAT
CCACTTTGGTATACTTTCTTCACAATCTTCAGCAGCCCATTATTCTTACGGCTGGTGG
AGTCTTTCCTATTTCCATGCAAACAAATTTAAATATGGTGAAGCTTGCCTTTTACTGTG
GTTACAATAGTGAAACAATTTAACTTGGCAGAAAAGTTTCAATAAGTTAAGATATGCA
AGCTCTGCTATTATAAACCTACACTCGAGAAAATATTTCTTCACATTAATAAACCTTC
AGTACTTACTGCTTGTGGCGCCCCCGGAAAAAAAAAAAAAAAAAAAA

DOR68
MSKLIEVFLGNLWTQRFTFARMGLDLQPDKKGNVLRSPLLYCIMCLTTSFELCTVCAF (SEQ ID NO: 82)
MVQNRNQIVLCSEALMHGLQMVSSLLKMAIFLAKSHDLVDLIQQIQSPFTEEDLVGTE
WRSQNQRGQLMAAIYFMMCAGTSVSFLLMPVALTMLKYHSTGEFAPVSSFRVLLPYDV
TQPHVYAMDCCLMVFVLSFFCCSTTGVDTLYGWCALGVSLQYRRLGQQLKRIPSCFNP
SRSDFGLSGIFVEHARLLKIVQHFNYSFMEIAFVEVVIICGLYCSVICQYIMPHTNQN
FAFLGFFSLVVTTQLCIYLFGAEQVRLEAERFSRLLYEVIPWQNLPPKHRKLFLFPIE
RAQRETVLGAYFFELGRPLLVWVSIFLFIVLLF

DOR68nt
ATGTCAAAGCTAATCGAGGTGTTTCTGGGTAATCTGTGGACCCAGCGTTTTACCTTCG (SEQ ID NO: 81)
CCCGAATGGGTTTGGATTTGCAGCCCGATAAAAAGGGCAATGTTTTGCGATCTCCGCT
TCTTTATTGTATTATGTGTCTGACAACAAGCTTTGAGCTCTGCACCGTGTGCGCCTTT
ATGGTCCAAAATCGCAACCAAATCGTGCTTTGTTCCGAGGCCCTGATGCACGGACTAC
AGATGGTCTCCTCGCTACTGAAGATGGCTATATTCTTGGCCAAATCTCACGACCTGGT
GGACCTAATTCAACAGATTCAGTCGCCTTTTACAGAGGAGGATCTTGTAGGTACAGAG
TGGAGATCCCAAAATCAAAGGGGACAACTAATGGCTGCCATTTACTTTATGATGTGTG
CCGGTACGAGTGTGTCATTTCTGTTGATGCCAGTGGCTTTGACCATGCTTAAGTACCA
TTCCACTGGGGAATTCGCGCCTGTCAGCTCGTTCCGGGTTCTGCTTCCATACGATGTG
ACACAACCGCATGTTTATGCCATGGACTGCTGCTTGATGGTATTTGTGTTAAGTTTTT
TTTGCTGCTCCACCACCGGAGTGGATACCTTATATGGATGGTGTGCTTTAGGCGTGAG
TTTACAATACCGTCGCCTCGGTCAACAACTTAAAAGGATACCCTCCTGTTTCAATCCA
TCTCGGTCTGACTTTGGATTAAGTGGGATTTTTGTGGAGCATGCTCGTCTGCTTAAAA
TAGTCCAACATTTTAATTATAGTTTTATGGAGATCGCATTTGTGGAGGTTGTTATAAT
CTGTGGACTCTATTGCTCAGTAATTTGTCAGTATATAATGCCACACACCAACCAAAAC
TTCGCCTTTCTGGGTTTCTTTTCATTGGTAGTTACCACACAGCTGTGCATCTATCTTT
TCGGTGCCGAACAGGTCCGTTTGGAGGCTGAGCGATTTTCCCGGCTGCTATACGAAGT
AATTCCTTGGCAAAACCTTCCTCCTAAACACCGGAAACTTTTCCTTTTTCCAATTGAG
CGCGCCCAACGAGAAACTGTTCTCGGTGCTTATTTCTTCGAACTAGGCAGACCTCTTC
TTGTTTGGGTAAGCATATTCCTTTTTATTGTATTATTATTT

DOR71g
MVIIDSLSFYRPFWICMRLLVPTFFKDSSRPVQLYVVLLHILVTLWFPLHLLLHLLLL (SEQ ID NO: 14)
PSTAEFFKNLTMSLTCVACSLKHVAHLYHLPQIVEIESLIEQLDTFIASEQEHRYYRD
HVHCHARRFTRCLYISFGMIYALFLFGVFVQVISGNWELLYPAYFPFDLESNRFLGAV
ALGYQVFSMLVEGFQGLGNDTYTPLTLCLLAGHVHLWSIRMGQLGYFDDETVVNHQRL
LDYIEQHKLLVRFHNLVSRTISEVQLVQLGGCGATLCIIVSYMLFFVGDTISLVYYLV
FFGVVCVQLFPSCYFASEVAEELERLPYAIFSSRWYDQSRDHRFDLLIFTQLTLGNRG
WIIKAGGLIELNLNAFFATLKMAYSLFAVVHRETGNPLQREH

DOR71gnt
ATGGTCATTATCGACAGTCTTAGTTTTTATCGTCCATTCTGGATCTGCATGCGATTGC (SEQ ID NO: 13)
TGGTACCGACTTTCTTCAAGGATTCCTCACGTCCTGTCCAGCTGTACGTGGTGTTGCT
GCACATCCTGGTCACCTTGTGGTTTCCACTGCATCTGCTGCTGCATCTTCTGCTACTT
CCATCTACCGCTGAGTTCTTTAAGAACCTGACCATGTCTCTGACTTGTGTGGCCTGCA
GTCTGAAGCATGTGGCCCACTTGTATCACTTGCCGCAGATTGTGGAAATCGAATCACT
GATCGAGCAATTAGACACATTTATTGCCAGCGAACAGGAGCATCGTTACTATCGGGAT
CACGTACATTGCCATGCTAGGCGCTTTACAAGATGTCTCTATATTAGCTTTGGCATGA
TCTATGCGCTTTTCCTGTTCGGCGTCTTCGTTCAGGTTATTAGCGGAAATTGGGAACT
TCTCTATCCAGCCTATTTCCCATTCGACTTGGAGAGCAATCGCTTTCTCGGCGCAGTA
GCCTTGGGCTATCAGGTATTCAGCATGTTAGTTGAAGGCTTCCAGGGGCTGGGCAACG
ATACCTATACCCCACTGACCCTATGCCTTCTGGCCGGACATGTCCATTTGTGGTCCAT
ACGAATGGGTCAACTGGGATACTTCGATGACGAGACGGTGGTGAATCATCAGCGTTTG
CTGGATTACATTGAGCAGCATAAACTCTTGGTGCGGTTCCACAACCTGGTGAGCCGGA
CCATCAGCGAAGTGCAACTGGTGCAGCTGGGCGGATGTGGAGCCACTCTGTGCATCAT -continued
```
TGTCTCCTACATGCTCTTCTTTGTGGGCGACACAATCTCGCTGGTCTACTACTTGGTG
TTCTTTGGAGTGGTCTGCGTGCAGCTCTTTCCCAGCTGCTATTTTGCCAGCGAAGTAG
CCGAGGAGTTGGAACGGCTGCCATATGCGATCTTCTCCAGCAGATGGTACGATCAATC
GCGGGATCATCGATTCGATTTGCTCATCTTTACACAATTAACACTGGGAAACCGGGGG
TGGATCATCAAGGCAGGAGGTCTTATCGAGCTGAATTTGAATGCCTTTTTCGCCACCC
TGAAGATGGCCTATTCCCTTTTTGCAGTTGTGGTGCGGGCAAAGGGTATATA
```

DOR72g
```
MDLKPRVIRSEDIYRTYWLYWHLLGLESNFFLNRLLDLVITIFVTIWYPIHLILGLFM   (SEQ ID NO: 16)
ERSLGDVCKGLPITAACFFASFKFICFRFKLSEIKEIEILFKELDQRALSREECEFFN
QNTRREANFIWKSFIVAYGLSNISAIASVLFGGGHKLLYPAWFPYDVQATELIFWLSV
TYQIAGVSLAILQNLANDSYPPMTFCVVAGHVRLLAMRLSRIGQGPEETIYLTGKQLI
ESIEDHRKLMKIVELLRSTMNISQLGQFISSGVNISITLVNILFFADNNFAITYYGVY
FLSMVLELFPCCYYGTLISVEMNQLTYAIYSSNWMSMNRSYSRILLIFMQLTLAEVQI
KAGGMIGIGMNAFFATVRLAYSFFTLAMSLR
```

DOR72gnt
```
ATGGACTTAAAACCGCGAGTCATTCGAAGTGAAGATATCTACAGAACCTATTGGTTAT   (SEQ ID NO: 15)
ATTTGGCATCTTTTGGGCCTGGAAAGCAATTTCTTTCTGAATCGCTTGTTGGATTTGGT
GATTACAATTTTCGTAACCATTTGGTATCCAATTCACCTGATTCTGGGACTGTTTATG
GAAAGATCTTTGGGGGATGTCTGCAAGGGTCTACCAATTACGGCAGCATGCTTTTTCG
CCAGCTTTAAATTTATTTGTTTTCGCTTCAAGCTATCTGAAATTAAAGAAATCGAAAT
ATTATTTAAAGAGCTGGATCAGCGAGCTTTAAGTCGAGAGGAATGCGAGTTTTTCAAT
CAAAATACGAGACGTGAGGCGAATTTCATTTGGAAAAGTTTCATTGTGGCCTATGGAC
TGTCGAATATCTCGGCTATTGCATCAGTTCTTTTCGGCGGTGGACATAAGCTATTATA
TCCCGCCTGGTTTCCATACGATGTGCAGGCCACGGAACTAATATTTTGGCTAAGTGTA
ACATACCAAATTGCCGGAGTAAGTTTGGCCATACTTCAGAATTTGGCCAATGATTCCT
ATCCACCGATGACATTTTGCGTGGTTGCCGGTCATGTAAGACTTTTTGGCGATGCGCTT
GAGTAGAATTGGCCAAGGTCCAGAGGAAACAATATACTTAACCGGAAAGCAATTAATC
GAAAGCATCGAGGATCACCGAAAACTAATGAAGATAGTGGAATTACTGCGCAGCACCA
TGAATATTTCGCAGCTCGGCCAGTTTATTTCAAGTGGTGTTAATATTTCCATAACACT
AGTCAACATTCTCTTCTTTGCGGATAATAATTTCGCTATAACCTACTACGGAGTGTAC
TTCCTATCGATGGTGTTGGAATTATTCCCGTGCTGCTATTACGGCACCCTGATATCCG
TGGAGATGAACCAGCTGACCTATGCGATTTACTCAAGTAACTGGATGAGTATGAATCG
GAGCTACAGCCGCATCCTACTGATCTTCATGCAACTCACCCTGGCGAAGTGCAGATC
AAGGCCGGTGGGATGATTGGCATCGGAATGAACGCCTTCTTTGCCACCGTGCGATTGG
CCTACTCCTTCTTCACTTTGGCCATGTCGCTGCGT
```

DOR73g
```
MDSRRKVRSENLYKTYWLYWRLLGVEGDYPFRRLVDFTITSFITILFPVHLILGMYKK   (SEQ ID NO: 18)
PQIQVFRSLHFTSECLFCSYKFFCFRWKLKEIKTIEGLLQDLDSRVESEEERNYFNQN
PSRVARMLSKSYLVAAISAIITATVAGLFSTGRNLMYLGWFPYDFQATAAIYWISFSY
QAIGSSLLILENLANDSYPPITFCVVSGHVRLLIMRLSRIGHDVKLSSSENTRKLIEG
IQDHRKLMKIIRLLRSTLHLSQLGQFLSSGINISITLINILFFAENNFAMLYYAVFFA
AMLIELFPSCYYGILMTMEFDKLPYAIFSSNWLKMDKRYNRSLIILMQLTLVPVNIKA
GGIVGIDMSAFFATVRMAYSFYTLALSFRV
```

DOR73gnt
```
ATGGATTCAAGAAGGAAAGTCCGAAGTGAAAATCTTTACAAAACCTATTGGCTTTACT   (SEQ ID NO: 17)
GGCGACTTCTGGGAGTCGAGGGCGATTATCCTTTTCGACGGCTAGTGGATTTTACAAT
CACGTCTTTCATTACGATTTTATTTCCCGTGCATCTTATACTGGGAATGTATAAAAAG
CCCCAGATTCAAGTCTTCAGGAGTCTGCATTTCACATCGGAATGCCTTTTCTGCAGCT
ATAAGTTTTTCTGTTTTCGTTGGAAACTTAAAGAAATAAAGACCATCGAAGAATTGCT
CCAGGATCTCGATAGTCGAGTTGAAAGTGAAGAAGAACGCAACTACTTTAATCAAAAT
CCAAGTCGTGTGGCTCGAATGCTTTCGAAAAGTTACTTGGTAGCTGCTATATCGGCCA
TAATCACTGCAACTGTAGCTGGTTTATTTAGTACTGGTCGAAATTTAATGTATCTGGG
TTGGTTTCCCTACGATTTTCAAGCAACCGCCGCAATCTATTGGATTAGTTTTTCCTAT
CAGGCGATTGGCTCTAGTCTGTTGATTCTGGAAAATCTGGCCAACGATTCATATCCGC
CGATTACATTTTGTGTGGCTCTCGGACATGTGAGACTATTGATAATGCGTTTAAGTCG
AATTGGTCACGATGTAAAATTATCAAGTTCGGAAAATACCAGAAAACTCATCGAAGGT
ATCCAGGATCACAGGAAACTAATGAAGATAATACGCCTACTTCGCAGCACTTTACATC
TTAGCCAACTGGGCCAGTTCCTTTCTAGTGGAATCAACATTTCCATAACACTCATCAA
CATCCTGTTCTTTGCGGAAAACAACTTTGCAATGCTTTATTATGCGGTGTTCTTTGCT
GCAATGTTAATAGAACTATTTCCAAGTTGTTACTATGGAATTCTGATGACAATGGAGT
TTGATAAGCTACCATATGCCATCTTCTCCAGCAACTGGCTTAAAATGGATAAAAGATA
CAATCGATCCTTGATAATTCTGATGCAACTAACACTGGTTCCAGTGAATATAAAAGCA
GGTGGGTATTGTTGGGATCGATATGAGTGCATTTTTTGCCACAGTTCGGATGGCATATT
CCTTTTACACTTTAGCCTTGTCATTTCGAGTA
```

DOR77
```
MELMRVPVQFYRTIGEDIYAHRSTNPLKSLLFKIYLYAGFINFNLLVIGELVFFYNSI   (SEQ ID NO: 84)
QDEFETIRLAIVAPCIGFSLVADFKQAAMIRGLKKTLIMLDDLENMHPKTLAKQMEYK
LPDFEKTMKRVINIFTFLCLAYTTTFSFYPAIKASVKFNFLGYDTFDRNFGFLIWFPF
DATRNNLIYWIMYWDIAHGAYLAAFQVTESTVEVIIIYCIFLMTSMVQVFMVCYYGDT
LIAASSLKVGDAAYNQKWFQCSKSYCTMLKLLIMRSQKPASIRPPTFPPISLVTYMKNP
FNNLPKHSSSLQINANRYI
```

DOR77nt
```
ATGGAATTGATGCGAGTGCCAGTACAGTTTTACAGAACGATTGGAGAGGATATCTACG   (SEQ ID NO: 83)
CCCATCGATCCACGAATCCCCTAAAATCGCTTCTCTTCAAGATCTATCTATATGCGGG
```

-continued
```
ATTCATAAATTTTAATCTGTTGGTAATCGGTGAACTGGTGTTCTTCTACAACTCAATT
CAGGACTTTGAAACCATTCGATTGGCCATCGCGGTGGCTCCATGTATCGGATTTTCTC
TGGTTGCTGATTTTAAACAAGCTGCCATGATTAGAGGCAAGAAAACACTAATTATGCT
ACTCGATGATTTGGAGAACATGCATCCGAAAACCCTGGCAAAGCAAATGGAATACAAA
TTGCCGGACTTTGAAAAGACCATGAAACGTGTGATCAATATATTCACCTTTCTCTGCT
TGGCCTATACGACTACGTTCTCCTTTTATCCGGCCATCAAGGCATCCGTGAAATTTAA
TTTCTTGGGCTACGACACCTTTGATCGAAATTTTGGTTTCCTCATCTGGTTTCCCTTC
GATGCAACAAGGAATAATTTGATATACTGGATCATGTACTGGGACATAGCCCATGGGG
CCTATCTAGCGGCCTTTCAGGTCACCGAATCAACAGTGGAAGTGATTATTATTTACTG
CATTTTTTTGATGACCTCGATGGTTCAGGTATTTATGGTGTGCTACTATGGGGATACT
TTAATTGCCGCGAGCTTGAAAGTGGGCGATGCCGCTTACAACCAAAAGTGGTTTCAGT
GCAGCAAATCCTATTGCACCATGTTGAAGTTGCTAATCATGAGGAGTCAGAAACCAGC
TTCAATAAGACCGCCGACTTTTCCCCCCATATCCTTGGTTACCTATATGAAGAATCCC
TTCAACAATCTACCCAAACACAGCTCTTCCCTGCAAATCAACGCCAATCGCTATATC
```

DOR78
```
MKFMKYAVFFYTSVGIEPYTIDSRSKKASLWSHLLFWANVINLSVIVFGEILYLGVAY       (SEQ ID NO: 86)
SDGKFIDAVTVLSYIGFVIVGMSKMFFIWWKKTDLSDLVKELEHIYPNGKAEEEMYRL
DRYLRSCSRISITYALLYSVLTWTFNLFSIMQFLVYEKLLKTRVVGQTLPYLMYFPWN
WHENWTYYVLLFCQNFAGHTSASGQISTDLLLCAVATQVVMHFDYLARVVEKQVLDRD
WSENSRFLAKTVQYHQRILRLMDVLNDIFGIPLLLNFMVSTFVICFVGFQMTVGVPPD
IMIKLFLFSSLSQVYLICHYGQLIADAVRDFRSSSLSISAYKQNWQNADIRYRRAL
VFFIARPQRTTYLKATIEMNITRATMTDVRYNLKCH
```

DOR78nt
```
ATGAAGTTCATGAAGTACGCAGTTTTCTTTTACACATCGGTGGGCATTGAGCCGTATA       (SEQ ID NO: 85)
CGATTGACTCGCGGTCCAAAAAAGCGAGCCTATGGTCACATCTTCTCTTCTGGGCCAA
TGTGATCAATTTAAGTGTCATTGTTTTCGGAGAGATCCTCTATCTGGGAGTGGCCTAT
TCCGATGGAAAGTTCATTGATGCCGTCACTGTACTGTCATATATCGGATTCGTAATCG
TGGGCATGAGCAAGATGTTCTTCATATGGTGGAAGAAGACCGATCTAAGCGATTTGGT
TAAGGAATTGGAGCACATCTATCCAAATGGCAAAGCTGAGGAGGAGATGTATCGGTTG
GATAGGTATCTGCGATCTTGTTCACGAATTAGCATTACCTATGCACTACTCTACTCCG
TACTCATCTGGACCTTCAATCTGTTCAGTATCATGCAATTCCTTGTCTATGAAAAGTT
GCTTAAAATCCAGTGGTCGGCCAACGCTGCCATATTTGATGTACTTTCCCTGGAAC
TGGCATGAAAACTGGACGTATTATGTGCTGCTGTTCTGTCAAAACTTCGCAGGACATA
CTTCGGCATCGGGACAGATCTCTACGGATCTTTTGCTTTGTGCTGTTGCTACCCAGGT
GGTAATGCACTTCGATTACTTGGCCAGAGTGGTGGAAAAACAAGTGTTAGATCGCGAT
TGGAGCGAAAACTCCAGATTTTTGGCAAAAACTGTACAATATCATCAGCGCATTCTTC
GGCTAATGGACGTTCTCAACGATATATTCGGGATACCGCTACTGCTTAACTTTATGGT
CTCCACATTTGTCATCTGCTTTGTGGGATTCCAAATGACCGTGGGTGTCCCGCCGGAC
ATCATGATTAAGCTCTTCTTGTTCCTGTTCTCGTCCTTGTCGCAAGTGTACTTGATAT
GCCACTACGGCCAGCTGATTGCCGATGCGGTAAGAGACTTTCGAAGCTCTAGCTTATC
GATTTCTGCATATAAGCAGAATTGGCAAAATGCTGACATTCGCTATCGTCGGCTCTG
GTATTCTTTATAGCTCGACCTCAGAGGACAACTTATCTAAAAGCTACAATTTTCATGA
ATATAACAAGGGCCACCATGACGGACGTAAGATACAATTTGAAATGTCAT
```

DOR81
```
MMETLRNSGLNLKNDFGIGRKIWRVFSFTYNMVILPVSFPINYVIHLAEFPPELLLQS       (SEQ ID NO: 88)
LQLCLNTWCFALKFFTLIVYTHRLELANKHFDELDKYCVKPAEKRKVRDMVATITRLY
LTFVVVYVLYATSTLLDGLLHHRVPYNTYYPFINWRVDRTQMYIQSFLEYFTVGYAIY
VATATDSYPVIYVAALRTHILLLKDRIIYLGDPSNEGSSDPSYMFKSLVDCIKAHRTM
LNFCDAIQPIISGTIFAQFIICGSILGTTMINMVLFADQSTRFGIVIYVMAVLLQTFP
LCFYCNAIVDDCKELAHALFHSAWWVQDKRYQRTVIQFLQKLQQPMTFTAMNIFNINL
ATNTNVSPLLSVRTGKEAKSELQSLQVAKFAFTVYAIASGMNLDQKLSIKE
```

DOR81nt
```
ATGATGGAGACGCTGCGAAATTCGGGCTTGAATTTGAAGAACGATTTCGGTATAGGCC       (SEQ ID NO: 87)
GCAAGATTTGGAGGGTGTTTTCGTTCACCTACAATATGGTGATACTTCCCGTAAGTTT
CCCAATCAACTATGTGATACATCTGGCGGAGTTCCCGCCGGAGCTGCTGCTGCAATCC
CTGCAACTGTGCCTCAACACTTGGTGCTTCGCTCTGAAGTTCTTCACTCTGATCGTCT
ATACGCACCGCTTGGAGCTGGCCAACAAGCACTTTGACGAATTGGATAAGTACTGCGT
GAAGCCGGCGGAGAAGCGCAAGGTTCGCGACATGGTGGCCACTATTACAAGACTGTAC
CTGACCTTCGTCGTGGTCTACGTCCTCTACGCCACCTCCACGCTACTGGACGGACTAC
TGCACCACCGTGTTCCCTACAATACGTACTATCCGTTCATAAACTGGCGAGTCGATCG
GACCCAGATGTACATCCAGAGTTTTCTGGAGTACTTCACCGTGGGTTATGCCATATAT
GTGGCCACCGCCACCGATTCCTACCCTGTGATTTACGTGGCAGCCCTGCGAACTCATA
TTCTCTTGCTCAAGGACCGTATCATTTACTTGGGCGATCCCAGCAACGAGGGTAGCAG
CGACCCGAGCTACATGTTTAAATCGTTGGTGGATTGTATCAAGGCACACAGAACCATG
CTAAAGTGCAGTTTTTGTGATGCCATTCAACCAATCATCTCTGGCACGATATTTGCCc
AATTCATCATATGCGGATCGATCCTGGGCATAATTATGATCAACATGGTATTGTTCGC
TGATCAATCGACCCGATTCGGCATAGTCATCTACGTTATGGCCGTCCTTCTGCAGACT
TTTCCGCTTTGCTTCTACTGCAACGCCATCGTGGACGACTGCAAAGAACTGGCCCACG
CACTTTTCCATTCCGCCTGGTGGGTGCAGGACAAGCGATACCAGCGGACTGTCATCCA
GTTCCTGCAGAAACTGCAGCAGCCCATGACCTTCACCGCCATGAACATATTTAACATT
AATTTGGCCACTAACATCAATGTAAGTCCACTGCTCTCGGTTAGAACGGGGAAGGAAG
CAAAGTCCGAACTTCAATCCTTGCAGGTAGCCAAGTTCGCCTTCACCGTGTACGCCAT
CGCGAGCGGTATGAACCTGGACCAAAAAGTTAAGCATTAAGGAA
```

-continued

DOR82
MACIPRYQWKGRPTERQFYASEQRIVFLLGTICQIFQITGVLIYWYCNGRLATETGTG (SEQ ID NO: 90)
VAQLSEMCSSFCLTFVGFCNVYAISTNRNQIETLLEELHQIYPRYRKNHYRCQHYFDM
AMTIMRIEFLFYMILYVYYNSAPLWVLLWEHLHEEYDLSFKTQTNTWFPWKVHGSALG
FGMAVLSITVGSFVGVGFSIVTQNLICLLTFQLKLHYDGISSQLVSLDCRRPGAHKEL
SILIAHHSRILQLGDQVNDIMNFVFGSSLVGATIAICMSSVSIMLLDLASAFKYASGL
VAFVLYNFVICYMGTEVTLAVKIGSYMDGRRWIPKDSLLRSQRLQVLVAVGFFNTCVL
SNRRPKIEILLRYYYHIMFYSFKLYFSLRKGSLWKTLSSFTLLRI

DOR82nt
ATGGCATGCATACCAAGATATCAATGGAAAGGACGCCCTACTGAAAGACAGTTCTACG (SEQ ID NO: 89)
CTTCGGAGCAAAGGATAGTGTTCCTTCTTGGAACCATTTGCCAGATATTCCAGATTAC
TGGAGTGCTTATCTATTGGTATTGCAATGGCCGTCTTGCCACGGAAACGGGCACCTTT
GTGGCACAATTATCTGAAATGTGCAGTTCTTTTTGTCTAACATTTGTGGGATTCTGTA
ACGTTTATGCGATCTCTACAAACCGCAATCAATTGAAACATTACTCGAGGAGCTTCA
TCAGATATATCCGAGATACAGGAAAAATCACTATCGCTGCCAGCATTATTTTGACATG
GCCATGACAATAATGAGAATTGAGTTTCTTTTCTATATGATCTTGTACGTGTACTACA
ATAGTGCACCATTATGGGTGCTTCTTTGGGAACACTTGCACGAGGAATATGATCTTAG
CTTCAAGACGCAGACCAACACTTGGTTTCCATGGAAAGTCCATGGGTCGGCACTTGGA
TTTGGTATGGCTGTACTAAGCATAACCGTGGGATCCTTTGTCGGCGTAGGTTTCAGTA
TTGTCACCCAGAATCTTATCTGTTTGTTAACCTTCCAACTAAAGTTGCACTACGATGG
AATATCCAGTCAGTTAGTATCTCTCGATTGCCGTCGTCCTGGAGCTCATAAGGAGTTG
AGCATCCTCATCGCCCACCACACCCGAATCCTTCAGCTGGGCGACCAAGTCAATGACA
TAATQAACTTTGTATTCGGCTCTAGCCTAGTAGGTGCCACTATTGCCATTTGTATGTC
AAGTGTTTCTATAATGCTACTGGACTTAGCATCTGCCTTCAAATATGCCAGTGGTCTA
GTGGCATTCGTCCTCTACAACTTTGTCATCTGCTACATGGGAACCGAGGTCACTTTAG
CTGTGAAGATTGGTTCATATATGGACGGAAGGCGGTGGATACCCAAAGATTCGTTGCT
GAGATCTCAGAGGCTACAGGTGCTCGTCGCAGTTGGATTTTTTAATATATGTGTCCTC
TCGAATCGTCGTCCTAAAATTGAAATTTTGCTTAGATATTATTACCATATTATGTTTT
ATTCATTTAAATTATATTTTTCTTTAAGGAAAGGTAGCCTTTGGAAAATCTTGTCTTC
TTTCACCTTATTGAGGATC

DOR83
MQLEDFMRYPDLVCQAAQLPRYTWNGRRSLEVKRNLAKRIIFWLGAVNLVYHNIGCVM (SEQ ID NO: 92)
YGYFGDGRTKDPIAYLAELASVASMLGFTIVGTLNLWKMLSLKTHFENLLNEFEELFQ
LIKHRAYRIHHYQEKYTRHIRNTFIFHTSAVVYYNSLPILLMIREHFSNSQQLGYRIQ
SNTWYPWQVQGSIPGFFAAVACQIFSCQTNMCVNMFIQFLINFFGIQLEIHFDGLARQ
LETIDARNPHAKDQLKYLIVYHTKLLNLADRVNRSFNFTFLISLSVSMISNCFLAFSM
TMFDFGTSLKHLLGLLLFITYNFSMCRSGTHLILTSGKVLPAAFYNNWYEGDLVYRRM
LLILMMRATKPYMWKTYKLAPVSITTYMAECKTKEAHEQRHFRRHERQKPRVARI

DOR83nt
ATGCAGTTGGAGGACTTTATGCGGTACCCGGACCTCGTGTGTCAAGCGGCCCAACTTC (SEQ ID NO: 91)
CCAGATACACGTGGAATGGCAGACGATCCTTGGAAGTTAAACGCAACTTGGCAAAACG
CATTATCTTCTGGCTTGGAGCAGTAAATTTGGTTTATCACAATATTGGCTGCGTCATG
TATGGCTATTTCGGTGATGGAAGAACAAAGGATCCAATTGCGTATTTAGCTGAATTGG
CATCTGTGGCCAGCATGCTTGGTTTCACCATTGTGGGCACCCTCAACTTGTGGAAGAT
GCTGAGCCTTAAGACCCATTTTGAGAACCTACTAAATGAATTCGAGGAATTATTTCAA
CTAATCAAGCACAGGGCGTATCGCATACACCACTATCAAGAAAAGTATACGCGTCATA
TACGAAATACATTTATTTTCCATACCTCTGCCGTTGTCTACTACAACTCACTACCAAT
TCTTCTAATGATTCGGGAACATTTCTCGAACTCACAGCAGTTGGGCTATAGAATTCAG
AGTAATACCTGGTATCCCTGGCAGGTTCAGGGATCAATTCCTGGATTTTTTGCTGCAG
TCGCCTGTCAAATCTTTTCGTGCCAAACCAATATGTGCGTCAATATGTTTATCCAGTT
TCTGATCAACTTTTTTGGTATCCAGCTAGAAATACACTTCGATGGTTTGGCCAGGCAG
CTGGAGACCATCGATGCCCGCAATCCCCATGCCAAGGATCAATTGAAGTATCTGATTG
TATATCACACAAAATTGCTTAATCTAGCCGACAGAGTTAATCGATCGTTTAACTTTAC
GTTTCTCATAAGTCTGTCGGTATCCATGATATCCAACTGTTTTCTGGCATTTTCCATG
ACCATGTTCGACTTTGGCACCTCTCTAAAACATTTACTCGGACTTTTGCTATTCATCA
CATATAATTTTTCAATGTGCCGCAGTGGTACGCACTTGATTTTAACGAGTGGCAAAGT
ATTGCCAGCGGCCTTTTATAACAATTGGTATGAAGGCGATCTTGTTTATCGAAGGATG
CTCCTCATCCTGATGATGCGTGCTACGAAACCTTATATGTGGAAAACCTACAAGCTGG
CACCTGTATCCATAACTACATATATGGCAGAATGCAAAACAAAAGAAGCCCATGAACA
ACGCCATTTTAGACGCCATQAAAGACAAAAACCTCGGGTTGCACGAATA

DOR84
MVFSFYAEVATLVDRLRDNENFLESCILLSYVSFVVMGLSKIGAVMKKKPKMTALVRQ (SEQ ID NO: 94)
LETCFPSPSAKVQEEYAVKSWLKRCHIYTKGFGGLFMIMYFAHALIPLFIYFIQRVLL
HYPDAKQIMPFYQLEPWEFRDSWLFYPSYFHQSSAGYTATCGSIAGDLMIFAVVLQVI
MHYERLAKVLREFKIQAHNAPNGAKEDIRKLQSLVANHIDILRLTDLMNEVFGIPLLL
NFIASALLVCLVGVQLTIALSPEYFCKQMLFLISVLLEVYLLCSFSQRLIDAVC

DOR84nt
ATGGTGTTTAGTTTTTATGCCGAGGTAGCGACTCTGGTGGACAGGTTACGCGATAATG (SEQ ID NO: 93)
AAAATTTTCTCGAGAGCTGCATCTTACTGAGCTACGTGTCCTTTGTGGTCATGGGCCT
CTCCAAGATAGGTGCTGTAATGAAAAAAAAGCCAAAAATGACAGCTTTGGTCAGGCAA
TTGGAGACCTGCTTTCCGTCGCCAAGTGCAAAGGTTCAAGAGGAATATGCTGTGAAGT
CCTGGCTGAAACGCTGCCATATATACACAAAGGGATTTGGTGGTCTCTTCATGATCAT
GTATTTCGCTCACGCTCTGATTCCCTTATTCATATACTTCATTCAAAGAGTGCTGCTC
CACTATCCGGATGCCAAGCAGATTATGCCGTTTTACCAACTCGAACCTTGGGAATTTC
GCGACTCCTGGTTGTTTTATCCAAGCTATTTTCACCAGTCGTCGGCCGGATATACGGC

-continued

TACATGTGGATCCATTGCCGGTGACCTAATGATCTTCGCTGTGGTCCTGCAGGTCATC
ATGCACTACGAAAGACTGGCCAAGGTTCTTAGGGAGTTTAAGATTCAAGCCCATAACG
CACCCAATGGAGCTAAGGAGGATATAAGGAAGTTGCAGTCCCTAGTCGCCAATCACAT
TGATATACTTCGACTCACTGATCTGATGAACGAGGTCTTTGGAATTCCCTTGTTGCTA
AACTTTATTGCATCTGCCTGCTGGTCTGCCTGGTGGGAGTTCAATTAACCATCGCTT
TAAGTCCAGAGTATTTTTGCAAGCAGATGCTATTTCTGATTTCCGTACTGCTTGAGGT
CTATCTCCTTTGCTCCTTCAGCCAGAGGTTAATAGATGCTGTATGT

DOR87
MTIEDTGLVGINVRMWRHLAVLYPTPGSSWRKFAFVLPVTANNLMQFVYLLRMWGDLP    (SEQ ID NO: 6)
AFTLNMFFFSATFNALMRTWLVIIKRRQFEEFLGQLATLFHSILDSTDEWGRGTLRPA
ERERARNLAILNLSASFLDIVGALVSPLFREEPAHPFGVALPGVSMTSSPVYEVIYLAQ
LPTPLLLSMMYMPFVSLFAGLATFGKANLQILVHRLGQIGGEEQSEEERFQRLASCIA
YHTQVMRYVWQLNKLVANIVAVEAIIFGSIICSLLFCLNIITSPTQVISIVMYTLTML
YVLFTYYNRANEICLENNRVAEAVYNVPWYEAGTRFRKTLLIFLMQTQHPMEIRVGNV
YPMTLANFQSLLNASYSYFTMLRGVTGK

DOR87nt
GGCACGAGGCTTATAGAAAGTGCCGAGCAATGACAATCGAGGATATCGGCCTGGTGGG    (SEQ ID NO: 5)
CATCAACGTGCGGATGTGGCGACACTTGGCCGTGCTGTACCCCACTCCGGGCTCCAGC
TGGCGCAAGTTCGCCTTCGTGCTGCCGGTGACTGCGATGAATCTGATGCAGTTCGTCT
ACCTGCTGCGGATGTGGGGCGACCTGCCCGCCTTCATTCTGAACATGTTCTTCTTCTC
GGCCATTTTCAACGCCCTGATGCGCACGTGGCTGGTCATAATCAAGCGGCGCCAGTTC
GAGGAGTTTCTCGGCCAACTGGCCACTCTGTTCCATTCGATTCTCGACTCCACCGACG
AGTGGGGGCGTGGCATCCTGCGGAGGGCGGAACGGGAGGCTCGGAACCTGCCCATCCT
TAATTTGAGTGCCTCCTTCCTGGACATTGTCGGTGCTCTGGTATCGCCGCTTTTCAGG
GAGGAGAGAGCTCATCCCTTCGGCGTAGCTCTACCAGGAGTGAGCATGACCAGTTCAC
CCGTCTACGAGGTTATCTACTTGGCCCAACTGCCTACGCCCCTGCTGCTGTCCATGAT
GTACATGCCTTTCGTCAGCCTTTTTGCCGGCCTGGCCATCTTTGGGAAGGCCATGCTG
CAGATCCTGGTACACAGGCTGGGCCAGATTGGCGGAGAAGAGCAGTCGGAGGAGGAGC
GCTTCCAAAGGCTGGCCTCCTGCATTGCGTACCACACGCAGGTGATGCGCTATGTGTG
GCAGCTCAACAAACTGGTGGCCAACATTGTGGCGGTGGAAGCAATTATTTTTGGCTCG
ATAATCTGCTCACTGCTCTTCTGTCTGAATATTATAACCTCACCCACCCAGGTGATCT
CGATAGTGATGTACATTCTGACCATGCTGTACGTTCTCTTCACCTACTACAATGGGC
CAATGAAATATGCCTCGAGAACAACCGGGTGGCGGAGGCTGTTTACAATGTGCCCTGG
TACGAGGCAGGAACTCGGTTTCGCAAAACCCTCCTGATCTTCTTGATGCAAACACAAC
ACCCGATGGAGATAAGAGTCGGCAACGTTTACCCCATGACATTGGCCATGTTCCAGAG
TCTGTTGAATGCGTCCTACTCCTACTTTACCATGCTGCGTGGCGTCACCGGCAAATGA
GCTGAAAGACCGAAAAAACCGGAGTATCCCCTTCCATATTCCCCCTGCTCCTTTATTT
TCCTTTCCTTTTCCCTTTCCGTTTTCCCATTCGCTTTTCCAGCAATCCGGGTAATGCA
AAAAGTTGTTGCTGGCTGTGGTCCTGGCTGCTTGTTTGGCATTTGCATATGCTTGTCG
TTTGAAAGGATTTAATCGGACTGCTGGCACGGAGTCGGCATCCTGGCTCCTGGATCCT
GGCATGCAAATAGTTGGCTTCTTAGATTGTTACACAAAATAGATTGTAGATTGCAGCT
GAATGTTGTGCTTGGAATAAAGTCAAAAGGATGTGGAGTCGGCCCAAGGCTCTGCCCA
TTCTGTTTGCTCGGGATGCCCGAAAGTATGAAAAAAAAAAAAAAAAAA

DOR91
MVRYVPRFADGQKVKLAWPLAVFRLNHIFWPLDPSTGKWGRYLDKVLAVANSLVFMQH    (SEQ ID NO: 96)
NDAELRYLRFEASNRNLDAFLTGMPTYLILVEAQFRSLHILLHFEKLQKFLEIFYANI
YIDPRKEPEMFRKVDGKMIINRLVSANYGAVISLYLIAPVFSIINQSKDFLYSMIFPF
DSDPLYIFVPLLLTNVWVGIVIDTMMFGETNLLCELIVHLNGSYMLLKRDLQLAIEKI
LVARDRPHMAKQLKVLITKTLRKNVALNQFGQQLEAQYTVRVFIMFAFAAGLLCALSF
KAYTTDSLSTMYYLTHWEQILQYSTNPSENLRLLKLINLAIEMNSKPFYVTGLKYFRV
SLQAGLKRQKFLRSASSSTLSTADVLAFAFAFTRWLL

DOR91nt
ATGGTTCGTTACGTGCCCCGGTTCGCTGATGGTCAGAAAGTAAAGTTGGCTTGGCCCT    (SEQ ID NO: 95)
TGGCCGGTTTTTCGGTTAAATCACATATTCTGGCCATTGGATCCGAGCACAGGGAAATG
GGGCCGATATCTGGACAAGGTTCTAGCTGTTGCGATGTCCTTGGTTTTTATGCAACAC
AACGATGCAGAGCTGAGGTACTTGCGCTTCAGGCAAGTAATCGGAATTTGGATGCCT
TTCTCACAGGAATGCCAACGTATTTAATCCTCGTGGAGGCTCAATTTAGAAGTCTTCA
CATTCTACTGCACTTCGAGAAGCTTCAGAAGTTTTTAGAAATATTCTACGCAAATATT
TATATTGATCCCCGTAAGGAACCCGAAATGTTTCGAAAAGTGGATGGAAAGATGATAA
TTAACAGATTAGTTTCGGCCATGTACGGTGCAGTTATCTCTCTGTATCTAATCGCACC
CGTTTTTTCCATCATTAACCAAAGCAAAGATTTTCTATACTCTATGATCTTTCCGTTC
GATTCGGATCCCTTGTACATATTTGTGCCACTGCTTTTGACAAACGTATGGGTTGGCA
TTGTAATAGATACCATGATGTTCGGGGAGACGAATTTGTTGTGTGAACTAATTGTCCA
CCTAAATGGTAGTTATATGTTGCTCAAGAGGGACTTGCAOTTGGCCATTGAAAAGATA
TTAGTTGCAAGGGACCGTCCGCATATGGCCAAACAGCTAAAGGTTTTAATTACAAAAA
CTCTCCGAAAGAATGTGGCTCTAAATCAGTTTGGCCAGCAGCTGGAGGCTCAGTATAC
TGTGCGGGTTTTTATTATGTTTGCATTCGCTGCGGGCCTTTTATGTGCTCTTTCTTTT
AAGGCTTATACGACGGATTCCCTCAGCACAATGTACTACCTTACCCATTGGGAGCAAA
TCCTGCAGTACTCTACAAATCCCAGCGAAATCTGCGATTACTAAAGCTCATTAACTT
GGCCATTGAGATGAACAGCAAGCCCTTCTATGTGACAGGGCTAAAATATTTTCGCGTT
AGTCTGCAGGCTGGCTTAAAACGTCAAAAGTTTCTGCGGTCTGCCAGCTCATCCACCC
TTAGCACCGCTGATGTGTTGGCATTTGCTTTTGCTTTTACTCGCTOGCTGCTT

-continued

DOR92
MSEWLRFLKRDQQLDVYFFAVPRLSLDIMGYWPGKTGDTWPWRSLIHFAILAIGVATE (SEQ ID NO: 98)
LHAGMCFLDRQQITLALETLCPAGTSAVTLLKMFLMLRFRQDLSIMWNRLRGLLFDPN
WERPEQRDIRLKHSAMAARINFWPLSAGFFTCTTYNLKPILIAMILYLQNRYEDFVWF
TPFNMTMPKVLLNYPFFPLTYIFIAYTGYVTIFMFGGCDGFYFEFCAHLSALFEVLQA
EIESMFRPYTDHLELSPVQLYILEQKMRSVITRHNAIIDLTRFFRDRYTIITLAHFVS
AAMVIGFSMVNLLTLGNNGLGAMLYVAYTVAALSQLLVYCYGGTLVAESSTGLCRAMF
SCPWQLFKPKQRRLVQLLILRSQRPVSMAVPFFSPSLATFAAILQTSGSIIALVKSFQ

DOR92nt
ATGTCCGAGTGGTTACGCTTTCTGAAACGCGATCAACAGCTGGATGTGTACTTTTTTG (SEQ ID NO: 97)
CAGTGCCCCGCTTGAGTTTAGACATAATGGGCTATTGGCCGGGCAAAACTGGTGATAC
ATGGCCCTGGAGATCCCTGATTCACTTCGCAATCCTGGCCATTGGCGTGGCCACCGAA
CTGCATGCTGGCATGTGTTTTCTAGACCGACAGCAGATTACCTTGGCACTGGAGACCC
TCTGTCCAGCTGGCACATCGGCGGTCACGCTGCTCAAGATGTTCCTAATGCTGCGCTT
TCGTCAGGATCTCTCCATTATGTGGAACCGCCTGAGGGGCCTGCTCTTCGATCCCAAC
TGGGAGCGACCCGAGCAGCGGGACATCCGGCTAAAGCACTCGGCCATGGCGGCTCGCA
TCAATTTCTGGCCCCTGTCAGCCGGATTCTTCACATGCACCACCTACAACCTAAAGCC
GATACTGATCGCAATGATATTGTATCTCCAGAATCGTTACGAGGACTTCGTTTGGTTT
ACACCCTTCAATATGACTATGCCCAAAGTTCTGCTAAACTATCCATTTTTTCCCCTGA
CCTACATATTTATTGCCTATACGGGCTATGTGACCATCTTTATGTTCGGCGGCTGTGA
TGGTTTTTATTTCGAGTTCTGTGCCCACCTATCAGCTCTTTTCGAAGTGCTCCAGGCG
GAGATAGAATCAATGTTTAGACCCTACACTGATCACTTGGAACTGTCGCCAGTGCAGC
TTTACATTTTAGAGCAAAAGATGCGATCAGTAATCATTAGGCACAATGCCATCATCGA
TTTGACCAGATTTTTTCGTGATCGCTATACCATTATTACCCTGGCCCATTTTGTGTCC
GCCGCCATGGTGATTGGATTCAGCATGGTTAATCTCCTGACATTGGGCAATAATGGTC
TGGGCGCAATGCTCTATGTGGCCTACACGGTTGCCGCTTTGAGCCAACTGCTGGTTTA
TTGCTATGGCGGAACTCTGGTGGCCGAAAGTAGCACTGGTCTGTGCCGAGCCATGTTC
TCCCTGTCCGTGGCAGCTTTTTAAGCCTPAACAACGTCGACTCGTTCAGCTTTTGATTC
TCAGATCGCAGCGTCCTGTTTCCATGGCAGTGCCATTCTTTTCGCCATCGTTGGCTAC
CTTTGCTGCGATTCTTCAAACTTCGGCTTCCATAATTGCGCTGGTTAAGTCCTTTCAG

DOR95
MSDKVKGKKQEEKDQSLRVQILVYRCMGIDLWSPTMANDRPWLTFVTMGPLFLFMVPM (SEQ ID NO: 100)
FLAAHEYITQVSLLSDTLGSTFASMLTLVKFLLFCYHRKEFVGLIYHIPAILAKEIEV
WPDAREIIEVENQSDQMLSLTYTRCFGLAGIFAALKPFVGIILSSIRGDEIHLELPHN
GVYPYDLQVVMFYVPTYLWNVMASYSAVTMALCVDSLLFFFTYNVCAIFKIAKHRMIH
LPAVGGKEELEGLVQVLLLHQKGLQIADHTADKYRPLIFLQFFLSALQICFTGFQVAD
LFPNPQSLYFIAFVGSLLIALFIYSKCGENIKSASLDFGNGLYETNWTDFSPPTKRAL
LTAAMRAQRPCQMKGYFFEASMATFSTIVRSAVSYIMMLRSFNA

DOR95nt
ATGAGCGACAAGGTGAAGGGAAAAAAGCAGGAGGAAAAGGATCAATCCTTGCGGGTGC (SEQ ID NO: 99)
AAATTCTCGTTTATCGCTGCATGGGCATCGATTTGTGGAGCCCCACGATGGCGAATGA
CCGCCCCGTGGCTGACCTTTGTCACAATGGGACCACTTTTCCTGTTTATGGTGCCCATG
TTCCTGGCCGCCCACGAGTACATCACCCAGGTGAGCCTGCTCTCCGACACCCTGGGCT
CCACCTTCGCCAGCATGCTCACCCTGGTCAAATTCCTGCTCTTCTGCTATCATCGCAA
GGAGTTCGTCGGCCTGATCTACCACATCAGGGCCATTCTGGCTAAAGAAATCGAAGTG
TGGCCTGATGCGCGGGAAATCATCGAGGTGGAGAACCAAAGTGACCAAATGCTCAGTC
TTACGTACACTCGCTGTTTTGGACTGGCTGGAATCTTTGCGGCCCTGAAGCCCTTTGT
GGGCATCATACTCTCCTCGATTCGCGGCGACGAGATTCACCTGGAGCTGCCCCACAAC
GGCGTTTACCCGTACGATCTCCAGGTGGTCATGTTTTATGTGCCCACCTATCTGTGGA
ATGTGATGGCCAGCTATAGTGCTGTAACCATGGCACTCTGCGTGGACTCGCTGCTCTT
CTTTTTTCACCTACAACGTGTGCGCCATTTTCAAGATCGCCAAGCACCGGATGATCCAT
CTGCCGGCGGTGGGCGGAAAGGAGGAGCTGGAGGGGCTCGTCCAGGTGCTGCTGCTGC
ACCAGAAGGGCCTCCAGATCGCCGATCACATTGCGGACAAGTACCGGCCGCTGATCTT
TTTGCAGTTCTTTCTGTCCGCCTTGCAGATCTGCTTCATTGGATTCCAGGTGGCTGAT
CTGTTTCCCAATCCGCAGAGTCTCTACTTTATCGCCTTTGTGGGCTCGCTGCTCATCG
CACTGTTCATCTACTCGAAGTGCGGCGAAAATATCAAGAGTGCCAGCCTGGATTTCGG
AAACGGGCTGTACGAGACCAACTGGACCGACTTCTCGCCACCCACTAAAAGAGCCCTC
CTCATTGCCGCCATGCGCGCCCAGCGACCTTGCCAGATGAAGGGCTACTTTTTCGAGG
CCAGCATGGCCACCTTCTCGACGATTGTTCGCTCTGCCGTGTCGTACATCATGATGTT
GCGCTCCTTTAATGCC

DOR99
MEEFLRPQMFQEVAQMVHFQWRRNPVDNSMVNASMVPFCLSAFLNVLFFGCNGWDIIG (SEQ ID NO: 102)
HFWLGHPANQNPPVLSITIYFSIRGLMLYLKRKEIVEFVNDLDRECPRDLVSQLDMQN
DETYPNFWQRYRFIRIYSHLGGPMFCVVPLALFLLTHEGKDTPVAQHEQLLGGWLPCG
VRKDPNFYLLVWSFDLMCTTCGVSFFVTFDNLFNVMQGHLVMHLGHLARQFSAIDPRQ
SLTDEKRFFVDLRLLVQRQQLLNGLCRKYNDIFKVAFLVSNFVGAGSLCFYLFMLSET
SDVLIIAQYILPTLVLVGFTFEICLRGTQLEKASEGLESSLRSQEWYLGSRRYRKFYL
LWTQYCQRTQQLGAFGLIQVNMVHFTEIMQLAYRLFTFLKSH

DOR99nt
ATGGAGGAGTTTCTGCGTCCGCAGATGTTCCAGGAGGTGGCTCAGATGGTGCATTTCC (SEQ ID NO: 101)
AGTGGCGGAGAAATCCGGTGGACAACAGCATGGTGAACGCATCCATGGTCCCCTTCTG
CTTGTCGGCGTTTCTTAATGTCCTGTTTTTCGGCTGCAATGGTTGGGACATCATAGGA
CATTTTTGGCTGGGACATCCTGCCAACCAGAATCCGCCCGTGCTTAGCATCACCATTT
ACTTCTCGATCAGGGGATTGATGCTATACCTGAAACGAAAGGAAATCGTTGAGTTTGT
TAACGACTTGGATCGGGAGTGTCCGCGGGACTTGGTCAGCCAGTTGGACATGCAAATG

```
-continued
GATGAGACGTACCGAAACTTTTGGCAGCGCTATCGCTTCATCCGTATCTACTCCCATT
TGGGTGGTCCGATGTTCTGCGTTGTGCCATTAGCTCTATTCCTCCTGACCCACGAGGG
TAAAGATACTCCTGTTGCCCAGCACGAGCAGCTCCTTGGAGGATGGCTGCCATGCGGT
GTGCGAAAGGACCCAAATTTCTACCTTTTAGTCTGGTCCTTCGACCTGATGTGCACCA
CTTGCGGCGTCTCCTTTTTCGTTACCTTCGACAACCTATTCAATGTGATGCAGGGACA
TTTGGTCATGCATTTGGGCCATCTTGCTCGCCAGTTTTCGGCCATCGATCCTCGACAG
AGTTTGACCGATGAGAAGCGATTCTTTGTGGATCTTAGGTTATTAGTTCAGAGGCAGC
AGCTTCTTAATGGATTGTGCAGAAAATACAACGACATCTTTAAAGTGGCCTTCCTGGT
GAGCAATTTTGTAGGCGCCGGTTCCCTCTGCTTCTACCTCTTTATGCTCTCGGAGACA
TCAGATGTCCTTATCATCGCCCAGTATATATTACCCACTTTGGTCCTGGTGGGCTTCA
CATTTGAGATTTGTCTACGGGGAACCCAACTGGAAAAGGCGTCGGAGGGACTGGAATC
GTCGTTGCGAAGCCAGGAATGGTATTTGGGAAGTAGGCGGTACCGGAAGTTCTATTTG
CTCTGGACGCAATATTGCCAGCGAACACAGCAACTGGGCGCCTTTGGGCTAATCCAAG
TCAATATGGTGCACTTCACTGAAATAATGCAGCTGGCCTATAGACTCTTCACTTTTCT
CAAATCTCAT DORA45
MTTSMQPSKYTGLVADLMPNIRAMKYSGLFMHNFTGGSAFMKKVYSSVHLVFLLMQFT    (SEQ ID NO: 104)
FILVNMALNAEEVNELSGNTITTLFFTHCTTKFTYLAVNQKNFYRTLNIWNQVNTHPL
FAESDARYHSIALAKMRKLFFLVMLTTVASATAWTTITFFGDSVKMVVDHETNSSIPV
EIPRLPIKSFYPWNASHGMFYMISFAFQIYYVLFSMIHSNLCDVMFCSWLIFACEQLQ
HLKGIMKPLMELSASLDTYRPNSAALFRSLSANSKSELIHNEEKDPGTDMDMSGIYSS
KADWGAQFPAPSTLQSFGGNGGGNGLVNGANPNGLTKKQEMMVRSAIKYWVERHKHV
VRLVAAIGDTYGAALLLHMLTSTIKLTLLAYQATKINGVNVYAFTVVGYLGYAIAQVF
HFCIFGNRLIEESSSVMEAAYSCHWYDGSEEAKTFVQIVCQQCQKAMSISGAKFFTVS
LDLFASVLGAVVTYFMVLVQLK DORA45nt
GGCACGAGCTGGTTCCGGAAAGCCTCATATCTCOTATCTTAAAGTATCCCGGTTAAGC    (SEQ ID NO: 103)
CTTAAAGAGTGAAATGATTGCCTAGACGATTGCTGCATTACTGGCACTCAATTAACCC
AAGTGTACCAGACAACAATTACATTTGTATTTTTAAAGTTCAATAGCAAGGATGACAA
CCTCGATGCAGCCGAGCAAGTACACGGGCCTGGTCGCCGACCTGATGCCCAACATCCG
GGCGATGAAGTACTCCGGCCTGTTCATGCACAACTTCACGGGCGGCAGTGCCTTCATG
AAGAAGGTGTACTCCTCCGTGCACCTGGTGTTCCTCCTCATGCAGTTCACCTTCATCC
TGGTCAACATGGCCCTGAACGCCGAGGAGGTCAACGAGCTGTCGGGCAACACGATCAC
GACCCTCTTCTTCACCCACTGCATCACGAAGTTTATCTACCTGGCTGTTAACCAGAAG
AATTTCTACAGAACATTGAATATATGGAACCAGGTGAACACGCATCCCTTGTTCGCCG
AGTCGGATGCTCGTTACCATTCGATCGCACTGGCGAAGATGAGGAAGCTGTTCTTTCT
GGTGATGCTGACCACAGTCGCCTCGGCCACCGCCTGGACCACGATCACCTTCTTTGGC
GACAGCGTAAAAATGGTGGTGGACCATGAGACGAACTCCAGCATCCCGGTGGAGATAC
CCCGGCTGCCGATTAAGTCCTTCTACCCGTGGAACGCCAGCCACGGCATGTTCTACAT
GATCAGCTTTGCCTTTCAGATCTACTACGTGCTCTTCTCGATGATCCACTCCAATCTA
TGCGACGTGATGTTCTGCTCTTGGCTGATATTCGCCTGCGAGCAGCTGCAGCACTTGA
AGGGCATCATGAAGCCGCTGATGGAGCTGTCCGCCTCGCTGGACACCTACAGGCCCAA
CTCGGCGGCCCCTCTTCAGGTCCCTGTCGGCCAACTCCAAGTCGGAGCTAATTCATAAT
GAAGAAAAGGATCCCGGCACCGACATGGACATGTCGGGCATCTACAGCTCGAAAGCGG
ATTGGGGCGCTCAGTTTCGAGCACCCTCGACACTGCAGTCCTTTGGCGGGAACGGGGG
CGGAGGCAACGGGTTGGTGAACGGCGCTAATCCCAACGGGCTGACCAAAAAGCAGGAG
ATGATGGTGCGCAGTGCCATCAAOTACTGGGTCGAGCGGCACAAGCACGTGGTGCGAC
TGGTGGCTGCCATCGGCGATACTTACGGAGCCGCCCTCCTCCTCCACATGCTGACCTC
GACCATCAAGCTGACCCTGCTGGCATACCAGGCCACCAAAATCAACGGAGTGAATGTC
TACGCCTTCACAGTCGTCGGATACCTAGGATACGCGCTGOCCCAGGTGTTCCACTTTT
GCATCTTTGGCAATCGTCTGATTGAAGAGAGTTCATCCGTCATGGAGGCCGCCTACTC
GTGCCACTGGTACGATGGCTCCGAGGAGGCCAAGACCTTCGTCCAGATCGTGTGCCAG
CAGTGCCAGAAGGCGATGAGCATATCGGGAGCOAAATTCTTCACCGTCTCCCTGGATT
TGTTTGCTTCGGTTCTGGGTGCCGTCGTCACCTACTTTATGGTGCTGGTGCAGCTCAA
GTAAGTTGCTGCGAAGCTGATGGATTTTTGTACCAGAAAAGCGAATGCCAAGAAGCCA
CCTACCGCCCCTTGCCCCCTCCGCACTGTGCAACCAGCAATATCACAGAGCAATTATA
ACGCAAATTATATATTTTATACCTGCGACGAGCGAGCCTCGTGGGGCATAATGGAGAC
ATTCTGGGGCACATAGAAGCCTGCAAATACTTATCGATTTTGTACACGCGTAGAGCTT
TTAATGTAACTCAAGATGCAAACTAAATAAATGTGTAGTGAAAAAAAAAAAAAAAAAA
AAA GENBANK ACCESSION NUMBERS
The accession numbers for the sequences reported in this
paper are AF127921-AF127926.
```

REFERENCES

Altschul, S. F., Gish, W., Miller, W., Myers, E. W., and Lipman, D. J. (1990) Basic local alignment search tool. J. Mol. Biol. 215, 403–410.

Altschul, S. F., Madden, T. L., Schaffer, A. A., Zhang, J., Zhang, Z., Miller, W., and Lipman, D. J. (1997) Gapped BLAST and PSI-BLAST: a new generation of protein database search programs. Nucleic Acids Res. 25, 3389–3402.

Amrein, H., Gorman, M., and Nothiger, R. (1988) The sex-determining gene tra-2 of *Drosophila* encodes a putative RNA binding protein [published erratum appears in Cell Jul. 28, 1989;58(2):following 419]. Cell 55, 1025–1035.

Ayer, R. K., Jr., and Carlson, J. (1992) Olfactory physiology in the *Drosophila* antenna and maxillary palp: acj6 distinguishes two classes of odorant pathways. J. Neurobiol. 23, 965–982.

Bargmann, C. I., and Kaplan, J. M. (1998) Signal transduction in the *Caenorhabditis elegans* nervous system. Annu Rev Neurosci 21, 279–308.

Bargmann, C. I., Hartwieg, E., and Horvitz, H. R. (1993) Odorant-selective genes and neurons mediate olfaction in *C. elegans*. Cell 74, 515–527.

Bargmann, C. I., and Horvitz, H. R. (1991) Chemosensory neurons with overlapping functions direct chemotaxis to multiple chemicals in *C. elegans*. Neuron 7, 729–742.

Ben-Arie, N., Lancet, D., Taylor, C., Khen, M., Walker, N., Ledbetter, D. H., Carrozzo, R., Patel, K., Sheer, D., Lehrach, H., and et al. (1994) Olfactory receptor gene cluster on human chromosome 17: possible duplication of an ancestral receptor repertoire. Hum. Mol. Genet. 3, 229–235.

Buck, L. B. (1996) Information coding in the vertebrate olfactory system. Annu. Rev. Neurosci. 19, 517–44.

Buck, L., and Axel, R. (1991) A novel multigene family may encode odorant receptors: a molecular basis for odor recognition. Cell 65, 175–187.

Burge, C., and Karlin, S. (1997) Prediction of complete gene structures in human genomic DNA. J. Mol. Biol. 268, 78–94.

Carlson, J. R. (1996) Olfaction in *Drosophila*: from odor to behavior. Trends Genet. 12, 175–180.

Chess, A., Simon, I., Cedar, H., and Axel, R. (1994) Allelic inactivation regulates olfactory receptor gene expression. Cell 78, 823–834.

Colbert, H. A., and Bargmann, C. I. (1995) Odorant-specific adaptation pathways generate olfactory plasticity in *C. elegans*. Neuron 14, 803–812.

Cserzo, M., Wallin, E., Simon, I., von Heijne, G., and Elofsson, A. (1997) Prediction of transmembrane-helices in prokaryotic membrane proteins: the dense alignment surface method. Protein Eng. 10, 673–676.

Doe, C. Q., and Skeath, J. B. (1996) Neurogenesis in the insect central nervous system. Curr. Opin. Neurobiol. 6, 18–24.

Dulac, C., and Axel, R. (1995) A novel family of genes encoding putative pheromone receptors in mammals. Cell 83, 195–206.

Faber, T., Joerges, J., and Menzel, R. (1998) Associative learning modifies neural representations of odors in the insect brain. Nature Neurosci. 2, 74–78.

Friedrich, R. W., and Korsching, S. I. (1997) Combinatorial and chemotopic odorant coding in the zebrafish olfactory bulb visualized by optical imaging. Neuron 18, 737–752.

Grillenzoni, N., van Helden, J., Dambly-Chaudiere, C., and Ghysen, A. (1998) The iroquois complex controls the somatotopy of *Drosophila* notum mechanosensory projections. Development 125, 3563–9.

Hartl, D. L., Nurminsky, D. I., Jones, R. W., and Lozovskaya, E. R. (1994) Genome structure and evolution in *Drosophila*: applications of the framework P1 map. Proc. Natl. Acad. Sci. USA 91, 6824–6829.

Herrada, G., and Dulac, C. (1997) A novel family of putative pheromone receptors in mammals with a topographically organized and sexually dimorphic distribution. Cell 90, 763–773.

Imamura, K., Mataga, N., and Mori, K. (1992) Coding of odor molecules by mitral/tufted cells in rabbit olfactory bulb. I. Aliphatic compounds. J. Neurophysiol. 68, 1986–2002.

Joerges, J., Kuttner, A., Galizia, C. G., and Menzel, R. (1997) Presentations of odours and odour mixtures visualized in the honeybee brain. Nature 387, 285–288.

Katoh, K., Koshimoto, H., Tani, A., and Mori, K. (1993) Coding of odor molecules by mitral/tufted cells in rabbit olfactory bulb. II. Aromatic compounds. J. Neurophysiol. 70, 2161–2175.

Kauer, J. S., Senseman, D. M., and Cohen, L. B. (1987) Odor-elicited activity monitored simultaneously from 124 regions of the salamander olfactory bulb using a voltage-sensitive dye. Brain Res. 418, 255–261.

Kim, M. S., Repp, A., and Smith, D. P. (1998) LUSH odorant-binding protein mediates chemosensory responses to alcohols in *Drosophila* melanogaster. Genetics 150, 711–21.

Kimmerly, W., Stultz, K., Lewis, S., Lewis, K., Lustre, V., Romero, R., Benke, J., Sun, D., Shirley, G., Martin, C., and Palazzolo, M. (1996) A P1-based physical map of the *Drosophila* euchromatic genome. Genome Res. 6, 414–430.

Kyte, J., and Doolittle, R. F. (1982) A simple method for displaying the hydropathic character of a protein. J Mol. Biol. 157, 105–132.

Laissue, P. P., Reiter, C., Hiesinger, P. R., Halter, S., Fischbach, K. F., and Stocker, R. F. (1999) Three-dimensional reconstruction of the antennal lobe in *Drosophila melanogaster*. J. Comp. Neurol. 405, 543–552.

Lancet, D., Greer, C. A., Kauer, J. S., and Shepherd, G. M. (1982) Mapping of odor-related neuronal activity in the olfactory bulb by high-resolution 2-deoxyglucose autoradiography. Proc. Natl. Acad. Sci. USA 79, 670–674.

Levy, N. S., Bakalyar, H. A., and Reed, R. R. (1991) Signal transduction in olfactory neurons. J. Steroid Biochem. Mol. Biol. 39, 633–637.

Lin, D. M., and Goodman, C. S. (1994) Ectopic and increased expression of Fasciclin II alters motoneuron growth cone guidance. Neuron 13, 507–523.

Matsunami, H., and Buck, L. B. (1997) A multigene family encoding a diverse array of putative pheromone receptors in mammals. Cell 90, 775–84.

McKenna, M. P., Hekmat-Scafe, D. S., Gaines, P., and Carlson, J. R. (1994) Putative *Drosophila* pheromone-binding proteins expressed in a subregion of the olfactory system. J Biol. Chem. 269, 16340–16347.

McLatchie, L. M., Fraser, N. J., Main, M. J., Wise, A., Brown, J., Thompson, N., Solari, R., Lee, M. G., and Foord, S. M. (1998) RAMPs regulate the transport and ligand specificity of the calcitonin-receptor-like receptor. Nature 393, 333–9.

Merritt, D. J., and Whitington, P. M. (1995) Central projections of sensory neurons in the *Drosophila* embryo correlate with sensory modality, soma position, and proneural gene function. J. Neurosci. 15, 1755–67.

Mitchell, R., McCulloch, D., Lutz, E., Johnson, M., MacKenzie, C., Fennell, M., Fink, G., Zhou, W., and Sealfon, S. C. (1998) Rhodopsin-family receptors associate with small G proteins to activate phospholipase D. Nature 392, 411–4.

Mombaerts, P., Wang, F., Dulac, C., Chao, S. K., Nemes, A., Mendelsohn, M., Edmondson, J., and Axel, R. (1996). Visualizing an olfactory sensory map. Cell 87, 675–686.

Mori, K., Mataga, N., and Imamura, K. (1992) Differential specificities of single mitral cells in rabbit olfactory bulb for a homologous series of fatty acid odor molecules. J. Neurophysiol. 67, 786–789.

Ngai, J., Chess, A., Dowling, M. M., Necles, N., Macagno, E. R., and Axel, R. (1993) Coding of olfactory information: topography of odorant receptor expression in the catfish olfactory epithelium. Cell 72, 667–680.

Parmentier, M., Libert, F., Schurmans, S., Schiffmann, S., Lefort, A., Eggericks, D., Ledent, C., Molleareau, C., Gerard, D., and et al. (1992) Expression of members of the putative olfactory receptor gene family in mammalian germ cells. Nature 355, 453–455.

Pelosi, P. (1994) Odorant-binding proteins. Crit. Rev. Biochem. Mol. Biol. 29, 199–228.

Persson, B., and Argos, P. (1994) Prediction of transmembrane segments in proteins utilizing multiple sequence alignments. J. Mol. Biol. 237, 182–192.

Pikielny, C. W., Hasan, G., Rouyer, F., and Rosbash, M. (1994) Members of a family of Drosophila putative odorant-binding proteins are expressed in different subsets of olfactory hairs. Neuron 12, 35–49.

Ray, K., and Rodrigues, V. (1995) Cellular events during development of the olfactory sense organs in Drosophila melanogaster. Dev. Biol. 167, 426–38.

Reddy, G. V., Gupta, B., Ray, K., and Rodrigues, V. (1997) Development of the Drosophila olfactory sense organs utilizes cell-cell interactions as well as lineage. Development 124, 703–712.

Ressler, K. J., Sullivan, S. L., and Buck, L. B. (1993) A zonal organization of odorant receptor gene expression in the olfactory epithelium. Cell 73, 597–609.

Ressler, K. J., Sullivan, S. L., and Buck, L. B. (1994) Information coding in the olfactory system: evidence for a stereotyped and highly organized epitope map in the olfactory bulb. Cell 79, 1245–1255.

Robertson, H. M. (1998) Two large families of chemoreceptor genes in the nematodes Caenorhabditis elegans and Caenorhabditis briggsae reveal extensive gene duplication, diversification, movement, and intron loss. Genome Res. 8, 449–463.

Robinow, S. and White, K. (1988) The locus elav of Drosophila melanogaster is expressed in neurons at all developmental stages. Dev. Biol. 126, 294–303.

Rodrigues, V. (1988) Spatial coding of olfactory information in the antennal lobe of Drosophila melanogaster. Brain Res. 453, 299–307.

Ryba, N. J., and Tirindelli, R. (1997) A new multigene family of putative pheromone receptors. Neuron 19, 371–379.

Sambrook, J., Fritsch, E. F., and Maniatis, T. (1989). Molecular Cloning: A Laboratory Manual, Second Edition (Cold Spring Harbor, N.Y.: Cold Spring Harbor Laboratory Press).

Schaeren-Wiemers, N., and Gerfin-Moser, A. (1993) A single protocol to detect transcripts of various types and expression levels in neural tissue and cultured cells: in situ hybridization using digoxigenin-labelled cRNA probes. Histochemistry 100, 431–440.

Sengupta, P., Chou, J. H., and Bargmann, C. I. (1996) odr-10 encodes a seven transmembrane domain olfactory receptor required for responses to the odorant diacetyl. Cell 84, 899–909.

Siddiqi, O. (1987) Neurogenetics of olfaction in Drosophila melanogaster. Trends Genet. 3, 137–142.

Siden-Kiamos, I., Saunders, R. D., Spanos, L., Majerus, T., Treanear, J., Savakis, C., Louis, C., Glover, D. M., Ashburner, M., and Kafatos, F. C. (1990) Towards a physical map of the Drosophila melanogaster genome: mapping of cosmid clones within defined genomic divisions. Nucleic Acids Res. 18, 6261–6270.

Singh, R. N., and Nayak, S. (1985) Fine structure and primary sensory projections of sensilla on the maxillary palp of Drosophila melanogaster Meigen (Diptera: Drosophilidae). Int. J. Insect Morphol. Embryol. 14, 291–306.

Stewart, W. B., Kauer, J. S., and Shepherd, G. M. (1979) Functional organization of rat olfactory bulb analyzed by the 2-deoxyglucose method. J. Comp. Neurol. 185, 715–734.

Stocker, R. F. (1994) The organization of the chemosensory system in Drosophila melanogaster: a review. Cell Tissue Res. 275, 3–26.

Stocker, R. F., Lienhard, M. C., Borst, A., and Fischbach, K. F. (1990) Neuronal architecture of the antennal lobe in Drosophila melanogaster. Cell Tissue Res. 262, 9–34.

Stocker, R. F., Singh, R. N., Schorderet, M., and Siddiqi, O. (1983) Projection patterns of different types of antennal sensilla in the antennal glomeruli of Drosophila melanogaster. Cell Tissue Res. 232, 237–248.

Thummel, C. S., Boulet, A. M., and Lipshitz, H. D. (1988) Vectors for Drosophila melanogaster P-element-mediated transformation and tissue culture transfection. Gene 74, 771–784.

Troemel, E. R., Chou, J. H., Dwyer, N. D., Colbert, H. A., and Bargmann, C. I. (1995) Divergent seven transmembrane receptors are candidate chemosensory receptors in C. elegans. Cell 83, 207–218.

Troemel, E. R., Kimmel, B. E., and Bargmann, C. I. (1997) Reprogramming chemotaxis responses: sensory neurons define olfactory preferences in C. elegans. Cell 91, 161–169.

Vassar, R., Chao, S. K., Sitcheran, R., Nuñez, J. M., Vosshall, L. B., and Axel, R. (1994) Topographic organization of sensory projections to the olfactory bulb. Cell 79, 981–991.

Vassar, R., Ngai, J., and Axel, R. (1993) Spatial segregation of odorant receptor expression in the mammalian olfactory epithelium. Cell 74, 309–318.

Venkatesh, S., and Singh, R. N. (1984) Sensilla on the third antennal segment of Drosophila melanogaster Meigen (Diptera: Drosophilidae). Int. J. Insect Morphol. Embryol. 13, 51–63.

Wang, F., Nemes, A., Mendelsohn, M., and Axel, R. (1998) Odorant receptors govern the formation of a precise topographic map. Cell 93, 47–60.

What is claimed is:

1. An isolated nucleic acid encoding a polypeptide present in an insect odorant receptor, wherein the polypeptide comprises consecutive amino acids having a sequence identical to that set forth for DORA45 in SEQ ID NO: 104.

2. A vector which comprises the isolated nucleic acid of claim 1.

3. A method of transforming a cell which comprises transfecting a host cell with the vector of claim 2.

4. A transformed cell produced by the method of claim 3.

5. The transformed cell of claim 4, wherein prior to being transfected with the vector the host cell does not express an insect odorant receptor.

6. The transformed cell of claim 4, wherein prior to being transfected with the vector the host cell does express an insect odorant receptor.

7. The isolated nucleic acid of claim 1, wherein the nucleic acid is DNA or RNA.

8. The isolated nucleic acid of claim 4, wherein the DNA is cDNA, genomic DNA, or synthetic DNA.

9. The isolated nucleic acid of claim 1, wherein the nucleic acid encodes a *Drosophila* odorant receptor.

* * * * *

SEQUENCE LISTING

<160> NUMBER OF SEQ ID NOS: 112

<210> SEQ ID NO 1
<211> LENGTH: 1285
<212> TYPE: DNA
<213> ORGANISM: DROSOPHILA MELANOGASTER DOR62

<400> SEQUENCE: 1

```
atggagaagc aagaggattt caaactgaac acccacagtg ctgtgtacta ccactggcgc    60
gtttgggagc tcactggcct gatgcgtcct ccgggcgttt caagcctgct ttacgtggta   120
tactccatta cggtcaactt ggtggtcacc gtgctgtttc ccttgagctt gctggccagg   180
ctgctgttca ccaccaacat ggccggattg tgcgagaacc tgaccataac tattaccgat   240
attgtggcca atttgaagtt tgcgaatgtg tacatggtga ggaagcagct ccatgagatt   300
cgctctctcc taaggctcat ggacgctaga gcccggctgg tgggcgatcc cgaggagatt   360
tctgccttga ggaaggaagt gaatatcgca cagggcactt ccgcaccctt gccagtatt    420
ttcgtatttg gcactacttt gagttgcgtc cgcgtggtcg ttcgcccgga tcgagagctc   480
ctgtatccgg cctggttcgg cgttgactgg atgcactcca ccagaaacta tgtgctcatc   540
aatatctacc agctcttcgg cttgatagtg caggctatac agaactgcgc tagtgactcc   600
tatccgcctg cgtttctctg cctgctcacg ggtcatatgc gtgctttgga gctgagggtg   660
cggcggattg gctgcaggac ggaaaagtcc aataaaggc agacatatga agcctggcgg    720
gaggaggtgt accaggaact catcgagtgc atccgcgatc tggcgcgggt ccatcggctg   780
agggagatca ttcagcgggt cctttcagtg ccctgcatgg cccagttcgt ctgctccgcc   840
gccgtccagt gtaccgtcgc catgcacttc ctgtacgtag cggatgacca cgaccacacc   900
gccatgatca tctcgattgt atttttctcg gccgtcacct ggaggtgtt tgtaatctgc    960
tatttggggg acaggatgcg gacacagagc gaggcgctgt gcgatgcctt ctacgattgc  1020
aactggatag aacagctgcc caagttcaag cgcgaactgc tcttcaccct ggccaggacg  1080
cagcggcctt ctcttattta cgcaggcaac tacatcgcac tctcgctgga gaccttcgag  1140
caggtcatga ggttcacata ctctgttttc acactcttgc tgagggccaa gtaagaactt  1200
tataatctct ttttggggag aaaaatttta agcacaata gcagaaaaat atatcagata   1260
atataacaaa aaaaaaaaaa aaaaa                                        1285
```

<210> SEQ ID NO 2
<211> LENGTH: 397
<212> TYPE: PRT
<213> ORGANISM: DROSOPHILA MELANOGASTER DOR62

<400> SEQUENCE: 2

```
Met Glu Lys Gln Glu Asp Phe Lys Leu Asn Thr His Ser Ala Val Tyr
1               5                   10                  15

Tyr His Trp Arg Val Trp Glu Leu Thr Gly Leu Met Arg Pro Pro Gly
            20                  25                  30

Val Ser Ser Leu Leu Tyr Val Tyr Ser Ile Thr Val Asn Leu Val
        35                  40                  45

Val Thr Val Leu Phe Pro Leu Ser Leu Ala Arg Leu Leu Phe Thr
    50                  55                  60

Thr Asn Met Ala Gly Leu Cys Glu Asn Leu Thr Ile Thr Ile Thr Asp
65                  70                  75                  80

Ile Val Ala Asn Leu Lys Phe Ala Asn Val Tyr Met Val Arg Lys Gln
                85                  90                  95

Leu His Glu Ile Arg Ser Leu Leu Arg Leu Met Asp Ala Arg Ala Arg
            100                 105                 110

Leu Val Gly Asp Pro Glu Glu Ile Ser Ala Leu Arg Lys Glu Val Asn
        115                 120                 125
```

-continued

```
Ile Ala Gln Gly Thr Phe Arg Thr Phe Ala Ser Ile Phe Val Phe Gly
130                 135                 140

Thr Thr Leu Ser Cys Val Arg Val Val Arg Pro Asp Arg Glu Leu
145                 150                 155                 160

Leu Tyr Pro Ala Trp Phe Gly Val Asp Trp Met His Ser Thr Arg Asn
                165                 170                 175

Tyr Val Leu Ile Asn Ile Tyr Gln Leu Phe Gly Leu Ile Val Gln Ala
            180                 185                 190

Ile Gln Asn Cys Ala Ser Asp Ser Tyr Pro Pro Ala Phe Leu Cys Leu
        195                 200                 205

Leu Thr Gly His Met Arg Ala Leu Glu Leu Arg Val Arg Arg Ile Gly
210                 215                 220

Cys Arg Thr Glu Lys Ser Asn Lys Gly Gln Thr Tyr Glu Ala Trp Arg
225                 230                 235                 240

Glu Glu Val Tyr Gln Glu Leu Ile Glu Cys Ile Arg Asp Leu Ala Arg
                245                 250                 255

Val His Arg Leu Arg Glu Ile Ile Gln Arg Val Leu Ser Val Pro Cys
            260                 265                 270

Met Ala Gln Phe Val Cys Ser Ala Ala Val Gln Cys Thr Val Ala Met
        275                 280                 285

His Phe Leu Tyr Val Ala Asp Asp His Asp His Thr Ala Met Ile Ile
290                 295                 300

Ser Ile Val Phe Phe Ser Ala Val Thr Leu Glu Val Phe Val Ile Cys
305                 310                 315                 320

Tyr Phe Gly Asp Arg Met Arg Thr Gln Ser Glu Ala Leu Cys Asp Ala
                325                 330                 335

Phe Tyr Asp Cys Asn Trp Ile Glu Gln Leu Pro Lys Phe Lys Arg Glu
            340                 345                 350

Leu Leu Phe Thr Leu Ala Arg Thr Gln Arg Pro Ser Leu Ile Tyr Ala
        355                 360                 365

Gly Asn Tyr Ile Ala Leu Ser Leu Glu Thr Phe Glu Gln Val Met Arg
370                 375                 380

Phe Thr Tyr Ser Val Phe Thr Leu Leu Leu Arg Ala Lys
385                 390                 395
```

<210> SEQ ID NO 3
<211> LENGTH: 1499
<212> TYPE: DNA
<213> ORGANISM: DROSOPHILA MELANOGASTER DOR104

<400> SEQUENCE: 3

```
gaattcggca cgagcagtcg atggccagtc ttcagttcca cggcaacgtc gatgcggaca      60
tcaggtatga tattagcctg gatccggcta gggaatcgaa tctcttccgt ctgctaatgg     120
gactccagtt ggcgaatggc acgaagccat cgccgcggtt acccaaatgg tggccaaagc     180
ggctggaaat gattggtaaa gtgctgccca agcctattg ttccatggtg attttcacct      240
ccctgcattt gggtgtcctg ttcacgaaaa ccacactgga tgtcctgccg acggggagc      300 tgcaggccat aacggatgcc ctcaccatga ccataatata cttttttcacg ggctacggca    360 ccatctactg gtgcctgcgc tcccggcgcc tcttggccta catggagcac atgaaccggg     420
agtatcgcca tcattcgctg gccggggtga cctttgtgag tagccatgcg gcctttagga     480
tgtccagaaa cttcacggtg gtgtggataa tgtcctgcct gctgggcgtg atttcctggg     540
gcgtttcgcc actgatgctg gcatccgga tgctgccgct ccaatgttgg tatcccttcg      600
```

```
                                          -continued
acgccctggg tcccggcaca tatacggcgg tctatgctac acaacttttc ggtcagatca      660
tggtgggcat gacctttgga ttcgggggat cactgtttgt caccctgagc ctgctactcc      720
tgggacaatt cgatgtgctc tactgcagcc tgaagaacct ggatgcccat accaagttgc      780
tgggcgggga gtctgtaaat ggcctgagtt cgctgcaaga ggagttgctg ctgggggact      840
cgaagaggga attaaatcag tacgttttgc tccaggagca tccgacggat ctgctgagat      900
tgtcggcagg acgaaaatgt cctgaccaag gaaatgcgtt tcacaacgcc ttggtggaat      960
gcattcgctt gcatcgcttc attctgcact gctcacagga gttggagaat ctattcagtc     1020
catattgtct ggtcaagtca ctgcagatca cctttcagct ttgcctgctg gtctttgtgg     1080
gcgtttcggg tactcgagag gtcctgcgga ttgtcaacca gctacagtac ttgggactga     1140
ccatcttcga gctcctaatg ttcacctatt gtggcgaact cctcagtcgg catagtattc     1200
gatctggcga cgccttttgg agggtgcgt ggtggaagca cgcccatttc atccgccagg      1260
acatcctcat ctttctggtc aatagtagac gtgcagttca cgtgactgcc ggcaagtttt     1320
atgtgatgga tgtgaatcgt ctaagatcgg ttataacgca ggcgttcagc ttcttgactt     1380
tgctgcaaaa gttggctgcc aagaagacgg aatcggagct ctaaactggt accacgcatc     1440
gatatttatt tagcgcatta aaaaaagtc gagtaaaagc aaaaaaaaaa aaaaaaaa       1499

<210> SEQ ID NO 4
<211> LENGTH: 467
<212> TYPE: PRT
<213> ORGANISM: DROSOPHILA MELANOGASTER DOR104

<400> SEQUENCE: 4

Met Ala Ser Leu Gln Phe His Gly Asn Val Asp Ala Asp Ile Arg Tyr
1               5                   10                  15

Asp Ile Ser Leu Asp Pro Ala Arg Glu Ser Asn Leu Phe Arg Leu Leu
            20                  25                  30

Met Gly Leu Gln Leu Ala Asn Gly Thr Lys Pro Ser Pro Arg Leu Pro
        35                  40                  45

Lys Trp Trp Pro Lys Arg Leu Glu Met Ile Gly Lys Val Leu Pro Lys
    50                  55                  60

Ala Tyr Cys Ser Met Val Ile Phe Thr Ser Leu His Leu Gly Val Leu
65                  70                  75                  80

Phe Thr Lys Thr Thr Leu Asp Val Leu Pro Thr Gly Glu Leu Gln Ala
                85                  90                  95

Ile Thr Asp Ala Leu Thr Met Thr Ile Ile Tyr Phe Phe Thr Gly Tyr
            100                 105                 110

Gly Thr Ile Tyr Trp Cys Leu Arg Ser Arg Arg Leu Leu Ala Tyr Met
        115                 120                 125

Glu His Met Asn Arg Glu Tyr Arg His His Ser Leu Ala Gly Val Thr
    130                 135                 140

Phe Val Ser Ser His Ala Ala Phe Arg Met Ser Arg Asn Phe Thr Val
145                 150                 155                 160

Val Trp Ile Met Ser Cys Leu Leu Gly Val Ile Ser Trp Gly Val Ser
                165                 170                 175

Pro Leu Met Leu Gly Ile Arg Met Leu Pro Leu Gln Cys Trp Tyr Pro
            180                 185                 190

Phe Asp Ala Leu Gly Pro Gly Thr Tyr Thr Ala Val Tyr Ala Thr Gln
        195                 200                 205

Leu Phe Gly Gln Ile Met Val Gly Met Thr Phe Gly Phe Gly Gly Ser
    210                 215                 220
```

```
Leu Phe Val Thr Leu Ser Leu Leu Leu Gly Gln Phe Asp Val Leu
225                 230                 235                 240

Tyr Cys Ser Leu Lys Asn Leu Asp Ala His Thr Lys Leu Leu Gly Gly
                245                 250                 255

Glu Ser Val Asn Gly Leu Ser Ser Leu Gln Glu Leu Leu Leu Gly
            260                 265                 270

Asp Ser Lys Arg Glu Leu Asn Gln Tyr Val Leu Leu Gln Glu His Pro
        275                 280                 285

Thr Asp Leu Leu Arg Leu Ser Ala Gly Arg Lys Cys Pro Asp Gln Gly
    290                 295                 300

Asn Ala Phe His Asn Ala Leu Val Glu Cys Ile Arg Leu His Arg Phe
305                 310                 315                 320

Ile Leu His Cys Ser Gln Glu Leu Glu Asn Leu Phe Ser Pro Tyr Cys
                325                 330                 335

Leu Val Lys Ser Leu Gln Ile Thr Phe Gln Leu Cys Leu Leu Val Phe
            340                 345                 350

Val Gly Val Ser Gly Thr Arg Glu Val Leu Arg Ile Val Asn Gln Leu
        355                 360                 365

Gln Tyr Leu Gly Leu Thr Ile Phe Glu Leu Leu Met Phe Thr Tyr Cys
    370                 375                 380

Gly Glu Leu Leu Ser Arg His Ser Ile Arg Ser Gly Asp Ala Phe Trp
385                 390                 395                 400

Arg Gly Ala Trp Trp Lys His Ala His Phe Ile Arg Gln Asp Ile Leu
                405                 410                 415

Ile Phe Leu Val Asn Ser Arg Arg Ala Val His Val Thr Ala Gly Lys
            420                 425                 430

Phe Tyr Val Met Asp Val Asn Arg Leu Arg Ser Val Ile Thr Gln Ala
        435                 440                 445

Phe Ser Phe Leu Thr Leu Leu Gln Lys Leu Ala Ala Lys Lys Thr Glu
    450                 455                 460

Ser Glu Leu
465

<210> SEQ ID NO 5
<211> LENGTH: 1556
<212> TYPE: DNA
<213> ORGANISM: DROSOPHILA MELANOGASTER DOR87

<400> SEQUENCE: 5
ggcacgaggc ttatagaaag tgccgagcaa tgacaatcga ggatatcggc ctggtgggca      60
tcaacgtgcg gatgtggcga cacttggccg tgctgtaccc cactccgggc tccagctggc     120
gcaagttcgc cttcgtgctg ccggtgactg cgatgaatct gatgcagttc gtctacctgc     180
tgcggatgtg gggcgacctg cccgccttca ttctgaacat gttcttcttc tcggccattt     240
tcaacgccct gatgcgcacg tggctggtca taatcaagcg gcgccagttc gaggagtttc     300
tcggccaact ggccactctg ttccattcga ttctcgactc caccgacgag tgggggcgtg     360
gcatcctgcg gagggcggaa cgggaggctc ggaacctggc catccttaat ttgagtgcct     420
ccttcctgga cattgtcggt gctctggtat cgccgctttt cagggaggag agagctcatc     480
ccttcggcgt agctctacca ggagtgagca tgaccagttc acccgtctac gaggttatct     540
acttggccca actgcctacg cccctgctgc tgtccatgat gtacatgcct tcgtcagcc      600 tttttgccgg cctggccatc tttgggaagg ccatgctgca gatcctggta cacaggctgg     660
```

```
gccagattgg cggagaagag cagtcggagg aggagcgctt ccaaaggctg gcctcctgca      720
ttgcgtacca cacgcaggtg atgcgctatg tgtggcagct caacaaactg gtggccaaca      780
ttgtggcggt ggaagcaatt attttggct cgataatctg ctcactgctc ttctgtctga       840
atattataac ctcacccacc caggtgatct cgatagtgat gtacattctg accatgctgt      900
acgttctctt cacctactac aatcgggcca atgaaatatg cctcgagaac aaccgggtgg      960
cggaggctgt ttacaatgtg ccctggtacg aggcaggaac tcggtttcgc aaaaccctcc     1020
tgatcttctt gatgcaaaca caacacccga tggagataag agtcggcaac gtttacccca     1080
tgacattggc catgttccag agtctgttga atgcgtccta ctcctacttt accatgctgc     1140
gtggcgtcac cggcaaatga gctgaaagac cgaaaaaacc ggagtatccc cttccatatt     1200 cccctgctc ctttatttc ctttcctttt ccctttccgt tttcccattc gcttttccag        1260
caatccgggt aatgcaaaaa gttgttgctg ctgtggtcc tggctgcttg tttggcattt      1320
gcatatgctt gtcgtttgaa aggatttaat cggactgctg cacggagtc ggcatcctgg      1380 ctcctggatc ctggcatgca aatagttggc ttcttagatt gttacacaaa atagattgta     1440
gattgcagct gaatgttgtg cttggaataa agtcaaaagg atgtggagtc ggcccaaggc     1500
tctgcccatt ctgtttgctc gggatgcccg aaagtatgaa aaaaaaaaaa aaaaaa         1556
```

<210> SEQ ID NO 6
<211> LENGTH: 376
<212> TYPE: PRT
<213> ORGANISM: DROSOPHILA MELANOGASTER DOR87

<400> SEQUENCE: 6

```
Met Thr Ile Glu Asp Ile Gly Leu Val Gly Ile Asn Val Arg Met Trp
1               5                   10                  15

Arg His Leu Ala Val Leu Tyr Pro Thr Pro Gly Ser Ser Trp Arg Lys
            20                  25                  30

Phe Ala Phe Val Leu Pro Val Thr Ala Met Asn Leu Met Gln Phe Val
        35                  40                  45

Tyr Leu Leu Arg Met Trp Gly Asp Leu Pro Ala Phe Ile Leu Asn Met
    50                  55                  60

Phe Phe Phe Ser Ala Ile Phe Asn Ala Leu Met Arg Thr Trp Leu Val
65                  70                  75                  80

Ile Ile Lys Arg Arg Gln Phe Glu Glu Phe Leu Gly Gln Leu Ala Thr
                85                  90                  95

Leu Phe His Ser Ile Leu Asp Ser Thr Asp Glu Trp Gly Arg Gly Ile
            100                 105                 110

Leu Arg Arg Ala Glu Arg Glu Ala Arg Asn Leu Ala Ile Leu Asn Leu
        115                 120                 125

Ser Ala Ser Phe Leu Asp Ile Val Gly Ala Leu Val Ser Pro Leu Phe
    130                 135                 140

Arg Glu Glu Arg Ala His Pro Phe Gly Val Ala Leu Pro Gly Val Ser
145                 150                 155                 160

Met Thr Ser Ser Pro Val Tyr Glu Val Ile Tyr Leu Ala Gln Leu Pro
                165                 170                 175

Thr Pro Leu Leu Leu Ser Met Met Tyr Met Pro Phe Val Ser Leu Phe
            180                 185                 190

Ala Gly Leu Ala Ile Phe Gly Lys Ala Met Leu Gln Ile Leu Val His
        195                 200                 205

Arg Leu Gly Gln Ile Gly Gly Glu Glu Gln Ser Glu Glu Glu Arg Phe
    210                 215                 220
```

```
Gln Arg Leu Ala Ser Cys Ile Ala Tyr His Thr Gln Val Met Arg Tyr
225                 230                 235                 240

Val Trp Gln Leu Asn Lys Leu Val Ala Asn Ile Val Ala Val Glu Ala
                245                 250                 255

Ile Ile Phe Gly Ser Ile Ile Cys Ser Leu Leu Phe Cys Leu Asn Ile
            260                 265                 270

Ile Thr Ser Pro Thr Gln Val Ile Ser Ile Val Met Tyr Ile Leu Thr
        275                 280                 285

Met Leu Tyr Val Leu Phe Thr Tyr Tyr Asn Arg Ala Asn Glu Ile Cys
    290                 295                 300

Leu Glu Asn Asn Arg Val Ala Glu Ala Val Tyr Asn Val Pro Trp Tyr
305                 310                 315                 320

Glu Ala Gly Thr Arg Phe Arg Lys Thr Leu Leu Ile Phe Leu Met Gln
                325                 330                 335

Thr Gln His Pro Met Glu Ile Arg Val Gly Asn Val Tyr Pro Met Thr
            340                 345                 350

Leu Ala Met Phe Gln Ser Leu Leu Asn Ala Ser Tyr Ser Tyr Phe Thr
        355                 360                 365

Met Leu Arg Gly Val Thr Gly Lys
    370                 375

<210> SEQ ID NO 7
<211> LENGTH: 1338
<212> TYPE: DNA
<213> ORGANISM: DROSOPHILA MELANOGASTER DOR53

<400> SEQUENCE: 7
tcaaacaaag ccacggacaa gatgttaagc aagttttttc cccacataaa agaaaagcca      60
ttgagcgagc gggttaagtc ccgagatgcc ttcatttact tggatcgggt gatgtggtcc     120
tttggctgga cagagcctga aaacaaaagg tggatccttc cttataaact gtggttagcg     180
ttcgtgaaca tagtaatgct catccttctg ccgatctcga taagcatcga gtacctccac     240
cgatttaaaa ccttctcggc gggggagttc cttagttccc tcgagattgg agtcaacatg     300
tacggaagct cttttaagtg cgccttcacc ttgattggat tcaagaaaag acaggaagct     360
aaggttttac tggatcagct ggacaagaga tgccttagcg ataaggagag gtccactgtt     420
catcgctatg tcgccatggg aaacttttc gatattttgt atcacatttt ttactccacc     480
ttcgtggtaa tgaacttccc gtattttctg cttgagagac gccatgcttg gcgcatgtac     540
tttccatata tcgattccga cgaacagttt tacatctcca gcatcgccga gtgttttctg     600
atgacggagg ccatctacat ggatctctgt acggacgtgt gtcccttgat ctccatgctt     660
atggctcgat gccacatcag cctcctgaaa cagcgactga gaaatctccg atcgaagcca     720
ggaaggaccg aagatgagta cttggaggag ctcaccgagt gcattcggga tcatcgattg     780
ctattggact atgttgacgc attgcgaccc gtcttttcgg aaccatttt tgtgcagttc     840 ctcctgatcg gtactgtact gggtctctca atgataaatc taatgttctt ctcgacattt     900
tggactggtg tcgccacttg cctttttatg ttcgacgtgt ccatggagac gttcccttt      960 tgctatttgt gcaacatgat tatcgatgac tgccaggaaa tgtccaattg cctcttttcaa    1020 tcggactgga cctctgccga tcgtcgctac aaatccactt tggtatactt tcttcacaat    1080
cttcagcaac ccattactct cacggctggt ggagtgtttc ctatttccat gcaaacaaat    1140
ttggctatgg tgaagctggc attttctgtg gttacggtaa ttaagcaatt taacttggcc    1200
```

-continued

```
gaaaggtttc aataagttga gagggacgag ctctgctact attatattat atattatatt    1260
atattatata tatattattt tatattatat attgctgtac cctaataaat atttagtaat    1320
aaaaaaaaaa aaaaaaaa                                                  1338
```

<210> SEQ ID NO 8
<211> LENGTH: 397
<212> TYPE: PRT
<213> ORGANISM: DROSOPHILA MELANOGASTER DOR53

<400> SEQUENCE: 8

```
Met Leu Ser Lys Phe Phe Pro His Ile Lys Glu Lys Pro Leu Ser Glu
1               5                   10                  15

Arg Val Lys Ser Arg Asp Ala Phe Ile Tyr Leu Asp Arg Val Met Trp
            20                  25                  30

Ser Phe Gly Trp Thr Glu Pro Glu Asn Lys Arg Trp Ile Leu Pro Tyr
        35                  40                  45

Lys Leu Trp Leu Ala Phe Val Asn Ile Val Met Leu Ile Leu Leu Pro
    50                  55                  60

Ile Ser Ile Ser Ile Glu Tyr Leu His Arg Phe Lys Thr Phe Ser Ala
65                  70                  75                  80

Gly Glu Phe Leu Ser Ser Leu Glu Ile Gly Val Asn Met Tyr Gly Ser
                85                  90                  95

Ser Phe Lys Cys Ala Phe Thr Leu Ile Gly Phe Lys Lys Arg Gln Glu
            100                 105                 110

Ala Lys Val Leu Leu Asp Gln Leu Asp Lys Arg Cys Leu Ser Asp Lys
        115                 120                 125

Glu Arg Ser Thr Val His Arg Tyr Val Ala Met Gly Asn Phe Phe Asp
    130                 135                 140

Ile Leu Tyr His Ile Phe Tyr Ser Thr Phe Val Val Met Asn Phe Pro
145                 150                 155                 160

Tyr Phe Leu Leu Glu Arg Arg His Ala Trp Arg Met Tyr Phe Pro Tyr
                165                 170                 175

Ile Asp Ser Asp Glu Gln Phe Tyr Ile Ser Ser Ile Ala Glu Cys Phe
            180                 185                 190

Leu Met Thr Glu Ala Ile Tyr Met Asp Leu Cys Thr Asp Val Cys Pro
        195                 200                 205

Leu Ile Ser Met Leu Met Ala Arg Cys His Ile Ser Leu Leu Lys Gln
    210                 215                 220

Arg Leu Arg Asn Leu Arg Ser Lys Pro Gly Arg Thr Glu Asp Glu Tyr
225                 230                 235                 240

Leu Glu Glu Leu Thr Glu Cys Ile Arg Asp His Arg Leu Leu Leu Asp
                245                 250                 255

Tyr Val Asp Ala Leu Arg Pro Val Phe Ser Gly Thr Ile Phe Val Gln
            260                 265                 270

Phe Leu Leu Ile Gly Thr Val Leu Gly Leu Ser Met Ile Asn Leu Met
        275                 280                 285

Phe Phe Ser Thr Phe Trp Thr Gly Val Ala Thr Cys Leu Phe Met Phe
    290                 295                 300

Asp Val Ser Met Glu Thr Phe Pro Phe Cys Tyr Leu Cys Asn Met Ile
305                 310                 315                 320

Ile Asp Asp Cys Gln Glu Met Ser Asn Cys Leu Phe Gln Ser Asp Trp
                325                 330                 335

Thr Ser Ala Asp Arg Arg Tyr Lys Ser Thr Leu Val Tyr Phe Leu His
            340                 345                 350
```

Asn Leu Gln Gln Pro Ile Thr Leu Thr Ala Gly Gly Val Phe Pro Ile
        355                 360                 365

Ser Met Gln Thr Asn Leu Ala Met Val Lys Leu Ala Phe Ser Val Val
        370                 375                 380

Thr Val Ile Lys Gln Phe Asn Leu Ala Glu Arg Phe Gln
385                 390                 395

<210> SEQ ID NO 9
<211> LENGTH: 1321
<212> TYPE: DNA
<213> ORGANISM: DROSOPHILA MELANOGASTER DOR67

<400> SEQUENCE: 9

| | | | | | |
|---|---|---|---|---|---|
| ggcacgagga | aatgttaagc | cagttctttc | cccacattaa | agaaaagcca | ttgagcgagc | 60 |
| gggttaagtc | ccgagatgcc | ttcgtttact | tagatcgggt | gatgtggtcc | tttggctgga | 120 |
| cagtgcctga | aaacaaaagg | tgggatctac | attacaaact | gtggtcaact | ttcgtgacat | 180 |
| tggtgatatt | tatccttctg | ccgatatcgg | taagcgttga | gtatattcag | cggttcaaga | 240 |
| ccttctcggc | gggtgagttt | cttagctcaa | tccagattgg | cgttaacatg | tacggaagca | 300 |
| gcttttaaaag | ttatttgacc | atgatgggat | ataagaagag | acaggaggct | aagatgtcac | 360 |
| tggatgagct | ggacaagaga | tgcgtttgtg | atgaggagag | gaccattgta | catcgacatg | 420 |
| tcgccctggg | aaacttttgc | tatattttct | atcacattgc | gtacactagc | tttttgattt | 480 |
| caaactttt | gtcatttata | atgaagagaa | tccatgcctg | gcgcatgtac | tttccctacg | 540 |
| tcgaccccga | aaagcaattt | tacatctcta | gcatcgccga | agtcattctt | agggggtggg | 600 |
| ccgtcttcat | ggatctctgc | acggatgtgt | gtcctttgat | ctccatggta | atagcacgat | 660 |
| gccacatcac | ccttctgaaa | cagcgcctgc | gaaatctacg | atcggaacca | ggaaggacgg | 720 |
| aagatgagta | cttgaaggag | ctcgccgact | gcgttcgaga | tcaccgcttg | atattggact | 780 |
| atgtcgacgc | attgcgatcc | gtcttttcgg | ggacaatttt | tgtgcagttc | ctcttgatcg | 840 |
| gtattgtact | gggtctgtca | atgataaata | taatgttttt | ctcaacactt | tcgactggtg | 900 |
| tcgccgttgt | cctttttatg | tcctgcgtat | ctatgcagac | gttcccctt | tgctatttgt | 960 |
| gtaacatgat | tatggatgac | tgccaagaga | tggccgactc | ccttttttcaa | tcggactgga | 1020 |
| catctgccga | tcgtcgctac | aaatccactt | tggtatactt | tcttcacaat | cttcagcagc | 1080 |
| ccattattct | tacggctggt | ggagtctttc | ctatttccat | gcaaacaaat | ttaaatatgg | 1140 |
| tgaagctggc | ctttactgtg | gttacaatag | tgaaacaatt | taacttggca | gaaaagtttc | 1200 |
| aataagttaa | gatatgcaag | ctctgctatt | ataaacctac | actcgagaaa | atatttcttc | 1260 |
| acattaataa | accttcagta | cttactgctt | gtggcgcccc | cggaaaaaaa | aaaaaaaaaa | 1320 |
| a | | | | | | 1321 |

<210> SEQ ID NO 10
<211> LENGTH: 397
<212> TYPE: PRT
<213> ORGANISM: DROSOPHILA MELANOGASTER DOR67

<400> SEQUENCE: 10

Met Leu Ser Gln Phe Phe Pro His Ile Lys Glu Lys Pro Leu Ser Glu
1               5                   10                  15

Arg Val Lys Ser Arg Asp Ala Phe Val Tyr Leu Asp Arg Val Met Trp
            20                  25                  30

Ser Phe Gly Trp Thr Val Pro Glu Asn Lys Arg Trp Asp Leu His Tyr

|    |    |    |    | 35 |    |    |    | 40 |    |    |    | 45 |    |    |
|----|----|----|----|----|----|----|----|----|----|----|----|----|----|----|

Lys Leu Trp Ser Thr Phe Val Thr Leu Val Ile Phe Ile Leu Leu Pro
50                   55                  60

Ile Ser Val Ser Val Glu Tyr Ile Gln Arg Phe Lys Thr Phe Ser Ala
65                   70                  75                  80

Gly Glu Phe Leu Ser Ser Ile Gln Ile Gly Val Asn Met Tyr Gly Ser
                85                  90                  95

Ser Phe Lys Ser Tyr Leu Thr Met Met Gly Tyr Lys Lys Arg Gln Glu
                100                 105                 110

Ala Lys Met Ser Leu Asp Glu Leu Asp Lys Arg Cys Val Cys Asp Glu
                115                 120                 125

Glu Arg Thr Ile Val His Arg His Val Ala Leu Gly Asn Phe Cys Tyr
130                 135                 140

Ile Phe Tyr His Ile Ala Tyr Thr Ser Phe Leu Ile Ser Asn Phe Leu
145                 150                 155                 160

Ser Phe Ile Met Lys Arg Ile His Ala Trp Arg Met Tyr Phe Pro Tyr
                165                 170                 175

Val Asp Pro Glu Lys Gln Phe Tyr Ile Ser Ser Ile Ala Glu Val Ile
                180                 185                 190

Leu Arg Gly Trp Ala Val Phe Met Asp Leu Cys Thr Asp Val Cys Pro
                195                 200                 205

Leu Ile Ser Met Val Ile Ala Arg Cys His Ile Thr Leu Leu Lys Gln
210                 215                 220

Arg Leu Arg Asn Leu Arg Ser Glu Pro Gly Arg Thr Glu Asp Glu Tyr
225                 230                 235                 240

Leu Lys Glu Leu Ala Asp Cys Val Arg Asp His Arg Leu Ile Leu Asp
                245                 250                 255

Tyr Val Asp Ala Leu Arg Ser Val Phe Ser Gly Thr Ile Phe Val Gln
                260                 265                 270

Phe Leu Leu Ile Gly Ile Val Leu Gly Leu Ser Met Ile Asn Ile Met
                275                 280                 285

Phe Phe Ser Thr Leu Ser Thr Gly Val Ala Val Val Leu Phe Met Ser
290                 295                 300

Cys Val Ser Met Gln Thr Phe Pro Phe Cys Tyr Leu Cys Asn Met Ile
305                 310                 315                 320

Met Asp Asp Cys Gln Glu Met Ala Asp Ser Leu Phe Gln Ser Asp Trp
                325                 330                 335

Thr Ser Ala Asp Arg Arg Tyr Lys Ser Thr Leu Val Tyr Phe Leu His
                340                 345                 350

Asn Leu Gln Gln Pro Ile Ile Leu Thr Ala Gly Gly Val Phe Pro Ile
                355                 360                 365

Ser Met Gln Thr Asn Leu Asn Met Val Lys Leu Ala Phe Thr Val Val
370                 375                 380

Thr Ile Val Lys Gln Phe Asn Leu Ala Glu Lys Phe Gln
385                 390                 395

<210> SEQ ID NO 11
<211> LENGTH: 1308
<212> TYPE: DNA
<213> ORGANISM: DROSOPHILA MELANOGASTER DOR64

<400> SEQUENCE: 11
ggcacgagcc aagaattcaa aatgaaactc agcgaaaccc taaaaatcga ctatttcga        60 gtccagttga atgcctggcg aatttgtggt gccttggatc tcagcgaggg taggtactgg      120

-continued

```
agttggtcga tgctattgtg catcttggtg tacctgccga cacccatgct actgagagga    180
gtatacagtt tcgaggatcc ggtggaaaat aatttcagct tgagcctgac ggtcacatcg    240
ctgtccaatc tcatgaagtt ctgcatgtac gtggcccaac taacaaagat ggtcgaggtc    300
cagagtctta ttggtcagct ggatgcccgg gtttctggcg agagccagtc tgagcgtcat    360
agaaatatga ccgagcacct gctaaggatg tccaagctgt tccagatcac ctacgctgta    420
gtcttcatca ttgctgcagt tcccttcgtt ttcgaaactg agctaagctt acccatgccc    480
atgtggtttc ccttcgactg gaagaactcg atggtggcct catcggagc tctggttttc    540
caggagattg gctatgtctt tcaaattatg caatgctttg cagctgactc gtttcccccg    600
ctcgtactgt acctgatctc cgagcaatgt caattgctga tcctgagaat ctctgaaatc    660
ggatatggtt acaagactct ggaggagaac gaacaggatc tggtcaactg catcagggat    720
caaaacgcgc tgtatagatt actcgatgtg accaagagtc tcgtttcgta tcccatgatg    780
gtgcagttta tggttattgg catcaacatc gccatcaccc tatttgtcct gatattttac    840
gtggagacct tgtacgatcg catctattat ctttgctttc tcttgggcat caccgtgcag    900
acatatccat tgtgctacta tggaaccatg gtgcaggaga gttttgctga gcttcactat    960
gcggtattct gcagcaactg ggtggatcaa agtgccagct atcgtgggca catgctcatc   1020
ctggcggagc gcactaagcg gatgcagctt ctcctcgccg gcaacctggt gcccatccac   1080
ctgagcacct acgtgccctg ttggaaggga gcctactcct tcttcaccct gatggccgat   1140
cgagatggcc tgggttctta gtagcccagt catttcactc acattctaca tcaagtagta   1200
ctaccactga acacgaacac gaatatttca aagtaaaca cataatattc acaatagtgt   1260
atcactttaa taaatttttt ggttaccatg aaaaaaaaaa aaaaaaa            1308
```

<210> SEQ ID NO 12
<211> LENGTH: 379
<212> TYPE: PRT
<213> ORGANISM: DROSOPHILA MELANOGASTER DOR64

<400> SEQUENCE: 12

```
Met Lys Leu Ser Glu Thr Leu Lys Ile Asp Tyr Phe Arg Val Gln Leu
1               5                   10                  15

Asn Ala Trp Arg Ile Cys Gly Ala Leu Asp Leu Ser Glu Gly Arg Tyr
            20                  25                  30

Trp Ser Trp Ser Met Leu Leu Cys Ile Leu Val Tyr Leu Pro Thr Pro
        35                  40                  45

Met Leu Leu Arg Gly Val Tyr Ser Phe Glu Asp Pro Val Glu Asn Asn
    50                  55                  60

Phe Ser Leu Ser Leu Thr Val Thr Ser Leu Ser Asn Leu Met Lys Phe
65                  70                  75                  80

Cys Met Tyr Val Ala Gln Leu Thr Lys Met Val Glu Val Gln Ser Leu
                85                  90                  95

Ile Gly Gln Leu Asp Ala Arg Val Ser Gly Glu Ser Gln Ser Glu Arg
            100                 105                 110

His Arg Asn Met Thr Glu His Leu Leu Arg Met Ser Lys Leu Phe Gln
        115                 120                 125

Ile Thr Tyr Ala Val Val Phe Ile Ile Ala Ala Val Pro Phe Val Phe
    130                 135                 140

Glu Thr Glu Leu Ser Leu Pro Met Pro Met Trp Phe Pro Phe Asp Trp
145                 150                 155                 160
```

```
Lys Asn Ser Met Val Ala Tyr Ile Gly Ala Leu Val Phe Gln Glu Ile
                165                 170                 175
Gly Tyr Val Phe Gln Ile Met Gln Cys Phe Ala Ala Asp Ser Phe Pro
            180                 185                 190
Pro Leu Val Leu Tyr Leu Ile Ser Glu Gln Cys Gln Leu Leu Ile Leu
        195                 200                 205
Arg Ile Ser Glu Ile Gly Tyr Gly Tyr Lys Thr Leu Glu Glu Asn Glu
    210                 215                 220
Gln Asp Leu Val Asn Cys Ile Arg Asp Gln Asn Ala Leu Tyr Arg Leu
225                 230                 235                 240
Leu Asp Val Thr Lys Ser Leu Val Ser Tyr Pro Met Met Val Gln Phe
                245                 250                 255
Met Val Ile Gly Ile Asn Ile Ala Ile Thr Leu Phe Val Leu Ile Phe
                260                 265                 270
Tyr Val Glu Thr Leu Tyr Asp Arg Ile Tyr Tyr Leu Cys Phe Leu Leu
            275                 280                 285
Gly Ile Thr Val Gln Thr Tyr Pro Leu Cys Tyr Tyr Gly Thr Met Val
        290                 295                 300
Gln Glu Ser Phe Ala Glu Leu His Tyr Ala Val Phe Cys Ser Asn Trp
305                 310                 315                 320
Val Asp Gln Ser Ala Ser Tyr Arg Gly His Met Leu Ile Leu Ala Glu
                325                 330                 335
Arg Thr Lys Arg Met Gln Leu Leu Ala Gly Asn Leu Val Pro Ile
                340                 345                 350
His Leu Ser Thr Tyr Val Ala Cys Trp Lys Gly Ala Tyr Ser Phe Phe
            355                 360                 365
Thr Leu Met Ala Asp Arg Asp Gly Leu Gly Ser
    370                 375

<210> SEQ ID NO 13
<211> LENGTH: 1152
<212> TYPE: DNA
<213> ORGANISM: DROSOPHILA MELANOGASTER DOR71g

<400> SEQUENCE: 13
atggtcatta tcgacagtct tagttttat cgtccattct ggatctgcat gcgattgctg      60
gtaccgactt tcttcaagga ttcctcacgt cctgtccagc tgtacgtggt gttgctgcac    120
atcctggtca ccttgtggtt tccactgcat ctgctgctgc atcttctgct acttccatct    180
accgctgagt tctttaagaa cctgaccatg tctctgactt gtgtggcctg cagtctgaag    240
catgtggccc acttgtatca cttgccgcag attgtggaaa tcgaatcact gatcgagcaa    300
ttagacacat ttattgccag cgaacaggag catcgttact atcgggatca cgtacattgc    360
catgctaggc gctttacaag atgtctctat attagctttg gcatgatcta tgcgcttttc    420
ctgttcggcg tcttcgttca ggttattagc ggaaattggg aacttctcta ccagcctat    480
ttcccattcg acttggagag caatcgcttt ctcggcgcag tagccttggg ctatcaggta    540
ttcagcatgt tagttgaagg cttccagggg ctgggcaacg ataccctatac cccactgacc    600
ctatgccttc tggccggaca tgtccatttg tggtccatac gaatgggtca actgggatac    660
ttcgatgacg agacggtggt gaatcatcag cgtttgctgg attacattga gcagcataaa    720
ctcttggtgc ggttccacaa cctggtgagc cggaccatca gcgaagtgca actggtgcag    780
ctgggcggat gtggagccac tctgtgcatc attgtctcct acatgctctt ctttgtgggc    840
gacacaatct cgctggtcta ctacttggtg ttctttggag tggtctgcgt gcagctcttt    900
```

-continued

```
cccagctgct attttgccag cgaagtagcc gaggagttgg aacggctgcc atatgcgatc    960
ttctccagca gatggtacga tcaatcgcgg gatcatcgat tcgatttgct catctttaca   1020
caattaacac tgggaaaccg ggggtggatc atcaaggcag aggtcttat cgagctgaat    1080 ttgaatgcct ttttcgccac cctgaagatg gcctattccc tttttgcagt tgtggtgcgg   1140
gcaaagggta ta                                                       1152
```

<210> SEQ ID NO 14
<211> LENGTH: 390
<212> TYPE: PRT
<213> ORGANISM: DROSOPHILA MELANOGASTER DOR71g

<400> SEQUENCE: 14

```
Met Val Ile Ile Asp Ser Leu Ser Phe Tyr Arg Pro Phe Trp Ile Cys
1               5                   10                  15

Met Arg Leu Leu Val Pro Thr Phe Phe Lys Asp Ser Ser Arg Pro Val
            20                  25                  30

Gln Leu Tyr Val Val Leu Leu His Ile Leu Val Thr Leu Trp Phe Pro
        35                  40                  45

Leu His Leu Leu Leu His Leu Leu Leu Pro Ser Thr Ala Glu Phe
    50                  55                  60

Phe Lys Asn Leu Thr Met Ser Leu Thr Cys Val Ala Cys Ser Leu Lys
65                  70                  75                  80

His Val Ala His Leu Tyr His Leu Pro Gln Ile Val Glu Ile Glu Ser
                85                  90                  95

Leu Ile Glu Gln Leu Asp Thr Phe Ile Ala Ser Glu Gln Glu His Arg
            100                 105                 110

Tyr Tyr Arg Asp His Val His Cys His Ala Arg Arg Phe Thr Arg Cys
        115                 120                 125

Leu Tyr Ile Ser Phe Gly Met Ile Tyr Ala Leu Phe Leu Phe Gly Val
    130                 135                 140

Phe Val Gln Val Ile Ser Gly Asn Trp Glu Leu Leu Tyr Pro Ala Tyr
145                 150                 155                 160

Phe Pro Phe Asp Leu Glu Ser Asn Arg Phe Leu Gly Ala Val Ala Leu
                165                 170                 175

Gly Tyr Gln Val Phe Ser Met Leu Val Glu Gly Phe Gln Gly Leu Gly
            180                 185                 190

Asn Asp Thr Tyr Thr Pro Leu Thr Leu Cys Leu Leu Ala Gly His Val
        195                 200                 205

His Leu Trp Ser Ile Arg Met Gly Gln Leu Gly Tyr Phe Asp Asp Glu
    210                 215                 220

Thr Val Val Asn His Gln Arg Leu Leu Asp Tyr Ile Glu Gln His Lys
225                 230                 235                 240

Leu Leu Val Arg Phe His Asn Leu Val Ser Arg Thr Ile Ser Glu Val
                245                 250                 255

Gln Leu Val Gln Leu Gly Gly Cys Gly Ala Thr Leu Cys Ile Ile Val
            260                 265                 270

Ser Tyr Met Leu Phe Phe Val Gly Asp Thr Ile Ser Leu Val Tyr Tyr
        275                 280                 285

Leu Val Phe Phe Gly Val Val Cys Val Gln Leu Phe Pro Ser Cys Tyr
    290                 295                 300

Phe Ala Ser Glu Val Ala Glu Glu Leu Glu Arg Leu Pro Tyr Ala Ile
305                 310                 315                 320
```

```
Phe Ser Ser Arg Trp Tyr Asp Gln Ser Arg Asp His Arg Phe Asp Leu
            325                 330                 335

Leu Ile Phe Thr Gln Leu Thr Leu Gly Asn Arg Gly Trp Ile Ile Lys
        340                 345                 350

Ala Gly Gly Leu Ile Glu Leu Asn Leu Asn Ala Phe Phe Ala Thr Leu
            355                 360                 365

Lys Met Ala Tyr Ser Leu Phe Ala Val Val His Arg Glu Thr Gly Asn
    370                 375                 380

Pro Leu Gln Arg Glu His
385                 390

<210> SEQ ID NO 15
<211> LENGTH: 1137
<212> TYPE: DNA
<213> ORGANISM: DROSOPHILA MELANOGASTER DOR72g

<400> SEQUENCE: 15
atggacttaa aaccgcgagt cattcgaagt gaagatatct acagaaccta ttggttatat      60
tggcatcttt tgggcctgga aagcaatttc tttctgaatc gcttgttgga tttggtgatt     120
acaattttcg taaccatttg gtatccaatt cacctgattc tgggactgtt tatggaaaga     180
tctttggggg atgtctgcaa gggtctacca attacggcag catgcttttt cgccagcttt     240
aaatttattt gttttcgctt caagctatct gaaattaaag aaatcgaaat attatttaaa     300
gagctggatc agcgagcttt aagtcgagag gaatgcgagt ttttcaatca aaatacgaga     360
cgtgaggcga atttcatttg gaaaagtttc attgtggcct atggactgtc gaatatctcg     420
gctattgcat cagttctttt cggcggtgga cataagctat tatatcccgc ctggtttcca     480
tacgatgtgc aggccacgga actaatattt tggctaagtg taacatacca aattgccgga     540
gtaagtttgg ccatacttca gaatttggcc aatgattcct atccaccgat gacattttgc     600
gtggttgccg tcatgtaag acttttggcg atgcgcttga gtagaattgg ccaaggtcca     660
gaggaaacaa tatacttaac cggaaagcaa ttaatcgaaa gcatcgagga tcaccgaaaa     720
ctaatgaaga tagtggaatt actgcgcagc accatgaata tttcgcagct cggccagttt     780
atttcaagtg gtgttaatat ttccataaca ctagtcaaca ttctcttctt tgcggataat     840
aatttcgcta taacctacta cggagtgtac ttcctatcga tggtgttgga attattcccg     900
tgctgctatt acggcaccct gatatccgtg agatgaacc agctgaccta tgcgatttac     960
tcaagtaact ggatgagtat gaatcggagc tacagccgca tcctactgat cttcatgcaa    1020
ctcaccctgg cggaagtgca gatcaaggcc ggtgggatga ttggcatcgg aatgaacgcc    1080
ttctttgcca ccgtgcgatt ggcctactcc ttcttcactt tggccatgtc gctgcgt      1137

<210> SEQ ID NO 16
<211> LENGTH: 379
<212> TYPE: PRT
<213> ORGANISM: DROSOPHILA MELANOGASTER DOR72g

<400> SEQUENCE: 16

Met Asp Leu Lys Pro Arg Val Ile Arg Ser Glu Asp Ile Tyr Arg Thr
1               5                   10                  15

Tyr Trp Leu Tyr Trp His Leu Leu Gly Leu Glu Ser Asn Phe Phe Leu
            20                  25                  30

Asn Arg Leu Leu Asp Leu Val Ile Thr Ile Phe Val Thr Ile Trp Tyr
        35                  40                  45

Pro Ile His Leu Ile Leu Gly Leu Phe Met Glu Arg Ser Leu Gly Asp
```

|  |  |  |  | 50 |  |  |  |  | 55 |  |  |  |  | 60 |  |
| Val | Cys | Lys | Gly | Leu | Pro | Ile | Thr | Ala | Ala | Cys | Phe | Phe | Ala | Ser | Phe |
| 65 |  |  |  | 70 |  |  |  |  | 75 |  |  |  |  | 80 |  |
| Lys | Phe | Ile | Cys | Phe | Arg | Phe | Lys | Leu | Ser | Glu | Ile | Lys | Glu | Ile | Glu |
|  |  |  |  | 85 |  |  |  |  | 90 |  |  |  |  | 95 |  |
| Ile | Leu | Phe | Lys | Glu | Leu | Asp | Gln | Arg | Ala | Leu | Ser | Arg | Glu | Glu | Cys |
|  |  |  | 100 |  |  |  |  | 105 |  |  |  |  | 110 |  |  |
| Glu | Phe | Phe | Asn | Gln | Asn | Thr | Arg | Arg | Glu | Ala | Asn | Phe | Ile | Trp | Lys |
|  |  | 115 |  |  |  |  | 120 |  |  |  |  | 125 |  |  |  |
| Ser | Phe | Ile | Val | Ala | Tyr | Gly | Leu | Ser | Asn | Ile | Ser | Ala | Ile | Ala | Ser |
| 130 |  |  |  |  | 135 |  |  |  |  | 140 |  |  |  |  |  |
| Val | Leu | Phe | Gly | Gly | His | Lys | Leu | Leu | Tyr | Pro | Ala | Trp | Phe | Pro |  |
| 145 |  |  |  | 150 |  |  |  |  | 155 |  |  |  |  | 160 |  |
| Tyr | Asp | Val | Gln | Ala | Thr | Glu | Leu | Ile | Phe | Trp | Leu | Ser | Val | Thr | Tyr |
|  |  |  | 165 |  |  |  |  | 170 |  |  |  |  | 175 |  |  |
| Gln | Ile | Ala | Gly | Val | Ser | Leu | Ala | Ile | Leu | Gln | Asn | Leu | Ala | Asn | Asp |
|  |  | 180 |  |  |  |  | 185 |  |  |  |  | 190 |  |  |  |
| Ser | Tyr | Pro | Pro | Met | Thr | Phe | Cys | Val | Val | Ala | Gly | His | Val | Arg | Leu |
|  | 195 |  |  |  |  | 200 |  |  |  |  | 205 |  |  |  |  |
| Leu | Ala | Met | Arg | Leu | Ser | Arg | Ile | Gly | Gln | Gly | Pro | Glu | Glu | Thr | Ile |
| 210 |  |  |  |  | 215 |  |  |  |  | 220 |  |  |  |  |  |
| Tyr | Leu | Thr | Gly | Lys | Gln | Leu | Ile | Glu | Ser | Ile | Glu | Asp | His | Arg | Lys |
| 225 |  |  |  | 230 |  |  |  |  | 235 |  |  |  |  | 240 |  |
| Leu | Met | Lys | Ile | Val | Glu | Leu | Leu | Arg | Ser | Thr | Met | Asn | Ile | Ser | Gln |
|  |  |  | 245 |  |  |  |  | 250 |  |  |  |  | 255 |  |  |
| Leu | Gly | Gln | Phe | Ile | Ser | Ser | Gly | Val | Asn | Ile | Ser | Ile | Thr | Leu | Val |
|  |  | 260 |  |  |  |  | 265 |  |  |  |  | 270 |  |  |  |
| Asn | Ile | Leu | Phe | Phe | Ala | Asp | Asn | Asn | Phe | Ala | Ile | Thr | Tyr | Tyr | Gly |
|  | 275 |  |  |  |  | 280 |  |  |  |  | 285 |  |  |  |  |
| Val | Tyr | Phe | Leu | Ser | Met | Val | Leu | Glu | Leu | Phe | Pro | Cys | Cys | Tyr | Tyr |
| 290 |  |  |  |  | 295 |  |  |  |  | 300 |  |  |  |  |  |
| Gly | Thr | Leu | Ile | Ser | Val | Glu | Met | Asn | Gln | Leu | Thr | Tyr | Ala | Ile | Tyr |
| 305 |  |  |  | 310 |  |  |  |  | 315 |  |  |  |  | 320 |  |
| Ser | Ser | Asn | Trp | Met | Ser | Met | Asn | Arg | Ser | Tyr | Ser | Arg | Ile | Leu | Leu |
|  |  |  | 325 |  |  |  |  | 330 |  |  |  |  | 335 |  |  |
| Ile | Phe | Met | Gln | Leu | Thr | Leu | Ala | Glu | Val | Gln | Ile | Lys | Ala | Gly | Gly |
|  |  | 340 |  |  |  |  | 345 |  |  |  |  | 350 |  |  |  |
| Met | Ile | Gly | Ile | Gly | Met | Asn | Ala | Phe | Phe | Ala | Thr | Val | Arg | Leu | Ala |
|  | 355 |  |  |  |  | 360 |  |  |  |  | 365 |  |  |  |  |
| Tyr | Ser | Phe | Phe | Thr | Leu | Ala | Met | Ser | Leu | Arg |  |  |  |  |  |
| 370 |  |  |  |  | 375 |  |  |  |  |  |  |  |  |  |  |

<210> SEQ ID NO 17
<211> LENGTH: 1134
<212> TYPE: DNA
<213> ORGANISM: DROSOPHILA MELANOGASTER DOR73g

<400> SEQUENCE: 17

```
atggattcaa gaaggaaagt ccgaagtgaa atctttaca  aaacctattg gctttactgg      60
cgacttctgg gagtcgaggg cgattatcct tttcgacggc tagtggattt tacaatcacg     120
tctttcatta cgattttatt tcccgtgcat cttatactgg gaatgtataa aaagccccag     180
attcaagtct tcaggagtct gcatttcaca tcggaatgcc ttttctgcag ctataagttt     240
ttctgttttc gttggaaact taagaaaata aagaccatcg aaggattgct ccaggatctc     300
```

-continued

```
gatagtcgag ttgaaagtga agaagaacgc aactacttta atcaaaatcc aagtcgtgtg      360
gctcgaatgc tttcgaaaag ttacttggta gctgctatat cggccataat cactgcaact      420
gtagctggtt tatttagtac tggtcgaaat ttaatgtatc tgggttggtt tccctacgat      480
tttcaagcaa ccgccgcaat ctattggatt agttttccct atcaggcgat tggctctagt      540
ctgttgattc tggaaaatct ggccaacgat tcatatccgc cgattacatt ttgtgtggtc      600
tctggacatg tgagactatt gataatgcgt ttaagtcgaa ttggtcacga tgtaaaatta      660
tcaagttcgg aaaataccag aaaactcatc gaaggtatcc aggatcacag gaaactaatg      720
aagataatac gcctacttcg cagcacttta catcttagcc aactgggcca gttcctttct      780
agtggaatca acatttccat aacactcatc aacatcctgt tctttgcgga aaacaacttt      840
gcaatgcttt attatgcggt gttctttgct gcaatgttaa tagaactatt tccaagttgt      900
tactatggaa ttctgatgac aatggagttt gataagctac catatgccat cttctccagc      960
aactggctta aaatggataa agatacaat cgatccttga taattctgat gcaactaaca     1020
ctggttccag tgaatataaa agcaggtggt attgttggca tcgatatgag tgcattttt      1080 gccacagttc ggatggcata ttcctttac actttagcct tgtcatttcg agta            1134
```

<210> SEQ ID NO 18
<211> LENGTH: 378
<212> TYPE: PRT
<213> ORGANISM: Drosophila Melanogaster DOR73g

<400> SEQUENCE: 18

```
Met Asp Ser Arg Arg Lys Val Arg Ser Glu Asn Leu Tyr Lys Thr Tyr
1               5                   10                  15

Trp Leu Tyr Trp Arg Leu Leu Gly Val Glu Gly Asp Tyr Pro Phe Arg
            20                  25                  30

Arg Leu Val Asp Phe Thr Ile Thr Ser Phe Ile Thr Ile Leu Phe Pro
        35                  40                  45

Val His Leu Ile Leu Gly Met Tyr Lys Lys Pro Gln Ile Gln Val Phe
    50                  55                  60

Arg Ser Leu His Phe Thr Ser Glu Cys Leu Phe Cys Ser Tyr Lys Phe
65                  70                  75                  80

Phe Cys Phe Arg Trp Lys Leu Lys Glu Ile Lys Thr Ile Glu Gly Leu
                85                  90                  95

Leu Gln Asp Leu Asp Ser Arg Val Glu Ser Glu Glu Arg Asn Tyr
            100                 105                 110

Phe Asn Gln Asn Pro Ser Arg Val Ala Arg Met Leu Ser Lys Ser Tyr
        115                 120                 125

Leu Val Ala Ala Ile Ser Ala Ile Ile Thr Ala Thr Val Ala Gly Leu
    130                 135                 140

Phe Ser Thr Gly Arg Asn Leu Met Tyr Leu Gly Trp Phe Pro Tyr Asp
145                 150                 155                 160

Phe Gln Ala Thr Ala Ala Ile Tyr Trp Ile Ser Phe Ser Tyr Gln Ala
                165                 170                 175

Ile Gly Ser Ser Leu Leu Ile Leu Glu Asn Leu Ala Asn Asp Ser Tyr
            180                 185                 190

Pro Pro Ile Thr Phe Cys Val Val Ser Gly His Val Arg Leu Leu Ile
        195                 200                 205

Met Arg Leu Ser Arg Ile Gly His Asp Val Lys Leu Ser Ser Ser Glu
    210                 215                 220
```

```
Asn Thr Arg Lys Leu Ile Glu Gly Ile Gln Asp His Arg Lys Leu Met
225                 230                 235                 240

Lys Ile Ile Arg Leu Leu Arg Ser Thr Leu His Leu Ser Gln Leu Gly
            245                 250                 255

Gln Phe Leu Ser Ser Gly Ile Asn Ile Ser Ile Thr Leu Ile Asn Ile
                260                 265                 270

Leu Phe Phe Ala Glu Asn Asn Phe Ala Met Leu Tyr Tyr Ala Val Phe
            275                 280                 285

Phe Ala Ala Met Leu Ile Glu Leu Phe Pro Ser Cys Tyr Tyr Gly Ile
        290                 295                 300

Leu Met Thr Met Glu Phe Asp Lys Leu Pro Tyr Ala Ile Phe Ser Ser
305                 310                 315                 320

Asn Trp Leu Lys Met Asp Lys Arg Tyr Asn Arg Ser Leu Ile Ile Leu
                325                 330                 335

Met Gln Leu Thr Leu Val Pro Val Asn Ile Lys Ala Gly Gly Ile Val
                340                 345                 350

Gly Ile Asp Met Ser Ala Phe Phe Ala Thr Val Arg Met Ala Tyr Ser
            355                 360                 365

Phe Tyr Thr Leu Ala Leu Ser Phe Arg Val
        370                 375

<210> SEQ ID NO 19
<211> LENGTH: 1191
<212> TYPE: DNA
<213> ORGANISM: DROSOPHILA MELANOGASTER DOR46

<400> SEQUENCE: 19
atggcagagg tcagagtgga cagtctggag ttttttcaaga gccattggac cgcctggcgg     60
tacttgggag tggctcattt tcgggtcgag aactggaaga acctttacgt gttttacagc    120
attgtgtcga atcttctcgt gaccctgtgc taccccgttc acctgggaat atccctcttt    180
cgcaaccgca ccatcaccga ggacatcctc aacctgacca cctttgcgac ctgcacagcc    240
tgttcggtga agtgcctgct ctacgcctac aacatcaagg atgtgctgga gatggagcgg    300
ctgttgaggc ttttggatga acgcgtcgtg ggtccggagc aacgcagcat ctacggacaa    360
gtgagggtcc agctgcgaaa tgtgctatac gtgttcatcg gcatctacat gccgtgtgcc    420
ctgttcgccg agctatcctt tctgttcaag gaggagcgcg gtctgatgta tcccgcctgg    480
tttcccttcg actggctgca ctccaccagg aactattaca tagcgaacgc ctatcagata    540
gtgggcatct cgtttcagct gctgcaaaac tatgttagcg actgctttcc ggcggtggtg    600
ctgtgcctga tctcatccca catcaaaatg ttgtacaaca gattcgagga ggtgggcctg    660
gatccagcca gagatgcgga gaaggacctg gaggcctgca tcaccgatca aagcatatt    720 ctagagtggg caggcggctc attggttcgt gttctattca ctttccaact ttttttccaga    780 ctattccgac gcatcgaggc cttcatttcc ctgcccatgc taattcagtt cacagtgacc    840
gccttgaatg tgtgcatcgg tttagcagcc ctggtgtttt cgtcagcga gcccatggca    900 cggatgtact tcatcttcta ctccctggcc atgccgctgc agatctttcc gtcctgcttt    960
ttcggcaccg acaacgagta ctggttcgga cgcctccact acgcggcctt cagttgcaat   1020
tggcacacac agaacaggag ctttaagcgg aaaatgatgc tgttcgttga caatcgttg    1080 aagaagagca ccgctgtggc tggcggaatg atgcgtatcc acctggacac gttctttccc    1140
accctaaagg gggcctactc cctctttacc atcattattc ggatgagaaa g           1191
```

<210> SEQ ID NO 20
<211> LENGTH: 379
<212> TYPE: PRT
<213> ORGANISM: DROSOPHILA MELANOGASTER DOR46

<400> SEQUENCE: 20

```
Met Ala Glu Val Arg Val Asp Ser Leu Glu Phe Phe Lys Ser His Trp
1               5                   10                  15

Thr Ala Trp Arg Tyr Leu Gly Val Ala His Phe Arg Val Glu Asn Trp
            20                  25                  30

Lys Asn Leu Tyr Val Phe Tyr Ser Ile Val Ser Asn Leu Leu Val Thr
        35                  40                  45

Leu Cys Tyr Pro Val His Leu Gly Ile Ser Leu Phe Arg Asn Arg Thr
    50                  55                  60

Ile Thr Glu Asp Ile Leu Asn Leu Thr Thr Phe Ala Thr Cys Thr Ala
65                  70                  75                  80

Cys Ser Val Lys Cys Leu Leu Tyr Ala Tyr Asn Ile Lys Asp Val Leu
                85                  90                  95

Glu Met Glu Arg Leu Leu Arg Leu Leu Asp Glu Arg Val Val Gly Pro
            100                 105                 110

Glu Gln Arg Ser Ile Tyr Gly Gln Val Arg Val Gln Leu Arg Asn Val
        115                 120                 125

Leu Tyr Val Phe Ile Gly Ile Tyr Met Pro Cys Ala Leu Phe Ala Glu
    130                 135                 140

Leu Ser Phe Leu Phe Lys Glu Glu Arg Gly Leu Met Tyr Pro Ala Trp
145                 150                 155                 160

Phe Pro Phe Asp Trp Leu His Ser Thr Arg Asn Tyr Tyr Ile Ala Asn
                165                 170                 175

Ala Tyr Gln Ile Val Gly Ile Ser Phe Gln Leu Leu Gln Asn Tyr Val
            180                 185                 190

Ser Asp Cys Phe Pro Ala Val Val Leu Cys Leu Ile Ser Ser His Ile
        195                 200                 205

Lys Met Leu Tyr Asn Arg Phe Glu Glu Val Gly Leu Asp Pro Ala Arg
    210                 215                 220

Asp Ala Glu Lys Asp Leu Glu Ala Cys Ile Thr Asp His Lys His Ile
225                 230                 235                 240

Leu Glu Leu Phe Arg Arg Ile Glu Ala Phe Ile Ser Leu Pro Met Leu
                245                 250                 255

Ile Gln Phe Thr Val Thr Ala Leu Asn Val Cys Ile Gly Leu Ala Ala
            260                 265                 270

Leu Val Phe Phe Val Ser Glu Pro Met Ala Arg Met Tyr Phe Ile Phe
        275                 280                 285

Tyr Ser Leu Ala Met Pro Leu Gln Ile Phe Pro Ser Cys Phe Phe Gly
    290                 295                 300

Thr Asp Asn Glu Tyr Trp Phe Gly Arg Leu His Tyr Ala Ala Phe Ser
305                 310                 315                 320

Cys Asn Trp His Thr Gln Asn Arg Ser Phe Lys Arg Lys Met Met Leu
                325                 330                 335

Phe Val Glu Gln Ser Leu Lys Lys Ser Thr Ala Val Ala Gly Gly Met
            340                 345                 350

Met Arg Ile His Leu Asp Thr Phe Phe Ser Thr Leu Lys Gly Ala Tyr
        355                 360                 365

Ser Leu Phe Thr Ile Ile Ile Arg Met Arg Lys
    370                 375
```

<210> SEQ ID NO 21
<211> LENGTH: 1290
<212> TYPE: DNA
<213> ORGANISM: DROSOPHILA MELANOGASTER DOR19g

<400> SEQUENCE: 21

| | | | | | |
|---|---|---|---|---|---|
| atggttacgg | aggactttta | taagtaccag | gtgtggtact | tccaaatcct | tggtgtttgg | 60 |
| cagctcccca | cttgggccgc | agaccaccag | cgtcgttttc | agtccatgag | gtttggcttc | 120 |
| atcctggtca | tcctgttcat | catgctgctg | cttttctcct | tcgaaatgtt | gaacaacatt | 180 |
| tcccaagtta | gggagatcct | aaaggtattc | ttcatgttcg | ccacggaaat | atcctgcatg | 240 |
| gccaaattat | tgcatttgaa | gttgaagagc | cgcaaactcg | ctggcttggt | tgatgcgatg | 300 |
| ttgtccccag | agttcggcgt | taaaagtgaa | caggaaatgc | agatgctgga | attggataga | 360 |
| gtggcggttg | tccgcatgag | gaactcctac | ggcatcatgt | ccctgggcgc | ggcttccctg | 420 |
| atccttatag | ttccctgttt | cgacaacttt | ggcgagctac | cactggccat | gttggaggta | 480 |
| tgcagcatcg | agggatggat | ctgctattgg | tcgcagtacc | ttttccactc | gatttgcctg | 540 |
| ctgcccactt | gtgtgctgaa | ataacctac | gactcggtgg | cctactcgtt | gctctgtttc | 600 |
| ttgaaggttc | agctacaaat | gctggtcctg | cgattagaaa | agttgggtcc | tgtgatcgaa | 660 |
| ccccaggata | tgagaaaat | cgcaatggaa | ctgcgtgagt | gtgccgccta | ctacaacagg | 720 |
| attgttcgtt | tcaaggacct | ggtggagctg | ttcataaagg | ggccaggatc | tgtgcagctc | 780 |
| atgtgttctg | ttctggtgct | ggtgtccaac | ctgtacgaca | tgtccaccat | gtccattgca | 840 |
| aacggcgatg | ccatctttat | gctcaagacc | tgtatctatc | agctggtgat | gctctggcag | 900 |
| atcttcatca | tttgctacgc | ctccaacgag | gtaactgtcc | agagctctag | gttgtgtcac | 960 |
| agcatctaca | gctcccaatg | gacgggatgg | aacagggcaa | accgccggat | tgtccttctc | 1020 |
| atgatgcagc | gctttaattc | cccgatgctc | ctgagcacct | taacccccac | ctttgctttc | 1080 |
| agcttggagg | cctttggttc | tgtagggcag | cagaaattcc | tttatatatc | atttattact | 1140 |
| ggttatgctc | ttctccttc | agatcgtcaa | ctgctcctac | agctacttcg | cactgctgaa | 1200 |
| gcgcgtcaac | agttaaattt | cgaaacaccg | cagcacctaa | agattttcaa | gccgatttt | 1260 |
| aaaagcactc | aaaacgttat | gcacgtacat | | | | 1290 |

<210> SEQ ID NO 22
<211> LENGTH: 430
<212> TYPE: PRT
<213> ORGANISM: DROSOPHILA MELANOGASTER DOR19g

<400> SEQUENCE: 22

Met Val Thr Glu Asp Phe Tyr Lys Tyr Gln Val Trp Tyr Phe Gln Ile
1               5                   10                  15

Leu Gly Val Trp Gln Leu Pro Thr Trp Ala Ala Asp His Gln Arg Arg
            20                  25                  30

Phe Gln Ser Met Arg Phe Gly Phe Ile Leu Val Ile Leu Phe Ile Met
        35                  40                  45

Leu Leu Leu Phe Ser Phe Glu Met Leu Asn Asn Ile Ser Gln Val Arg
    50                  55                  60

Glu Ile Leu Lys Val Phe Phe Met Phe Ala Thr Glu Ile Ser Cys Met
65                  70                  75                  80

Ala Lys Leu Leu His Leu Lys Leu Lys Ser Arg Lys Leu Ala Gly Leu
                85                  90                  95

Val Asp Ala Met Leu Ser Pro Glu Phe Gly Val Lys Ser Glu Gln Glu

-continued

```
                           100                 105                 110
Met Gln Met Leu Glu Leu Asp Arg Val Ala Val Arg Met Arg Asn
            115                 120                 125
Ser Tyr Gly Ile Met Ser Leu Gly Ala Ala Ser Leu Ile Leu Ile Val
        130                 135                 140
Pro Cys Phe Asp Asn Phe Gly Glu Leu Pro Leu Ala Met Leu Glu Val
145                 150                 155                 160
Cys Ser Ile Glu Gly Trp Ile Cys Tyr Trp Ser Gln Tyr Leu Phe His
                165                 170                 175
Ser Ile Cys Leu Leu Pro Thr Cys Val Leu Asn Ile Thr Tyr Asp Ser
            180                 185                 190
Val Ala Tyr Ser Leu Leu Cys Phe Leu Lys Val Gln Leu Gln Met Leu
        195                 200                 205
Val Leu Arg Leu Glu Lys Leu Gly Pro Val Ile Glu Pro Gln Asp Asn
210                 215                 220
Glu Lys Ile Ala Met Glu Leu Arg Glu Cys Ala Ala Tyr Tyr Asn Arg
225                 230                 235                 240
Ile Val Arg Phe Lys Asp Leu Val Glu Leu Phe Ile Lys Gly Pro Gly
                245                 250                 255
Ser Val Gln Leu Met Cys Ser Val Leu Val Leu Val Ser Asn Leu Tyr
            260                 265                 270
Asp Met Ser Thr Met Ser Ile Ala Asn Gly Asp Ala Ile Phe Met Leu
        275                 280                 285
Lys Thr Cys Ile Tyr Gln Leu Val Met Leu Trp Gln Ile Phe Ile Ile
        290                 295                 300
Cys Tyr Ala Ser Asn Glu Val Thr Val Gln Ser Ser Arg Leu Cys His
305                 310                 315                 320
Ser Ile Tyr Ser Ser Gln Trp Thr Gly Trp Asn Arg Ala Asn Arg Arg
                325                 330                 335
Ile Val Leu Leu Met Met Gln Arg Phe Asn Ser Pro Met Leu Leu Ser
            340                 345                 350
Thr Phe Asn Pro Thr Phe Ala Phe Ser Leu Glu Ala Phe Gly Ser Val
        355                 360                 365
Gly Gln Gln Lys Phe Leu Tyr Ile Ser Phe Ile Thr Gly Tyr Ala Leu
    370                 375                 380
Leu Leu Ser Asp Arg Gln Leu Leu Leu Gln Leu Leu Arg Thr Ala Glu
385                 390                 395                 400
Ala Arg Gln Gln Leu Asn Phe Glu Thr Pro Gln His Leu Lys Ile Phe
                405                 410                 415
Lys Pro Ile Phe Lys Ser Thr Gln Asn Val Met His Val His
            420                 425                 430

<210> SEQ ID NO 23
<211> LENGTH: 1391
<212> TYPE: DNA
<213> ORGANISM: DROSOPHILA MELANOGASTER DOR24

<400> SEQUENCE: 23
ggcacgagcc ttgtcgacat ggacagtttt ctgcaagtac agaagagcac cattgctctt    60
ctgggctttg atctctttag tgaaaatcga gaaatgtgga acgcccctaa tagagcaatg   120
aatgtgttta gcatagctgc cattttccc tttatcctgg cagctgtgct ccataattgg    180
aagaatgtat tgctgctggc cgatgccatg gtggccctac taataaccat tctgggccta   240
ttcaagttta gcatgatact ttacttacgt cgcgatttca agcgactgat tgacaaattt   300
```

-continued

```
cgtttgctca tgtcgaatga ggcggaacag ggcgaggaat acgccgagat tctcaacgca      360
gcaaacaagc aggatcaacg aatgtgcact ctgtttagga cttgtttcct cctcgcctgg      420
gccttgaata gtgttctgcc cctcgtgaga atgggtctca gctattggtt agcaggtcat      480
gcagagcccg agttgccttt tccctgtctt tttccctgga atatccacat cattcgcaat      540
tatgttttga gcttcatctg gagcgctttc gcctcgacag gtgtggtttt acctgctgtc      600
agcttggata ccatattctg ttccttcacc agcaacctgt gcgccttctt caaaattgcg      660
cagtacaagg tggttagatt taagggcgga tcccttaaag aatcacaggc acattgaac      720 aaagtctttg ccctgtacca gaccagcttg gatatgtgca acgatctgaa tcagtgctac      780
caaccgatta tctgcgccca gttcttcatt tcatctctgc aactctgcat gctgggatat      840
ctgttctcca ttacttttgc ccagacagag ggcgtgtact atgcctcttt catagccacc      900
atcattatac aagcctatat ctactgctac tgcggggaga acctgaagac ggagagtgcc      960
agcttcgagt gggccatcta cgacagtccg tggcacgaga gtttgggtgc tggtggagcc     1020
tctacctcga tctgccgatc cttgctgatc agcatgatgc gggctcatcg gggattccgc     1080
attacgggat acttcttcga ggcaaacatg gaggccttct catcgattgt tcgcacggct     1140
atgtcctaca tcacaatgct gagatcattc tcctaaatgt ggtttgacca caaggctttg     1200
gattgatttt tgtgcaattt ttgttttatt gctgagcatg cgttgccgta cgacatttaa     1260
caatcgatct tacgtaattt acatatgata atctcacata ttgttcgtta agcactaagt     1320
agaatgtaga atgtgaattg gctgtagaaa tgcacagatg aagcacgaaa aaaaaaaaa     1380 aaaaaaaaa a                                                            1391
```

<210> SEQ ID NO 24
<211> LENGTH: 385
<212> TYPE: PRT
<213> ORGANISM: DROSOPHILA MELANOGASTER DOR24

<400> SEQUENCE: 24

```
Met Asp Ser Phe Leu Gln Val Gln Lys Ser Thr Ile Ala Leu Leu Gly
 1               5                  10                  15

Phe Asp Leu Phe Ser Glu Asn Arg Glu Met Trp Lys Arg Pro Tyr Arg
            20                  25                  30

Ala Met Asn Val Phe Ser Ile Ala Ala Ile Phe Pro Phe Ile Leu Ala
        35                  40                  45

Ala Val Leu His Asn Trp Lys Asn Val Leu Leu Ala Asp Ala Met
    50                  55                  60

Val Ala Leu Leu Ile Thr Ile Leu Gly Leu Phe Lys Phe Ser Met Ile
65                  70                  75                  80

Leu Tyr Leu Arg Arg Asp Phe Lys Arg Leu Ile Asp Lys Phe Arg Leu
                85                  90                  95

Leu Met Ser Asn Glu Ala Glu Gln Gly Glu Glu Tyr Ala Glu Ile Leu
            100                 105                 110

Asn Ala Ala Asn Lys Gln Asp Gln Arg Met Cys Thr Leu Phe Arg Thr
        115                 120                 125

Cys Phe Leu Leu Ala Trp Ala Leu Asn Ser Val Leu Pro Leu Val Arg
    130                 135                 140

Met Gly Leu Ser Tyr Trp Leu Ala Gly His Ala Glu Pro Glu Leu Pro
145                 150                 155                 160

Phe Pro Cys Leu Phe Pro Trp Asn Ile His Ile Ile Arg Asn Tyr Val
                165                 170                 175
```

-continued

Leu Ser Phe Ile Trp Ser Ala Phe Ala Ser Thr Gly Val Val Leu Pro
            180                 185                 190

Ala Val Ser Leu Asp Thr Ile Phe Cys Ser Phe Thr Ser Asn Leu Cys
        195                 200                 205

Ala Phe Phe Lys Ile Ala Gln Tyr Lys Val Val Arg Phe Lys Gly Gly
    210                 215                 220

Ser Leu Lys Glu Ser Gln Ala Thr Leu Asn Lys Val Phe Ala Leu Tyr
225                 230                 235                 240

Gln Thr Ser Leu Asp Met Cys Asn Asp Leu Asn Gln Cys Tyr Gln Pro
                245                 250                 255

Ile Ile Cys Ala Gln Phe Phe Ile Ser Ser Leu Gln Leu Cys Met Leu
            260                 265                 270

Gly Tyr Leu Phe Ser Ile Thr Phe Ala Gln Thr Glu Gly Val Tyr Tyr
        275                 280                 285

Ala Ser Phe Ile Ala Thr Ile Ile Gln Ala Tyr Ile Tyr Cys Tyr
    290                 295                 300

Cys Gly Glu Asn Leu Lys Thr Glu Ser Ala Ser Phe Glu Trp Ala Ile
305                 310                 315                 320

Tyr Asp Ser Pro Trp His Glu Ser Leu Gly Ala Gly Ala Ser Thr
                325                 330                 335

Ser Ile Cys Arg Ser Leu Leu Ile Ser Met Met Arg Ala His Arg Gly
            340                 345                 350

Phe Arg Ile Thr Gly Tyr Phe Phe Glu Ala Asn Met Glu Ala Phe Ser
        355                 360                 365

Ser Ile Val Arg Thr Ala Met Ser Tyr Ile Thr Met Leu Arg Ser Phe
    370                 375                 380

Ser
385

<210> SEQ ID NO 25
<211> LENGTH: 900
<212> TYPE: DNA
<213> ORGANISM: Drosophila Melanogaster DOR10

<400> SEQUENCE: 25
atggaaaaac tacgttccta tgaggatttc atcttcatgg ccaacatgat gttcaagacc      60
cttggctacg atctattcca tacacccaaa ccctggtggc gctatctgct tgtgcgagga     120
tacttcgttt tgtgcacgat cagcaacttt tacgaggctt ccatggtgac gacaaggata     180
attgagtggg aatccttggc cggaagtccc tccaaaataa tgcgacaggg tctgcacttc     240
ttttacatgt tgagtagcca attgaaattt atcacattca tgataaatcg caaacgccta     300
ctgcagctga gccatcgttt gaaagagttg tatcctcata agagcaaaa tcaaaggaag     360
tacgaggtga ataaatacta cctatcctgt tccacgcgca atgttttgta cgtgtactac     420
tttgtaatgg tcgtcatggc actggaaccc ctcgttcagt cccagttcat agtgaatgtg     480
agcctgggca cagatctgtg gatgatgtgc gtctcaagcc aaatatcgat gcacttgggc     540
tatctggcca atatgttggc ctccattcga ccaagtccag aaacggaaca acaagactgt     600
gacttcttgg ccagcattat aaagagacat caactaatga tcaggcttca aaaggacgtg     660
aactatgttt ttggactctt attggcatct aatctgttta ccacatcctg tttactttgc     720
tgcatggcgt actataccgt cgtcgaaggt tcaattggg agggcatttc ctatatgatg     780
ctctttgcta gtgtagctgc ccagttctac gttgtcagct cacacggaca aatgttaata     840

-continued

```
gatttgttga tgaccatcac atacagattt ttcgcggtta tacgacaaac tgtagaaaag    900
```

<210> SEQ ID NO 26
<211> LENGTH: 300
<212> TYPE: PRT
<213> ORGANISM: Drosophila Melanogaster DOR10

<400> SEQUENCE: 26

| Met | Glu | Lys | Leu | Arg | Ser | Tyr | Glu | Asp | Phe | Ile | Phe | Met | Ala | Asn | Met |
|---|---|---|---|---|---|---|---|---|---|---|---|---|---|---|---|
| 1 | | | | 5 | | | | | 10 | | | | | 15 | |

| Met | Phe | Lys | Thr | Leu | Gly | Tyr | Asp | Leu | Phe | His | Thr | Pro | Lys | Pro | Trp |
|---|---|---|---|---|---|---|---|---|---|---|---|---|---|---|---|
| | | | 20 | | | | | 25 | | | | | 30 | | |

| Trp | Arg | Tyr | Leu | Leu | Val | Arg | Gly | Tyr | Phe | Val | Leu | Cys | Thr | Ile | Ser |
|---|---|---|---|---|---|---|---|---|---|---|---|---|---|---|---|
| | | 35 | | | | | 40 | | | | | 45 | | | |

| Asn | Phe | Tyr | Glu | Ala | Ser | Met | Val | Thr | Thr | Arg | Ile | Ile | Glu | Trp | Glu |
|---|---|---|---|---|---|---|---|---|---|---|---|---|---|---|---|
| | 50 | | | | | 55 | | | | | 60 | | | | |

| Ser | Leu | Ala | Gly | Ser | Pro | Ser | Lys | Ile | Met | Arg | Gln | Gly | Leu | His | Phe |
|---|---|---|---|---|---|---|---|---|---|---|---|---|---|---|---|
| 65 | | | | | 70 | | | | | 75 | | | | | 80 |

| Phe | Tyr | Met | Leu | Ser | Ser | Gln | Leu | Lys | Phe | Ile | Thr | Phe | Met | Ile | Asn |
|---|---|---|---|---|---|---|---|---|---|---|---|---|---|---|---|
| | | | | 85 | | | | | 90 | | | | | 95 | |

| Arg | Lys | Arg | Leu | Leu | Gln | Leu | Ser | His | Arg | Leu | Lys | Glu | Leu | Tyr | Pro |
|---|---|---|---|---|---|---|---|---|---|---|---|---|---|---|---|
| | | | 100 | | | | | 105 | | | | | 110 | | |

| His | Lys | Glu | Gln | Asn | Gln | Arg | Lys | Tyr | Glu | Val | Asn | Lys | Tyr | Tyr | Leu |
|---|---|---|---|---|---|---|---|---|---|---|---|---|---|---|---|
| | | 115 | | | | | 120 | | | | | 125 | | | |

| Ser | Cys | Ser | Thr | Arg | Asn | Val | Leu | Tyr | Val | Tyr | Phe | Val | Met | Val |
|---|---|---|---|---|---|---|---|---|---|---|---|---|---|---|
| | 130 | | | | | 135 | | | | | 140 | | | |

| Val | Met | Ala | Leu | Glu | Pro | Leu | Val | Gln | Ser | Gln | Phe | Ile | Val | Asn | Val |
|---|---|---|---|---|---|---|---|---|---|---|---|---|---|---|---|
| 145 | | | | | 150 | | | | | 155 | | | | | 160 |

| Ser | Leu | Gly | Thr | Asp | Leu | Trp | Met | Met | Cys | Val | Ser | Gln | Ile | Ser |
|---|---|---|---|---|---|---|---|---|---|---|---|---|---|---|
| | | | | 165 | | | | | 170 | | | | | 175 |

| Met | His | Leu | Gly | Tyr | Leu | Ala | Asn | Met | Leu | Ala | Ser | Ile | Arg | Pro | Ser |
|---|---|---|---|---|---|---|---|---|---|---|---|---|---|---|---|
| | | | 180 | | | | | 185 | | | | | 190 | | |

| Pro | Glu | Thr | Glu | Gln | Gln | Asp | Cys | Asp | Phe | Leu | Ala | Ser | Ile | Ile | Lys |
|---|---|---|---|---|---|---|---|---|---|---|---|---|---|---|---|
| | | 195 | | | | | 200 | | | | | 205 | | | |

| Arg | His | Gln | Leu | Met | Ile | Arg | Leu | Gln | Lys | Asp | Val | Asn | Tyr | Val | Phe |
|---|---|---|---|---|---|---|---|---|---|---|---|---|---|---|---|
| | 210 | | | | | 215 | | | | | 220 | | | | |

| Gly | Leu | Leu | Leu | Ala | Ser | Asn | Leu | Phe | Thr | Thr | Ser | Cys | Leu | Leu | Cys |
|---|---|---|---|---|---|---|---|---|---|---|---|---|---|---|---|
| 225 | | | | | 230 | | | | | 235 | | | | | 240 |

| Cys | Met | Ala | Tyr | Tyr | Thr | Val | Val | Glu | Gly | Phe | Asn | Trp | Glu | Gly | Ile |
|---|---|---|---|---|---|---|---|---|---|---|---|---|---|---|---|
| | | | 245 | | | | | 250 | | | | | 255 | | |

| Ser | Tyr | Met | Met | Leu | Phe | Ala | Ser | Val | Ala | Ala | Gln | Phe | Tyr | Val | Val |
|---|---|---|---|---|---|---|---|---|---|---|---|---|---|---|---|
| | | 260 | | | | | 265 | | | | | 270 | | | |

| Ser | Ser | His | Gly | Gln | Met | Leu | Ile | Asp | Leu | Leu | Met | Thr | Ile | Thr | Tyr |
|---|---|---|---|---|---|---|---|---|---|---|---|---|---|---|---|
| | 275 | | | | | 280 | | | | | 285 | | | | |

| Arg | Phe | Phe | Ala | Val | Ile | Arg | Gln | Thr | Val | Glu | Lys |
|---|---|---|---|---|---|---|---|---|---|---|---|
| | 290 | | | | | 295 | | | | | 300 |

<210> SEQ ID NO 27
<211> LENGTH: 1125
<212> TYPE: DNA
<213> ORGANISM: Drosophila Melanogaster DOR105

<400> SEQUENCE: 27

```
atgtttgaag acattcagct aatctacatg aatatcaaga tattgcgatt ctgggccctg    60
ctctatgaca aaaacttgag gcgttatgtg tgcattggac tggcctcatt ccacatcttc   120
```

-continued

```
acccaaatcg tctacatgat gagtaccaat gaaggactaa ccgggataat tcgtaactca    180
tatatgctcg tcctttggat taatacggtg ctgcgagctt atctcttgct ggcggatcac    240
gacagatatt tggctttgat ccaaaaacta actgaggcct attacgattt actgaatctg    300
aacgattcgt atatatcgga aatattggac caggtgaaca aggtgggaaa gttgatggct    360 agggcaatc tgttctttgg catgctcaca tccatgggat tcggtctgta cccattgtcc     420
tccagcgaaa gagtcctgcc atttggcagc aaaattcctg gtctaaatga gtacgagagt    480
ccgtactatg agatgtggta catctttcag atgctcatca ccccgatggg ctgttgcatg    540
tacattccgt acaccagtct gattgtgggc ttgataatgt tcggcattgt gaggtgcaag    600
gctttgcagc atcgcctccg ccaggtggcg cttaagcatc cgtacggaga tcgcgatccc    660
cgtgaactga gggaggagat catagcctgc atacgttacc agcagagcat tatcgagtac    720
atggatcaca taaacgagct gaccaccatg atgttcctat tcgaactgat ggccttttcg    780
gcgctgctct gtgcgctgct ctttatgctg attatcgtca gcggcaccag tcagctgata    840
attgtttgca tgtacattaa catgattctg gcccaaatac tggccctcta ttggtatgca    900
aatgagttaa gggaacagaa tctggcggtg ccaccgcag cctacgaaac ggagtggttc      960
accttcgacg ttccactgcg caaaaacatc ctgttcatga tgatgagggc acagcggcca    1020
gctgcaatac tactgggcaa tatacgcccc atcactttgg aactgttcca aaacctactg    1080
aacacaacct atacattttt tacggttctc aagcgagtct acgga                   1125
```

<210> SEQ ID NO 28
<211> LENGTH: 375
<212> TYPE: PRT
<213> ORGANISM: Drosophila Melanogaster DOR105

<400> SEQUENCE: 28

```
Met Phe Glu Asp Ile Gln Leu Ile Tyr Met Asn Ile Lys Ile Leu Arg
1               5                   10                  15

Phe Trp Ala Leu Leu Tyr Asp Lys Asn Leu Arg Arg Tyr Val Cys Ile
            20                  25                  30

Gly Leu Ala Ser Phe His Ile Phe Thr Gln Ile Val Tyr Met Met Ser
        35                  40                  45

Thr Asn Glu Gly Leu Thr Gly Ile Ile Arg Asn Ser Tyr Met Leu Val
    50                  55                  60

Leu Trp Ile Asn Thr Val Leu Arg Ala Tyr Leu Leu Ala Asp His
65                  70                  75                  80

Asp Arg Tyr Leu Ala Leu Ile Gln Lys Leu Thr Glu Ala Tyr Tyr Asp
                85                  90                  95

Leu Leu Asn Leu Asn Asp Ser Tyr Ile Ser Glu Ile Leu Asp Gln Val
            100                 105                 110

Asn Lys Val Gly Lys Leu Met Ala Arg Gly Asn Leu Phe Phe Gly Met
        115                 120                 125

Leu Thr Ser Met Gly Phe Gly Leu Tyr Pro Leu Ser Ser Ser Glu Arg
    130                 135                 140

Val Leu Pro Phe Gly Ser Lys Ile Pro Gly Leu Asn Glu Tyr Glu Ser
145                 150                 155                 160

Pro Tyr Tyr Glu Met Trp Tyr Ile Phe Gln Met Leu Ile Thr Pro Met
                165                 170                 175

Gly Cys Cys Met Tyr Ile Pro Tyr Thr Ser Leu Ile Val Gly Leu Ile
            180                 185                 190

Met Phe Gly Ile Val Arg Cys Lys Ala Leu Gln His Arg Leu Arg Gln
```

```
                        195                 200                 205
Val Ala Leu Lys His Pro Tyr Gly Asp Arg Asp Pro Arg Glu Leu Arg
    210                 215                 220

Glu Glu Ile Ile Ala Cys Ile Arg Tyr Gln Gln Ser Ile Ile Glu Tyr
225                 230                 235                 240

Met Asp His Ile Asn Glu Leu Thr Thr Met Met Phe Leu Phe Glu Leu
                245                 250                 255

Met Ala Phe Ser Ala Leu Leu Cys Ala Leu Leu Phe Met Leu Ile Ile
            260                 265                 270

Val Ser Gly Thr Ser Gln Leu Ile Ile Val Cys Met Tyr Ile Asn Met
        275                 280                 285

Ile Leu Ala Gln Ile Leu Ala Leu Tyr Trp Tyr Ala Asn Glu Leu Arg
    290                 295                 300

Glu Gln Asn Leu Ala Val Ala Thr Ala Ala Tyr Glu Thr Glu Trp Phe
305                 310                 315                 320

Thr Phe Asp Val Pro Leu Arg Lys Asn Ile Leu Phe Met Met Met Arg
                325                 330                 335

Ala Gln Arg Pro Ala Ala Ile Leu Leu Gly Asn Ile Arg Pro Ile Thr
            340                 345                 350

Leu Glu Leu Phe Gln Asn Leu Leu Asn Thr Thr Tyr Thr Phe Phe Thr
        355                 360                 365

Val Leu Lys Arg Val Tyr Gly
    370                 375

<210> SEQ ID NO 29
<211> LENGTH: 1188
<212> TYPE: DNA
<213> ORGANISM: Drosophila Melanogaster DOR107

<400> SEQUENCE: 29
atgtatccgc gattcctcag ccgtaactat ccgctggcca agcatttgtt cttcgtcacc      60
agatactcct ttggcctgct gggcctgaga tttggcaaag cagtcgtg gcttcacctc      120 ttgtggctgg tgttcaattt cgttaacctg gcgcactgct gccaggcgga gttcgtcttc      180
ggctggagtc acttgcgcac cagtcccgtg gatgccatgg acgccttttg tcctctggcc      240
tgcagtttca ccacgctctt caagctggga tggatgtggt ggcgtcgcca ggaagtagct      300
gatctaatgg accgcatccg cttgctcatc ggggagcagg agaagaggga ggactcccgg      360
agaaaggtgg ctcaaaggag ctactatctc atggtcacca ggtgcggtat gctggtcttc      420
accctgggca gcattaccac tggagccttc gttctgcgtt ccctttggga aatgtgggtg      480
cgtcgtcatc aggagttcaa attcgatatg cccttccgca tgctgttcca cgactttgcg      540
catcgcatgc cctggtttcc agttttctat ctctactcca catggagtgg ccaggtcact      600
gtgtacgcct tgctggtac agatggtttc ttctttggct ttaccctcta catggccttc      660
ttgctgcagg ccttaagata cgatatccag gatgccctca gccaataag agatccctcg      720 cttagggaat ccaaaatctg ctgtcagcga ttggcggaca tcgtggatcg ccacaatgag      780
atagagaaga tagtcaagga attttctgga attatggctg ctccaacttt tgttcacttc      840
gtatcagcca gctagtgat agccaccagc gtcattgata tactattgta ttccggctat      900
aacatcatcc gttacgtggt gtacaccttc acggtttcct cggccatctt cctctattgc      960 tacgaggca cagaaatgtc aactgagagc ctttccttgg gagaagcagc ctacagcagt      1020
gcctggtata cttgggatcg agagacccgc aggcgggtct ttctcattat cctgcgtgct      1080
```

```
caacgaccca ttacggtgag ggtgcccttt tttgcaccat cgttaccagt cttcacatcg    1140
gtcatcaagt ttacaggttc gattgtggca ctggctaaga cgatactg                  1188

<210> SEQ ID NO 30
<211> LENGTH: 396
<212> TYPE: PRT
<213> ORGANISM: Drosophila Melanogaster DOR107

<400> SEQUENCE: 30
```

| | | | | | | | | | | | | | | |
|---|---|---|---|---|---|---|---|---|---|---|---|---|---|---|
| Met | Tyr | Pro | Arg | Phe | Leu | Ser | Arg | Asn | Tyr | Pro | Leu | Ala | Lys | His | Leu |
| 1 | | | | 5 | | | | | 10 | | | | | 15 | |
| Phe | Phe | Val | Thr | Arg | Tyr | Ser | Phe | Gly | Leu | Leu | Gly | Leu | Arg | Phe | Gly |
| | | | 20 | | | | | 25 | | | | | 30 | | |
| Lys | Glu | Gln | Ser | Trp | Leu | His | Leu | Leu | Trp | Leu | Val | Phe | Asn | Phe | Val |
| | | | 35 | | | | | 40 | | | | | 45 | | |
| Asn | Leu | Ala | His | Cys | Cys | Gln | Ala | Glu | Phe | Val | Phe | Gly | Trp | Ser | His |
| | 50 | | | | | 55 | | | | | 60 | | | | |
| Leu | Arg | Thr | Ser | Pro | Val | Asp | Ala | Met | Asp | Ala | Phe | Cys | Pro | Leu | Ala |
| 65 | | | | | 70 | | | | | 75 | | | | | 80 |
| Cys | Ser | Phe | Thr | Thr | Leu | Phe | Lys | Leu | Gly | Trp | Met | Trp | Trp | Arg | Arg |
| | | | | 85 | | | | | 90 | | | | | 95 | |
| Gln | Glu | Val | Ala | Asp | Leu | Met | Asp | Arg | Ile | Arg | Leu | Leu | Ile | Gly | Glu |
| | | | 100 | | | | | 105 | | | | | 110 | | |
| Gln | Glu | Lys | Arg | Glu | Asp | Ser | Arg | Arg | Lys | Val | Ala | Gln | Arg | Ser | Tyr |
| | | | 115 | | | | | 120 | | | | | 125 | | |
| Tyr | Leu | Met | Val | Thr | Arg | Cys | Gly | Met | Leu | Val | Phe | Thr | Leu | Gly | Ser |
| | 130 | | | | | 135 | | | | | 140 | | | | |
| Ile | Thr | Thr | Gly | Ala | Phe | Val | Leu | Arg | Ser | Leu | Trp | Glu | Met | Trp | Val |
| 145 | | | | | 150 | | | | | 155 | | | | | 160 |
| Arg | Arg | His | Gln | Glu | Phe | Lys | Phe | Asp | Met | Pro | Phe | Arg | Met | Leu | Phe |
| | | | | 165 | | | | | 170 | | | | | 175 | |
| His | Asp | Phe | Ala | His | Arg | Met | Pro | Trp | Phe | Pro | Val | Phe | Tyr | Leu | Tyr |
| | | | 180 | | | | | 185 | | | | | 190 | | |
| Ser | Thr | Trp | Ser | Gly | Gln | Val | Thr | Val | Tyr | Ala | Phe | Ala | Gly | Thr | Asp |
| | | | 195 | | | | | 200 | | | | | 205 | | |
| Gly | Phe | Phe | Gly | Phe | Thr | Leu | Tyr | Met | Ala | Phe | Leu | Leu | Gln | Ala |
| | 210 | | | | | 215 | | | | | 220 | | | | |
| Leu | Arg | Tyr | Asp | Ile | Gln | Asp | Ala | Leu | Lys | Pro | Ile | Arg | Asp | Pro | Ser |
| 225 | | | | | 230 | | | | | 235 | | | | | 240 |
| Leu | Arg | Glu | Ser | Lys | Ile | Cys | Cys | Gln | Arg | Leu | Ala | Asp | Ile | Val | Asp |
| | | | | 245 | | | | | 250 | | | | | 255 | |
| Arg | His | Asn | Glu | Ile | Glu | Lys | Ile | Val | Lys | Glu | Phe | Ser | Gly | Ile | Met |
| | | | 260 | | | | | 265 | | | | | 270 | | |
| Ala | Ala | Pro | Thr | Phe | Val | His | Phe | Val | Ser | Ala | Ser | Leu | Val | Ile | Ala |
| | | | 275 | | | | | 280 | | | | | 285 | | |
| Thr | Ser | Val | Ile | Asp | Ile | Leu | Leu | Tyr | Ser | Gly | Tyr | Asn | Ile | Ile | Arg |
| | 290 | | | | | 295 | | | | | 300 | | | | |
| Tyr | Val | Val | Tyr | Thr | Phe | Thr | Val | Ser | Ser | Ala | Ile | Phe | Leu | Tyr | Cys |
| 305 | | | | | 310 | | | | | 315 | | | | | 320 |
| Tyr | Gly | Gly | Thr | Glu | Met | Ser | Thr | Glu | Ser | Leu | Ser | Leu | Gly | Glu | Ala |
| | | | | 325 | | | | | 330 | | | | | 335 | |
| Ala | Tyr | Ser | Ser | Ala | Trp | Tyr | Thr | Trp | Asp | Arg | Glu | Thr | Arg | Arg |
| | | | 340 | | | | | 345 | | | | | 350 | | |
| Val | Phe | Leu | Ile | Ile | Leu | Arg | Ala | Gln | Arg | Pro | Ile | Thr | Val | Arg | Val |

```
                355                360                365
    Pro Phe Phe Ala Pro Ser Leu Pro Val Phe Thr Ser Val Ile Lys Phe
        370                375                380

Thr Gly Ser Ile Val Ala Leu Ala Lys Thr Ile Leu
    385                390                395
```

<210> SEQ ID NO 31
<211> LENGTH: 1161
<212> TYPE: DNA
<213> ORGANISM: Drosophila Melanogaster DOR108

<400> SEQUENCE: 31

| | | |
|---|---|---|
| atggataaac acaaggatcg cattgaatcc atgcgcctaa ttcttcaggt catgcaacta | 60 |
| tttggcctct ggccgtggtc cttgaaatcg aagaggagt ggactttcac cggttttgta | 120 |
| aagcgcaact atcgcttcct gctccatctg cccattacct tcacctttat tggactcatg | 180 |
| tggctggagg ccttcatctc gagcaatctg agcaggctg gccaggttct gtacatgtcc | 240 |
| atcaccgaga tggctttggt ggtgaaaatc ctgagcattt ggcactatcg caccgaagct | 300 |
| tggcggctga tgtacgaact ccaacatgct ccggactacc aactccacaa ccaggaggag | 360 |
| gtagactttt ggcgccggga gcaacgattc ttcaagtggt tcttctacat ctacattctg | 420 |
| attagcttgg gcgtggtata tagtggctgc actggagtac tttttctgga gggctacgaa | 480 |
| ctgcccttg cctactacgt gcccttcgaa tggcagaacg agagaaggta ctggttcgcc | 540 |
| tatggttacg atatggcggg catgacgctg acctgcatct caaacattac cctggacacc | 600 |
| ctgggttgct atttcctgtt ccatatctct cttttgtacc gactgcttgg tctgcgattg | 660 |
| agggaaacga agaatatgaa gaatgatacc atttttggcc agcagttgcg tgccatcttc | 720 |
| attatgcatc agaggattag aagcctaacc ctgacctgcc agagaatcgt atctccctat | 780 |
| atcctatctc agatcatttt gagtgccctg atcatctgct ttagtggata ccgcttgcag | 840 |
| catgtgggaa ttcgcgataa tcccggccag tttatatcca tgttgcagtt tgtcagtgtg | 900 |
| atgatcctgc agatttactt gccctgctac tatggaaacg agataaccgt gtatgccaat | 960 |
| cagctgacca acgaggttta ccataccaat tggctggaat gtcggccacc gattcgaaag | 1020 |
| ttactcaatg cctacatgga gcacctgaag aaaccggtga ccatccgggc tggcaactcc | 1080 |
| ttcgccgtgg gactaccaat ttttgttaag accatcaaca cgcctacag tttcttggct | 1140 |
| ttattactaa atgtatcgaa t | 1161 |

<210> SEQ ID NO 32
<211> LENGTH: 387
<212> TYPE: PRT
<213> ORGANISM: Drosophila Melanogaster DOR108

<400> SEQUENCE: 32

```
Met Asp Lys His Lys Asp Arg Ile Glu Ser Met Arg Leu Ile Leu Gln
1               5                   10                  15

Val Met Gln Leu Phe Gly Leu Trp Pro Trp Ser Leu Lys Ser Glu Glu
            20                  25                  30

Glu Trp Thr Phe Thr Gly Phe Val Lys Arg Asn Tyr Arg Phe Leu Leu
        35                  40                  45

His Leu Pro Ile Thr Phe Thr Phe Ile Gly Leu Met Trp Leu Glu Ala
    50                  55                  60

Phe Ile Ser Ser Asn Leu Glu Gln Ala Gly Gln Val Leu Tyr Met Ser
65                  70                  75                  80
```

| | | | | | | | | | | | |
|---|---|---|---|---|---|---|---|---|---|---|---|
|Ile|Thr|Glu|Met|Ala|Leu|Val|Val|Lys|Ile|Leu|Ser|Ile|Trp|His|Tyr|
| | | | |85| | | |90| | | |95| | | |

Ile Thr Glu Met Ala Leu Val Val Lys Ile Leu Ser Ile Trp His Tyr
                85                  90                  95

Arg Thr Glu Ala Trp Arg Leu Met Tyr Glu Leu Gln His Ala Pro Asp
            100                 105                 110

Tyr Gln Leu His Asn Gln Glu Glu Val Asp Phe Trp Arg Arg Glu Gln
        115                 120                 125

Arg Phe Phe Lys Trp Phe Phe Tyr Ile Tyr Ile Leu Ile Ser Leu Gly
130                 135                 140

Val Val Tyr Ser Gly Cys Thr Gly Val Leu Phe Leu Glu Gly Tyr Glu
145                 150                 155                 160

Leu Pro Phe Ala Tyr Tyr Val Pro Phe Glu Trp Gln Asn Glu Arg Arg
                165                 170                 175

Tyr Trp Phe Ala Tyr Gly Tyr Asp Met Ala Gly Met Thr Leu Thr Cys
                180                 185                 190

Ile Ser Asn Ile Thr Leu Asp Thr Leu Gly Cys Tyr Phe Leu Phe His
            195                 200                 205

Ile Ser Leu Leu Tyr Arg Leu Leu Gly Leu Arg Leu Arg Glu Thr Lys
        210                 215                 220

Asn Met Lys Asn Asp Thr Ile Phe Gly Gln Leu Arg Ala Ile Phe
225                 230                 235                 240

Ile Met His Gln Arg Ile Arg Ser Leu Thr Leu Thr Cys Gln Arg Ile
                245                 250                 255

Val Ser Pro Tyr Ile Leu Ser Gln Ile Ile Leu Ser Ala Leu Ile Ile
                260                 265                 270

Cys Phe Ser Gly Tyr Arg Leu Gln His Val Gly Ile Arg Asp Asn Pro
                275                 280                 285

Gly Gln Phe Ile Ser Met Leu Gln Phe Val Ser Val Met Ile Leu Gln
            290                 295                 300

Ile Tyr Leu Pro Cys Tyr Tyr Gly Asn Glu Ile Thr Val Tyr Ala Asn
305                 310                 315                 320

Gln Leu Thr Asn Glu Val Tyr His Thr Asn Trp Leu Glu Cys Arg Pro
                325                 330                 335

Pro Ile Arg Lys Leu Leu Asn Ala Tyr Met Glu His Leu Lys Lys Pro
            340                 345                 350

Val Thr Ile Arg Ala Gly Asn Ser Phe Ala Val Gly Leu Pro Ile Phe
                355                 360                 365

Val Lys Thr Ile Asn Asn Ala Tyr Ser Phe Leu Ala Leu Leu Leu Asn
370                 375                 380

Val Ser Asn
385

<210> SEQ ID NO 33
<211> LENGTH: 1149
<212> TYPE: DNA
<213> ORGANISM: Drosophila Melanogaster DOR109

<400> SEQUENCE: 33

```
atggagtcta caaatcgcct aagtgccatc caaacacttt tagtaatcca acgttggata      60
ggacttctta aatgggaaaa cgagggcgag gatggagtat taacctggct aaaacgaata     120
tatccttttg tactgcacct tccactgacc ttcacgtata ttgccttaat gtggtatgaa     180
gctattacat cgtcagattt tgaggaagct ggtcaagttc tgtacatgtc catcaccgaa     240
ctggcattgg tcactaaact gctgaatatt tggtatcgtc gtcatgaagc tgctagtcta     300
atccacgaat tgcaacacga tcccgcattt aatctgcgca attcggagga aatcaaattc     360
```

```
tggcagcaaa atcagaggaa ctttaagaga atattttact ggtacatctg gggcagcctt      420
ttcgtggctg taatgggtta tataagcgtg ttttccagg aggattacga gctgccctt        480 ggctactacg tgccattcga gtggcgcacc agggaacgat acttctacgc ttggggctat      540
aatgtggtgg ccatgaccct gtgctgtcta tccaacatcc tactggacac actaggctgt     600
tatttcatgt tccacatcgc ctcgcttttc aggcttttgg gaatgcgact ggaggccttg     660
aaaaatgcag ccgaagagaa agccagaccg gagttgcgcc gcattttcca actgcacact     720
aaagtccgcc gattgacgag ggaatgcgaa gtgttagttt caccctatgt tctatcccaa     780
gtggtcttca gtgccttcat catctgcttc agtgcctatc gactggtgca catgggcttc     840
aagcagcgac ctggactctt cgtgaccacc gtgcaattcg tggccgtcat gatcgtccag     900
attttcttgc cctgttacta cggcaatgag ttgacctttc atgccaatgc actcactaat     960
agtgtcttcg gtaccaattg gctggagtac tccgtgggca ctcgcaagct gcttaactgc    1020
tacatggagt tcctcaagcg accggttaaa gtgcgagctg gggtgttctt tgaaatagga    1080
ctacccatct ttgtgaagac catcaacaat gcctacagtt tcttcgccct gctgctaaag    1140
atatccaag                                                            1149
```

<210> SEQ ID NO 34
<211> LENGTH: 383
<212> TYPE: PRT
<213> ORGANISM: Drosophila Melanogaster DOR109

<400> SEQUENCE: 34

```
Met Glu Ser Thr Asn Arg Leu Ser Ala Ile Gln Thr Leu Leu Val Ile
1               5                   10                  15

Gln Arg Trp Ile Gly Leu Leu Lys Trp Glu Asn Glu Gly Glu Asp Gly
            20                  25                  30

Val Leu Thr Trp Leu Lys Arg Ile Tyr Pro Phe Val Leu His Leu Pro
        35                  40                  45

Leu Thr Phe Thr Tyr Ile Ala Leu Met Trp Tyr Glu Ala Ile Thr Ser
    50                  55                  60

Ser Asp Phe Glu Glu Ala Gly Gln Val Leu Tyr Met Ser Ile Thr Glu
65                  70                  75                  80

Leu Ala Leu Val Thr Lys Leu Leu Asn Ile Trp Tyr Arg Arg His Glu
                85                  90                  95

Ala Ala Ser Leu Ile His Glu Leu Gln His Asp Pro Ala Phe Asn Leu
            100                 105                 110

Arg Asn Ser Glu Glu Ile Lys Phe Trp Gln Gln Asn Gln Arg Asn Phe
        115                 120                 125

Lys Arg Ile Phe Tyr Trp Tyr Ile Trp Gly Ser Leu Phe Val Ala Val
    130                 135                 140

Met Gly Tyr Ile Ser Val Phe Phe Gln Glu Asp Tyr Glu Leu Pro Phe
145                 150                 155                 160

Gly Tyr Tyr Val Pro Phe Glu Trp Arg Thr Arg Glu Arg Tyr Phe Tyr
                165                 170                 175

Ala Trp Gly Tyr Asn Val Val Ala Met Thr Leu Cys Cys Leu Ser Asn
            180                 185                 190

Ile Leu Leu Asp Thr Leu Gly Cys Tyr Phe Met Phe His Ile Ala Ser
        195                 200                 205

Leu Phe Arg Leu Leu Gly Met Arg Leu Glu Ala Leu Lys Asn Ala Ala
    210                 215                 220
```

```
Glu Lys Ala Arg Pro Glu Leu Arg Arg Ile Phe Gln Leu His Thr
225                 230                 235                 240

Lys Val Arg Arg Leu Thr Arg Glu Cys Glu Val Leu Val Ser Pro Tyr
                245                 250                 255

Val Leu Ser Gln Val Val Phe Ser Ala Phe Ile Ile Cys Phe Ser Ala
            260                 265                 270

Tyr Arg Leu Val His Met Gly Phe Lys Gln Arg Pro Gly Leu Phe Val
        275                 280                 285

Thr Thr Val Gln Phe Val Ala Val Met Ile Val Gln Ile Phe Leu Pro
    290                 295                 300

Cys Tyr Tyr Gly Asn Glu Leu Thr Phe His Ala Asn Ala Leu Thr Asn
305                 310                 315                 320

Ser Val Phe Gly Thr Asn Trp Leu Glu Tyr Ser Val Gly Thr Arg Lys
                325                 330                 335

Leu Leu Asn Cys Tyr Met Glu Phe Leu Lys Arg Pro Val Lys Val Arg
            340                 345                 350

Ala Gly Val Phe Phe Glu Ile Gly Leu Pro Ile Phe Val Lys Thr Ile
        355                 360                 365

Asn Asn Ala Tyr Ser Phe Phe Ala Leu Leu Leu Lys Ile Ser Lys
    370                 375                 380

<210> SEQ ID NO 35
<211> LENGTH: 1161
<212> TYPE: DNA
<213> ORGANISM: Drosophila Melanogaster DOR110

<400> SEQUENCE: 35
atgttgttca actatctgcg aaagccgaat cccacaaacc ttttgacttc tccggactca      60
tttagatact ttgagtatgg aatgttttgc atgggatggc acacaccagc aacgcataag     120
ataatctact atataacatc ctgtttgatt tttgcttggt gtgccgtata cttgccaatc     180
ggaatcatca ttagtttcaa aacggatatt aacacattca caccgaatga actgttgaca     240
gttatgcaat tattttttcaa ttcagtggga atgccattca aggttctgtt cttcaatttg     300
tatatttctg gattttacaa ggccaaaaag ctccttagcg aaatggacaa acgttgcacc     360
actttgaagg agcgagtgga agtgcaccaa ggtgtggtcc gttgcaacaa ggcctacctc     420
atttaccagt tcatttatac cgcgtacact atttcaacat ttctatcggc ggctcttagt     480
ggaaaattgc catggcgcat ctataatcct tttgtggatt ttcgagaaag tagatccagt     540
ttttggaaag ctgccctcaa cgagacagca cttatgctat ttgctgtgac tcaaacccta     600
atgagtgata tatatccact gctttatggt ttgatcctga gagttcacct caaacttttg     660
cgactaagag tggagagcct gtgcacagat tctggaaaaa gcgatgctga aaacgagcaa     720
gatttgatta actatgctgc agcaatacga ccagcggtta cccgcacaat tttcgttcaa     780
tccctcttga tcggaatttg ccttggcctt tcaatgatca atctactctt ctttgccgac     840
atctggacag gattggccac agtggcttac atcaatggtc taatggtgca gacatttcca     900
ttttgcttcg tttgtgatct actcaaaaag gattgtgaac ttcttgtgtc ggccatattt     960
cattccaact ggattaattc aagccgcagt tacaagtcat ctttgagata ttttctgaag    1020
aacgcccaga aatcaattgc ttttacagcc ggctctatttt tcccatttc tactggctcg    1080
aatattaagg tggctaagct ggcatttttcg gtggttactt ttgtcaatca acttaacata    1140
gctgacagat tgacaaagaa c                                              1161
```

<210> SEQ ID NO 36
<211> LENGTH: 387
<212> TYPE: PRT
<213> ORGANISM: Drosophila Melanogaster DOR110

<400> SEQUENCE: 36

```
Met Leu Phe Asn Tyr Leu Arg Lys Pro Asn Pro Thr Asn Leu Leu Thr
 1               5                  10                  15

Ser Pro Asp Ser Phe Arg Tyr Phe Glu Tyr Gly Met Phe Cys Met Gly
            20                  25                  30

Trp His Thr Pro Ala Thr His Lys Ile Ile Tyr Tyr Ile Thr Ser Cys
        35                  40                  45

Leu Ile Phe Ala Trp Cys Ala Val Tyr Leu Pro Ile Gly Ile Ile Ile
    50                  55                  60

Ser Phe Lys Thr Asp Ile Asn Thr Phe Thr Pro Asn Glu Leu Leu Thr
65                  70                  75                  80

Val Met Gln Leu Phe Phe Asn Ser Val Gly Met Pro Phe Lys Val Leu
                85                  90                  95

Phe Phe Asn Leu Tyr Ile Ser Gly Phe Tyr Lys Ala Lys Lys Leu Leu
            100                 105                 110

Ser Glu Met Asp Lys Arg Cys Thr Thr Leu Lys Glu Arg Val Glu Val
        115                 120                 125

His Gln Gly Val Val Arg Cys Asn Lys Ala Tyr Leu Ile Tyr Gln Phe
    130                 135                 140

Ile Tyr Thr Ala Tyr Thr Ile Ser Thr Phe Leu Ser Ala Ala Leu Ser
145                 150                 155                 160

Gly Lys Leu Pro Trp Arg Ile Tyr Asn Pro Phe Val Asp Phe Arg Glu
                165                 170                 175

Ser Arg Ser Ser Phe Trp Lys Ala Ala Leu Asn Glu Thr Ala Leu Met
            180                 185                 190

Leu Phe Ala Val Thr Gln Thr Leu Met Ser Asp Ile Tyr Pro Leu Leu
        195                 200                 205

Tyr Gly Leu Ile Leu Arg Val His Leu Lys Leu Leu Arg Leu Arg Val
    210                 215                 220

Glu Ser Leu Cys Thr Asp Ser Gly Lys Ser Asp Ala Glu Asn Glu Gln
225                 230                 235                 240

Asp Leu Ile Asn Tyr Ala Ala Ala Ile Arg Pro Ala Val Thr Arg Thr
                245                 250                 255

Ile Phe Val Gln Phe Leu Leu Ile Gly Ile Cys Leu Gly Leu Ser Met
            260                 265                 270

Ile Asn Leu Leu Phe Phe Ala Asp Ile Trp Thr Gly Leu Ala Thr Val
        275                 280                 285

Ala Tyr Ile Asn Gly Leu Met Val Gln Thr Phe Pro Phe Cys Phe Val
    290                 295                 300

Cys Asp Leu Leu Lys Lys Asp Cys Glu Leu Leu Val Ser Ala Ile Phe
305                 310                 315                 320

His Ser Asn Trp Ile Asn Ser Ser Arg Ser Tyr Lys Ser Ser Leu Arg
                325                 330                 335

Tyr Phe Leu Lys Asn Ala Gln Lys Ser Ile Ala Phe Thr Ala Gly Ser
            340                 345                 350

Ile Phe Pro Ile Ser Thr Gly Ser Asn Ile Lys Val Ala Lys Leu Ala
        355                 360                 365

Phe Ser Val Val Thr Phe Val Asn Gln Leu Asn Ile Ala Asp Arg Leu
    370                 375                 380
```

Thr Lys Asn
385

<210> SEQ ID NO 37
<211> LENGTH: 1050
<212> TYPE: DNA
<213> ORGANISM: Drosophila Melanogaster DOR111

<400> SEQUENCE: 37

| | | |
|---|---|---|
| atgctgttcc gcaaacgtaa gccaaaaagt gacgatgaag tcatcacctt cgacgaactt | 60 |
| acccggtttc cgatgacttt ctacaagacc atcggcgagg atctgtactc cgataggga t | 120 |
| ccgaatgtga taaggcgtta cctgctacgt ttttatctgg tactcggttt tctcaacttc | 180 |
| aatgcctatg tggtgggcga atcgcgtac tttatagtcc atataatgtc gacgactact | 240 |
| cttttggagg ccactgcagt ggcaccgtgc attggcttca gcttcatggc cgactttaag | 300 |
| cagttcggtc tcacagtgaa tagaaagcga ttggtcagat tgctggatga tctcaaggag | 360 |
| atatttcctt tagatttaga agcgcagcgg aagtataacg tatcgtttta ccggaaacac | 420 |
| atgaacaggg tcatgaccct attccaccatc tctgcatga cctacacctc gtcatttagc | 480 |
| ttttatccag ccatcaagtc gaccataaag tattaccttta tgggatcgga atctttgag | 540 |
| cgcaactacg gatttcacat tttgtttccc tacgacgcag aaacggatct gacggtctac | 600 |
| tggttttcct actggggatt ggctcattgt gcctatgtgg ccggagtttc ctacgtctgc | 660 |
| gtggatctcc tgctgatcgc gaccataacc cagctgacca tgcacttcaa ctttatagcg | 720 |
| aatgatttgg aggcctacga aggaggtgat catacggatg aagaaaatat caaatacctg | 780 |
| cacaacttgg tcgtctatca tgccagggcg ctggatatta caagaaatg tacatttcag | 840 |
| agctctcgga ttggccattc ggcatttaat cagaactggt tgccatgcag caccaaatac | 900 |
| aaacgcatcc tgcaatttat tatcgcgcgc agccagaagc ccgcctctat aagaccgcct | 960 |
| acctttccac ccatatctttt taatacccttt atgaaggtaa tcagcatgtc gtatcagttt | 1020 |
| tttgcactgc tccgcaccac atattatggt | 1050 |

<210> SEQ ID NO 38
<211> LENGTH: 350
<212> TYPE: PRT
<213> ORGANISM: Drosophila Melanogaster DOR111

<400> SEQUENCE: 38

Met Leu Phe Arg Lys Arg Lys Pro Lys Ser Asp Asp Glu Val Ile Thr
1               5                   10                  15

Phe Asp Glu Leu Thr Arg Phe Pro Met Thr Phe Tyr Lys Thr Ile Gly
            20                  25                  30

Glu Asp Leu Tyr Ser Asp Arg Asp Pro Asn Val Ile Arg Arg Tyr Leu
        35                  40                  45

Leu Arg Phe Tyr Leu Val Leu Gly Phe Leu Asn Phe Asn Ala Tyr Val
    50                  55                  60

Val Gly Glu Ile Ala Tyr Phe Ile Val His Ile Met Ser Thr Thr Thr
65                  70                  75                  80

Leu Leu Glu Ala Thr Ala Val Ala Pro Cys Ile Gly Phe Ser Phe Met
                85                  90                  95

Ala Asp Phe Lys Gln Phe Gly Leu Thr Val Asn Arg Lys Arg Leu Val
            100                 105                 110

Arg Leu Leu Asp Asp Leu Lys Glu Ile Phe Pro Leu Asp Leu Glu Ala
        115                 120                 125

```
Gln Arg Lys Tyr Asn Val Ser Phe Tyr Arg Lys His Met Asn Arg Val
    130                 135                 140
Met Thr Leu Phe Thr Ile Leu Cys Met Thr Tyr Thr Ser Ser Phe Ser
145                 150                 155                 160
Phe Tyr Pro Ala Ile Lys Ser Thr Ile Lys Tyr Leu Met Gly Ser
                165                 170                 175
Glu Ile Phe Glu Arg Asn Tyr Gly Phe His Ile Leu Phe Pro Tyr Asp
                180                 185                 190
Ala Glu Thr Asp Leu Thr Val Tyr Trp Phe Ser Tyr Trp Gly Leu Ala
                195                 200                 205
His Cys Ala Tyr Val Ala Gly Val Ser Tyr Val Cys Val Asp Leu Leu
    210                 215                 220
Leu Ile Ala Thr Ile Thr Gln Leu Thr Met His Phe Asn Phe Ile Ala
225                 230                 235                 240
Asn Asp Leu Glu Ala Tyr Glu Gly Gly Asp His Thr Asp Glu Glu Asn
                245                 250                 255
Ile Lys Tyr Leu His Asn Leu Val Tyr His Ala Arg Ala Leu Asp
                260                 265                 270
Ile Asn Lys Lys Cys Thr Phe Gln Ser Ser Arg Ile Gly His Ser Ala
            275                 280                 285
Phe Asn Gln Asn Trp Leu Pro Cys Ser Thr Lys Tyr Lys Arg Ile Leu
290                 295                 300
Gln Phe Ile Ile Ala Arg Ser Gln Lys Pro Ala Ser Ile Arg Pro Pro
305                 310                 315                 320
Thr Phe Pro Pro Ile Ser Phe Asn Thr Phe Met Lys Val Ile Ser Met
                325                 330                 335
Ser Tyr Gln Phe Phe Ala Leu Leu Arg Thr Thr Tyr Tyr Gly
                340                 345                 350

<210> SEQ ID NO 39
<211> LENGTH: 1236
<212> TYPE: DNA
<213> ORGANISM: Drosophila Melanogaster DOR114

<400> SEQUENCE: 39
atgttgacta agaaggatac tcaaagtgcc aaggagcagg aaaagttgaa ggccattcca    60
ttgcacagct ttctgaaata tgccaacgtg ttctatttat cgattggaat gatggcctac   120
gatcacaagt acagtcaaaa gtggaaggag gtcctgctgc actggacatt cattgcccag   180
atggtcaatc tgaatacagt gctcatctcg gaactgattt acgtattcct ggcgatcggc   240
aaaggtagca tttttctgga ggccaccatg aatctgtctt tcattggatt tgtcatcgtt   300
ggtgacttca aaatctggaa catttcgcgg cagagaaaga gactcaccca gtggtcagc   360
cgattggaag aactgcatcc gcaaggcttg gctcaacaag aaccctataa tatagggcat   420
catctgagcg gctatagccg atatagcaaa ttttacttcg gcatgcacat ggtgctgata   480
tggacgtaca acctgtattg ggccgtttac tatctggtct gtgatttctg gctgggaatg   540
cgtcaatttg agaggatgct gccctactac tgctgggttc cctgggattg gagtaccgga   600
tatagctact atttcatgta tatctcacag aatatcggcg gtcaggcttg tctgtccggt   660
cagctagcag ctgacatgtt aatgtgcgcc ctggtcactt tggtggtgat gcacttcatc   720
cggctttccg ctcacatcga gagtcatgtt gcgggcattg gctcattcca gcacgatttg   780
gagttcctcc aagcgacggt ggcgtatcac cagagcttga tccacctctg ccaggatatc   840
aatgagatat tcggtgtttc actgttgtcc aactttgtat cctcgtcgtt tatcatctgc   900
```

```
ttcgtgggtt tccagatgac catcggcagc aagatcgaca acctggtaat gcttgtgctt    960
ttcctgtttt gtgccatggt tcaggtcttc atgattgcca cccatgctca gaggctcgtt   1020
gatgcgagtg aacagattgg tcaagcggtc tataatcacg actggttccg tgctgatctg   1080
cggtatcgta aaatgctgat cctgattatt aagagggccc aacagccgag tcgactcaag   1140
gccacaatgt tcctgaacat ctcactggtc accgtgtcgg atctcttgca actctcgtac   1200
aaattctttg cccttctgcg cacaatgtac gtgaat                             1236
```

<210> SEQ ID NO 40
<211> LENGTH: 412
<212> TYPE: PRT
<213> ORGANISM: Drosophila Melanogaster DOR114

<400> SEQUENCE: 40

```
Met Leu Thr Lys Lys Asp Thr Gln Ser Ala Lys Glu Gln Glu Lys Leu
1               5                   10                  15

Lys Ala Ile Pro Leu His Ser Phe Leu Lys Tyr Ala Asn Val Phe Tyr
            20                  25                  30

Leu Ser Ile Gly Met Met Ala Tyr Asp His Lys Tyr Ser Gln Lys Trp
        35                  40                  45

Lys Glu Val Leu Leu His Trp Thr Phe Ile Ala Gln Met Val Asn Leu
    50                  55                  60

Asn Thr Val Leu Ile Ser Glu Leu Ile Tyr Val Phe Leu Ala Ile Gly
65                  70                  75                  80

Lys Gly Ser Asn Phe Leu Glu Ala Thr Met Asn Leu Ser Phe Ile Gly
                85                  90                  95

Phe Val Ile Val Gly Asp Phe Lys Ile Trp Asn Ile Ser Arg Gln Arg
            100                 105                 110

Lys Arg Leu Thr Gln Val Val Ser Arg Leu Glu Glu Leu His Pro Gln
        115                 120                 125

Gly Leu Ala Gln Gln Glu Pro Tyr Asn Ile Gly His His Leu Ser Gly
    130                 135                 140

Tyr Ser Arg Tyr Ser Lys Phe Tyr Phe Gly Met His Met Val Leu Ile
145                 150                 155                 160

Trp Thr Tyr Asn Leu Tyr Trp Ala Val Tyr Tyr Leu Val Cys Asp Phe
                165                 170                 175

Trp Leu Gly Met Arg Gln Phe Glu Arg Met Leu Pro Tyr Tyr Cys Trp
            180                 185                 190

Val Pro Trp Asp Trp Ser Thr Gly Tyr Ser Tyr Tyr Phe Met Tyr Ile
        195                 200                 205

Ser Gln Asn Ile Gly Gly Gln Ala Cys Leu Ser Gly Gln Leu Ala Ala
    210                 215                 220

Asp Met Leu Met Cys Ala Leu Val Thr Leu Val Val Met His Phe Ile
225                 230                 235                 240

Arg Leu Ser Ala His Ile Glu Ser His Val Ala Gly Ile Gly Ser Phe
                245                 250                 255

Gln His Asp Leu Glu Phe Leu Gln Ala Thr Val Ala Tyr His Gln Ser
            260                 265                 270

Leu Ile His Leu Cys Gln Asp Ile Asn Glu Ile Phe Gly Val Ser Leu
        275                 280                 285

Leu Ser Asn Phe Val Ser Ser Ser Phe Ile Ile Cys Phe Val Gly Phe
    290                 295                 300

Gln Met Thr Ile Gly Ser Lys Ile Asp Asn Leu Val Met Leu Val Leu
```

-continued

```
            305                 310                 315                 320

Phe Leu Phe Cys Ala Met Val Gln Val Phe Met Ile Ala Thr His Ala
                325                 330                 335

Gln Arg Leu Val Asp Ala Ser Glu Gln Ile Gly Gln Ala Val Tyr Asn
            340                 345                 350

His Asp Trp Phe Arg Ala Asp Leu Arg Tyr Arg Lys Met Leu Ile Leu
        355                 360                 365

Ile Ile Lys Arg Ala Gln Gln Pro Ser Arg Leu Lys Ala Thr Met Phe
    370                 375                 380

Leu Asn Ile Ser Leu Val Thr Val Ser Asp Leu Leu Gln Leu Ser Tyr
385                 390                 395                 400

Lys Phe Phe Ala Leu Leu Arg Thr Met Tyr Val Asn
                405                 410

<210> SEQ ID NO 41
<211> LENGTH: 1140
<212> TYPE: DNA
<213> ORGANISM: Drosophila Melanogaster DOR115

<400> SEQUENCE: 41
atggagaagc taatgaagta cgctagcttc ttctacacag cagtgggcat acggccatat      60
accaatggtg aagaatccaa aatgaacaaa cttatatttc acatagtttt ttggtccaat     120
gtgattaacc tcagcttcgt tggattattt gagagcattt acgtttacag tgccttcatg     180
gataataagt tcctggaagc agtcactgcg ttgtcctaca ttggcttcgt aaccgtaggc     240
atgagcaaga tgttcttcat ccggtggaag aaaacggcta taactgaact gattaatgaa     300
ttgaaggaga tctatccgaa tggtttgatc cgagaggaaa gatacaatct gccgatgtat     360
ctgggcacct gctccagaat cagccttata tattccttgc tctactctgt tctcatctgg     420
acattcaact tgttttgtgt aatggagtat tgggtctatg caagtggct caacattcga      480 gtggtgggca acagttgcc gtacctcatg tacattcctt ggaaatggca ggataactgg      540
tcgtactatc cactgttatt ctcccagaat tttgcaggat acacatctgc agctggtcaa     600
atttcaaccg atgtcttgct ctgcgcggtg gccactcagt tggtaatgca cttcgacttt     660
ctctcaaata gtatggaacg ccacgaattg agtggagatt ggaagaagga ctcccgattt     720
ctggtggaca ttgttaggta tcacgaacgt atactccgcc tttcagatgc agtgaacgat     780
atatttggaa ttccactact actcaacttc atggtatcct cgttcgtcat ctgcttcgtg     840
ggattccaga tgactgttgg agttccgccg gatatagttg tgaagctctt cctcttcctt     900
gtctcttcga tgagtcaggt ctatttgatt tgtcactatg gtcaactggt ggccgatgct     960
agctacggat tttcggttgc cacctacaat cagaagtggt ataaagccga tgtgcgctat    1020
aaacgagcct tggttattat tatagctaga tcgcagaagg taacttttct aaaggccact    1080
atattcttgg atattaccag gtccactatg acagatgtac gcaactgtgt attgtcagtg    1140

<210> SEQ ID NO 42
<211> LENGTH: 380
<212> TYPE: PRT
<213> ORGANISM: Drosophila Melanogaster DOR115

<400> SEQUENCE: 42

Met Glu Lys Leu Met Lys Tyr Ala Ser Phe Phe Tyr Thr Ala Val Gly
1               5                   10                  15

Ile Arg Pro Tyr Thr Asn Gly Glu Glu Ser Lys Met Asn Lys Leu Ile
            20                  25                  30
```

```
Phe His Ile Val Phe Trp Ser Asn Val Ile Asn Leu Ser Phe Val Gly
            35                  40                  45

Leu Phe Glu Ser Ile Tyr Val Tyr Ser Ala Phe Met Asp Asn Lys Phe
 50                  55                  60

Leu Glu Ala Val Thr Ala Leu Ser Tyr Ile Gly Phe Val Thr Val Gly
 65                  70                  75                  80

Met Ser Lys Met Phe Phe Ile Arg Trp Lys Lys Thr Ala Ile Thr Glu
                 85                  90                  95

Leu Ile Asn Glu Leu Lys Glu Ile Tyr Pro Asn Gly Leu Ile Arg Glu
                100                 105                 110

Glu Arg Tyr Asn Leu Pro Met Tyr Leu Gly Thr Cys Ser Arg Ile Ser
            115                 120                 125

Leu Ile Tyr Ser Leu Leu Tyr Ser Val Leu Ile Trp Thr Phe Asn Leu
            130                 135                 140

Phe Cys Val Met Glu Tyr Trp Val Tyr Asp Lys Trp Leu Asn Ile Arg
145                 150                 155                 160

Val Val Gly Lys Gln Leu Pro Tyr Leu Met Tyr Ile Pro Trp Lys Trp
                165                 170                 175

Gln Asp Asn Trp Ser Tyr Tyr Pro Leu Leu Phe Ser Gln Asn Phe Ala
                180                 185                 190

Gly Tyr Thr Ser Ala Ala Gly Gln Ile Ser Thr Asp Val Leu Leu Cys
            195                 200                 205

Ala Val Ala Thr Gln Leu Val Met His Phe Asp Phe Leu Ser Asn Ser
            210                 215                 220

Met Glu Arg His Glu Leu Ser Gly Asp Trp Lys Lys Asp Ser Arg Phe
225                 230                 235                 240

Leu Val Asp Ile Val Arg Tyr His Glu Arg Ile Leu Arg Leu Ser Asp
                245                 250                 255

Ala Val Asn Asp Ile Phe Gly Ile Pro Leu Leu Leu Asn Phe Met Val
                260                 265                 270

Ser Ser Phe Val Ile Cys Phe Val Gly Phe Gln Met Thr Val Gly Val
            275                 280                 285

Pro Pro Asp Ile Val Val Lys Leu Phe Leu Phe Leu Val Ser Ser Met
 290                 295                 300

Ser Gln Val Tyr Leu Ile Cys His Tyr Gly Gln Leu Val Ala Asp Ala
305                 310                 315                 320

Ser Tyr Gly Phe Ser Val Ala Thr Tyr Asn Gln Lys Trp Tyr Lys Ala
                325                 330                 335

Asp Val Arg Tyr Lys Arg Ala Leu Val Ile Ile Ala Arg Ser Gln
                340                 345                 350

Lys Val Thr Phe Leu Lys Ala Thr Ile Phe Leu Asp Ile Thr Arg Ser
            355                 360                 365

Thr Met Thr Asp Val Arg Asn Cys Val Leu Ser Val
    370                 375                 380

<210> SEQ ID NO 43
<211> LENGTH: 759
<212> TYPE: DNA
<213> ORGANISM: Drosophila Melanogaster DOR116

<400> SEQUENCE: 43
atggaactcc tgccattggc catgctaatg tacgatggaa cccgggttac tgcgatgcag     60
tatttaattc cgggtctacc gcttgagaac aattattgct acgtagtcac gtacatgatt    120
```

|  |  |  |  |  | -continued |  |
|---|---|---|---|---|---|---|
| cagacggtga | caatgctcgt | gcaaggagtc | ggattctact | ccggtgattt | gttcgtattt | 180 |
| ctcggcttaa | cgcagatcct | aactttcgcc | gatatgctgc | aggtgaaggt | gaaagagcta | 240 |
| aacgatgccc | tggaacaaaa | agcggaatac | agagctctag | tccgagttgg | agcttctatt | 300 |
| gatggagcgg | aaaatcgtca | acgccttctc | ttggatgtta | aagatggca | tcaattattc | 360 |
| acggactact | gtcgcgccat | aaatgccctc | tactacgaat | tgatcgccac | tcaggttctt | 420 |
| tcgatggctt | tggccatgat | gctcagcttc | tgcattaatt | tgagcagctt | tcacatgcct | 480 |
| tcggctatct | ttttcgtggt | ttctgcctac | agcatgtcca | tctattgcat | tctgggcacc | 540 |
| attcttgagt | ttgcatatga | ccaggtgtac | gagagcatct | gtaatgtgac | ctggtatgag | 600 |
| ttgagtggcg | aacagcgaaa | gcttttggt | tttttgttgc | gggaatccca | gtatccgcac | 660 |
| aatattcaga | tacttggagt | tatgtcgctt | ccgtgagaa | cggctctgca | gattgttaaa | 720 |
| ctaatttata | gcgtatccat | gatgatgatg | aatcgggcg |  |  | 759 |

<210> SEQ ID NO 44
<211> LENGTH: 253
<212> TYPE: PRT
<213> ORGANISM: Drosophila Melanogaster DOR116

<400> SEQUENCE: 44

```
Met Glu Leu Leu Pro Leu Ala Met Leu Met Tyr Asp Gly Thr Arg Val
1               5                   10                  15

Thr Ala Met Gln Tyr Leu Ile Pro Gly Leu Pro Leu Glu Asn Asn Tyr
            20                  25                  30

Cys Tyr Val Val Thr Tyr Met Ile Gln Thr Val Thr Met Leu Val Gln
        35                  40                  45

Gly Val Gly Phe Tyr Ser Gly Asp Leu Phe Val Phe Leu Gly Leu Thr
    50                  55                  60

Gln Ile Leu Thr Phe Ala Asp Met Leu Gln Val Lys Val Lys Glu Leu
65                  70                  75                  80

Asn Asp Ala Leu Glu Gln Lys Ala Glu Tyr Arg Ala Leu Val Arg Val
                85                  90                  95

Gly Ala Ser Ile Asp Gly Ala Glu Asn Arg Gln Arg Leu Leu Leu Asp
            100                 105                 110

Val Ile Arg Trp His Gln Leu Phe Thr Asp Tyr Cys Arg Ala Ile Asn
        115                 120                 125

Ala Leu Tyr Tyr Glu Leu Ile Ala Thr Gln Val Leu Ser Met Ala Leu
    130                 135                 140

Ala Met Met Leu Ser Phe Cys Ile Asn Leu Ser Ser Phe His Met Pro
145                 150                 155                 160

Ser Ala Ile Phe Phe Val Val Ser Ala Tyr Ser Met Ser Ile Tyr Cys
                165                 170                 175

Ile Leu Gly Thr Ile Leu Glu Phe Ala Tyr Asp Gln Val Tyr Glu Ser
            180                 185                 190

Ile Cys Asn Val Thr Trp Tyr Glu Leu Ser Gly Glu Gln Arg Lys Leu
        195                 200                 205

Phe Gly Phe Leu Leu Arg Glu Ser Gln Tyr Pro His Asn Ile Gln Ile
    210                 215                 220

Leu Gly Val Met Ser Leu Ser Val Arg Thr Ala Leu Gln Ile Val Lys
225                 230                 235                 240

Leu Ile Tyr Ser Val Ser Met Met Met Asn Arg Ala
                245                 250
```

<210> SEQ ID NO 45
<211> LENGTH: 1152
<212> TYPE: DNA
<213> ORGANISM: Drosophila Melanogaster DOR117

<400> SEQUENCE: 45

```
atggatctgc gaaggtggtt tccgaccttg tacacccagt cgaaggattc gccagttcgc      60
tcccgagacg cgaccctgta cctcctacgc tgcgtcttct taatgggcgt ccgcaagcca     120
cctgccaagt ttttcgtggc ctacgtgctc tggtccttcg cactgaattt ctgctcaaca     180
ttttatcagc caattggctt ctcacaggc tatataagcc atttatcaga gttctccccg      240
ggagagtttc taacttcgct gcaggtggcc tttaatgctt ggtcctgctc tacaaaagtc     300
ctgatagtgt gggcactagt taagcgcttt gacgaggcta ataaccttct cgacgagatg     360
gataggcgta tcacagaccc cggagagcgt cttcagattc atcgcgctgt ctccctcagt     420
aaccgtatat tcttcttttt catggcagtc tacatggttt atgccactaa tacgtttctg     480
tcggcgatct tcattggaag gccaccgtac caaaattact accctttct ggactggcga      540
tctagcactc tgcatctagc tctgcaggcc ggtctggaat acttcgccat ggctggcgcc     600
tgcttccagg acgtttgcgt tgattgctac ccagtcaatt tcgttttggt cctgcgtgcc     660
cacatgtcga tcttcgcgga gcgccttcga cgtttgggaa cttatcctta tgaaagccag     720
gagcagaaat atgaacgatt ggttcagtgc atacaagatc acaaagtaat tttgcgattt     780
gttgactgcc tgcgtcctgt tatttctggt accatcttcg tgcaattctt ggttgtgggg     840
ttggtgctgg gctttaccct aattaacatt gtcctgttcg ccaacttggg atcggccatc     900
gcagcgctct cgtttatggc cgcagtgctt ctagagacga ctcccttctg catattgtgc     960
aattatctca cagaagactg ctacaagctg gccgatgccc tgtttcagtc aaactggatt    1020
gatgaggaga acgatacca aaagacactc atgtacttcc tacagaaact gcagcagcct     1080
ataaccttca tggctatgaa cgtgttccca atatctgtgg gaactaacat cagtgtaagc    1140
agatgtgccc tt                                                        1152
```

<210> SEQ ID NO 46
<211> LENGTH: 384
<212> TYPE: PRT
<213> ORGANISM: Drosophila Melanogaster DOR117

<400> SEQUENCE: 46

```
Met Asp Leu Arg Arg Trp Phe Pro Thr Leu Tyr Thr Gln Ser Lys Asp
1               5                   10                  15

Ser Pro Val Arg Ser Arg Asp Ala Thr Leu Tyr Leu Leu Arg Cys Val
            20                  25                  30

Phe Leu Met Gly Val Arg Lys Pro Pro Ala Lys Phe Phe Val Ala Tyr
        35                  40                  45

Val Leu Trp Ser Phe Ala Leu Asn Phe Cys Ser Thr Phe Tyr Gln Pro
    50                  55                  60

Ile Gly Phe Leu Thr Gly Tyr Ile Ser His Leu Ser Glu Phe Ser Pro
65                  70                  75                  80

Gly Glu Phe Leu Thr Ser Leu Gln Val Ala Phe Asn Ala Trp Ser Cys
                85                  90                  95

Ser Thr Lys Val Leu Ile Val Trp Ala Leu Val Lys Arg Phe Asp Glu
            100                 105                 110

Ala Asn Asn Leu Leu Asp Glu Met Asp Arg Arg Ile Thr Asp Pro Gly
        115                 120                 125
```

-continued

```
Glu Arg Leu Gln Ile His Arg Ala Val Ser Leu Ser Asn Arg Ile Phe
    130                 135                 140

Phe Phe Phe Met Ala Val Tyr Met Val Tyr Ala Thr Asn Thr Phe Leu
145                 150                 155                 160

Ser Ala Ile Phe Ile Gly Arg Pro Pro Tyr Gln Asn Tyr Tyr Pro Phe
                165                 170                 175

Leu Asp Trp Arg Ser Ser Thr Leu His Leu Ala Leu Gln Ala Gly Leu
            180                 185                 190

Glu Tyr Phe Ala Met Ala Gly Ala Cys Phe Gln Asp Val Cys Val Asp
        195                 200                 205

Cys Tyr Pro Val Asn Phe Val Leu Val Leu Arg Ala His Met Ser Ile
    210                 215                 220

Phe Ala Glu Arg Leu Arg Arg Leu Gly Thr Tyr Pro Tyr Glu Ser Gln
225                 230                 235                 240

Glu Gln Lys Tyr Glu Arg Leu Val Gln Cys Ile Gln Asp His Lys Val
                245                 250                 255

Ile Leu Arg Phe Val Asp Cys Leu Arg Pro Val Ile Ser Gly Thr Ile
            260                 265                 270

Phe Val Gln Phe Leu Val Val Gly Leu Val Leu Gly Phe Thr Leu Ile
        275                 280                 285

Asn Ile Val Leu Phe Ala Asn Leu Gly Ser Ala Ile Ala Ala Leu Ser
    290                 295                 300

Phe Met Ala Ala Val Leu Leu Glu Thr Thr Pro Phe Cys Ile Leu Cys
305                 310                 315                 320

Asn Tyr Leu Thr Glu Asp Cys Tyr Lys Leu Ala Asp Ala Leu Phe Gln
                325                 330                 335

Ser Asn Trp Ile Asp Glu Glu Lys Arg Tyr Gln Lys Thr Leu Met Tyr
            340                 345                 350

Phe Leu Gln Lys Leu Gln Gln Pro Ile Thr Phe Met Ala Met Asn Val
        355                 360                 365

Phe Pro Ile Ser Val Gly Thr Asn Ile Ser Val Ser Arg Cys Ala Leu
    370                 375                 380
```

<210> SEQ ID NO 47
<211> LENGTH: 1116
<212> TYPE: DNA
<213> ORGANISM: Drosophila Melanogaster DOR118

<400> SEQUENCE: 47

```
atgaagttta ttggatggct gcccccccaag cagggtgtgc tccggtatgt gtacctcacc      60
tggacgctaa tgacgttcgt gtggtgtaca acgtacctgc cgcttggctt ccttggtagc     120
tacatgacgc agatcaagtc cttctcccct ggagagtttc tcacttcact ccaggtgtgc     180
attaatgcct acggctcatc ggtaaaagtt gcaatcacat actccatgct ctggcgcctt     240
atcaaggcca agaacatttt ggaccagctg gacctgcgct gcaccgccat ggaggagcgc     300
gaaaagatcc acctagtggt ggcccgcagc aaccatgcct ttctcatctt caccttttgtc     360 tactgcggat atgccggctc cacctacctg agctcggttc tcagcgggcg tccgccctgg     420
cagctgtaca atccctttat tgattggcat gacggcacac tcaagctctg ggtggcctcc     480
acgttggagt acatggtgat gtcaggcgcc gttctgcagg atcaactctc ggactcttac     540
ccattgatct ataccctcat ccttcgtgct cacttggaca tgctaaggga gcgcatccga     600
cgcctccgtt ccgatgagaa cctgagcgag gccgagagct atgaagagct ggtcaaatgt     660
gtgatggacc acaagctcat tctaagatac tgcgcgatta ttaaaccagt aatccagggg     720
```

```
accatcttca cacagtttct gctgatcggc ctggttctgg gcttcacgct gatcaacgtg    780 ttttcttct  cagacatctg acgggcatc  gcatcattta tgtttgttat aaccattttg    840
ctgcagacct tcccttctg  ctacacatgc aacctcatca tggaggactg cgagtccttg    900
acccatgcta ttttccagtc caactgggtg gatgccagtc gtcgctacaa acaacacta    960 ctgtattttc tccaaaacgt gcagcagcct atcgttttca ttgcaggcgg tatctttcag   1020
atatccatga gcagcaacat aagtgtggca aagtttgctt tctccgtgat aaccattacc   1080
aagcaaatga atatagctga caaatttaag acggac                              1116
```

<210> SEQ ID NO 48
<211> LENGTH: 372
<212> TYPE: PRT
<213> ORGANISM: Drosophila Melanogaster DOR118

<400> SEQUENCE: 48

```
Met Lys Phe Ile Gly Trp Leu Pro Pro Lys Gln Gly Val Leu Arg Tyr
1               5                   10                  15

Val Tyr Leu Thr Trp Thr Leu Met Thr Phe Val Trp Cys Thr Thr Tyr
            20                  25                  30

Leu Pro Leu Gly Phe Leu Gly Ser Tyr Met Thr Gln Ile Lys Ser Phe
        35                  40                  45

Ser Pro Gly Glu Phe Leu Thr Ser Leu Gln Val Cys Ile Asn Ala Tyr
    50                  55                  60

Gly Ser Ser Val Lys Val Ala Ile Thr Tyr Ser Met Leu Trp Arg Leu
65                  70                  75                  80

Ile Lys Ala Lys Asn Ile Leu Asp Gln Leu Asp Leu Arg Cys Thr Ala
                85                  90                  95

Met Glu Glu Arg Glu Lys Ile His Leu Val Ala Arg Ser Asn His
            100                 105                 110

Ala Phe Leu Ile Phe Thr Phe Val Tyr Cys Gly Tyr Ala Gly Ser Thr
        115                 120                 125

Tyr Leu Ser Ser Val Leu Ser Gly Arg Pro Pro Trp Gln Leu Tyr Asn
    130                 135                 140

Pro Phe Ile Asp Trp His Asp Gly Thr Leu Lys Leu Trp Val Ala Ser
145                 150                 155                 160

Thr Leu Glu Tyr Met Val Met Ser Gly Ala Val Leu Gln Asp Gln Leu
                165                 170                 175

Ser Asp Ser Tyr Pro Leu Ile Tyr Thr Leu Ile Leu Arg Ala His Leu
            180                 185                 190

Asp Met Leu Arg Glu Arg Ile Arg Arg Leu Arg Ser Asp Glu Asn Leu
        195                 200                 205

Ser Glu Ala Glu Ser Tyr Glu Glu Leu Val Lys Cys Val Met Asp His
    210                 215                 220

Lys Leu Ile Leu Arg Tyr Cys Ala Ile Ile Lys Pro Val Ile Gln Gly
225                 230                 235                 240

Thr Ile Phe Thr Gln Phe Leu Leu Ile Gly Leu Val Leu Gly Phe Thr
                245                 250                 255

Leu Ile Asn Val Phe Phe Ser Asp Ile Trp Thr Gly Ile Ala Ser
            260                 265                 270

Phe Met Phe Val Ile Thr Ile Leu Gln Thr Phe Pro Phe Cys Tyr
        275                 280                 285

Thr Cys Asn Leu Ile Met Glu Asp Cys Glu Ser Leu Thr His Ala Ile
    290                 295                 300
```

```
Phe Gln Ser Asn Trp Val Asp Ala Ser Arg Arg Tyr Lys Thr Thr Leu
305                 310                 315                 320

Leu Tyr Phe Leu Gln Asn Val Gln Gln Pro Ile Val Phe Ile Ala Gly
            325                 330                 335

Gly Ile Phe Gln Ile Ser Met Ser Ser Asn Ile Ser Val Ala Lys Phe
            340                 345                 350

Ala Phe Ser Val Ile Thr Ile Thr Lys Gln Met Asn Ile Ala Asp Lys
            355                 360                 365

Phe Lys Thr Asp
    370
```

<210> SEQ ID NO 49
<211> LENGTH: 1194
<212> TYPE: DNA
<213> ORGANISM: Drosophila Melanogaster DOR119

<400> SEQUENCE: 49

| | | | | | |
|---|---|---|---|---|---|
| atggcggtgt | tcaagctaat | caaaccggct | ccgttgaccg | agaaggtgca | gtcccgccag | 60 |
| gggaatatat | atctgtaccg | tgccatgtgg | ctcatcggat | ggattccgcc | gaaggaggga | 120 |
| gtcctgcgct | acgtgtatct | cttctggacc | tgcgtgccct | tcgccttcgg | ggtgttttac | 180 |
| ctgcccgtgg | gcttcatcat | cagctacgtg | caggagttca | gaacttcac | gccgggcgag | 240 |
| ttccttacct | cgctgcaggt | gtgcatcaat | gtgtatggcg | cctcggtgaa | gtccaccatc | 300 |
| acctacctct | cctctggcg | actgcgcaag | acggagatcc | ttctggactc | cctggacaag | 360 |
| aggctggcga | acgacagcga | tcgcgagagg | atccacaata | tggtggcgcg | ctgcaactac | 420 |
| gcctttctca | tctacagctt | catctactgc | ggatacgcgg | gttccacttt | cctgtcctac | 480 |
| gccctcagtg | gtcgtcctcc | gtggtccgtc | tacaatccct | tcatcgattg | gcgcgatggc | 540 |
| atgggcagcc | tgtggatcca | ggccatattc | gagtacatca | ccatgtcctt | cgccgtgctg | 600 |
| caggaccagc | tatccgacac | gtatccctg | atgttcacca | ttatgttccg | ggcccacatg | 660 |
| gaggtcctca | aggatcacgt | gcggagcctg | cgcatggatc | ccgagcgcag | tgaggcagac | 720 |
| aactatcagg | atctggtgaa | ctgcgtgctg | gaccacaaga | ctatactgaa | atgctgtgac | 780 |
| atgattcgcc | ccatgatatc | ccgcaccatc | ttcgtgcaat | tcgcgctgat | tggttccgtt | 840 |
| ttgggcctga | ccctggtgaa | cgtgttcttc | ttctcgaact | tctggaaggg | cgtggcctcg | 900 |
| ctcctgttcg | tcatcaccat | cctgctgcag | accttcccgt | tctgctacac | ctgcaacatg | 960 |
| ctgatcgacg | atgcccagga | tctgtccaac | gagattttcc | agtccaactg | ggtggacgcg | 1020 |
| gagccgcgct | acaaggcgac | gctggtgctc | ttcatgcacc | atgttcagca | gcccataatc | 1080 |
| ttcattgccg | gaggcatctt | tcccatctct | atgaacagca | acataaccgt | ggccaagttc | 1140 |
| gccttcagca | tcattacaat | agtgcgacaa | atgaatctgg | ccgagcagtt | ccag | 1194 |

<210> SEQ ID NO 50
<211> LENGTH: 398
<212> TYPE: PRT
<213> ORGANISM: Drosophila Melanogaster DOR119

<400> SEQUENCE: 50

```
Met Ala Val Phe Lys Leu Ile Lys Pro Ala Pro Leu Thr Glu Lys Val
1               5                   10                  15

Gln Ser Arg Gln Gly Asn Ile Tyr Leu Tyr Arg Ala Met Trp Leu Ile
            20                  25                  30

Gly Trp Ile Pro Pro Lys Glu Gly Val Leu Arg Tyr Val Tyr Leu Phe
```

```
                35                  40                  45
Trp Thr Cys Val Pro Phe Ala Phe Gly Val Phe Tyr Leu Pro Val Gly
         50                  55                  60
Phe Ile Ile Ser Tyr Val Gln Glu Phe Lys Asn Phe Thr Pro Gly Glu
 65                  70                  75                  80
Phe Leu Thr Ser Leu Gln Val Cys Ile Asn Val Tyr Gly Ala Ser Val
                 85                  90                  95
Lys Ser Thr Ile Thr Tyr Leu Phe Leu Trp Arg Leu Arg Lys Thr Glu
                100                 105                 110
Ile Leu Leu Asp Ser Leu Asp Lys Arg Leu Ala Asn Asp Ser Asp Arg
            115                 120                 125
Glu Arg Ile His Asn Met Val Ala Arg Cys Asn Tyr Ala Phe Leu Ile
        130                 135                 140
Tyr Ser Phe Ile Tyr Cys Gly Tyr Ala Gly Ser Thr Phe Leu Ser Tyr
145                 150                 155                 160
Ala Leu Ser Gly Arg Pro Pro Trp Ser Val Tyr Asn Pro Phe Ile Asp
                165                 170                 175
Trp Arg Asp Gly Met Gly Ser Leu Trp Ile Gln Ala Ile Phe Glu Tyr
            180                 185                 190
Ile Thr Met Ser Phe Ala Val Leu Gln Asp Gln Leu Ser Asp Thr Tyr
        195                 200                 205
Pro Leu Met Phe Thr Ile Met Phe Arg Ala His Met Glu Val Leu Lys
    210                 215                 220
Asp His Val Arg Ser Leu Arg Met Asp Pro Glu Arg Ser Glu Ala Asp
225                 230                 235                 240
Asn Tyr Gln Asp Leu Val Asn Cys Val Leu Asp His Lys Thr Ile Leu
                245                 250                 255
Lys Cys Cys Asp Met Ile Arg Pro Met Ile Ser Arg Thr Ile Phe Val
            260                 265                 270
Gln Phe Ala Leu Ile Gly Ser Val Leu Gly Leu Thr Leu Val Asn Val
        275                 280                 285
Phe Phe Phe Ser Asn Phe Trp Lys Gly Val Ala Ser Leu Leu Phe Val
    290                 295                 300
Ile Thr Ile Leu Leu Gln Thr Phe Pro Phe Cys Tyr Thr Cys Asn Met
305                 310                 315                 320
Leu Ile Asp Asp Ala Gln Asp Leu Ser Asn Glu Ile Phe Gln Ser Asn
                325                 330                 335
Trp Val Asp Ala Glu Pro Arg Tyr Lys Ala Thr Leu Val Leu Phe Met
            340                 345                 350
His His Val Gln Gln Pro Ile Ile Phe Ile Ala Gly Gly Ile Phe Pro
        355                 360                 365
Ile Ser Met Asn Ser Asn Ile Thr Val Ala Lys Phe Ala Phe Ser Ile
    370                 375                 380
Ile Thr Ile Val Arg Gln Met Asn Leu Ala Glu Gln Phe Gln
385                 390                 395

<210> SEQ ID NO 51
<211> LENGTH: 1233
<212> TYPE: DNA
<213> ORGANISM: Drosophila Melanogaster DOR120

<400> SEQUENCE: 51
atgaccaagt tcttcttcaa gcgcctgcaa actgctccac ttgatcagga ggtgagttcc      60
cttgatgcca gcgactacta ctaccgcatc gcattttttcc tgggctggac cccgcccaag     120
```

-continued

```
ggggctctgc tccgatggat ctactccctg tggactctga ccacgatgtg gctgggtatc      180
gtgtacctgc cgctcggact gagcctcacc tatgtgaagc acttcgatag attcacgccg      240
acggagttcc tgacctccct gcaggtggat atcaactgca tcgggaacgt gatcaagtca      300
tgcgtaactt attcccagat gtggcgtttt cgccggatga atgagcttat ctcgtccctg      360
gacaagagat gtgtgactac gacacagcgt cgaattttcc ataagatggt ggcacgggtt      420
aatctcatcg tgattctgtt cttgtccacg tacttgggct tctgctttct aactctgttc      480
acttcggttt tcgctggcaa agctccttgg cagctgtaca cccactggt ggactggcgg      540 aaaggccatt ggcagctatg gattgcctcc atcctggagt actgtgtggt ctccattggc      600
accatgcagg agttgatgtc cgacacctac gccatagtgt tcatctcctt gttccgctgc      660
cacctggcta ttctcagaga tcgcatagct aatctgcggc aggatccgaa actcagtgag      720
atggaacact atgagcagat ggtggcctgc attcaggatc atcgaaccat catacagtgc      780
tcccagatta ttcgacccat cctgtcgatc actatctttg cccagttcat gctggttggc      840
attgacttgg gtctggcggc catcagcatc ctcttctttc cgaacaccat ttggacgatc      900
atggcaaacg tgtcgttcat cgtggccatc tgtacagagt cctttccatg ctgcatgctc      960
tgcgagcatc tgatcgagga ctccgtccat gtgagcaacg ccctgttcca ctcaaactgg     1020
ataaccgcgg acaggagcta caagtcggcg ttctgtatt tcctgcaccg ggctcagcaa     1080
cccattcaat tcacggccgg ctccatattt cccatttcgg tgcagagcaa catagccgtg     1140
gccaagttcg cgttcacaat catcacaatc gtgaaccaaa tgaatctggg cgagaagttc     1200
ttcagtgaca ggagcaatgg cgatataaat cct                                  1233
```

<210> SEQ ID NO 52
<211> LENGTH: 411
<212> TYPE: PRT
<213> ORGANISM: Drosophila Melanogaster DOR120

<400> SEQUENCE: 52

```
Met Thr Lys Phe Phe Lys Arg Leu Gln Thr Ala Pro Leu Asp Gln
1               5                   10                  15

Glu Val Ser Ser Leu Asp Ala Ser Asp Tyr Tyr Arg Ile Ala Phe
                20                  25                  30

Phe Leu Gly Trp Thr Pro Lys Gly Ala Leu Leu Arg Trp Ile Tyr
            35                  40                  45

Ser Leu Trp Thr Leu Thr Thr Met Trp Leu Gly Ile Val Tyr Leu Pro
        50                  55                  60

Leu Gly Leu Ser Leu Thr Tyr Val Lys His Phe Asp Arg Phe Thr Pro
65                  70                  75                  80

Thr Glu Phe Leu Thr Ser Leu Gln Val Asp Ile Asn Cys Ile Gly Asn
                85                  90                  95

Val Ile Lys Ser Cys Val Thr Tyr Ser Gln Met Trp Arg Phe Arg Arg
            100                 105                 110

Met Asn Glu Leu Ile Ser Ser Leu Asp Lys Arg Cys Val Thr Thr Thr
        115                 120                 125

Gln Arg Arg Ile Phe His Lys Met Val Ala Arg Val Asn Leu Ile Val
    130                 135                 140

Ile Leu Phe Leu Ser Thr Tyr Leu Gly Phe Cys Phe Leu Thr Leu Phe
145                 150                 155                 160

Thr Ser Val Phe Ala Gly Lys Ala Pro Trp Gln Leu Tyr Asn Pro Leu
                165                 170                 175
```

| | | | | | | | | | | | |
|---|---|---|---|---|---|---|---|---|---|---|---|
|Val|Asp|Trp|Arg|Lys|Gly|His|Trp|Gln|Leu|Trp|Ile|Ala|Ser|Ile|Leu|
| | | |180| | | |185| | | |190| | | | |

Val Asp Trp Arg Lys Gly His Trp Gln Leu Trp Ile Ala Ser Ile Leu
            180                 185                 190

Glu Tyr Cys Val Val Ser Ile Gly Thr Met Gln Glu Leu Met Ser Asp
        195                 200                 205

Thr Tyr Ala Ile Val Phe Ile Ser Leu Phe Arg Cys His Leu Ala Ile
        210                 215                 220

Leu Arg Asp Arg Ile Ala Asn Leu Arg Gln Asp Pro Lys Leu Ser Glu
225                 230                 235                 240

Met Glu His Tyr Glu Gln Met Val Ala Cys Ile Gln Asp His Arg Thr
            245                 250                 255

Ile Ile Gln Cys Ser Gln Ile Ile Arg Pro Ile Leu Ser Ile Thr Ile
        260                 265                 270

Phe Ala Gln Phe Met Leu Val Gly Ile Asp Leu Gly Leu Ala Ala Ile
        275                 280                 285

Ser Ile Leu Phe Phe Pro Asn Thr Ile Trp Thr Ile Met Ala Asn Val
        290                 295                 300

Ser Phe Ile Val Ala Ile Cys Thr Glu Ser Phe Pro Cys Cys Met Leu
305                 310                 315                 320

Cys Glu His Leu Ile Glu Asp Ser Val His Val Ser Asn Ala Leu Phe
            325                 330                 335

His Ser Asn Trp Ile Thr Ala Asp Arg Ser Tyr Lys Ser Ala Val Leu
            340                 345                 350

Tyr Phe Leu His Arg Ala Gln Gln Pro Ile Gln Phe Thr Ala Gly Ser
        355                 360                 365

Thr Phe Pro Ile Ser Val Gln Ser Asn Ile Ala Val Ala Lys Phe Ala
370                 375                 380

Phe Thr Ile Ile Thr Ile Val Asn Gln Met Asn Leu Gly Glu Lys Phe
385                 390                 395                 400

Phe Ser Asp Arg Ser Asn Gly Asp Ile Asn Pro
            405                 410

```
<210> SEQ ID NO 53
<211> LENGTH: 1203
<212> TYPE: DNA
<213> ORGANISM: Drosophila Melanogaster DOR121

<400> SEQUENCE: 53
atgctgacgg acaagttcct ccgactgcag tccgctttat ttcgccttct cggactcgaa      60
ttgttgcacg agcaggatgt tggccatcga tatccttggc gcagcatctg ctgcattctc     120
tcggtggcca gtttcatgcc cctgaccatt gcgtttggcc tgcaaaacgt ccaaaatgtg     180
gagcaattaa ccgactcact ctgctcggtt ctcgtggatt tgctggccct gtgcaaaatc     240
gggcttttcc tttggcttta caaggacttc aagttcctaa tagggcagtt ctattgtgtt     300
ttgcaaacgg aaacccacac cgctgtcgct gaaatgatag tgaccaggga agtcgtcgg     360 gatcagttca tcagtgctat gtatgcctac tgtttcatta cggctggcct ttcggcctgc     420
ctgatgtccc tctatccat gctgattagc taccacgaac aggtgaattg cagccgaaat     480
ttccatttcc cagtgtgtaa gaaaaagtac tgcttaatat ccagaatatt aagatacagt     540
ttctgcagat atccctggga caatatgaag ctgtccaact catcatttc ctatttctgg     600 aatgtgtgtg ctgcattggg cgtggcactg cccaccgttt gtgtggacac actgttctgt     660
tctctgagcc ataatctctg tgccctattc cagattgcca ggcacaaaat gatgcacttt     720
gagggcagaa ataccaaaga gactcatgag aacttaaagc acgtgtttca actatatgcg     780
```

-continued

```
ttgtgtttga acctgggcca tttcttaaac gaatatttca gaccgctcat ctgccagttt    840
gtggcagcct cactgcactt gtgtgtcctg tgctaccaac tgtctgccaa tatcctgcag    900
ccagcgttac tcttctatgc cgcatttacg gcagcagttg ttggccaggt gtctatatac    960
tgcttctgcg gatcgagcat ccattcggag tgtcagctat ttggccaggc catctacgag   1020
tccagctggc cccatctgct gcaggaaaac ctgcagcttg taagctcctt aaaaattgcc   1080
atgatgcgat cgagtttggg atgtcccatc gatggttact tcttcgaggc caatcgggag   1140
acgctcatca cggtgagtaa agcgtttata aaagtgtcca aaaagacacc tcaagtgaat   1200
gat                                                                 1203
```

<210> SEQ ID NO 54
<211> LENGTH: 401
<212> TYPE: PRT
<213> ORGANISM: Drosophila Melanogaster DOR121

<400> SEQUENCE: 54

```
Met Leu Thr Asp Lys Phe Leu Arg Leu Gln Ser Ala Leu Phe Arg Leu
1               5                   10                  15

Leu Gly Leu Glu Leu Leu His Glu Gln Asp Val Gly His Arg Tyr Pro
            20                  25                  30

Trp Arg Ser Ile Cys Cys Ile Leu Ser Val Ala Ser Phe Met Pro Leu
        35                  40                  45

Thr Ile Ala Phe Gly Leu Gln Asn Val Gln Asn Val Glu Gln Leu Thr
    50                  55                  60

Asp Ser Leu Cys Ser Val Leu Val Asp Leu Leu Ala Leu Cys Lys Ile
65                  70                  75                  80

Gly Leu Phe Leu Trp Leu Tyr Lys Asp Phe Lys Phe Leu Ile Gly Gln
                85                  90                  95

Phe Tyr Cys Val Leu Gln Thr Glu Thr His Thr Ala Val Ala Glu Met
            100                 105                 110

Ile Val Thr Arg Glu Ser Arg Arg Asp Gln Phe Ile Ser Ala Met Tyr
        115                 120                 125

Ala Tyr Cys Phe Ile Thr Ala Gly Leu Ser Ala Cys Leu Met Ser Pro
    130                 135                 140

Leu Ser Met Leu Ile Ser Tyr His Glu Gln Val Asn Cys Ser Arg Asn
145                 150                 155                 160

Phe His Phe Pro Val Cys Lys Lys Lys Tyr Cys Leu Ile Ser Arg Ile
                165                 170                 175

Leu Arg Tyr Ser Phe Cys Arg Tyr Pro Trp Asp Asn Met Lys Leu Ser
            180                 185                 190

Asn Tyr Ile Ile Ser Tyr Phe Trp Asn Val Cys Ala Ala Leu Gly Val
        195                 200                 205

Ala Leu Pro Thr Val Cys Val Asp Thr Leu Phe Cys Ser Leu Ser His
    210                 215                 220

Asn Leu Cys Ala Leu Phe Gln Ile Ala Arg His Lys Met Met His Phe
225                 230                 235                 240

Glu Gly Arg Asn Thr Lys Glu Thr His Glu Asn Leu Lys His Val Phe
                245                 250                 255

Gln Leu Tyr Ala Leu Cys Leu Asn Leu Gly His Phe Leu Asn Glu Tyr
            260                 265                 270

Phe Arg Pro Leu Ile Cys Gln Phe Val Ala Ala Ser Leu His Leu Cys
        275                 280                 285
```

```
Val Leu Cys Tyr Gln Leu Ser Ala Asn Ile Leu Gln Pro Ala Leu Leu
    290                 295                 300

Phe Tyr Ala Ala Phe Thr Ala Ala Val Val Gly Gln Val Ser Ile Tyr
305                 310                 315                 320

Cys Phe Cys Gly Ser Ser Ile His Ser Glu Cys Gln Leu Phe Gly Gln
                    325                 330                 335

Ala Ile Tyr Glu Ser Ser Trp Pro His Leu Leu Gln Glu Asn Leu Gln
                340                 345                 350

Leu Val Ser Ser Leu Lys Ile Ala Met Met Arg Ser Ser Leu Gly Cys
            355                 360                 365

Pro Ile Asp Gly Tyr Phe Phe Glu Ala Asn Arg Glu Thr Leu Ile Thr
    370                 375                 380

Val Ser Lys Ala Phe Ile Lys Val Ser Lys Lys Thr Pro Gln Val Asn
385                 390                 395                 400

Asp

<210> SEQ ID NO 55
<211> LENGTH: 1122
<212> TYPE: DNA
<213> ORGANISM: Drosophila Melanogaster DOR14

<400> SEQUENCE: 55
atggactacg atcgaattcg accggtgcga ttttgacgg gagtgctgaa atggtggcgt      60
ctctggccga ggaaggaatc ggtgtccaca ccggactgga ctaactgca ggcatatgcc     120 ttgcacgttc catttacatt cttgtttgtg ttgcttttgt ggttggaggc aatcaagagc     180
agggatatac agcataccgc cgatgtcctt ttgatttgcc taaccaccac tgccttggga     240
ggtaaagtta tcaatatctg gaagtatgcc catgtggccc aaggcatttt gtccgagtgg     300
agcacgtggg atcttttcga gctgaggagc aaacaggaag tggatatgtg gcgattcgag     360
catcgacgtt tcaatcgtgt ttttatgttt tactgttttgt gcagtgctgg tgtaatccca     420
tttattgtga ttcaaccgtt gtttgatatc ccaaatcgat tgcccttctg gatgtggaca     480
ccattcgatt ggcagcagcc tgttctcttc tggtatgcat tcatctatca ggccacaacc     540
attcctattg cctgtgcttg caacgtaacc atggacgctg ttaattggta cttgatgctg     600
catctgtcct tgtgttttgcg tatgttgggc cagcgattga gtaagcttca gcatgatgac     660
aaggatctga gggagaagtt cctggaactg atccatctgc accagcgact caagcaacag     720
gccttgagca ttgaaatctt tatttcgaag agcacgttca cccaaattct ggtcagttcc     780
cttatcattt gcttcaccat ttacagcatg cagatggact tgccaggatt tgccgccatg     840
atgcagtacc tagtggccat gatcatgcag gtcatgctgc ccaccatata tggtaacgcc     900
gtcatcgatt ctgcaaatat gttgaccgat tccatgtaca attcggattg gccggatatg     960
aattgccgaa tgcgtcgcct agttttaatg tttatggtgt acttaaatcg accggtgacc    1020
ttaaaagccg gtggcttttt tcatattggt ttacctctgt ttaccaaggt tgtatttct     1080 actctggaaa atccttgtat aagttatctt tatttcagac ca                      1122

<210> SEQ ID NO 56
<211> LENGTH: 374
<212> TYPE: PRT
<213> ORGANISM: Drosophila Melanogaster DOR14

<400> SEQUENCE: 56

Met Asp Tyr Asp Arg Ile Arg Pro Val Arg Phe Leu Thr Gly Val Leu
1               5                   10                  15
```

```
Lys Trp Trp Arg Leu Trp Pro Arg Lys Glu Ser Val Ser Thr Pro Asp
            20                  25                  30

Trp Thr Asn Trp Gln Ala Tyr Ala Leu His Val Pro Phe Thr Phe Leu
        35                  40                  45

Phe Val Leu Leu Leu Trp Leu Glu Ala Ile Lys Ser Arg Asp Ile Gln
    50                  55                  60

His Thr Ala Asp Val Leu Leu Ile Cys Leu Thr Thr Thr Ala Leu Gly
65                  70                  75                  80

Gly Lys Val Ile Asn Ile Trp Lys Tyr Ala His Val Ala Gln Gly Ile
                85                  90                  95

Leu Ser Glu Trp Ser Thr Trp Asp Leu Phe Glu Leu Arg Ser Lys Gln
            100                 105                 110

Glu Val Asp Met Trp Arg Phe Glu His Arg Arg Phe Asn Arg Val Phe
        115                 120                 125

Met Phe Tyr Cys Leu Cys Ser Ala Gly Val Ile Pro Phe Ile Val Ile
    130                 135                 140

Gln Pro Leu Phe Asp Ile Pro Asn Arg Leu Pro Phe Trp Met Trp Thr
145                 150                 155                 160

Pro Phe Asp Trp Gln Gln Pro Val Leu Phe Trp Tyr Ala Phe Ile Tyr
                165                 170                 175

Gln Ala Thr Thr Ile Pro Ile Ala Cys Ala Cys Asn Val Thr Met Asp
            180                 185                 190

Ala Val Asn Trp Tyr Leu Met Leu His Leu Ser Leu Cys Leu Arg Met
        195                 200                 205

Leu Gly Gln Arg Leu Ser Lys Leu Gln His Asp Asp Lys Asp Leu Arg
    210                 215                 220

Glu Lys Phe Leu Glu Leu Ile His Leu His Gln Arg Leu Lys Gln Gln
225                 230                 235                 240

Ala Leu Ser Ile Glu Ile Phe Ile Ser Lys Ser Thr Phe Thr Gln Ile
                245                 250                 255

Leu Val Ser Ser Leu Ile Ile Cys Phe Thr Ile Tyr Ser Met Gln Met
            260                 265                 270

Asp Leu Pro Gly Phe Ala Ala Met Met Gln Tyr Leu Val Ala Met Ile
        275                 280                 285

Met Gln Val Met Leu Pro Thr Ile Tyr Gly Asn Ala Val Ile Asp Ser
    290                 295                 300

Ala Asn Met Leu Thr Asp Ser Met Tyr Asn Ser Asp Trp Pro Asp Met
305                 310                 315                 320

Asn Cys Arg Met Arg Arg Leu Val Leu Met Phe Met Val Tyr Leu Asn
                325                 330                 335

Arg Pro Val Thr Leu Lys Ala Gly Gly Phe Phe His Ile Gly Leu Pro
            340                 345                 350

Leu Phe Thr Lys Val Val Phe Ser Thr Leu Glu Asn Pro Cys Ile Ser
        355                 360                 365

Tyr Leu Tyr Phe Arg Pro
    370

<210> SEQ ID NO 57
<211> LENGTH: 1140
<212> TYPE: DNA
<213> ORGANISM: Drosophila Melanogaster DOR16

<400> SEQUENCE: 57
atgactgaca gcgggcagcc tgccattgcc gaccactttt atcggattcc ccgcatctcc      60
```

-continued

```
ggcctcattg tcggcctctg ccgcaaagg ataaggggcg ggggcggtcg tccttggcac    120
gcccatctgc tcttcgtgtt cgccttcgcc atggtggtgg tgggtgcggt gggcgaggtg    180
tcgtacggct gtgtccacct ggacaacctg gtggtggcgc tggaggcctt ctgccccgga    240
accaccaagg cggtctgcgt tttgaagctg tgggtcttct ccgctccaa tcgccggtgg    300 gcggagttgg tccagcgcct gcgggctatt ttgtgggaat cgcggcggca ggaggcccag    360
aggatgctgg tcggactggc caccacggcc aacaggctca gcctgttgtt gctcagctct    420
ggcacggcga caaatgccgc cttcaccttg caaccgctga ttatgggtct ctaccgctgg    480
attgtgcagc tgccaggtca aaccgagctg ccctttaata tcatactgcc ctcgtttgcc    540
gtgcagccag gagtctttcc gctcacctac gtgctgctga ccgcttccgg tgcctgcacc    600
gttttcgcct tcagcttcgt ggacggattc ttcatttgct cgtgcctcta catctgcggc    660
gctttccggc tggtgcagca ggacattcgc aggatatttg ccgatttgca tgcgactca    720 gtggatgtgt tcaccgagga gatgaacgcg gaggtgcggc acagactggc ccaagttgtc    780
gagcggcaca atgcgattat cgatttctgc acgacctaa cacgccagtt caccgttatc    840
gttttaatgc atttcctgtc cgccgccttc gtcctctgct cgaccatcct ggacatcatg    900
ttggtgagcc cctttcaga ggccttcctt tggggcgggt atccttgggt tgtcgcgcc    960 actggctttt cgcatcgcct gcattcggcg gctgttttaa aagtttttcc ctgtttttcac   1020 tgtttgctgt ttttccctgg cttttccagc cgctccgttc tgattcggtt ttcccgatttt   1080 gtttgtttgc tttgtggctg cggctgcggc tctctccggt ggcaattat aagcgcatga   1140
```

<210> SEQ ID NO 58
<211> LENGTH: 379
<212> TYPE: PRT
<213> ORGANISM: Drosophila Melanogaster DOR16

<400> SEQUENCE: 58

```
Met Thr Asp Ser Gly Gln Pro Ala Ile Ala Asp His Phe Tyr Arg Ile
1               5                   10                  15

Pro Arg Ile Ser Gly Leu Ile Val Gly Leu Trp Pro Gln Arg Ile Arg
            20                  25                  30

Gly Gly Gly Gly Arg Pro Trp His Ala His Leu Leu Phe Val Phe Ala
        35                  40                  45

Phe Ala Met Val Val Val Gly Ala Val Gly Glu Val Ser Tyr Gly Cys
    50                  55                  60

Val His Leu Asp Asn Leu Val Val Ala Leu Glu Ala Phe Cys Pro Gly
65                  70                  75                  80

Thr Thr Lys Ala Val Cys Val Leu Lys Leu Trp Val Phe Phe Arg Ser
                85                  90                  95

Asn Arg Arg Trp Ala Glu Leu Val Gln Arg Leu Arg Ala Ile Leu Trp
            100                 105                 110

Glu Ser Arg Arg Gln Glu Ala Gln Arg Met Leu Val Gly Leu Ala Thr
        115                 120                 125

Thr Ala Asn Arg Leu Ser Leu Leu Leu Ser Ser Gly Thr Ala Thr
    130                 135                 140

Asn Ala Ala Phe Thr Leu Gln Pro Leu Ile Met Gly Leu Tyr Arg Trp
145                 150                 155                 160

Ile Val Gln Leu Pro Gly Gln Thr Glu Leu Pro Phe Asn Ile Ile Leu
                165                 170                 175

Pro Ser Phe Ala Val Gln Pro Gly Val Phe Pro Leu Thr Tyr Val Leu
```

-continued

```
                 180                 185                 190
Leu Thr Ala Ser Gly Ala Cys Thr Val Phe Ala Phe Ser Phe Val Asp
            195                 200                 205

Gly Phe Phe Ile Cys Ser Cys Leu Tyr Ile Cys Gly Ala Phe Arg Leu
        210                 215                 220

Val Gln Gln Asp Ile Arg Arg Ile Phe Ala Asp Leu His Gly Asp Ser
225                 230                 235                 240

Val Asp Val Phe Thr Glu Glu Met Asn Ala Glu Val Arg His Arg Leu
                245                 250                 255

Ala Gln Val Val Glu Arg His Asn Ala Ile Ile Asp Phe Cys Thr Asp
            260                 265                 270

Leu Thr Arg Gln Phe Thr Val Ile Val Leu Met His Phe Leu Ser Ala
        275                 280                 285

Ala Phe Val Leu Cys Ser Thr Ile Leu Asp Ile Met Leu Val Ser Pro
    290                 295                 300

Phe Ser Glu Ala Phe Leu Trp Gly Gly Tyr Pro Trp Val Cys Arg Ala
305                 310                 315                 320

Thr Gly Phe Ser His Arg Leu His Ser Ala Ala Val Leu Lys Val Phe
                325                 330                 335

Pro Cys Phe His Cys Leu Leu Phe Phe Pro Gly Phe Ser Ser Arg Ser
            340                 345                 350

Val Leu Ile Arg Phe Ser Arg Phe Val Cys Leu Leu Cys Gly Cys Gly
        355                 360                 365

Cys Gly Ser Leu Arg Trp Gln Phe Ile Ser Ala
    370                 375
```

<210> SEQ ID NO 59
<211> LENGTH: 1215
<212> TYPE: DNA
<213> ORGANISM: Drosophila Melanogaster DOR20

<400> SEQUENCE: 59

```
atgagcaaag gagtagaaat cttttacaag ggccagaagg cattcttgaa catcctctcg      60
ttgtggcctc agatagaacg ccggtggaga atcatccacc aggtgaacta tgtccacgta     120
attgtgtttt gggtgctgct cttttgatctc ctcttggtgc tccatgtgat ggctaatttg     180
agctacatgt ccgaggttgt gaaagccatc tttatcctgg ccaccagtgc agggcacacc     240
accaagctgc tgtccataaa ggcgaacaat gtgcagatgg aggagctctt taggagattg     300
gataacgaag agttccgtcc tagaggcgcc aacgaagagt tgatctttgc agcagcctgt     360
gaaagaagta ggaagcttcg ggacttctat ggagcgcttt cgtttgccgc cttgagcatg     420
attctcatac cccagttcgc cttggactgg tcccaccttc cgctcaaaac atacaatccg     480
cttggcgaga taccggctc acctgcttat tggctcctct actgctatca gtgtctggcc     540
ttgtccgtat cctgcatcac caacatagga ttcgactcac tctgctcctc actgttcatc     600
ttcctcaagt gccagctgga cattctggcc gtgcgactgg acaagatcgg tcggttaatc     660
actacttctg gtggcactgt ggaacagcaa cttaaggaaa atatccgcta tcacatgacc     720
atcgttgaac tgtcgaaaac cgtggagcgt ctactttgca agccgatttc ggtgcagatc     780
ttctgctcgg ttttggtgct gactgccaat tctatgcca ttgctgtggt gagctgtgaa     840
ttcgcaacaa gaagactatc agtatgtgac ctatcaggcg tgcatgttga ttcagatttt     900
tatattgtgc tactatgccg ggtgggtatt ccatatccga aatgcctccc caggccagta     960
atgaatttca tcgtcagtga ggtaacccag cgcagcctgg accttccgca cgagctgtac    1020
```

-continued

```
aagacctcct gggtggactg ggactacagg agccgaagga ttgcgctcct ctttatgcaa    1080
cgccttcact cgaccttgag gattaggaca cttaatccaa gtcttggttt tgacttaatg    1140
ctcttcagct cggtgagttc tttccgtgtt ttgactttt tgtgcactgt agccaatttc     1200
cataatgagg ctcat                                                     1215
```

<210> SEQ ID NO 60
<211> LENGTH: 405
<212> TYPE: PRT
<213> ORGANISM: Drosophila Melanogaster DOR20

<400> SEQUENCE: 60

```
Met Ser Lys Gly Val Glu Ile Phe Tyr Lys Gly Gln Lys Ala Phe Leu
1               5                   10                  15

Asn Ile Leu Ser Leu Trp Pro Gln Ile Glu Arg Arg Trp Arg Ile Ile
            20                  25                  30

His Gln Val Asn Tyr Val His Val Ile Val Phe Trp Val Leu Leu Phe
        35                  40                  45

Asp Leu Leu Leu Val Leu His Val Met Ala Asn Leu Ser Tyr Met Ser
    50                  55                  60

Glu Val Val Lys Ala Ile Phe Ile Leu Ala Thr Ser Ala Gly His Thr
65                  70                  75                  80

Thr Lys Leu Leu Ser Ile Lys Ala Asn Asn Val Gln Met Glu Glu Leu
                85                  90                  95

Phe Arg Arg Leu Asp Asn Glu Glu Phe Arg Pro Arg Gly Ala Asn Glu
            100                 105                 110

Glu Leu Ile Phe Ala Ala Ala Cys Glu Arg Ser Arg Lys Leu Arg Asp
        115                 120                 125

Phe Tyr Gly Ala Leu Ser Phe Ala Ala Leu Ser Met Ile Leu Ile Pro
    130                 135                 140

Gln Phe Ala Leu Asp Trp Ser His Leu Pro Leu Lys Thr Tyr Asn Pro
145                 150                 155                 160

Leu Gly Glu Asn Thr Gly Ser Pro Ala Tyr Trp Leu Leu Tyr Cys Tyr
                165                 170                 175

Gln Cys Leu Ala Leu Ser Val Ser Cys Ile Thr Asn Ile Gly Phe Asp
            180                 185                 190

Ser Leu Cys Ser Ser Leu Phe Ile Phe Leu Lys Cys Gln Leu Asp Ile
        195                 200                 205

Leu Ala Val Arg Leu Asp Lys Ile Gly Arg Leu Ile Thr Thr Ser Gly
    210                 215                 220

Gly Thr Val Glu Gln Gln Leu Lys Glu Asn Ile Arg Tyr His Met Thr
225                 230                 235                 240

Ile Val Glu Leu Ser Lys Thr Val Glu Arg Leu Leu Cys Lys Pro Ile
                245                 250                 255

Ser Val Gln Ile Phe Cys Ser Val Leu Val Leu Thr Ala Asn Phe Tyr
            260                 265                 270

Ala Ile Ala Val Val Ser Cys Glu Phe Ala Thr Arg Arg Leu Ser Val
        275                 280                 285

Cys Asp Leu Ser Gly Val His Val Asp Ser Asp Phe Tyr Ile Val Leu
    290                 295                 300

Leu Cys Arg Val Gly Ile Pro Tyr Pro Lys Cys Leu Pro Arg Pro Val
305                 310                 315                 320

Met Asn Phe Ile Val Ser Glu Val Thr Gln Arg Ser Leu Asp Leu Pro
                325                 330                 335
```

His Glu Leu Tyr Lys Thr Ser Trp Val Asp Trp Asp Tyr Arg Ser Arg
            340                 345                 350

Arg Ile Ala Leu Leu Phe Met Gln Arg Leu His Ser Thr Leu Arg Ile
        355                 360                 365

Arg Thr Leu Asn Pro Ser Leu Gly Phe Asp Leu Met Leu Phe Ser Ser
    370                 375                 380

Val Ser Ser Phe Arg Val Leu Thr Phe Leu Cys Thr Val Ala Asn Phe
385                 390                 395                 400

His Asn Glu Ala His
            405

<210> SEQ ID NO 61
<211> LENGTH: 1203
<212> TYPE: DNA
<213> ORGANISM: Drosophila Melanogaster DOR25

<400> SEQUENCE: 61

| | |
|---|---|
| atgaacgact cgggttatca atcaaatctc agccttctgc gggttttcct cgacgagttc | 60 |
| cgatcggttc tgcggcagga agtcccggt ctcatcccac gcctggcttt ttactatgtt | 120 |
| cgcgcctttc tgagcttgcc cctgtaccga tggatcaact tgttcatcat gtgcaatgtg | 180 |
| atgaccattt tctggaccat gttcgtggcc ctgcccgagt cgaagaacgt gatcgaaatg | 240 |
| ggcgacgact tggtttggat ttcggggatg gcactggtgt tcaccaagat cttttacatg | 300 |
| catttgcgtt gcgacgagat cgatgaactt atttcggatt ttgaatacta caaccgggag | 360 |
| ctgagacccc ataatatcga tgaggaggtg ttgggttggc agagactgtg ctacgtgata | 420 |
| gaatcgggtc tatatatcaa ctgcttttgc ctggtcaact tcttcagtgc cgctattttc | 480 |
| ctgcaacctc tgttgggcga gggaaagctg cccttccaca gcgtctatcc gtttcaatgg | 540 |
| catcgcttgg atctgcatcc ctacacgttc tggttcctct acatctggca gagtctgacc | 600 |
| tcgcagcaca acctaatgag cattctaatg gtggatatgg taggcatttc cacgttcctc | 660 |
| cagacggcgc tcaatctcaa gttgcttttgc atcgagataa ggaaactggg ggacatggag | 720 |
| gtcagtgata agaggttcca cgaggagttt tgtcgtgtgg ttcgcttcca ccagcacatt | 780 |
| atcaagttgg tggggaaagc caatagagct ttcaatggcg ccttcaatgc acaattaatg | 840 |
| gccagtttct ccctgatttc catatccact ttcgagacca tggctgcagc ggctgtggat | 900 |
| cccaaaatgg ccgccaagtt cgtgcttctc atgctggtgg cattcattca actgtcgctt | 960 |
| tggtgcgtct ctggaacttt ggtttatact cagtcagtga aggtggctca ggctgctttt | 1020 |
| gatatcaacg attggcacac caaatcgcca ggcatccaga gggatatatc ctttgtgata | 1080 |
| ctacgagccc agaaaccct gatgtatgtg gccgaaccat ttctgccctt cacccctggga | 1140 |
| acctatatgc ttgtactgaa gaactgctat cgtttgctgg ccctgatgca agaatcgatg | 1200 |
| tag | 1203 |

<210> SEQ ID NO 62
<211> LENGTH: 400
<212> TYPE: PRT
<213> ORGANISM: Drosophila Melanogaster DOR25

<400> SEQUENCE: 62

Met Asn Asp Ser Gly Tyr Gln Ser Asn Leu Ser Leu Leu Arg Val Phe
1               5                   10                  15

Leu Asp Glu Phe Arg Ser Val Leu Arg Gln Glu Ser Pro Gly Leu Ile
            20                  25                  30

```
Pro Arg Leu Ala Phe Tyr Tyr Val Arg Ala Phe Leu Ser Leu Pro Leu
        35                  40                  45

Tyr Arg Trp Ile Asn Leu Phe Ile Met Cys Asn Val Met Thr Ile Phe
    50                  55                  60

Trp Thr Met Phe Val Ala Leu Pro Glu Ser Lys Asn Val Ile Glu Met
65                  70                  75                  80

Gly Asp Asp Leu Val Trp Ile Ser Gly Met Ala Leu Val Phe Thr Lys
                    85                  90                  95

Ile Phe Tyr Met His Leu Arg Cys Asp Glu Ile Asp Glu Leu Ile Ser
                100                 105                 110

Asp Phe Glu Tyr Tyr Asn Arg Glu Leu Arg Pro His Asn Ile Asp Glu
            115                 120                 125

Glu Val Leu Gly Trp Gln Arg Leu Cys Tyr Val Ile Glu Ser Gly Leu
        130                 135                 140

Tyr Ile Asn Cys Phe Cys Leu Val Asn Phe Phe Ser Ala Ala Ile Phe
145                 150                 155                 160

Leu Gln Pro Leu Leu Gly Glu Gly Lys Leu Pro Phe His Ser Val Tyr
                    165                 170                 175

Pro Phe Gln Trp His Arg Leu Asp Leu His Pro Tyr Thr Phe Trp Phe
                180                 185                 190

Leu Tyr Ile Trp Gln Ser Leu Thr Ser Gln His Asn Leu Met Ser Ile
            195                 200                 205

Leu Met Val Asp Met Val Gly Ile Ser Thr Phe Leu Gln Thr Ala Leu
        210                 215                 220

Asn Leu Lys Leu Leu Cys Ile Glu Ile Arg Lys Leu Gly Asp Met Glu
225                 230                 235                 240

Val Ser Asp Lys Arg Phe His Glu Glu Phe Cys Arg Val Val Arg Phe
                    245                 250                 255

His Gln His Ile Ile Lys Leu Val Gly Lys Ala Asn Arg Ala Phe Asn
                260                 265                 270

Gly Ala Phe Asn Ala Gln Leu Met Ala Ser Phe Ser Leu Ile Ser Ile
            275                 280                 285

Ser Thr Phe Glu Thr Met Ala Ala Ala Val Asp Pro Lys Met Ala
        290                 295                 300

Ala Lys Phe Val Leu Leu Met Leu Val Ala Phe Ile Gln Leu Ser Leu
305                 310                 315                 320

Trp Cys Val Ser Gly Thr Leu Val Tyr Thr Gln Ser Val Glu Val Ala
                    325                 330                 335

Gln Ala Ala Phe Asp Ile Asn Asp Trp His Thr Lys Ser Pro Gly Ile
                340                 345                 350

Gln Arg Asp Ile Ser Phe Val Ile Leu Arg Ala Gln Lys Pro Leu Met
            355                 360                 365

Tyr Val Ala Glu Pro Phe Leu Pro Phe Thr Leu Gly Thr Tyr Met Leu
        370                 375                 380

Val Leu Lys Asn Cys Tyr Arg Leu Leu Ala Leu Met Gln Glu Ser Met
385                 390                 395                 400

<210> SEQ ID NO 63
<211> LENGTH: 1368
<212> TYPE: DNA
<213> ORGANISM: Drosophila Melanogaster DOR28

<400> SEQUENCE: 63
atgtactcac cggaagaggc ggccgaactg aagaggcgca actatcgcag catcagggag      60
```

-continued

```
atgatccgac tctcctatac ggtgggcttc aacctgttgg atccttcccg atgcggacag    120
gtgctcagaa tctggacaat tgtccttagc gtgagtagct tggcatcgct ttatgggcac    180
tggcaaatgt tagccaggta cattcatgat attccacgca ttggagagac cgctggaact    240
gccctgcagt tcctaacatc gatagcaaag atgtggtact ttctgtttgc ccatagacag    300
atatacgaat tgctacgaaa ggcgcgctgc catgaattac tccaaaagtg tgagctcttt    360
gaaaggatgt cagatctacc tgttatcaaa gagattcgcc agcaggttga gtccacgatg    420
aatcggtact gggccagcac tcgtcggcaa attcttatct atttgtacag ctgtatttgt    480
attactacaa actactttat caactccttc gtaatcaacc tctatcgcta tttcactaaa    540
ccgaaaggat cctacgacat aatgttacct ctgccatctc tgtatcccgc ctgggagcac    600
aagggattag agtttcccta ctatcatata cagatgtacc tggaaacctg ttctctgtat    660
atctgcggca tgtgtgccgt tagctttgat ggagtcttta ttgtcctgtg ccttcatagc    720
gtgggactta tgaggtcact taaccaaatg gtggaacaag ccacatctga gttggttcct    780
ccagatcgca gggttgaata cttgcgatgc tgtatttatc agtaccaacg agtggcgaac    840
tttgcaaccg aggttaacaa ctgctttcgg cacatcactt tcacgcagtt cctgcttagc    900
cttttcaact ggggcctggc cttgttccaa atgagcgtcg gattgggcaa caacagcagc    960
atcaccatga tccggatgac catgtacctg gtggcagccg gctatcagat agttgtgtac   1020
tgctacaatg ccagcgatt tgcgactgct agcgaggaga ttgccaacgc ctttttaccag   1080 gtgcgatggt acggagagtc cagggagttc cgccacctca tccgcatgat gctgatcgc   1140 acgaaccggg gattcaggct ggacgtgtcc tggttcatgc aaatgtcctt gcccacactc   1200
atggcggtga gtagcggagc agagcagagc agggggtcctg caggtcctgc aggtcctgca   1260
ggtccacccc caagggtccc ctcctacagc cagttccact tgattgattc gcagatggtc   1320
cggacaagtg gacagtactt cctgctgctg cagaacgtca accagaaa              1368
```

<210> SEQ ID NO 64
<211> LENGTH: 456
<212> TYPE: PRT
<213> ORGANISM: Drosophila Melanogaster DOR28

<400> SEQUENCE: 64

```
Met Tyr Ser Pro Glu Ala Ala Glu Leu Lys Arg Arg Asn Tyr Arg
1               5                   10                  15

Ser Ile Arg Glu Met Ile Arg Leu Ser Tyr Thr Val Gly Phe Asn Leu
            20                  25                  30

Leu Asp Pro Ser Arg Cys Gly Gln Val Leu Arg Ile Trp Thr Ile Val
        35                  40                  45

Leu Ser Val Ser Ser Leu Ala Ser Leu Tyr Gly His Trp Gln Met Leu
    50                  55                  60

Ala Arg Tyr Ile His Asp Ile Pro Arg Ile Gly Glu Thr Ala Gly Thr
65                  70                  75                  80

Ala Leu Gln Phe Leu Thr Ser Ile Ala Lys Met Trp Tyr Phe Leu Phe
                85                  90                  95

Ala His Arg Gln Ile Tyr Glu Leu Leu Arg Lys Ala Arg Cys His Glu
            100                 105                 110

Leu Leu Gln Lys Cys Glu Leu Phe Glu Arg Met Ser Asp Leu Pro Val
        115                 120                 125

Ile Lys Glu Ile Arg Gln Gln Val Glu Ser Thr Met Asn Arg Tyr Trp
    130                 135                 140
```

```
Ala Ser Thr Arg Arg Gln Ile Leu Ile Tyr Leu Tyr Ser Cys Ile Cys
145                 150                 155                 160

Ile Thr Thr Asn Tyr Phe Ile Asn Ser Phe Val Ile Asn Leu Tyr Arg
            165                 170                 175

Tyr Phe Thr Lys Pro Lys Gly Ser Tyr Asp Ile Met Leu Pro Leu Pro
        180                 185                 190

Ser Leu Tyr Pro Ala Trp Glu His Lys Gly Leu Glu Phe Pro Tyr Tyr
    195                 200                 205

His Ile Gln Met Tyr Leu Glu Thr Cys Ser Leu Tyr Ile Cys Gly Met
210                 215                 220

Cys Ala Val Ser Phe Asp Gly Val Phe Ile Val Leu Cys Leu His Ser
225                 230                 235                 240

Val Gly Leu Met Arg Ser Leu Asn Gln Met Val Glu Gln Ala Thr Ser
                245                 250                 255

Glu Leu Val Pro Pro Asp Arg Arg Val Glu Tyr Leu Arg Cys Cys Ile
            260                 265                 270

Tyr Gln Tyr Gln Arg Val Ala Asn Phe Ala Thr Glu Val Asn Asn Cys
        275                 280                 285

Phe Arg His Ile Thr Phe Thr Gln Phe Leu Ser Leu Phe Asn Trp
290                 295                 300

Gly Leu Ala Leu Phe Gln Met Ser Val Gly Leu Gly Asn Asn Ser Ser
305                 310                 315                 320

Ile Thr Met Ile Arg Met Thr Met Tyr Leu Val Ala Ala Gly Tyr Gln
                325                 330                 335

Ile Val Val Tyr Cys Tyr Asn Gly Gln Arg Phe Ala Thr Ala Ser Glu
            340                 345                 350

Glu Ile Ala Asn Ala Phe Tyr Gln Val Arg Trp Tyr Gly Glu Ser Arg
        355                 360                 365

Glu Phe Arg His Leu Ile Arg Met Met Leu Met Arg Thr Asn Arg Gly
370                 375                 380

Phe Arg Leu Asp Val Ser Trp Phe Met Gln Met Ser Leu Pro Thr Leu
385                 390                 395                 400

Met Ala Val Ser Ser Gly Ala Glu Gln Ser Arg Gly Pro Ala Gly Pro
                405                 410                 415

Ala Gly Pro Ala Gly Pro Pro Arg Val Pro Ser Tyr Ser Gln Phe
            420                 425                 430

His Leu Ile Asp Ser Gln Met Val Arg Thr Ser Gly Gln Tyr Phe Leu
        435                 440                 445

Leu Leu Gln Asn Val Asn Gln Lys
450                 455
```

<210> SEQ ID NO 65
<211> LENGTH: 1239
<212> TYPE: DNA
<213> ORGANISM: Drosophila Melanogaster DOR30

<400> SEQUENCE: 65

```
atggcggtga gcactcgtgt ggccacaaag caggaagtgc ccgaatcccg gcgagcgttt      60
aggaatctct tcaattgctt ctatgccctt ggcatgcagg caccggatgg cagtcgaccg     120
accacgagca gcacatggca acgcatctac gcctgcttct cggtggtcat gtacgtgtgg     180
caactgctgc tggtgcccac attctttgtg atcagctatc ggtacatggg cggcatggag     240
attacccagg tgctgacctc cgcccaggtg gccatcgatg cggtcattct gccggccaag     300
```

-continued

```
attgtggcac tggcgtggaa tttgccattg ctgcgcagag cagagcatca tctggccgcc    360
ttggatgcgc ggtgcaggga acaggaggag ttccaattga tcctcgatgc ggtgaggttt    420
tgcaactatc tggtatggtt ctaccagatc tgctatgcca tctactcctc gtcgacattt    480
gtgtgcgcct tcctgctggg ccaaccgcca tatgccctct atttgcctgg cctcgattgg    540
cagcgttccc agatgcagtt ctgcatccag gcctggattg agttccttat catgaactgg    600
acgtgcctgc accaagctag cgatgatgtg tacgccgtta tctatctgta tgtggtccgg    660
attcaagtgc aattgctggc caggcgggtg gagaagctgg gcacggatga tagtggccag    720
gtggagatct atcccgatga gcggcggcag gaggagcatt gcgcggaact gcagcgctgc    780
attgtagatc accagacgat gctgcagctg ctcgactgca ttagtcccgt catctcgcgt    840
accatattcg ttcagttcct gatcaccgcc gccatcatgg gcaccaccat gatcaacatt    900
ttcattttcg ccaatacgaa cacgaagatc gcatcgatca tttacctgct ggcggtgacc    960
ctgcagacgc tccatgttg ctatcaggcc acctcgctga tgttggacaa cgagaggctg   1020
gccctggcca tcttccagtg ccagtggctg ggccagagtg cccggttccg taagatgctg   1080
ctctactatc ttcatcgcgc ccagcagccc atcacgctga ccgccatgaa gctgtttccc   1140
atcaatctgg ccacgtactt cagtatagcc aagttctcgt tttcgctcta cacgctcatc   1200
aagggggatga atctcggcga gcgattcaac aggacaaat                         1239
```

<210> SEQ ID NO 66
<211> LENGTH: 413
<212> TYPE: PRT
<213> ORGANISM: Drosophila Melanogaster DOR30

<400> SEQUENCE: 66

```
Met Ala Val Ser Thr Arg Val Ala Thr Lys Gln Glu Val Pro Glu Ser
1               5                   10                  15

Arg Arg Ala Phe Arg Asn Leu Phe Asn Cys Phe Tyr Ala Leu Gly Met
            20                  25                  30

Gln Ala Pro Asp Gly Ser Arg Pro Thr Thr Ser Ser Thr Trp Gln Arg
        35                  40                  45

Ile Tyr Ala Cys Phe Ser Val Val Met Tyr Val Trp Gln Leu Leu Leu
    50                  55                  60

Val Pro Thr Phe Phe Val Ile Ser Tyr Arg Tyr Met Gly Gly Met Glu
65                  70                  75                  80

Ile Thr Gln Val Leu Thr Ser Ala Gln Val Ala Ile Asp Ala Val Ile
                85                  90                  95

Leu Pro Ala Lys Ile Val Ala Leu Ala Trp Asn Leu Pro Leu Leu Arg
            100                 105                 110

Arg Ala Glu His His Leu Ala Ala Leu Asp Ala Arg Cys Arg Glu Gln
        115                 120                 125

Glu Glu Phe Gln Leu Ile Leu Asp Ala Val Arg Phe Cys Asn Tyr Leu
    130                 135                 140

Val Trp Phe Tyr Gln Ile Cys Tyr Ala Ile Tyr Ser Ser Ser Thr Phe
145                 150                 155                 160

Val Cys Ala Phe Leu Leu Gly Gln Pro Pro Tyr Ala Leu Tyr Leu Pro
                165                 170                 175

Gly Leu Asp Trp Gln Arg Ser Gln Met Gln Phe Cys Ile Gln Ala Trp
            180                 185                 190

Ile Glu Phe Leu Ile Met Asn Trp Thr Cys Leu His Gln Ala Ser Asp
        195                 200                 205
```

```
Asp Val Tyr Ala Val Ile Tyr Leu Tyr Val Val Arg Ile Gln Val Gln
        210                 215                 220

Leu Leu Ala Arg Arg Val Glu Lys Leu Gly Thr Asp Asp Ser Gly Gln
225                 230                 235                 240

Val Glu Ile Tyr Pro Asp Glu Arg Arg Gln Glu His Cys Ala Glu
                245                 250                 255

Leu Gln Arg Cys Ile Val Asp His Gln Thr Met Leu Gln Leu Leu Asp
                260                 265                 270

Cys Ile Ser Pro Val Ile Ser Arg Thr Ile Phe Val Gln Phe Leu Ile
                275                 280                 285

Thr Ala Ala Ile Met Gly Thr Thr Met Ile Asn Ile Phe Ile Phe Ala
        290                 295                 300

Asn Thr Asn Thr Lys Ile Ala Ser Ile Ile Tyr Leu Leu Ala Val Thr
305                 310                 315                 320

Leu Gln Thr Ala Pro Cys Cys Tyr Gln Ala Thr Ser Leu Met Leu Asp
                325                 330                 335

Asn Glu Arg Leu Ala Leu Ala Ile Phe Gln Cys Gln Trp Leu Gly Gln
                340                 345                 350

Ser Ala Arg Phe Arg Lys Met Leu Leu Tyr Tyr Leu His Arg Ala Gln
        355                 360                 365

Gln Pro Ile Thr Leu Thr Ala Met Lys Leu Phe Pro Ile Asn Leu Ala
370                 375                 380

Thr Tyr Phe Ser Ile Ala Lys Phe Ser Phe Ser Leu Tyr Thr Leu Ile
385                 390                 395                 400

Lys Gly Met Asn Leu Gly Glu Arg Phe Asn Arg Thr Asn
                405                 410

<210> SEQ ID NO 67
<211> LENGTH: 1191
<212> TYPE: DNA
<213> ORGANISM: Drosophila Melanogaster DOR31

<400> SEQUENCE: 67 atgatttta agtacattca agagccagtc cttggatcct tatttcgatc ccgggattcg      60
ctgatctact taaacagatc catagatcaa atggatgga gactgccgcc acgaactaag     120
ccgtactggt ggctctatta catttggaca ttggtggtca tagtactcgt ctttatcttt     180
ataccctatg gactgataat gactggaata aaggagttca agaacttcac gaccacggat     240
ctgtttacgt atgtccaggt gccggttaac accaatgctt cgatcatgaa gggcattata     300
gtgttgttta tgcggcggcg attttcaagg gctcagaaga tgatggacgc catggacatt     360
cgatgcacca agatggagga gaaagtccag gtgcaccgag cagcagcctt atgcaatcgt     420
gttgttgtga tttaccattg catatacttc ggctatctat ccatggcctt aaccggagct     480
ctggtgattg ggaagactcc attctgtttg tacaatccac tggttaaccc cgacgatcat     540
ttctatctgg ccactgccat tgaatcggtc accatggctg gcattattct ggccaatctc     600
attttggacg tatatcccat catatatgtg gtcgttctgc ggatccacat ggagctcttg     660
agtgagcgaa tcaagacgct gcgtactgat gtggaaaaag gcgacgatca acattatgcc     720
gagctggtgg agtgtgtaaa ggatcacaag ctaattgtcg aatatggaaa cactctgcgt     780
cccatgatat ccgccacgat gttcatccaa ctactatccg ttggcttact tttgggtctg     840
gcagcggtgt ccatgcagtt ctataacacc gtaatggagc gtgttgtctc cggggtctac     900
accatagcca ttctatccca gacctttcca ttttgctatg tctgtgagca gctgagcagc     960
```

-continued

```
gattgcgaat ccctgaccaa cacactgttc cattccaagt ggattggagc tgagcgacga   1020
tacagaacca cgatgttgta cttcattcac aatgttcagc agtcgatttt gttcactgcg   1080
ggcggaattt tccccatatg tctaaacacc aatataaaga tggccaagtt cgctttctca   1140
gtggtgacca ttgtaaatga gatggacttg gccgagaaat tgagaaggga g            1191
```

<210> SEQ ID NO 68
<211> LENGTH: 397
<212> TYPE: PRT
<213> ORGANISM: Drosophila Melanogaster DOR31

<400> SEQUENCE: 68

```
Met Ile Phe Lys Tyr Ile Gln Glu Pro Val Leu Gly Ser Leu Phe Arg
1               5                  10                  15

Ser Arg Asp Ser Leu Ile Tyr Leu Asn Arg Ser Ile Asp Gln Met Gly
            20                  25                  30

Trp Arg Leu Pro Pro Arg Thr Lys Pro Tyr Trp Trp Leu Tyr Tyr Ile
        35                  40                  45

Trp Thr Leu Val Val Ile Val Leu Val Phe Ile Phe Ile Pro Tyr Gly
    50                  55                  60

Leu Ile Met Thr Gly Ile Lys Glu Phe Lys Asn Phe Thr Thr Thr Asp
65                  70                  75                  80

Leu Phe Thr Tyr Val Gln Val Pro Val Asn Thr Asn Ala Ser Ile Met
                85                  90                  95

Lys Gly Ile Ile Val Leu Phe Met Arg Arg Arg Phe Ser Arg Ala Gln
            100                 105                 110

Lys Met Met Asp Ala Met Asp Ile Arg Cys Thr Lys Met Glu Glu Lys
        115                 120                 125

Val Gln Val His Arg Ala Ala Ala Leu Cys Asn Arg Val Val Val Ile
    130                 135                 140

Tyr His Cys Ile Tyr Phe Gly Tyr Leu Ser Met Ala Leu Thr Gly Ala
145                 150                 155                 160

Leu Val Ile Gly Lys Thr Pro Phe Cys Leu Tyr Asn Pro Leu Val Asn
                165                 170                 175

Pro Asp Asp His Phe Tyr Leu Ala Thr Ala Ile Glu Ser Val Thr Met
            180                 185                 190

Ala Gly Ile Ile Leu Ala Asn Leu Ile Leu Asp Val Tyr Pro Ile Ile
        195                 200                 205

Tyr Val Val Leu Arg Ile His Met Glu Leu Leu Ser Glu Arg Ile
    210                 215                 220

Lys Thr Leu Arg Thr Asp Val Glu Lys Gly Asp Asp Gln His Tyr Ala
225                 230                 235                 240

Glu Leu Val Glu Cys Val Lys Asp His Lys Leu Ile Val Glu Tyr Gly
                245                 250                 255

Asn Thr Leu Arg Pro Met Ile Ser Ala Thr Met Phe Ile Gln Leu Leu
            260                 265                 270

Ser Val Gly Leu Leu Leu Gly Leu Ala Ala Val Ser Met Gln Phe Tyr
        275                 280                 285

Asn Thr Val Met Glu Arg Val Val Ser Gly Val Tyr Thr Ile Ala Ile
    290                 295                 300

Leu Ser Gln Thr Phe Pro Phe Cys Tyr Val Cys Glu Gln Leu Ser Ser
305                 310                 315                 320

Asp Cys Glu Ser Leu Thr Asn Thr Leu Phe His Ser Lys Trp Ile Gly
                325                 330                 335
```

```
Ala Glu Arg Arg Tyr Arg Thr Thr Met Leu Tyr Phe Ile His Asn Val
                340                 345                 350

Gln Gln Ser Ile Leu Phe Thr Ala Gly Gly Ile Phe Pro Ile Cys Leu
            355                 360                 365

Asn Thr Asn Ile Lys Met Ala Lys Phe Ala Phe Ser Val Val Thr Ile
        370                 375                 380

Val Asn Glu Met Asp Leu Ala Glu Lys Leu Arg Arg Glu
385                 390                 395
```

<210> SEQ ID NO 69
<211> LENGTH: 1176
<212> TYPE: DNA
<213> ORGANISM: Drosophila Melanogaster DOR32

<400> SEQUENCE: 69

| | | | | | |
|---|---|---|---|---|---|
| atggaacctg | tgcagtacag | ctacgaggat | ttcgctcgat | tgcccacgac | ggtgttctgg | 60 |
| atcatgggct | acgacatgct | gggcgttccg | aagacccgct | ctcgcaggat | actatactgg | 120 |
| atatatcgtt | tcctctgtct | cgccagccat | ggggtctgtg | taggagtcat | ggtatttcgt | 180 |
| atggtggagg | caaagaccat | tgacaatgtt | tcgctgatca | tgcggtatgc | cactctggtc | 240 |
| acctatatca | tcaactcgga | tacgaaattc | gcaactgtct | tacaaaggag | tgcaattcaa | 300 |
| agtctaaact | caaaactggc | cgaactatat | ccgaagacca | cgctggacag | gatctatcac | 360 |
| cgggtgaatg | atcactattg | gaccaagtca | tttgtatatt | tggttattat | ctacattggt | 420 |
| tcgtcgatta | tggttgttat | tggaccgatt | attacgtcga | ttatagctta | cttcacgcac | 480 |
| aacgttttca | cctacatgca | ctgctatccg | tacttttttgt | atgatcctga | aaggatccg | 540 |
| gtttggatct | acatcagcat | ctatgctctg | aatggttgc | acagcacaca | gatggtcatt | 600 |
| tcgaacattg | gcgcggatat | ctggctgctg | tactttcagg | tgcagataaa | tctccacttc | 660 |
| aggggcatta | tacgatcact | ggcggatcac | aagcccagtg | tgaagcacga | ccaggaggac | 720 |
| aggaaattca | ttgcgaaaat | tgtcgacaag | caggtgcacc | tggtcagttt | gcaaaacgat | 780 |
| ctgaatggta | tctttggaaa | atcgctgctt | ctaagcctgc | tgaccaccgc | agcggttatc | 840 |
| tgcacggtgg | cggtgtacac | tctgattcag | ggtcccacct | tggagggctt | cacctatgtg | 900 |
| atcttcatcg | ggacttctgt | gatgcaggtc | tacctggtgt | gctattacgg | tcagcaagtt | 960 |
| ctcgacttga | gcggcgaggt | ggcccacgcc | gtgtacaatc | atgattttca | cgatgcttct | 1020 |
| atagcgtaca | agaggtacct | gctcataatc | attatcaggg | cgcagcagcc | cgtggaactt | 1080 |
| aatgccatgg | gctacctgtc | catttcgctg | gacacctta | aacagctgat | gagcgtctcc | 1140 |
| taccgggtta | taaccatgct | catgcagatg | attcag | | | 1176 |

<210> SEQ ID NO 70
<211> LENGTH: 392
<212> TYPE: PRT
<213> ORGANISM: Drosophila Melanogaster DOR32

<400> SEQUENCE: 70

```
Met Glu Pro Val Gln Tyr Ser Tyr Glu Asp Phe Ala Arg Leu Pro Thr
1               5                   10                  15

Thr Val Phe Trp Ile Met Gly Tyr Asp Met Leu Gly Val Pro Lys Thr
            20                  25                  30

Arg Ser Arg Arg Ile Leu Tyr Trp Ile Tyr Arg Phe Leu Cys Leu Ala
        35                  40                  45

Ser His Gly Val Cys Val Gly Val Met Val Phe Arg Met Val Glu Ala
    50                  55                  60
```

```
Lys Thr Ile Asp Asn Val Ser Leu Ile Met Arg Tyr Ala Thr Leu Val
 65                  70                  75                  80

Thr Tyr Ile Ile Asn Ser Asp Thr Lys Phe Ala Thr Val Leu Gln Arg
                 85                  90                  95

Ser Ala Ile Gln Ser Leu Asn Ser Lys Leu Ala Glu Leu Tyr Pro Lys
            100                 105                 110

Thr Thr Leu Asp Arg Ile Tyr His Arg Val Asn Asp His Tyr Trp Thr
            115                 120                 125

Lys Ser Phe Val Tyr Leu Val Ile Tyr Ile Gly Ser Ser Ile Met
130                 135                 140

Val Val Ile Gly Pro Ile Ile Thr Ser Ile Ile Ala Tyr Phe Thr His
145                 150                 155                 160

Asn Val Phe Thr Tyr Met His Cys Tyr Pro Tyr Phe Leu Tyr Asp Pro
                165                 170                 175

Glu Lys Asp Pro Val Trp Ile Tyr Ile Ser Ile Tyr Ala Leu Glu Trp
            180                 185                 190

Leu His Ser Thr Gln Met Val Ile Ser Asn Ile Gly Ala Asp Ile Trp
            195                 200                 205

Leu Leu Tyr Phe Gln Val Gln Ile Asn Leu His Phe Arg Gly Ile Ile
210                 215                 220

Arg Ser Leu Ala Asp His Lys Pro Ser Val Lys His Asp Gln Glu Asp
225                 230                 235                 240

Arg Lys Phe Ile Ala Lys Ile Val Asp Lys Gln Val His Leu Val Ser
                245                 250                 255

Leu Gln Asn Asp Leu Asn Gly Ile Phe Gly Lys Ser Leu Leu Leu Ser
            260                 265                 270

Leu Leu Thr Thr Ala Ala Val Ile Cys Thr Val Ala Val Tyr Thr Leu
            275                 280                 285

Ile Gln Gly Pro Thr Leu Glu Gly Phe Thr Tyr Val Ile Phe Ile Gly
            290                 295                 300

Thr Ser Val Met Gln Val Tyr Leu Val Cys Tyr Tyr Gly Gln Gln Val
305                 310                 315                 320

Leu Asp Leu Ser Gly Glu Val Ala His Ala Val Tyr Asn His Asp Phe
                325                 330                 335

His Asp Ala Ser Ile Ala Tyr Lys Arg Tyr Leu Leu Ile Ile Ile Ile
            340                 345                 350

Arg Ala Gln Gln Pro Val Glu Leu Asn Ala Met Gly Tyr Leu Ser Ile
            355                 360                 365

Ser Leu Asp Thr Phe Lys Gln Leu Met Ser Val Ser Tyr Arg Val Ile
370                 375                 380

Thr Met Leu Met Gln Met Ile Gln
385                 390

<210> SEQ ID NO 71
<211> LENGTH: 795
<212> TYPE: DNA
<213> ORGANISM: Drosophila Melanogaster DOR38

<400> SEQUENCE: 71
atgcgtttga tcaaaatttc atattcggca cttaatgagg tgtgcgtttg gctgaaactg      60
aatggttctt ggccattaac cgaatcatcg aggccatgga ggagccaatc cttattggcc     120
accgcctaca tcgtgtgggc gtggtacgtc attgcatctg tggcataac aatcagctat     180 cagacggcct ttttgctgaa caacctttcg gacattatta tcaccacgga aaattgttgc     240
```

-continued

```
accaccttta tgggtgtcct gaactttgtc cgactcatcc atcttcgcct caatcagagg    300
aaattccgcc agcttattga gaactttccc tacgaaattt ggatacctaa ttcttccaaa    360
aacaatgttg ccgccgagtg tcgcagacgc atggttacct tcagcataat gacatccttg    420
ctagcgtgcc tgatcataat gtattgtgtc ctgccgctgg tggagatctt ctttggaccc    480
gccttcgatg cacagaacaa gccgtttccc tacaagatga tctttccgta cgatgcccag    540
agcagttgga tccgatatgt gatgacctac atcttcacct cctacgcggg aatctgtgtg    600
gtcaccacct tgtttgcaga ggacaccatt cttggcttct tcataaccta cacttgtggc    660
caatttcatt tgctacacca acgaatcgca ggtttatttg cgggttccaa tgcggaattg    720
gccgagagca ttcagctgga gcgactcaaa cgtattgtgg aaaaacacaa caatattatc    780
agcgcaaatt ctgta                                                     795
```

<210> SEQ ID NO 72
<211> LENGTH: 265
<212> TYPE: PRT
<213> ORGANISM: Drosophila Melanogaster DOR38

<400> SEQUENCE: 72

```
Met Arg Leu Ile Lys Ile Ser Tyr Ser Ala Leu Asn Glu Val Cys Val
 1               5                  10                  15

Trp Leu Lys Leu Asn Gly Ser Trp Pro Leu Thr Glu Ser Ser Arg Pro
                20                  25                  30

Trp Arg Ser Gln Ser Leu Leu Ala Thr Ala Tyr Ile Val Trp Ala Trp
            35                  40                  45

Tyr Val Ile Ala Ser Val Gly Ile Thr Ile Ser Tyr Gln Thr Ala Phe
        50                  55                  60

Leu Leu Asn Asn Leu Ser Asp Ile Ile Ile Thr Thr Glu Asn Cys Cys
65                  70                  75                  80

Thr Thr Phe Met Gly Val Leu Asn Phe Val Arg Leu Ile His Leu Arg
                85                  90                  95

Leu Asn Gln Arg Lys Phe Arg Gln Leu Ile Glu Asn Phe Ser Tyr Glu
                100                 105                 110

Ile Trp Ile Pro Asn Ser Ser Lys Asn Val Ala Ala Glu Cys Arg
            115                 120                 125

Arg Arg Met Val Thr Phe Ser Ile Met Thr Ser Leu Leu Ala Cys Leu
        130                 135                 140

Ile Ile Met Tyr Cys Val Leu Pro Leu Val Glu Ile Phe Phe Gly Pro
145                 150                 155                 160

Ala Phe Asp Ala Gln Asn Lys Pro Phe Pro Tyr Lys Met Ile Phe Pro
                165                 170                 175

Tyr Asp Ala Gln Ser Ser Trp Ile Arg Tyr Val Met Thr Tyr Ile Phe
            180                 185                 190

Thr Ser Tyr Ala Gly Ile Cys Val Val Thr Thr Leu Phe Ala Glu Asp
        195                 200                 205

Thr Ile Leu Gly Phe Phe Ile Thr Tyr Thr Cys Gly Gln Phe His Leu
    210                 215                 220

Leu His Gln Arg Ile Ala Gly Leu Phe Ala Gly Ser Asn Ala Glu Leu
225                 230                 235                 240

Ala Glu Ser Ile Gln Leu Glu Arg Leu Lys Arg Ile Val Glu Lys His
                245                 250                 255

Asn Asn Ile Ile Ser Ala Asn Ser Val
            260                 265
```

<210> SEQ ID NO 73
<211> LENGTH: 1409
<212> TYPE: DNA
<213> ORGANISM: Drosophila Melanogaster DOR48

<400> SEQUENCE: 73

| | | | | |
|---|---|---|---|---|
| atggagcgcc | attatttcat | ggtgccaaag | tttgcattat cgctgattgg ttttatccc | 60 |
| gaacagaagc | gaacggtttt | ggtgaaactt | tggagtttct tcaactttt catcctcacc | 120 |
| tacggctgtt | atgcagaggc | ttactatggc | atacactata taccgattaa catagccact | 180 |
| gcattggatg | cccttgtcc | tgtggcctcc | agcattttgt cgctggtgaa atggtcgcc | 240 |
| atttggtggt | atcaagatga | attaaggagt | tgatagagc gggtaagatt tttaacagag | 300 |
| caacagaagt | ccaagaggaa | actgggctat | aagaagaggt tctatacact ggcaacgcaa | 360 |
| ctaacattcc | tgctactatg | ctgtggattt | tgcaccagta cttcctattc cgtcagacat | 420 |
| tgattgata | atatcctgag | acgcacccat | ggcaaggact ggatctacga gactccgttc | 480 |
| aagatgatgt | aaggaaaggg | aagaatggtt | tatatatact tttggaacga ataatgatg | 540 |
| tgatctaaac | aagatgcact | tttttttagg | ttccccgatc ttctcctgcg tttgccactc | 600 |
| tatcccatca | cctatatact | cgtgcattgg | catggctaca ttactgtggt ttgttttgtc | 660 |
| ggcgcggatg | gtttcttcct | ggggttctgt | ttgtacttca ctgttttgct gctctgtctg | 720 |
| caggacgatg | tttgtgattt | actagaggtt | gaaaacatcg agaagagtcc ctccgaagcg | 780 |
| gaggaagctc | gcatagttcg | ggaaatggaa | aaactggtgg accggcataa cgaggtggcc | 840 |
| gagctgacag | aaagattgtc | gggtgttatg | gtggaaataa cactggccca ctttgttact | 900 |
| tcgagtttga | taatcggaac | cagcgtggtg | gatatttat tagtgggtat ttacatttga | 960 |
| ttagatcctt | tcgatatatg | ttcttaaatt | ctagttttcc ggcctgggaa tcattgtgta | 1020 |
| tgtggtctac | acttgtgccg | taggtgtgga | aatatttcta tactgtttag gaggatctca | 1080 |
| tattatggaa | gcggtatatt | cataagaaac | tactataaag ttacttttaa attcattgca | 1140 |
| tttcttagtg | ttccaatcta | gcgcgctcca | cattttccag ccactggtat ggccacagtg | 1200 |
| ttcgggtcca | aaagatgacc | cttttgatgg | tagctcgtgc tcaacgagtt ctcacaatta | 1260 |
| aaattccttt | cttttcccca | tcattagaga | ctctaacttc ggtaagctta tgcgaaaatg | 1320 |
| ttatggtaca | cacaagtcta | catttctatg | aggtcttgta gattttgcgc ttcactggat | 1380 |
| ctctgattgc | cctggcaaag | tcggttata | | 1409 |

<210> SEQ ID NO 74
<211> LENGTH: 369
<212> TYPE: PRT
<213> ORGANISM: Drosophila Melanogaster DOR48

<400> SEQUENCE: 74

Met Glu Arg His Tyr Phe Met Val Pro Lys Phe Ala Leu Ser Leu Ile
1               5                   10                  15

Gly Phe Tyr Pro Glu Gln Lys Arg Thr Val Leu Val Lys Leu Trp Ser
                20                  25                  30

Phe Phe Asn Phe Phe Ile Leu Thr Tyr Gly Cys Tyr Ala Glu Ala Tyr
            35                  40                  45

Tyr Gly Ile His Tyr Ile Pro Ile Asn Ile Ala Thr Ala Leu Asp Ala
        50                  55                  60

Leu Cys Pro Val Ala Ser Ser Ile Leu Ser Leu Val Lys Met Val Ala
65                  70                  75                  80

Ile Trp Trp Tyr Gln Asp Glu Leu Arg Ser Leu Ile Glu Arg Arg Phe
                85                  90                  95

Tyr Thr Leu Ala Thr Gln Leu Thr Phe Leu Leu Leu Cys Cys Gly Phe
            100                 105                 110

Cys Thr Ser Thr Ser Tyr Ser Val Arg His Leu Ile Asp Asn Ile Leu
            115                 120                 125

Arg Arg Thr His Gly Lys Asp Trp Ile Tyr Glu Thr Pro Phe Lys Met
        130                 135                 140

Met Phe Pro Asp Leu Leu Leu Arg Leu Pro Leu Tyr Pro Ile Thr Tyr
145                 150                 155                 160

Ile Leu Val His Trp His Gly Tyr Ile Thr Val Val Cys Phe Val Gly
                165                 170                 175

Ala Asp Gly Phe Phe Leu Gly Phe Cys Leu Tyr Phe Thr Val Leu Leu
            180                 185                 190

Leu Cys Leu Gln Asp Asp Val Cys Asp Leu Leu Glu Val Glu Asn Ile
        195                 200                 205

Glu Lys Ser Pro Ser Glu Ala Glu Glu Ala Arg Ile Val Arg Glu Met
    210                 215                 220

Glu Lys Leu Val Asp Arg His Asn Glu Val Ala Glu Leu Thr Glu Arg
225                 230                 235                 240

Leu Ser Gly Val Met Val Glu Ile Thr Leu Ala His Phe Val Thr Ser
                245                 250                 255

Ser Leu Ile Ile Gly Thr Ser Val Val Asp Ile Leu Leu Phe Ser Gly
            260                 265                 270

Leu Gly Ile Ile Val Tyr Val Tyr Thr Cys Ala Val Gly Val Glu
        275                 280                 285

Ile Phe Leu Tyr Cys Leu Gly Gly Ser His Ile Met Glu Ala Cys Ser
    290                 295                 300

Asn Leu Ala Arg Ser Thr Phe Ser Ser His Trp Tyr Gly His Ser Val
305                 310                 315                 320

Arg Val Gln Lys Met Thr Leu Leu Met Val Ala Arg Ala Gln Arg Val
                325                 330                 335

Leu Thr Ile Lys Ile Pro Phe Phe Ser Pro Ser Leu Glu Thr Leu Thr
            340                 345                 350

Ser Ile Leu Arg Phe Thr Gly Ser Leu Ile Ala Leu Ala Lys Ser Val
        355                 360                 365

Ile

<210> SEQ ID NO 75
<211> LENGTH: 891
<212> TYPE: DNA
<213> ORGANISM: Drosophila Melanogaster DOR56

<400> SEQUENCE: 75
atggatccgg tggagatgcc cattttggt agcactctga agctaatgaa gttctggtca      60
tatctgtttg ttcacaactg gcgccgctat gtcgcaatga ctccgtacat cattatcaac    120
tgtactcagt atgtggatat atatctgagc accgaatcct tggactttat catcagaaat    180
gtatacctgg ctgtattgtt taccaacacg gtggtcagag gtgtattgtt atgcgtacag    240
cggtttagct acgagcgttt cattaatatt ttgaaaagct tttacattga gttgttggtg    300
agtaccgaaa gattatctca aaaatgcata ttgcataaat gggcagttct gccatatggc    360
atgtatttgc ccactattga tgaatacaaa tacgcatcac cttactacga gatttctttt    420

| | |
|---|---|
| gtgattcaag ccattatggc tccaatgggg tgttgcatgt acataccata cacaaacatg | 480 |
| gtagtgacat ttacccttt cgccattctc atgtgtcgag tgttgcaaca taagttgaga | 540 |
| agcctagaaa agctgaaaaa tgaacaagta cgtggtgaaa tcgctcaaac aattgctcag | 600 |
| accgtcatag tcatcgcata catggtaatg atatttgcca acagtgtagt cctttactac | 660 |
| gtggccaatg agctatactt tcaaagcttt gatattgcca ttgctgccta tgagagcaat | 720 |
| tggatggact ttgatgtgga cacacaaaag actttgaagt tcctcatcat gcgctcgcaa | 780 |
| aagcccttgg cgagtctggt gggtggcaca tatcccatga acttgaaaat gcttcagtca | 840 |
| ctactaaatg ccatttactc cttcttcacc cttctgcgtc gcgtttacgg c | 891 |

<210> SEQ ID NO 76
<211> LENGTH: 297
<212> TYPE: PRT
<213> ORGANISM: Drosophila Melanogaster DOR56

<400> SEQUENCE: 76

```
Met Asp Pro Val Glu Met Pro Ile Phe Gly Ser Thr Leu Lys Leu Met
1               5                   10                  15

Lys Phe Trp Ser Tyr Leu Phe Val His Asn Trp Arg Arg Tyr Val Ala
            20                  25                  30

Met Thr Pro Tyr Ile Ile Ile Asn Cys Thr Gln Tyr Val Asp Ile Tyr
        35                  40                  45

Leu Ser Thr Glu Ser Leu Asp Phe Ile Ile Arg Asn Val Tyr Leu Ala
    50                  55                  60

Val Leu Phe Thr Asn Thr Val Val Arg Gly Val Leu Leu Cys Val Gln
65                  70                  75                  80

Arg Phe Ser Tyr Glu Arg Phe Ile Asn Ile Leu Lys Ser Phe Tyr Ile
                85                  90                  95

Glu Leu Leu Val Ser Thr Glu Arg Leu Ser Gln Lys Cys Ile Leu His
            100                 105                 110

Lys Trp Ala Val Leu Pro Tyr Gly Met Tyr Leu Pro Thr Ile Asp Glu
        115                 120                 125

Tyr Lys Tyr Ala Ser Pro Tyr Tyr Glu Ile Phe Phe Val Ile Gln Ala
    130                 135                 140

Ile Met Ala Pro Met Gly Cys Cys Met Tyr Ile Pro Tyr Thr Asn Met
145                 150                 155                 160

Val Val Thr Phe Thr Leu Phe Ala Ile Leu Met Cys Arg Val Leu Gln
                165                 170                 175

His Lys Leu Arg Ser Leu Glu Lys Leu Lys Asn Glu Gln Val Arg Gly
            180                 185                 190

Glu Ile Ala Gln Thr Ile Ala Gln Thr Val Ile Val Ala Tyr Met
        195                 200                 205

Val Met Ile Phe Ala Asn Ser Val Val Leu Tyr Tyr Val Ala Asn Glu
    210                 215                 220

Leu Tyr Phe Gln Ser Phe Asp Ile Ala Ile Ala Ala Tyr Glu Ser Asn
225                 230                 235                 240

Trp Met Asp Phe Asp Val Asp Thr Gln Lys Thr Leu Lys Phe Leu Ile
                245                 250                 255

Met Arg Ser Gln Lys Pro Leu Ala Ser Leu Val Gly Gly Thr Tyr Pro
            260                 265                 270

Met Asn Leu Lys Met Leu Gln Ser Leu Leu Asn Ala Ile Tyr Ser Phe
        275                 280                 285

Phe Thr Leu Leu Arg Arg Val Tyr Gly
```

-continued

| 290 | 295 |

<210> SEQ ID NO 77
<211> LENGTH: 1134
<212> TYPE: DNA
<213> ORGANISM: Drosophila Melanogaster DOR58

<400> SEQUENCE: 77

| atggacgcca gctactttgc cgtccagaga agagctctgg aaatagttgg attcgatccc | 60 |
| agtactccgc aactgagtct gaaacatccc atctgggccg ggattctcat cctgtccttg | 120 |
| atctctcaca actggcccat ggtagtctat gccctgcagg atctctccga cttgacccgt | 180 |
| ctgacggaca actttgcggt gtttatgcaa ggatcacaga gcaccttcaa gttcctggtc | 240 |
| atgatggcga acgaaggcg cattggatcg ttgattcacc gtttgcataa gctaaaccag | 300 |
| gcggccagtg ccacgcccaa tcacctggag aagatcgaga gggaaaacca actggatagg | 360 |
| tatgtcgcca ggtcctttag aaatgccgcc tacggagtga tttgtgcctc ggccatagcg | 420 |
| cccatgttgc ttggcctgtg gggatatgtg agacgggtg tatttacccc caccacaccc | 480 |
| atggagttca acttctggct ggacgagcga agcctcact tttattggcc catctacgtt | 540 |
| tgggcgtac tgggcgtggc agctgccgcc tggttggcca ttgcaacgga caccctgttc | 600 |
| tcctggctga ctcacaatgt ggtgattcag ttccaactac tggagcttgt tctcgaagag | 660 |
| aaggatctga atggcggaga ctctcgcctg accgggtttg ttagtcgtca tcgtatagct | 720 |
| ctggatttgg ccaaggaact aagttcgatt tccggggaga tcgtctttgt gaaatacatg | 780 |
| ctcagttacc tgcaactctg catgttggcc tttcgcttca gccgcagtgg ctggagtgcc | 840 |
| caggtgccat ttagagccac cttcctagtg gccatcatca tccaactgag ttcgtattgc | 900 |
| tatggaggcg agtatataaa gcagcaaagt ttggccatcg cacaagccgt ttatggtcaa | 960 |
| atcaattggc cagaaatgac gccaaagaaa agaagactct ggcaaatggt gatcatgagg | 1020 |
| gcgcagcgac cggctaagat ttttggattc atgttcgttg tggacttgcc actgctgctt | 1080 |
| tgggtcatca gaactgcggg ctcatttctg gccatgctta ggactttcga gcgt | 1134 |

<210> SEQ ID NO 78
<211> LENGTH: 378
<212> TYPE: PRT
<213> ORGANISM: Drosophila Melanogaster DOR58

<400> SEQUENCE: 78

Met Asp Ala Ser Tyr Phe Ala Val Gln Arg Arg Ala Leu Glu Ile Val
1               5                   10                  15

Gly Phe Asp Pro Ser Thr Pro Gln Leu Ser Leu Lys His Pro Ile Trp
                20                  25                  30

Ala Gly Ile Leu Ile Leu Ser Leu Ile Ser His Asn Trp Pro Met Val
            35                  40                  45

Val Tyr Ala Leu Gln Asp Leu Ser Asp Leu Thr Arg Leu Thr Asp Asn
        50                  55                  60

Phe Ala Val Phe Met Gln Gly Ser Gln Ser Thr Phe Lys Phe Leu Val
65                  70                  75                  80

Met Met Ala Lys Arg Arg Arg Ile Gly Ser Leu Ile His Arg Leu His
                85                  90                  95

Lys Leu Asn Gln Ala Ala Ser Ala Thr Pro Asn His Leu Glu Lys Ile
            100                 105                 110

Glu Arg Glu Asn Gln Leu Asp Arg Tyr Val Ala Arg Ser Phe Arg Asn
        115                 120                 125

```
Ala Ala Tyr Gly Val Ile Cys Ala Ser Ala Ile Ala Pro Met Leu Leu
        130                 135                 140

Gly Leu Trp Gly Tyr Val Glu Thr Gly Val Phe Thr Pro Thr Thr Pro
145                 150                 155                 160

Met Glu Phe Asn Phe Trp Leu Asp Glu Arg Lys Pro His Phe Tyr Trp
                165                 170                 175

Pro Ile Tyr Val Trp Gly Val Leu Gly Val Ala Ala Ala Trp Leu
                180                 185                 190

Ala Ile Ala Thr Asp Thr Leu Phe Ser Trp Leu Thr His Asn Val Val
                195                 200                 205

Ile Gln Phe Gln Leu Leu Glu Leu Val Leu Glu Glu Lys Asp Leu Asn
        210                 215                 220

Gly Gly Asp Ser Arg Leu Thr Gly Phe Val Ser Arg His Arg Ile Ala
225                 230                 235                 240

Leu Asp Leu Ala Lys Glu Leu Ser Ser Ile Phe Gly Glu Ile Val Phe
                245                 250                 255

Val Lys Tyr Met Leu Ser Tyr Leu Gln Leu Cys Met Leu Ala Phe Arg
                260                 265                 270

Phe Ser Arg Ser Gly Trp Ser Ala Gln Val Pro Phe Arg Ala Thr Phe
        275                 280                 285

Leu Val Ala Ile Ile Gln Leu Ser Ser Tyr Cys Tyr Gly Gly Glu
        290                 295                 300

Tyr Ile Lys Gln Gln Ser Leu Ala Ile Ala Gln Ala Val Tyr Gly Gln
305                 310                 315                 320

Ile Asn Trp Pro Glu Met Thr Pro Lys Lys Arg Arg Leu Trp Gln Met
                325                 330                 335

Val Ile Met Arg Ala Gln Arg Pro Ala Lys Ile Phe Gly Phe Met Phe
                340                 345                 350

Val Val Asp Leu Pro Leu Leu Leu Trp Val Ile Arg Thr Ala Gly Ser
        355                 360                 365

Phe Leu Ala Met Leu Arg Thr Phe Glu Arg
    370                 375

<210> SEQ ID NO 79
<211> LENGTH: 807
<212> TYPE: DNA
<213> ORGANISM: Drosophila Melanogaster DOR59

<400> SEQUENCE: 79
atgcacgaag cagataatcg ggagatggaa cttttggtcg ccactcaggc ttatacacga    60
accattaccc tgttgatctg gataccatcg gttattgctg gcctaatggc ctattcagac   120
tgcatctaca ggagtctgtt tctgccgaaa tcggttttca atgtgccagc tgtgcgacgt   180
ggtgaggagc atcccattct gctatttcag ctgtttccct tcggagaact ttgcgataac   240
ttcgttgttg atacttggg accttggtat gctctgggcc tgggaatcac ggctatccca   300
ttgtggcaca cctttatcac ttgcctcatg aagtacgtaa atctcaagct gcaaatactc   360
aacaagcgag tggaggagat ggatattacc cgacttaatt ccaaattggt aattggtcgc   420
ctaactgcca gtgagttaac cttctggcaa atgcaactct caaggaatt tgtaaaggaa   480 cagctgagga ttcgaaaatt tgtccaggaa ctacagtatc tgatttgcgt gcctgtgatg   540
gcagatttca ttatcttctc ggttctcatt tgctttctct tttttgcctt gacagttggc   600
cacgatgaac tgagccttgc ttactttct tgcggatggt acaacttcga aatgcctttg   660
```

```
cagaaaatgc tggtttttat gatgatgcat gcccaaaggc cgatgaagat gcgcgccctg    720
ctggtcgatt tgaatctgag gaccttcata gacattggcc gtggagccta cagctacttc    780
aatttgctgc gtagctccca cttgtat                                         807
```

<210> SEQ ID NO 80
<211> LENGTH: 269
<212> TYPE: PRT
<213> ORGANISM: Drosophila Melanogaster DOR59

<400> SEQUENCE: 80

```
Met His Glu Ala Asp Asn Arg Glu Met Glu Leu Leu Val Ala Thr Gln
1               5                   10                  15

Ala Tyr Thr Arg Thr Ile Thr Leu Leu Ile Trp Ile Pro Ser Val Ile
            20                  25                  30

Ala Gly Leu Met Ala Tyr Ser Asp Cys Ile Tyr Arg Ser Leu Phe Leu
        35                  40                  45

Pro Lys Ser Val Phe Asn Val Pro Ala Val Arg Arg Gly Glu Glu His
    50                  55                  60

Pro Ile Leu Leu Phe Gln Leu Phe Pro Phe Gly Glu Leu Cys Asp Asn
65                  70                  75                  80

Phe Val Val Gly Tyr Leu Gly Pro Trp Tyr Ala Leu Gly Leu Gly Ile
                85                  90                  95

Thr Ala Ile Pro Leu Trp His Thr Phe Ile Thr Cys Leu Met Lys Tyr
            100                 105                 110

Val Asn Leu Lys Leu Gln Ile Leu Asn Lys Arg Val Glu Glu Met Asp
        115                 120                 125

Ile Thr Arg Leu Asn Ser Lys Leu Val Ile Gly Arg Leu Thr Ala Ser
    130                 135                 140

Glu Leu Thr Phe Trp Gln Met Gln Leu Phe Lys Glu Phe Val Lys Glu
145                 150                 155                 160

Gln Leu Arg Ile Arg Lys Phe Val Gln Glu Leu Gln Tyr Leu Ile Cys
                165                 170                 175

Val Pro Val Met Ala Asp Phe Ile Ile Phe Ser Val Leu Ile Cys Phe
            180                 185                 190

Leu Phe Phe Ala Leu Thr Val Gly His Asp Glu Leu Ser Leu Ala Tyr
        195                 200                 205

Phe Ser Cys Gly Trp Tyr Asn Phe Glu Met Pro Leu Gln Lys Met Leu
    210                 215                 220

Val Phe Met Met Met His Ala Gln Arg Pro Met Lys Met Arg Ala Leu
225                 230                 235                 240

Leu Val Asp Leu Asn Leu Arg Thr Phe Ile Asp Ile Gly Arg Gly Ala
                245                 250                 255

Tyr Ser Tyr Phe Asn Leu Leu Arg Ser Ser His Leu Tyr
            260                 265
```

<210> SEQ ID NO 81
<211> LENGTH: 1143
<212> TYPE: DNA
<213> ORGANISM: Drosophila Melanogaster DOR68

<400> SEQUENCE: 81

```
atgtcaaagc taatcgaggt gtttctgggt aatctgtgga cccagcgttt taccttcgcc     60
cgaatgggtt tggatttgca gcccgataaa aagggcaatg ttttgcgatc tccgcttctt    120
tattgtatta tgtgtctgac aacaagcttt gagctctgca ccgtgtgcgc ctttatggtc    180
```

-continued

```
caaaatcgca accaaatcgt gctttgttcc gaggccctga tgcacggact acagatggtc      240
tcctcgctac tgaagatggc tatattcttg cccaaatctc acgacctggt ggacctaatt      300
caacagattc agtcgccttt tacagaggag gatcttgtag gtacagagtg gagatcccaa      360
aatcaaaggg gacaactaat ggctgccatt tactttatga tgtgtgccgg tacgagtgtg      420
tcatttctgt tgatgccagt ggctttgacc atgcttaagt accattccac tggggaattc      480
gcgcctgtca gctcgttccg ggttctgctt ccatacgatg tgacacaacc gcatgtttat      540
gccatggact gctgcttgat ggtatttgtg ttaagttttt tttgctgctc caccaccgga      600
gtggatacct tatatggatg gtgtgcttta ggcgtgagtt tacaataccg tcgcctcggt      660
caacaactta aaggatacc  ctcctgtttc aatccatctc ggtctgactt tggattaagt      720 gggattttttg tggagcatgc tcgtctgctt aaaatagtcc aacatttaa  ttatagtttt    780 atggagatcg catttgtgga ggttgttata atctgtggac tctattgctc agtaatttgt      840
cagtatataa tgccacacac caaccaaaac ttcgccttc  tgggtttctt ttcattggta      900
gttaccacac agctgtgcat ctatctttc  ggtgccgaac aggtccgttt ggaggctgag      960 cgatttttccc ggctgctata cgaagtaatt ccttggcaaa accttcctcc taaacaccgg     1020 aaactttttcc tttttccaat tgagcgcgcc caacgagaaa ctgttctcgg tgcttatttc     1080
ttcgaactag gcagacctct tcttgttttgg gtaagcatat tccttttttat tgtattatta   1140 ttt                                                                    1143
```

<210> SEQ ID NO 82
<211> LENGTH: 381
<212> TYPE: PRT
<213> ORGANISM: Drosophila Melanogaster DOR68

<400> SEQUENCE: 82

```
Met Ser Lys Leu Ile Glu Val Phe Leu Gly Asn Leu Trp Thr Gln Arg
1               5                   10                  15

Phe Thr Phe Ala Arg Met Gly Leu Asp Leu Gln Pro Asp Lys Lys Gly
            20                  25                  30

Asn Val Leu Arg Ser Pro Leu Leu Tyr Cys Ile Met Cys Leu Thr Thr
        35                  40                  45

Ser Phe Glu Leu Cys Thr Val Cys Ala Phe Met Val Gln Asn Arg Asn
    50                  55                  60

Gln Ile Val Leu Cys Ser Glu Ala Leu Met His Gly Leu Gln Met Val
65                  70                  75                  80

Ser Ser Leu Leu Lys Met Ala Ile Phe Leu Ala Lys Ser His Asp Leu
                85                  90                  95

Val Asp Leu Ile Gln Gln Ile Ser Pro Phe Thr Glu Glu Asp Leu
            100                 105                 110

Val Gly Thr Glu Trp Arg Ser Gln Asn Gln Arg Gly Gln Leu Met Ala
        115                 120                 125

Ala Ile Tyr Phe Met Met Cys Ala Gly Thr Ser Val Ser Phe Leu Leu
    130                 135                 140

Met Pro Val Ala Leu Thr Met Leu Lys Tyr His Ser Thr Gly Glu Phe
145                 150                 155                 160

Ala Pro Val Ser Ser Phe Arg Val Leu Pro Tyr Asp Val Thr Gln
                165                 170                 175

Pro His Val Tyr Ala Met Asp Cys Cys Leu Met Val Phe Val Leu Ser
            180                 185                 190

Phe Phe Cys Cys Ser Thr Thr Gly Val Asp Thr Leu Tyr Gly Trp Cys
```

|  |  | 195 |  |  | 200 |  |  | 205 |  |  |  |
|---|---|---|---|---|---|---|---|---|---|---|---|

Ala Leu Gly Val Ser Leu Gln Tyr Arg Arg Leu Gly Gln Gln Leu Lys
    210                     215                     220

Arg Ile Pro Ser Cys Phe Asn Pro Ser Arg Ser Asp Phe Gly Leu Ser
225                     230                     235                     240

Gly Ile Phe Val Glu His Ala Arg Leu Leu Lys Ile Val Gln His Phe
                245                     250                     255

Asn Tyr Ser Phe Met Glu Ile Ala Phe Val Glu Val Ile Ile Cys
            260                     265                     270

Gly Leu Tyr Cys Ser Val Ile Cys Gln Tyr Ile Met Pro His Thr Asn
                275                     280                     285

Gln Asn Phe Ala Phe Leu Gly Phe Ser Leu Val Val Thr Thr Gln
    290                     295                     300

Leu Cys Ile Tyr Leu Phe Gly Ala Glu Gln Val Arg Leu Glu Ala Glu
305                     310                     315                     320

Arg Phe Ser Arg Leu Leu Tyr Glu Val Ile Pro Trp Gln Asn Leu Pro
                325                     330                     335

Pro Lys His Arg Lys Leu Phe Leu Phe Pro Ile Glu Arg Ala Gln Arg
            340                     345                     350

Glu Thr Val Leu Gly Ala Tyr Phe Phe Glu Leu Gly Arg Pro Leu Leu
                355                     360                     365

Val Trp Val Ser Ile Phe Leu Phe Ile Val Leu Leu Phe
    370                     375                     380

<210> SEQ ID NO 83
<211> LENGTH: 927
<212> TYPE: DNA
<213> ORGANISM: Drosophila Melanogaster DOR77

<400> SEQUENCE: 83

| atggaattga tgcgagtgcc agtacagttt tacagaacga ttggagagga tatctacgcc | 60 |
| catcgatcca cgaatcccct aaaatcgctt ctcttcaaga tctatctata tgcgggattc | 120 |
| ataaatttta atctgttggt aatcggtgaa ctggtgttct tctacaactc aattcaggac | 180 |
| tttgaaacca ttcgattggc catcgcggtg gctccatgta tcggattttc tctggttgct | 240 |
| gattttaaac aagctgccat gattagaggc aagaaaacac taattatgct actcgatgat | 300 |
| ttggagaaca tgcatccgaa aaccctggca agcaaatgg aatacaaatt gccggacttt | 360 |
| gaaaagacca tgaaacgtgt gatcaatata ttcacctttc tctgcttggc ctatacgact | 420 |
| acgttctcct tttatccggc catcaaggca tccgtgaaat ttaatttctt gggctacgac | 480 |
| acctttgatc gaaattttgg tttcctcatc tggtttccct tcgatgcaac aaggaataat | 540 |
| ttgatatact ggatcatgta ctgggacata gcccatgggg cctatctagc ggcctttcag | 600 |
| gtcaccgaat caacagtgga agtgattatt atttactgca ttttttttgat gacctcgatg | 660 |
| gttcaggtat ttatggtgtg ctactatggg gatactttaa ttgccgcgag cttgaaagtg | 720 |
| ggcgatgccg cttacaacca aaagtggttt cagtgcagca atcctattg caccatgttg | 780 |
| aagttgctaa tcatgaggag tcagaaacca gcttcaataa gaccgccgac ttttccccccc | 840 |
| atatccttgg ttacctatat gaagaatccc ttcaacaatc tacccaaaca cagctcttcc | 900 |
| ctgcaaatca acgccaatcg ctatatc | 927 |

<210> SEQ ID NO 84
<211> LENGTH: 309
<212> TYPE: PRT

<213> ORGANISM: Drosophila Melanogaster DOR77

<400> SEQUENCE: 84

```
Met Glu Leu Met Arg Val Pro Val Gln Phe Tyr Arg Thr Ile Gly Glu
1               5                   10                  15

Asp Ile Tyr Ala His Arg Ser Thr Asn Pro Leu Lys Ser Leu Leu Phe
            20                  25                  30

Lys Ile Tyr Leu Tyr Ala Gly Phe Ile Asn Phe Asn Leu Leu Val Ile
        35                  40                  45

Gly Glu Leu Val Phe Phe Tyr Asn Ser Ile Gln Asp Phe Glu Thr Ile
    50                  55                  60

Arg Leu Ala Ile Ala Val Ala Pro Cys Ile Gly Phe Ser Leu Val Ala
65                  70                  75                  80

Asp Phe Lys Gln Ala Ala Met Ile Arg Gly Lys Lys Thr Leu Ile Met
                85                  90                  95

Leu Leu Asp Asp Leu Glu Asn Met His Pro Lys Thr Leu Ala Lys Gln
            100                 105                 110

Met Glu Tyr Lys Leu Pro Asp Phe Glu Lys Thr Met Lys Arg Val Ile
        115                 120                 125

Asn Ile Phe Thr Phe Leu Cys Leu Ala Tyr Thr Thr Thr Phe Ser Phe
    130                 135                 140

Tyr Pro Ala Ile Lys Ala Ser Val Lys Phe Asn Phe Leu Gly Tyr Asp
145                 150                 155                 160

Thr Phe Asp Arg Asn Phe Gly Phe Leu Ile Trp Phe Pro Phe Asp Ala
                165                 170                 175

Thr Arg Asn Asn Leu Ile Tyr Trp Ile Met Tyr Trp Asp Ile Ala His
            180                 185                 190

Gly Ala Tyr Leu Ala Ala Phe Gln Val Thr Glu Ser Thr Val Glu Val
        195                 200                 205

Ile Ile Ile Tyr Cys Ile Phe Leu Met Thr Ser Met Val Gln Val Phe
    210                 215                 220

Met Val Cys Tyr Tyr Gly Asp Thr Leu Ile Ala Ala Ser Leu Lys Val
225                 230                 235                 240

Gly Asp Ala Ala Tyr Asn Gln Lys Trp Phe Gln Cys Ser Lys Ser Tyr
                245                 250                 255

Cys Thr Met Leu Lys Leu Leu Ile Met Arg Ser Gln Lys Pro Ala Ser
            260                 265                 270

Ile Arg Pro Pro Thr Phe Pro Pro Ile Ser Leu Val Thr Tyr Met Lys
        275                 280                 285

Asn Pro Phe Asn Asn Leu Pro Lys His Ser Ser Ser Leu Gln Ile Asn
    290                 295                 300

Ala Asn Arg Tyr Ile
305
```

<210> SEQ ID NO 85
<211> LENGTH: 1152
<212> TYPE: DNA
<213> ORGANISM: Drosophila Melanogaster DOR78

<400> SEQUENCE: 85

```
atgaagttca tgaagtacgc agttttcttt tacacatcgg tgggcattga gccgtatacg      60
attgactcgc ggtccaaaaa agcgagccta tggtcacatc ttctcttctg ggccaatgtg     120
atcaatttaa gtgtcattgt tttcggagag atcctctatc tgggagtggc ctattccgat     180
ggaaagttca ttgatgccgt cactgtactg tcatatatcg gattcgtaat cgtgggcatg     240
```

-continued

| | |
|---|---|
| agcaagatgt tcttcatatg gtggaagaag accgatctaa gcgatttggt taaggaattg | 300 |
| gagcacatct atccaaatgg caaagctgag gaggagatgt atcggttgga taggtatctg | 360 |
| cgatcttgtt cacgaattag cattacctat gcactactct actccgtact catctggacc | 420 |
| ttcaatctgt tcagtatcat gcaattcctt gtctatgaaa agttgcttaa aatccgagtg | 480 |
| gtcggccaaa cgctgccata tttgatgtac tttccctgga actggcatga aaactggacg | 540 |
| tattatgtgc tgctgttctg tcaaaacttc gcaggacata cttcggcatc gggacagatc | 600 |
| tctacggatc ttttgctttg tgctgttgct acccaggtgg taatgcactt cgattacttg | 660 |
| gccagagtgg tggaaaaaca agtgttagat cgcgattgga gcgaaaactc cagattttg | 720 |
| gcaaaaactg tacaatatca tcagcgcatt cttcggctaa tggacgttct caacgatata | 780 |
| ttcgggatac cgctactgct taactttatg gtctccacat ttgtcatctg ctttgtggga | 840 |
| ttccaaatga ccgtgggtgt cccgccggac atcatgatta agctcttctt gttcctgttc | 900 |
| tcgtccttgt cgcaagtgta cttgatatgc cactacggcc agctgattgc cgatgcggta | 960 |
| agagactttc gaagctctag cttatcgatt tctgcatata agcagaattg gcaaaatgct | 1020 |
| gacattcgct atcgtcgggc tctggtattc tttatagctc gacctcagag gacaacttat | 1080 |
| ctaaaagcta caattttcat gaatataaca agggccacca tgacggacgt aagatacaat | 1140 |
| ttgaaatgtc at | 1152 |

<210> SEQ ID NO 86
<211> LENGTH: 384
<212> TYPE: PRT
<213> ORGANISM: Drosophila Melanogaster DOR78

<400> SEQUENCE: 86

```
Met Lys Phe Met Lys Tyr Ala Val Phe Phe Tyr Thr Ser Val Gly Ile
 1               5                  10                  15

Glu Pro Tyr Thr Ile Asp Ser Arg Ser Lys Lys Ala Ser Leu Trp Ser
            20                  25                  30

His Leu Leu Phe Trp Ala Asn Val Ile Asn Leu Ser Val Ile Val Phe
        35                  40                  45

Gly Glu Ile Leu Tyr Leu Gly Val Ala Tyr Ser Asp Gly Lys Phe Ile
    50                  55                  60

Asp Ala Val Thr Val Leu Ser Tyr Ile Gly Phe Val Ile Val Gly Met
65                  70                  75                  80

Ser Lys Met Phe Phe Ile Trp Trp Lys Lys Thr Asp Leu Ser Asp Leu
                85                  90                  95

Val Lys Glu Leu Glu His Ile Tyr Pro Asn Gly Lys Ala Glu Glu Glu
            100                 105                 110

Met Tyr Arg Leu Asp Arg Tyr Leu Arg Ser Cys Ser Arg Ile Ser Ile
        115                 120                 125

Thr Tyr Ala Leu Leu Tyr Ser Val Leu Ile Trp Thr Phe Asn Leu Phe
    130                 135                 140

Ser Ile Met Gln Phe Leu Val Tyr Glu Lys Leu Leu Lys Ile Arg Val
145                 150                 155                 160

Val Gly Gln Thr Leu Pro Tyr Leu Met Tyr Phe Pro Trp Asn Trp His
                165                 170                 175

Glu Asn Trp Thr Tyr Tyr Val Leu Leu Phe Cys Gln Asn Phe Ala Gly
            180                 185                 190

His Thr Ser Ala Ser Gly Gln Ile Ser Thr Asp Leu Leu Leu Cys Ala
        195                 200                 205
```

-continued

```
Val Ala Thr Gln Val Val Met His Phe Asp Tyr Leu Ala Arg Val Val
        210                 215                 220
Glu Lys Gln Val Leu Asp Arg Asp Trp Ser Glu Asn Ser Arg Phe Leu
225                 230                 235                 240
Ala Lys Thr Val Gln Tyr His Gln Arg Ile Leu Arg Leu Met Asp Val
                245                 250                 255
Leu Asn Asp Ile Phe Gly Ile Pro Leu Leu Asn Phe Met Val Ser
            260                 265                 270
Thr Phe Val Ile Cys Phe Val Gly Phe Gln Met Thr Val Gly Val Pro
        275                 280                 285
Pro Asp Ile Met Ile Lys Leu Phe Leu Phe Leu Phe Ser Ser Leu Ser
290                 295                 300
Gln Val Tyr Leu Ile Cys His Tyr Gly Gln Leu Ile Ala Asp Ala Val
305                 310                 315                 320
Arg Asp Phe Arg Ser Ser Leu Ser Ile Ser Ala Tyr Lys Gln Asn
                325                 330                 335
Trp Gln Asn Ala Asp Ile Arg Tyr Arg Arg Ala Leu Val Phe Phe Ile
            340                 345                 350
Ala Arg Pro Gln Arg Thr Thr Tyr Leu Lys Ala Thr Ile Phe Met Asn
        355                 360                 365
Ile Thr Arg Ala Thr Met Thr Asp Val Arg Tyr Asn Leu Lys Cys His
    370                 375                 380
```

<210> SEQ ID NO 87
<211> LENGTH: 1203
<212> TYPE: DNA
<213> ORGANISM: Drosophila Melanogaster DOR81

<400> SEQUENCE: 87

```
atgatggaga cgctgcgaaa ttcgggcttg aatttgaaga acgatttcgg tataggccgc      60
aagatttgga gggtgttttc gttcacctac aatatggtga tacttcccgt aagtttccca     120
atcaactatg tgatacatct ggcggagttc ccgccggagc tgctgctgca atccctgcaa     180
ctgtgcctca acacttggtg cttcgctctg aagttcttca ctctgatcgt ctatacgcac     240
cgcttggagc tggccaacaa gcactttgac gaattggata gtactgcgt gaagccggcg      300
gagaagcgca aggttcgcga catggtggcc actattacaa gactgtacct gaccttcgtc     360
gtggtctacg tcctctacgc cacctccacg ctactggacg gactactgca ccaccgtgtt     420
ccctacaata cgtactatcc gttcataaac tggcgagtcg atcggaccca gatgtacatc     480
cagagttttc tggagtactt caccgtgggt tatgccatat atgtggccac cgccaccgat     540
tcctaccctg tgatttacgt ggcagccctg cgaactcata ttctcttgct caaggaccgt     600
atcatttact gggcgatcc cagcaacgag ggtagcagcg acccgagcta catgtttaaa      660
tcgttggtgg attgtatcaa ggcacacaga accatgctaa agtgcagttt ttgtgatgcc     720
attcaaccaa tcatctctgg cacgatattt gcccaattca tcatatgcgg atcgatcctg     780
ggcataatta tgatcaacat ggtattgttc gctgatcaat cgaccgatt cggcatagtc     840
atctacgtta tggccgtcct tctgcagact tttccgcttt gcttctactg caacgccatc     900
gtggacgact gcaaagaact ggcccacgca cttttccatt ccgcctggtg ggtgcaggac     960
aagcgatacc agcggactgt catccagttc ctgcagaaac tgcagcagcc catgaccttc    1020
accgccatga acatatttaa cattaatttg gccactaaca tcaatgtaag tccactgctc    1080
tcggttagaa cggggaagga agcaaagtcc gaacttcaat ccttgcaggt agccaagttc    1140
```
gccttcaccg tgtacgccat cgcgagcggt atgaacctgg accaaaagtt aagcattaag    1200
gaa                                                                  1203

<210> SEQ ID NO 88
<211> LENGTH: 399
<212> TYPE: PRT
<213> ORGANISM: Drosophila Melanogaster DOR81

<400> SEQUENCE: 88

| Met | Met | Glu | Thr | Leu | Arg | Asn | Ser | Gly | Leu | Asn | Leu | Lys | Asn | Asp | Phe |
|-----|-----|-----|-----|-----|-----|-----|-----|-----|-----|-----|-----|-----|-----|-----|-----|
| 1 | | | | 5 | | | | | 10 | | | | | 15 | |

| Gly | Ile | Gly | Arg | Lys | Ile | Trp | Arg | Val | Phe | Ser | Phe | Thr | Tyr | Asn | Met |
|-----|-----|-----|-----|-----|-----|-----|-----|-----|-----|-----|-----|-----|-----|-----|-----|
| | | | 20 | | | | | 25 | | | | | 30 | | |

| Val | Ile | Leu | Pro | Val | Ser | Phe | Pro | Ile | Asn | Tyr | Val | Ile | His | Leu | Ala |
|-----|-----|-----|-----|-----|-----|-----|-----|-----|-----|-----|-----|-----|-----|-----|-----|
| | | 35 | | | | | 40 | | | | | 45 | | | |

| Glu | Phe | Pro | Pro | Glu | Leu | Leu | Leu | Gln | Ser | Leu | Gln | Leu | Cys | Leu | Asn |
|-----|-----|-----|-----|-----|-----|-----|-----|-----|-----|-----|-----|-----|-----|-----|-----|
| | 50 | | | | | 55 | | | | | 60 | | | | |

| Thr | Trp | Cys | Phe | Ala | Leu | Lys | Phe | Phe | Thr | Leu | Ile | Val | Tyr | Thr | His |
|-----|-----|-----|-----|-----|-----|-----|-----|-----|-----|-----|-----|-----|-----|-----|-----|
| 65 | | | | | 70 | | | | | 75 | | | | | 80 |

| Arg | Leu | Glu | Leu | Ala | Asn | Lys | His | Phe | Asp | Glu | Leu | Asp | Lys | Tyr | Cys |
|-----|-----|-----|-----|-----|-----|-----|-----|-----|-----|-----|-----|-----|-----|-----|-----|
| | | | | 85 | | | | | 90 | | | | | 95 | |

| Val | Lys | Pro | Ala | Glu | Lys | Arg | Lys | Val | Arg | Asp | Met | Val | Ala | Thr | Ile |
|-----|-----|-----|-----|-----|-----|-----|-----|-----|-----|-----|-----|-----|-----|-----|-----|
| | | | 100 | | | | | 105 | | | | | 110 | | |

| Thr | Arg | Leu | Tyr | Leu | Thr | Phe | Val | Val | Tyr | Val | Leu | Tyr | Ala | Thr |
|-----|-----|-----|-----|-----|-----|-----|-----|-----|-----|-----|-----|-----|-----|-----|
| | | 115 | | | | | 120 | | | | | 125 | | |

| Ser | Thr | Leu | Leu | Asp | Gly | Leu | Leu | His | His | Arg | Val | Pro | Tyr | Asn | Thr |
|-----|-----|-----|-----|-----|-----|-----|-----|-----|-----|-----|-----|-----|-----|-----|-----|
| | 130 | | | | | 135 | | | | | 140 | | | | |

| Tyr | Tyr | Pro | Phe | Ile | Asn | Trp | Arg | Val | Asp | Arg | Thr | Gln | Met | Tyr | Ile |
|-----|-----|-----|-----|-----|-----|-----|-----|-----|-----|-----|-----|-----|-----|-----|-----|
| 145 | | | | | 150 | | | | | 155 | | | | | 160 |

| Gln | Ser | Phe | Leu | Glu | Tyr | Phe | Thr | Val | Gly | Tyr | Ala | Ile | Tyr | Val | Ala |
|-----|-----|-----|-----|-----|-----|-----|-----|-----|-----|-----|-----|-----|-----|-----|-----|
| | | | | 165 | | | | | 170 | | | | | 175 | |

| Thr | Ala | Thr | Asp | Ser | Tyr | Pro | Val | Ile | Tyr | Val | Ala | Ala | Leu | Arg | Thr |
|-----|-----|-----|-----|-----|-----|-----|-----|-----|-----|-----|-----|-----|-----|-----|-----|
| | | | 180 | | | | | 185 | | | | | 190 | | |

| His | Ile | Leu | Leu | Leu | Lys | Asp | Arg | Ile | Ile | Tyr | Leu | Gly | Asp | Pro | Ser |
|-----|-----|-----|-----|-----|-----|-----|-----|-----|-----|-----|-----|-----|-----|-----|-----|
| | | 195 | | | | | 200 | | | | | 205 | | | |

| Asn | Glu | Gly | Ser | Ser | Asp | Pro | Ser | Tyr | Met | Phe | Lys | Ser | Leu | Val | Asp |
|-----|-----|-----|-----|-----|-----|-----|-----|-----|-----|-----|-----|-----|-----|-----|-----|
| | 210 | | | | | 215 | | | | | 220 | | | | |

| Cys | Ile | Lys | Ala | His | Arg | Thr | Met | Leu | Asn | Phe | Cys | Asp | Ala | Ile | Gln |
|-----|-----|-----|-----|-----|-----|-----|-----|-----|-----|-----|-----|-----|-----|-----|-----|
| 225 | | | | | 230 | | | | | 235 | | | | | 240 |

| Pro | Ile | Ile | Ser | Gly | Thr | Ile | Phe | Ala | Gln | Phe | Ile | Ile | Cys | Gly | Ser |
|-----|-----|-----|-----|-----|-----|-----|-----|-----|-----|-----|-----|-----|-----|-----|-----|
| | | | | 245 | | | | | 250 | | | | | 255 | |

| Ile | Leu | Gly | Ile | Ile | Met | Ile | Asn | Met | Val | Leu | Phe | Ala | Asp | Gln | Ser |
|-----|-----|-----|-----|-----|-----|-----|-----|-----|-----|-----|-----|-----|-----|-----|-----|
| | | | 260 | | | | | 265 | | | | | 270 | | |

| Thr | Arg | Phe | Gly | Ile | Val | Ile | Tyr | Val | Met | Ala | Val | Leu | Leu | Gln | Thr |
|-----|-----|-----|-----|-----|-----|-----|-----|-----|-----|-----|-----|-----|-----|-----|-----|
| | | 275 | | | | | 280 | | | | | 285 | | | |

| Phe | Pro | Leu | Cys | Phe | Tyr | Cys | Asn | Ala | Ile | Val | Asp | Asp | Cys | Lys | Glu |
|-----|-----|-----|-----|-----|-----|-----|-----|-----|-----|-----|-----|-----|-----|-----|-----|
| | 290 | | | | | 295 | | | | | 300 | | | | |

| Leu | Ala | His | Ala | Leu | Phe | His | Ser | Ala | Trp | Trp | Val | Gln | Asp | Lys | Arg |
|-----|-----|-----|-----|-----|-----|-----|-----|-----|-----|-----|-----|-----|-----|-----|-----|
| 305 | | | | | 310 | | | | | 315 | | | | | 320 |

| Tyr | Gln | Arg | Thr | Val | Ile | Gln | Phe | Leu | Gln | Lys | Leu | Gln | Gln | Pro | Met |
|-----|-----|-----|-----|-----|-----|-----|-----|-----|-----|-----|-----|-----|-----|-----|-----|
| | | | | 325 | | | | | 330 | | | | | 335 | |

| Thr | Phe | Thr | Ala | Met | Asn | Ile | Phe | Asn | Ile | Asn | Leu | Ala | Thr | Asn | Ile |
|-----|-----|-----|-----|-----|-----|-----|-----|-----|-----|-----|-----|-----|-----|-----|-----|
| | | | 340 | | | | | 345 | | | | | 350 | | |

```
Asn Val Ser Pro Leu Ser Val Arg Thr Gly Lys Glu Ala Lys Ser
            355                 360                 365

Glu Leu Gln Ser Leu Gln Val Ala Lys Phe Ala Phe Thr Val Tyr Ala
        370                 375                 380

Ile Ala Ser Gly Met Asn Leu Asp Gln Lys Leu Ser Ile Lys Glu
385                 390                 395
```

<210> SEQ ID NO 89
<211> LENGTH: 1179
<212> TYPE: DNA
<213> ORGANISM: Drosophila Melanogaster DOR82

<400> SEQUENCE: 89

| | | | | | |
|---|---|---|---|---|---|
| atggcatgca | taccaagata | tcaatggaaa | ggacgcccta | ctgaaagaca | gttctacgct | 60 |
| tcggagcaaa | ggatagtgtt | ccttcttgga | accatttgcc | agatattcca | gattactgga | 120 |
| gtgcttatct | attggtattg | caatggccgt | cttgccacgg | aaacgggcac | ctttgtggca | 180 |
| caattatctg | aaatgtgcag | ttcttttgt | ctaacatttg | tgggattctg | taacgtttat | 240 |
| gcgatctcta | caaaccgcaa | tcaaattgaa | acattactcg | aggagcttca | tcagatatat | 300 |
| ccgagataca | ggaaaaatca | ctatcgctgc | cagcattatt | ttgacatggc | catgacaata | 360 |
| atgagaattg | agtttctttt | ctatatgatc | ttgtacgtgt | actacaatag | tgcaccatta | 420 |
| tgggtgcttc | tttgggaaca | cttgcacgag | gaatatgatc | ttagcttcaa | gacgcagacc | 480 |
| aacacttggt | tccatggaa  | agtccatggg | tcggcacttg | gatttggtat | ggctgtacta | 540 |
| agcataaccg | tgggatcctt | tgtgggcgta | ggtttcagta | ttgtcaccca | gaatcttatc | 600 |
| tgtttgttaa | ccttccaact | aaagttgcac | tacgatggaa | tatccagtca | gttagtatct | 660 |
| ctcgattgcc | gtcgtcctgg | agctcataag | gagttgagca | tcctcatcgc | ccaccacagc | 720 |
| cgaatccttc | agctgggcga | ccaagtcaat | gacataatga | actttgtatt | cggctctagc | 780 |
| ctagtaggtg | ccactattgc | catttgtatg | tcaagtgttt | ctataatgct | actggactta | 840 |
| gcatctgcct | tcaaatatgc | cagtggtcta | gtggcattcg | tcctctacaa | ctttgtcatc | 900 |
| tgctacatgg | gaaccgaggt | cactttagct | gtgaagattg | gttcatatat | ggacggaagg | 960 |
| cggtggatac | ccaaagattc | gttgctgaga | tctcagaggc | tacaggtgct | cgtcgcagtt | 1020 |
| ggatttttta | atatatgtgt | cctctcgaat | cgtcgtccta | aaattgaaat | tttgcttaga | 1080 |
| tattattacc | atattatgtt | ttattcattt | aaattatatt | tttctttaag | gaaaggtagc | 1140 |
| ctttggaaaa | tcttgtcttc | tttcaccta  | ttgaggatc  |            |            | 1179 |

<210> SEQ ID NO 90
<211> LENGTH: 393
<212> TYPE: PRT
<213> ORGANISM: Drosophila Melanogaster DOR82

<400> SEQUENCE: 90

```
Met Ala Cys Ile Pro Arg Tyr Gln Trp Lys Gly Arg Pro Thr Glu Arg
1               5                   10                  15

Gln Phe Tyr Ala Ser Glu Gln Arg Ile Val Phe Leu Leu Gly Thr Ile
            20                  25                  30

Cys Gln Ile Phe Gln Ile Thr Gly Val Leu Ile Tyr Trp Tyr Cys Asn
        35                  40                  45

Gly Arg Leu Ala Thr Glu Thr Gly Thr Phe Val Ala Gln Leu Ser Glu
    50                  55                  60

Met Cys Ser Ser Phe Cys Leu Thr Phe Val Gly Phe Cys Asn Val Tyr
65                  70                  75                  80
```

-continued

```
Ala Ile Ser Thr Asn Arg Asn Gln Ile Glu Thr Leu Glu Glu Leu
            85                  90                  95

His Gln Ile Tyr Pro Arg Tyr Arg Lys Asn His Tyr Arg Cys Gln His
            100                 105                 110

Tyr Phe Asp Met Ala Met Thr Ile Met Arg Ile Glu Phe Leu Phe Tyr
        115                 120                 125

Met Ile Leu Tyr Val Tyr Tyr Asn Ser Ala Pro Leu Trp Val Leu Leu
130                 135                 140

Trp Glu His Leu His Glu Glu Tyr Asp Leu Ser Phe Lys Thr Gln Thr
145                 150                 155                 160

Asn Thr Trp Phe Pro Trp Lys Val His Gly Ser Ala Leu Gly Phe Gly
            165                 170                 175

Met Ala Val Leu Ser Ile Thr Val Gly Ser Phe Val Gly Val Gly Phe
            180                 185                 190

Ser Ile Val Thr Gln Asn Leu Ile Cys Leu Leu Thr Phe Gln Leu Lys
            195                 200                 205

Leu His Tyr Asp Gly Ile Ser Ser Gln Leu Val Ser Leu Asp Cys Arg
    210                 215                 220

Arg Pro Gly Ala His Lys Glu Leu Ser Ile Leu Ile Ala His His Ser
225                 230                 235                 240

Arg Ile Leu Gln Leu Gly Asp Gln Val Asn Asp Ile Met Asn Phe Val
            245                 250                 255

Phe Gly Ser Ser Leu Val Gly Ala Thr Ile Ala Ile Cys Met Ser Ser
            260                 265                 270

Val Ser Ile Met Leu Leu Asp Leu Ala Ser Ala Phe Lys Tyr Ala Ser
            275                 280                 285

Gly Leu Val Ala Phe Val Leu Tyr Asn Phe Val Ile Cys Tyr Met Gly
    290                 295                 300

Thr Glu Val Thr Leu Ala Val Lys Ile Gly Ser Tyr Met Asp Gly Arg
305                 310                 315                 320

Arg Trp Ile Pro Lys Asp Ser Leu Leu Arg Ser Gln Arg Leu Gln Val
            325                 330                 335

Leu Val Ala Val Gly Phe Phe Asn Ile Cys Val Leu Ser Asn Arg Arg
            340                 345                 350

Pro Lys Ile Glu Ile Leu Leu Arg Tyr Tyr His Ile Met Phe Tyr
            355                 360                 365

Ser Phe Lys Leu Tyr Phe Ser Leu Arg Lys Gly Ser Leu Trp Lys Ile
    370                 375                 380

Leu Ser Ser Phe Thr Leu Leu Arg Ile
385                 390
```

<210> SEQ ID NO 91
<211> LENGTH: 1209
<212> TYPE: DNA
<213> ORGANISM: Drosophila Melanogaster DOR83

<400> SEQUENCE: 91

| | | | | | |
|---|---|---|---|---|---|
| atgcagttgg | aggactttat | gcggtacccg | gacctcgtgt | gtcaagcggc | ccaacttccc | 60 |
| agatacacgt | ggaatggcag | acgatccttg | gaagttaaac | gcaacttggc | aaaacgcatt | 120 |
| atcttctggc | ttggagcagt | aaatttggtt | tatcacaata | ttggctgcgt | catgtatggc | 180 |
| tatttcggtg | atggaagaac | aaaggatcca | attgcgtatt | tagctgaatt | ggcatctgtg | 240 |
| gccagcatgc | ttggtttcac | cattgtgggc | accctcaact | tgtggaagat | gctgagcctt | 300 |
| aagacccatt | ttgagaacct | actaaatgaa | ttcgaggaat | tatttcaact | aatcaagcac | 360 |

```
aggggcgtatc gcatacacca ctatcaagaa aagtatacgc gtcatatacg aaatacattt      420
attttccata cctctgccgt tgtctactac aactcactac caattcttct aatgattcgg      480
gaacatttct cgaactcaca gcagttgggc tatagaattc agagtaatac ctggtatccc      540
tggcaggttc agggatcaat tcctggattt tttgctgcag tcgcctgtca aatcttttcg      600
tgccaaacca atatgtgcgt caatatgttt atccagtttc tgatcaactt ttttggtatc      660
cagctagaaa tacacttcga tggtttggcc aggcagctgg agaccatcga tgcccgcaat      720
ccccatgcca aggatcaatt gaagtatctg attgtatatc acacaaaatt gcttaatcta      780
gccgacagag ttaatcgatc gtttaacttt acgtttctca taagtctgtc ggtatccatg      840
atatccaact gttttctggc attttccatg accatgttcg actttggcac ctctctaaaa      900
catttactcg gacttttgct attcatcaca tataatttt caatgtgccg cagtggtacg       960
cacttgattt taacgagtgg caaagtattg ccagcggcct tttataacaa ttggtatgaa     1020
ggcgatcttg tttatcgaag gatgctcctc atcctgatga tgcgtgctac gaaacctat     1080 atgtggaaaa cctacaagct ggcacctgta tccataacta catatatggc agaatgcaaa     1140
acaaaagaag cccatgaaca acgccatttt agacgccatg aaagacaaaa acctcgggtt     1200
gcacgaata                                                              1209
```

<210> SEQ ID NO 92
<211> LENGTH: 403
<212> TYPE: PRT
<213> ORGANISM: Drosophila Melanogaster DOR83

<400> SEQUENCE: 92

```
Met Gln Leu Glu Asp Phe Met Arg Tyr Pro Asp Leu Val Cys Gln Ala
1               5                   10                  15

Ala Gln Leu Pro Arg Tyr Thr Trp Asn Gly Arg Arg Ser Leu Glu Val
            20                  25                  30

Lys Arg Asn Leu Ala Lys Arg Ile Ile Phe Trp Leu Gly Ala Val Asn
        35                  40                  45

Leu Val Tyr His Asn Ile Gly Cys Val Met Tyr Gly Tyr Phe Gly Asp
    50                  55                  60

Gly Arg Thr Lys Asp Pro Ile Ala Tyr Leu Ala Glu Leu Ala Ser Val
65                  70                  75                  80

Ala Ser Met Leu Gly Phe Thr Ile Val Gly Thr Leu Asn Leu Trp Lys
                85                  90                  95

Met Leu Ser Leu Lys Thr His Phe Glu Asn Leu Leu Asn Glu Phe Glu
            100                 105                 110

Glu Leu Phe Gln Leu Ile Lys His Arg Ala Tyr Arg Ile His His Tyr
        115                 120                 125

Gln Glu Lys Tyr Thr Arg His Ile Arg Asn Thr Phe Ile Phe His Thr
    130                 135                 140

Ser Ala Val Val Tyr Tyr Asn Ser Leu Pro Ile Leu Leu Met Ile Arg
145                 150                 155                 160

Glu His Phe Ser Asn Ser Gln Gln Leu Gly Tyr Arg Ile Gln Ser Asn
                165                 170                 175

Thr Trp Tyr Pro Trp Gln Val Gly Ser Ile Pro Gly Phe Phe Ala
            180                 185                 190

Ala Val Ala Cys Gln Ile Phe Ser Cys Gln Thr Asn Met Cys Val Asn
        195                 200                 205

Met Phe Ile Gln Phe Leu Ile Asn Phe Phe Gly Ile Gln Leu Glu Ile
```

```
         210                 215                 220
His Phe Asp Gly Leu Ala Arg Gln Leu Glu Thr Ile Asp Ala Arg Asn
225                 230                 235                 240

Pro His Ala Lys Asp Gln Leu Lys Tyr Leu Ile Val Tyr His Thr Lys
                245                 250                 255

Leu Leu Asn Leu Ala Asp Arg Val Asn Arg Ser Phe Asn Phe Thr Phe
            260                 265                 270

Leu Ile Ser Leu Ser Val Ser Met Ile Ser Asn Cys Phe Leu Ala Phe
        275                 280                 285

Ser Met Thr Met Phe Asp Phe Gly Thr Ser Leu Lys His Leu Leu Gly
290                 295                 300

Leu Leu Leu Phe Ile Thr Tyr Asn Phe Ser Met Cys Arg Ser Gly Thr
305                 310                 315                 320

His Leu Ile Leu Thr Ser Gly Lys Val Leu Pro Ala Ala Phe Tyr Asn
                325                 330                 335

Asn Trp Tyr Glu Gly Asp Leu Val Tyr Arg Arg Met Leu Leu Ile Leu
            340                 345                 350

Met Met Arg Ala Thr Lys Pro Tyr Met Trp Lys Thr Tyr Lys Leu Ala
        355                 360                 365

Pro Val Ser Ile Thr Thr Tyr Met Ala Glu Cys Lys Thr Lys Glu Ala
    370                 375                 380

His Glu Gln Arg His Phe Arg Arg His Glu Arg Gln Lys Pro Arg Val
385                 390                 395                 400

Ala Arg Ile

<210> SEQ ID NO 93
<211> LENGTH: 858
<212> TYPE: DNA
<213> ORGANISM: Drosophila Melanogaster DOR84

<400> SEQUENCE: 93
atggtgttta gttttttatgc cgaggtagcg actctggtgg acaggttacg cgataatgaa      60
aattttctcg agagctgcat cttactgagc tacgtgtcct tgtgtggtcat gggcctctcc    120 aagataggtg ctgtaatgaa aaaaaagcca aaatgacag ctttggtcag gcaattggag     180
acctgctttc cgtcgccaag tgcaaaggtt caagaggaat atgctgtgaa gtcctggctg     240
aaacgctgcc atatatacac aaagggattt ggtggtctct tcatgatcat gtatttcgct     300
cacgctctga ttcccttatt catatacttc attcaaagag tgctgctcca ctatccggat     360
gccaagcaga ttatgccgtt ttaccaactc gaaccttggg aatttcgcga ctcctggttg     420
ttttatccaa gctatttca ccagtcgtcg gccggatata cggctacatg tggatccatt     480
gccggtgacc taatgatctt cgctgtggtc ctgcaggtca tcatgcacta cgaaagactg     540
gccaaggttc ttagggagtt taagattcaa gcccataacg cacccaatgg agctaaggag     600
gatataagga agttgcagtc cctagtcgcc aatcacattg atatacttcg actcactgat     660
ctgatgaacg aggtctttgg aattcccttg ttgctaaact ttattgcatc tgcgctgctg     720
gtctgcctgg tgggagttca attaaccatc gctttaagtc cagagtattt ttgcaagcag     780
atgctatttc tgatttccgt actgcttgag gtctatctcc tttgctcctt cagccagagg     840
ttaatagatg ctgtatgt                                                   858

<210> SEQ ID NO 94
<211> LENGTH: 286
<212> TYPE: PRT
```

<213> ORGANISM: Drosophila Melanogaster DOR84

<400> SEQUENCE: 94

```
Met Val Phe Ser Phe Tyr Ala Glu Val Ala Thr Leu Val Asp Arg Leu
1               5                  10                  15
Arg Asp Asn Glu Asn Phe Leu Glu Ser Cys Ile Leu Leu Ser Tyr Val
            20                  25                  30
Ser Phe Val Val Met Gly Leu Ser Lys Ile Gly Ala Val Met Lys Lys
        35                  40                  45
Lys Pro Lys Met Thr Ala Leu Val Arg Gln Leu Glu Thr Cys Phe Pro
    50                  55                  60
Ser Pro Ser Ala Lys Val Gln Glu Glu Tyr Ala Val Lys Ser Trp Leu
65                  70                  75                  80
Lys Arg Cys His Ile Tyr Thr Lys Gly Phe Gly Gly Leu Phe Met Ile
                85                  90                  95
Met Tyr Phe Ala His Ala Leu Ile Pro Leu Phe Ile Tyr Phe Ile Gln
            100                 105                 110
Arg Val Leu Leu His Tyr Pro Asp Ala Lys Gln Ile Met Pro Phe Tyr
        115                 120                 125
Gln Leu Glu Pro Trp Glu Phe Arg Asp Ser Trp Leu Phe Tyr Pro Ser
    130                 135                 140
Tyr Phe His Gln Ser Ser Ala Gly Tyr Thr Ala Thr Cys Gly Ser Ile
145                 150                 155                 160
Ala Gly Asp Leu Met Ile Phe Ala Val Val Leu Gln Val Ile Met His
                165                 170                 175
Tyr Glu Arg Leu Ala Lys Val Leu Arg Glu Phe Lys Ile Gln Ala His
            180                 185                 190
Asn Ala Pro Asn Gly Ala Lys Glu Asp Ile Arg Lys Leu Gln Ser Leu
        195                 200                 205
Val Ala Asn His Ile Asp Ile Leu Arg Leu Thr Asp Leu Met Asn Glu
    210                 215                 220
Val Phe Gly Ile Pro Leu Leu Asn Phe Ile Ala Ser Ala Leu Leu
225                 230                 235                 240
Val Cys Leu Val Gly Val Gln Leu Thr Ile Ala Leu Ser Pro Glu Tyr
                245                 250                 255
Phe Cys Lys Gln Met Leu Phe Leu Ile Ser Val Leu Leu Glu Val Tyr
            260                 265                 270
Leu Leu Cys Ser Phe Ser Gln Arg Leu Ile Asp Ala Val Cys
        275                 280                 285
```

<210> SEQ ID NO 95
<211> LENGTH: 1155
<212> TYPE: DNA
<213> ORGANISM: Drosophila Melanogaster DOR91

<400> SEQUENCE: 95

```
atggttcgtt acgtgccccg gttcgctgat ggtcagaaag taaagttggc ttggcccttg     60
gcggtttttc ggttaaatca catattctgg ccattggatc cgagcacagg gaaatggggc    120
cgatatctgg acaaggttct agctgttgcg atgtccttgg tttttatgca acacaacgat    180
gcagagctga ggtacttgcg cttcgaggca agtaatcgga atttggatgc ctttctcaca    240
ggaatgccaa cgtatttaat cctcgtggag gctcaattta gaagtcttca cattctactg    300
cacttcgaga agcttcagaa gttttttagaa atattctacg caaatatttta tattgatccc    360
cgtaaggaac ccgaaatgtt tcgaaaagtg gatggaaaga tgataattaa cagattagtt    420
```

```
tcggccatgt acggtgcagt tatctctctg tatctaatcg cacccgtttt ttccatcatt    480
aaccaaagca aagattttct atactctatg atctttccgt tcgattcgga tcccttgtac    540
atatttgtgc cactgctttt gacaaacgta tgggttggca ttgtaataga taccatgatg    600
ttcggggaga cgaatttgtt gtgtgaacta attgtccacc taaatggtag ttatatgttg    660
ctcaagaggg acttgcagtt ggccattgaa aagatattag ttgcaaggga ccgtccgcat    720
atggccaaac agctaaaggt tttaattaca aaaactctcc gaaagaatgt ggctctaaat    780
cagtttggcc agcagctgga ggctcagtat actgtgcggg ttttattat gtttgcattc     840 gctgcgggcc ttttatgtgc tctttctttt aaggcttata cgacggattc cctcagcaca    900
atgtactacc ttacccattg ggagcaaatc ctgcagtact ctacaaatcc cagcgaaaat    960
ctgcgattac taaagctcat taacttggcc attgagatga acagcaagcc cttctatgtg    1020
acagggctaa atattttcg cgttagtctg caggctggct aaaacgtca aaagtttctg      1080 cggtctgcca gctcatccac ccttagcacc gctgatgtgt tggcatttgc ttttgctttt    1140
actcgctggc tgctt                                                      1155
```

<210> SEQ ID NO 96
<211> LENGTH: 385
<212> TYPE: PRT
<213> ORGANISM: Drosophila Melanogaster DOR91

<400> SEQUENCE: 96

```
Met Val Arg Tyr Val Pro Arg Phe Ala Asp Gly Gln Lys Val Lys Leu
1               5                   10                  15

Ala Trp Pro Leu Ala Val Phe Arg Leu Asn His Ile Phe Trp Pro Leu
            20                  25                  30

Asp Pro Ser Thr Gly Lys Trp Gly Arg Tyr Leu Asp Lys Val Leu Ala
        35                  40                  45

Val Ala Met Ser Leu Val Phe Met Gln His Asn Asp Ala Glu Leu Arg
    50                  55                  60

Tyr Leu Arg Phe Glu Ala Ser Asn Arg Asn Leu Asp Ala Phe Leu Thr
65                  70                  75                  80

Gly Met Pro Thr Tyr Leu Ile Leu Val Glu Ala Gln Phe Arg Ser Leu
                85                  90                  95

His Ile Leu Leu His Phe Glu Lys Leu Gln Lys Phe Leu Glu Ile Phe
            100                 105                 110

Tyr Ala Asn Ile Tyr Ile Asp Pro Arg Lys Glu Pro Glu Met Phe Arg
        115                 120                 125

Lys Val Asp Gly Lys Met Ile Ile Asn Arg Leu Val Ser Ala Met Tyr
    130                 135                 140

Gly Ala Val Ile Ser Leu Tyr Leu Ile Ala Pro Val Phe Ser Ile Ile
145                 150                 155                 160

Asn Gln Ser Lys Asp Phe Leu Tyr Ser Met Ile Phe Pro Phe Asp Ser
                165                 170                 175

Asp Pro Leu Tyr Ile Phe Val Pro Leu Leu Leu Thr Asn Val Trp Val
            180                 185                 190

Gly Ile Val Ile Asp Thr Met Met Phe Gly Glu Thr Asn Leu Leu Cys
        195                 200                 205

Glu Leu Ile Val His Leu Asn Gly Ser Tyr Met Leu Leu Lys Arg Asp
    210                 215                 220

Leu Gln Leu Ala Ile Glu Lys Ile Leu Val Ala Arg Asp Arg Pro His
225                 230                 235                 240
```

```
Met Ala Lys Gln Leu Lys Val Leu Ile Thr Lys Thr Leu Arg Lys Asn
                245                 250                 255

Val Ala Leu Asn Gln Phe Gly Gln Leu Glu Ala Gln Tyr Thr Val
            260                 265                 270

Arg Val Phe Ile Met Phe Ala Phe Ala Gly Leu Leu Cys Ala Leu
        275                 280                 285

Ser Phe Lys Ala Tyr Thr Thr Asp Ser Leu Ser Thr Met Tyr Tyr Leu
    290                 295                 300

Thr His Trp Glu Gln Ile Leu Gln Tyr Ser Thr Asn Pro Ser Glu Asn
305                 310                 315                 320

Leu Arg Leu Leu Lys Leu Ile Asn Leu Ala Ile Glu Met Asn Ser Lys
                325                 330                 335

Pro Phe Tyr Val Thr Gly Leu Lys Tyr Phe Arg Val Ser Leu Gln Ala
            340                 345                 350

Gly Leu Lys Arg Gln Lys Phe Leu Arg Ser Ala Ser Ser Ser Thr Leu
        355                 360                 365

Ser Thr Ala Asp Val Leu Ala Phe Ala Phe Ala Phe Thr Arg Trp Leu
    370                 375                 380

Leu
385

<210> SEQ ID NO 97
<211> LENGTH: 1218
<212> TYPE: DNA
<213> ORGANISM: Drosophila Melanogaster DOR92

<400> SEQUENCE: 97
atgtccgagt ggttacgctt tctgaaacgc gatcaacagc tggatgtgta cttttttgca      60
gtgccccgct tgagtttaga cataatgggc tattggccgg gcaaaactgg tgatacatgg     120
ccctggagat ccctgattca cttcgcaatc ctggccattg gcgtggccac cgaactgcat     180
gctggcatgt gttttctaga ccgacagcag attaccttgg cactggagac cctctgtcca     240
gctggcacat cggcggtcac gctgctcaag atgttcctaa tgctgcgctt cgtcaggat      300 ctctccatta tgtggaaccg cctgaggggc ctgctcttcg atcccaactg ggagcgaccc     360
gagcagcggg acatccggct aaagcactcg gccatggcgg ctcgcatcaa tttctggccc     420
ctgtcagccg gattcttcac atgcaccacc tacaacctaa agccgatact gatcgcaatg     480
atattgtatc tccagaatcg ttacgaggac ttcgtttggt ttacacccctt caatatgact     540 atgcccaaag ttctgctaaa ctatccattt tttcccctga cctacatatt tattgcctat     600
acgggctatg tgaccatctt tatgttcggc ggctgtgatg gttttttattt cgagttctgt     660 gcccacctat cagctctttt cgaagtgctc caggcggaga tagaatcaat gtttagaccc     720
tacactgatc acttggaact gtcgccagtg cagctttaca ttttagagca aaagatgcga     780
tcagtaatca ttaggcacaa tgccatcatc gatttgacca gattttttcg tgatcgctat     840
accattatta ccctggccca ttttgtgtcc gccgccatgg tgattggatt cagcatggtt     900
aatctcctga cattgggcaa taatggtctg ggcgcaatgc tctatgtggc ctacacggtt     960
gccgctttga gccaactgct ggtttattgc tatggcggaa ctctggtggc cgaaagtagc    1020
actggtctgt gccgagccat gttctcctgt ccgtggcagc ttttttaagcc taaacaacgt    1080 cgactcgttc agcttttgat tctcagatcg cagcgtcctg tttccatggc agtgccattc    1140
ttttcgccat cgttggctac ctttgctgcg attcttcaaa cttcgggttc cataattgcg    1200
```
ctggttaagt cctttcag                                             1218

<210> SEQ ID NO 98
<211> LENGTH: 406
<212> TYPE: PRT
<213> ORGANISM: Drosophila Melanogaster DOR92

<400> SEQUENCE: 98

```
Met Ser Glu Trp Leu Arg Phe Leu Lys Arg Asp Gln Gln Leu Asp Val
1               5                   10                  15

Tyr Phe Phe Ala Val Pro Arg Leu Ser Leu Asp Ile Met Gly Tyr Trp
            20                  25                  30

Pro Gly Lys Thr Gly Asp Thr Trp Pro Trp Arg Ser Leu Ile His Phe
        35                  40                  45

Ala Ile Leu Ala Ile Gly Val Ala Thr Glu Leu His Ala Gly Met Cys
    50                  55                  60

Phe Leu Asp Arg Gln Gln Ile Thr Leu Ala Leu Glu Thr Leu Cys Pro
65                  70                  75                  80

Ala Gly Thr Ser Ala Val Thr Leu Leu Lys Met Phe Leu Met Leu Arg
                85                  90                  95

Phe Arg Gln Asp Leu Ser Ile Met Trp Asn Arg Leu Arg Gly Leu Leu
            100                 105                 110

Phe Asp Pro Asn Trp Glu Arg Pro Glu Gln Arg Asp Ile Arg Leu Lys
        115                 120                 125

His Ser Ala Met Ala Ala Arg Ile Asn Phe Trp Pro Leu Ser Ala Gly
    130                 135                 140

Phe Phe Thr Cys Thr Thr Tyr Asn Leu Lys Pro Ile Leu Ile Ala Met
145                 150                 155                 160

Ile Leu Tyr Leu Gln Asn Arg Tyr Glu Asp Phe Val Trp Phe Thr Pro
                165                 170                 175

Phe Asn Met Thr Met Pro Lys Val Leu Leu Asn Tyr Pro Phe Phe Pro
            180                 185                 190

Leu Thr Tyr Ile Phe Ile Ala Tyr Thr Gly Tyr Val Thr Ile Phe Met
        195                 200                 205

Phe Gly Gly Cys Asp Gly Phe Tyr Phe Glu Phe Cys Ala His Leu Ser
    210                 215                 220

Ala Leu Phe Glu Val Leu Gln Ala Glu Ile Gly Ser Met Phe Arg Pro
225                 230                 235                 240

Tyr Thr Asp His Leu Glu Leu Ser Pro Val Gln Leu Tyr Ile Leu Glu
                245                 250                 255

Gln Lys Met Arg Ser Val Ile Ile Arg His Asn Ala Ile Ile Asp Leu
            260                 265                 270

Thr Arg Phe Phe Arg Asp Arg Tyr Thr Ile Ile Thr Leu Ala His Phe
        275                 280                 285

Val Ser Ala Ala Met Val Ile Gly Phe Ser Met Val Asn Leu Leu Thr
    290                 295                 300

Leu Gly Asn Asn Gly Leu Gly Ala Met Leu Tyr Val Ala Tyr Thr Val
305                 310                 315                 320

Ala Ala Leu Ser Gln Leu Leu Val Tyr Cys Tyr Gly Gly Thr Leu Val
                325                 330                 335

Ala Glu Ser Ser Thr Gly Leu Cys Arg Ala Met Phe Ser Cys Pro Trp
            340                 345                 350

Gln Leu Phe Lys Pro Lys Gln Arg Arg Leu Val Gln Leu Leu Ile Leu
        355                 360                 365
```

```
Arg Ser Gln Arg Pro Val Ser Met Ala Val Pro Phe Phe Ser Pro Ser
        370                 375                 380

Leu Ala Thr Phe Ala Ala Ile Leu Gln Thr Ser Gly Ser Ile Ile Ala
385                 390                 395                 400

Leu Val Lys Ser Phe Gln
            405
```

<210> SEQ ID NO 99
<211> LENGTH: 1176
<212> TYPE: DNA
<213> ORGANISM: Drosophila Melanogaster DOR95

<400> SEQUENCE: 99

```
atgagcgaca aggtgaaggg aaaaaagcag gaggaaaagg atcaatcctt gcgggtgcaa      60
attctcgttt atcgctgcat gggcatcgat ttgtggagcc ccacgatggc gaatgaccgc     120
ccgtggctga cctttgtcac aatgggacca cttttcctgt ttatggtgcc catgttcctg     180
gccgcccacg agtacatcac ccaggtgagc ctgctctccg acaccctggg ctccaccttc     240
gccagcatgc tcaccctggt caaattcctg ctcttctgct atcatcgcaa ggagttcgtc     300
ggcctgatct accacatcag ggccattctg gctaaagaaa tcgaagtgtg gcctgatgcg     360
cgggaaatca tcgaggtgga gaaccaaagt gaccaaatgc tcagtcttac gtacactcgc     420
tgttttggac tggctggaat ctttgcggcc ctgaagccct ttgtgggcat catactctcc     480
tcgattcgcg gcgacgagat tcacctggag ctgccccaca acggcgttta cccgtacgat     540
ctccaggtgg tcatgtttta tgtgcccacc tatctgtgga atgtgatggc cagctatagt     600
gctgtaacca tggcactctg cgtggactcg ctgctcttct ttttcaccta caacgtgtgc     660
gccattttca agatcgccaa gcaccggatg atccatctgc cggcggtggg cggaaaggag     720
gagctggagg ggctcgtcca ggtgctgctg ctgcaccaga agggcctcca gatcgccgat     780
cacattgcgg acaagtaccg gccgctgatc tttttgcagt tctttctgtc cgccttgcag     840
atctgcttca ttggattcca ggtggctgat ctgtttccca atccgcagag tctctacttt     900
atcgcctttg tgggctcgct gctcatcgca ctgttcatct actcgaagtg cggcgaaaat     960
atcaagagtg ccagcctgga tttcggaaac gggctgtacg agaccaactg gaccgacttc    1020
tcgccaccca ctaaaagagc cctcctcatt gccgccatgc gcgcccagcg accttgccag    1080
atgaagggct acttttttcga ggccagcatg gccaccttct cgacgattgt tcgctctgcc    1140
gtgtcgtaca tcatgatgtt gcgctccttt aatgcc                              1176
```

<210> SEQ ID NO 100
<211> LENGTH: 392
<212> TYPE: PRT
<213> ORGANISM: Drosophila Melanogaster DOR95

<400> SEQUENCE: 100

```
Met Ser Asp Lys Val Lys Gly Lys Lys Gln Glu Glu Lys Asp Gln Ser
1               5                   10                  15

Leu Arg Val Gln Ile Leu Val Tyr Arg Cys Met Gly Ile Asp Leu Trp
            20                  25                  30

Ser Pro Thr Met Ala Asn Asp Arg Pro Trp Leu Thr Phe Val Thr Met
        35                  40                  45

Gly Pro Leu Phe Leu Phe Met Val Pro Met Phe Leu Ala Ala His Glu
    50                  55                  60

Tyr Ile Thr Gln Val Ser Leu Leu Ser Asp Thr Leu Gly Ser Thr Phe
65                  70                  75                  80
```

-continued

```
Ala Ser Met Leu Thr Leu Val Lys Phe Leu Phe Cys Tyr His Arg
                85                  90                  95
Lys Glu Phe Val Gly Leu Ile Tyr His Ile Arg Ala Ile Leu Ala Lys
            100                 105                 110
Glu Ile Glu Val Trp Pro Asp Ala Arg Glu Ile Ile Glu Val Glu Asn
            115                 120                 125
Gln Ser Asp Gln Met Leu Ser Leu Thr Tyr Thr Arg Cys Phe Gly Leu
        130                 135                 140
Ala Gly Ile Phe Ala Ala Leu Lys Pro Phe Val Gly Ile Ile Leu Ser
145                 150                 155                 160
Ser Ile Arg Gly Asp Glu Ile His Leu Glu Leu Pro His Asn Gly Val
                165                 170                 175
Tyr Pro Tyr Asp Leu Gln Val Val Met Phe Tyr Val Pro Thr Tyr Leu
            180                 185                 190
Trp Asn Val Met Ala Ser Tyr Ser Ala Val Thr Met Ala Leu Cys Val
            195                 200                 205
Asp Ser Leu Leu Phe Phe Phe Thr Tyr Asn Val Cys Ala Ile Phe Lys
        210                 215                 220
Ile Ala Lys His Arg Met Ile His Leu Pro Ala Val Gly Gly Lys Glu
225                 230                 235                 240
Glu Leu Glu Gly Leu Val Gln Val Leu Leu His Gln Lys Gly Leu
                245                 250                 255
Gln Ile Ala Asp His Ile Ala Asp Lys Tyr Arg Pro Leu Ile Phe Leu
            260                 265                 270
Gln Phe Phe Leu Ser Ala Leu Gln Ile Cys Phe Ile Gly Phe Gln Val
        275                 280                 285
Ala Asp Leu Phe Pro Asn Pro Gln Ser Leu Tyr Phe Ile Ala Phe Val
        290                 295                 300
Gly Ser Leu Leu Ile Ala Leu Phe Ile Tyr Ser Lys Cys Gly Glu Asn
305                 310                 315                 320
Ile Lys Ser Ala Ser Leu Asp Phe Gly Asn Gly Leu Tyr Glu Thr Asn
                325                 330                 335
Trp Thr Asp Phe Ser Pro Pro Thr Lys Arg Ala Leu Leu Ile Ala Ala
            340                 345                 350
Met Arg Ala Gln Arg Pro Cys Gln Met Lys Gly Tyr Phe Phe Glu Ala
        355                 360                 365
Ser Met Ala Thr Phe Ser Thr Ile Val Arg Ser Ala Val Ser Tyr Ile
        370                 375                 380
Met Met Leu Arg Ser Phe Asn Ala
385                 390
```

<210> SEQ ID NO 101
<211> LENGTH: 1170
<212> TYPE: DNA
<213> ORGANISM: Drosophila Melanogaster DOR99

<400> SEQUENCE: 101

```
atggaggagt ttctgcgtcc gcagatgttc caggaggtgg ctcagatggt gcatttccag      60
tggcggagaa atccggtgga caacagcatg gtgaacgcat ccatggtccc cttctgcttg     120
tcggcgtttc ttaatgtcct gtttttcggc tgcaatggtt gggacatcat aggacatttt     180
tggctgggac atcctgccaa ccagaatccg cccgtgctta gcatcaccat ttacttctcg     240
atcaggggat tgatgctata cctgaaacga aggaaatcg ttgagtttgt taacgacttg     300
```

-continued

```
gatcgggagt gtccgcggga cttggtcagc cagttggaca tgcaaatgga tgagacgtac    360
cgaaactttt ggcagcgcta tcgcttcatc cgtatctact cccatttggg tggtccgatg    420
ttctgcgttg tgccattagc tctattcctc ctgacccacg agggtaaaga tactcctgtt    480
gcccagcacg agcagctcct tggaggatgg ctgccatgcg gtgtgcgaaa ggacccaaat    540
ttctaccttt tagtctggtc cttcgacctg atgtgcacca cttgcggcgt ctccttttc     600 gttaccttcg acaacctatt caatgtgatg cagggacatt tggtcatgca tttgggccat    660
cttgctcgcc agttttcggc catcgatcct cgacagagtt tgaccgatga aagcgattc     720 tttgtggatc ttaggttatt agttcagagg cagcagcttc ttaatggatt gtgcagaaaa    780
tacaacgaca tctttaaagt ggccttcctg gtgagcaatt tgtaggcgc cggttccctc     840 tgcttctacc tctttatgct ctcggagaca tcagatgtcc ttatcatcgc ccagtatata    900
ttacccactt tggtcctggt gggcttcaca tttgagattt gtctacgggg aacccaactg    960
gaaaaggcgt cggagggact ggaatcgtcg ttgcgaagcc aggaatggta tttgggaagt   1020
aggcggtacc ggaagttcta tttgctctgg acgcaatatt gccagcgaac acagcaactg   1080
ggcgcctttg ggctaatcca agtcaatatg gtgcacttca ctgaaataat gcagctggcc   1140
tatagactct tcactttct caaatctcat                                     1170
```

<210> SEQ ID NO 102
<211> LENGTH: 390
<212> TYPE: PRT
<213> ORGANISM: Drosophila Melanogaster DOR99

<400> SEQUENCE: 102

```
Met Glu Glu Phe Leu Arg Pro Gln Met Phe Gln Glu Val Ala Gln Met
1               5                  10                  15

Val His Phe Gln Trp Arg Arg Asn Pro Val Asp Asn Ser Met Val Asn
            20                  25                  30

Ala Ser Met Val Pro Phe Cys Leu Ser Ala Phe Leu Asn Val Leu Phe
        35                  40                  45

Phe Gly Cys Asn Gly Trp Asp Ile Ile Gly His Phe Trp Leu Gly His
    50                  55                  60

Pro Ala Asn Gln Asn Pro Pro Val Leu Ser Ile Thr Ile Tyr Phe Ser
65                  70                  75                  80

Ile Arg Gly Leu Met Leu Tyr Leu Lys Arg Lys Glu Ile Val Glu Phe
                85                  90                  95

Val Asn Asp Leu Asp Arg Glu Cys Pro Arg Asp Leu Val Ser Gln Leu
            100                 105                 110

Asp Met Gln Met Asp Glu Thr Tyr Arg Asn Phe Trp Gln Arg Tyr Arg
        115                 120                 125

Phe Ile Arg Ile Tyr Ser His Leu Gly Gly Pro Met Phe Cys Val Val
    130                 135                 140

Pro Leu Ala Leu Phe Leu Leu Thr His Glu Gly Lys Asp Thr Pro Val
145                 150                 155                 160

Ala Gln His Glu Gln Leu Leu Gly Gly Trp Leu Pro Cys Gly Val Arg
                165                 170                 175

Lys Asp Pro Asn Phe Tyr Leu Leu Val Trp Ser Phe Asp Leu Met Cys
            180                 185                 190

Thr Thr Cys Gly Val Ser Phe Phe Val Thr Phe Asp Asn Leu Phe Asn
        195                 200                 205

Val Met Gln Gly His Leu Val Met His Leu Gly His Leu Ala Arg Gln
    210                 215                 220
```

```
Phe Ser Ala Ile Asp Pro Arg Gln Ser Leu Thr Asp Glu Lys Arg Phe
225                 230                 235                 240

Phe Val Asp Leu Arg Leu Leu Val Gln Arg Gln Gln Leu Leu Asn Gly
                245                 250                 255

Leu Cys Arg Lys Tyr Asn Asp Ile Phe Lys Val Ala Phe Leu Val Ser
                260                 265                 270

Asn Phe Val Gly Ala Gly Ser Leu Cys Phe Tyr Leu Phe Met Leu Ser
                275                 280                 285

Glu Thr Ser Asp Val Leu Ile Ile Ala Gln Tyr Ile Leu Pro Thr Leu
                290                 295                 300

Val Leu Val Gly Phe Thr Phe Glu Ile Cys Leu Arg Gly Thr Gln Leu
305                 310                 315                 320

Glu Lys Ala Ser Glu Gly Leu Glu Ser Ser Leu Arg Ser Gln Glu Trp
                325                 330                 335

Tyr Leu Gly Ser Arg Arg Tyr Arg Lys Phe Tyr Leu Leu Trp Thr Gln
                340                 345                 350

Tyr Cys Gln Arg Thr Gln Gln Leu Gly Ala Phe Gly Leu Ile Gln Val
                355                 360                 365

Asn Met Val His Phe Thr Glu Ile Met Gln Leu Ala Tyr Arg Leu Phe
                370                 375                 380

Thr Phe Leu Lys Ser His
385                 390
```

<210> SEQ ID NO 103
<211> LENGTH: 1917
<212> TYPE: DNA
<213> ORGANISM: Drosophila Melanogaster DORA45

<400> SEQUENCE: 103

```
ggcacgagct ggttccggaa agcctcatat ctcgtatctt aaagtatccc ggttaagcct      60
taaagagtga atgattgcc tagacgattg ctgcattact ggcactcaat taacccaagt     120
gtaccagaca caattacat ttgtatttt aaagttcaat agcaaggatg acaacctcga      180
tgcagccgag caagtacacg ggcctggtcg ccgacctgat gcccaacatc cgggcgatga   240
agtactccgg cctgttcatg cacaacttca cgggcggcag tgccttcatg aagaaggtgt   300
actcctccgt gcacctggtg ttcctcctca tgcagttcac cttcatcctg gtcaacatgg   360
ccctgaacgc cgaggaggtc aacgagctgt cgggcaacac gatcacgacc ctcttcttca   420
cccactgcat cacgaagttt atctacctgg ctgttaacca aagaatttc tacagaacat    480
tgaatatatg gaaccaggtg aacacgcatc ccttgttcgc cgagtcggat gctcgttacc   540
attcgatcgc actggcgaag atgaggaagc tgttctttct ggtgatgctg accacagtcg   600
cctcggccac cgcctggacc acgatcacct tctttggcga cagcgtaaaa atggtggtgg   660
accatgagac gaactccagc atcccggtgg agataccccg gctgccgatt aagtccttct   720
acccgtggaa cgccagccac ggcatgttct acatgatcag ctttgccttt cagatctact   780
acgtgctctt ctcgatgatc cactccaatc tatgcgacgt gatgttctgc tcttggctga   840
tattcgcctg cgagcagctg cagcacttga agggcatcat gaagccgctg atggagctgt   900
ccgcctcgct ggacacctac aggcccaact cggcggccct cttcaggtcc ctgtcggcca   960
actccaagtc ggagctaatt cataatgaag aaaaggatcc cggcaccgac atggacatgt  1020
cgggcatcta cagctcgaaa gcggattggg gcgctcagtt tcgagcaccc tcgacactgc  1080
agtcctttgg cgggaacggg ggcggaggca acgggttggt gaacggcgct aatcccaacg  1140
```

-continued

```
ggctgaccaa aaagcaggag atgatggtgc gcagtgccat caagtactgg gtcgagcggc    1200
acaagcacgt ggtgcgactg gtggctgcca tcggcgatac ttacggagcc gccctcctcc    1260
tccacatgct gacctcgacc atcaagctga ccctgctggc ataccaggcc accaaaatca    1320
acggagtgaa tgtctacgcc ttcacagtcg tcggatacct aggatacgcg ctggcccagg    1380
tgttccactt tgcatctttt ggcaatcgtc tgattgaaga gagttcatcc gtcatggagg    1440
ccgcctactc gtgccactgg tacgatggct ccgaggaggc caagaccttc gtccagatcg    1500
tgtgccagca gtgccagaag gcgatgagca tcgggagc gaaattcttc accgtctccc    1560
tggatttgtt tgcttcggtt ctgggtgccg tcgtcaccta ctttatggtg ctggtgcagc    1620
tcaagtaagt tgctgcgaag ctgatggatt tttgtaccag aaaagcgaat gccaagaagc    1680
cacctaccgc cccttgcccc ctccgcactg tgcaaccagc aatatcacag agcaattata    1740
acgcaaatta tatattttat acctgcgacg agcgagcctc gtggggcata atggagacat    1800 tctgggcac atagaagcct gcaaatactt atcgattttg tacacgcgta gagcttttaa    1860
tgtaaactca agatgcaaac taaataaatg tgtagtgaaa aaaaaaaaaa aaaaaaa    1917
```

<210> SEQ ID NO 104
<211> LENGTH: 486
<212> TYPE: PRT
<213> ORGANISM: Drosophila Melanogaster DORA45

<400> SEQUENCE: 104

```
Met Thr Thr Ser Met Gln Pro Ser Lys Tyr Thr Gly Leu Val Ala Asp
 1               5                  10                  15

Leu Met Pro Asn Ile Arg Ala Met Lys Tyr Ser Gly Leu Phe Met His
                20                  25                  30

Asn Phe Thr Gly Gly Ser Ala Phe Met Lys Lys Val Tyr Ser Ser Val
            35                  40                  45

His Leu Val Phe Leu Leu Met Gln Phe Thr Phe Ile Leu Val Asn Met
        50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
    130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
    210                 215                 220

Ile Phe Ala Cys Glu Gln Leu Gln His Leu Lys Gly Ile Met Lys Pro
225                 230                 235                 240
```

```
Leu Met Glu Leu Ser Ala Ser Leu Asp Thr Tyr Arg Pro Asn Ser Ala
            245                 250                 255
Ala Leu Phe Arg Ser Leu Ser Ala Asn Ser Lys Ser Glu Leu Ile His
        260                 265                 270
Asn Glu Glu Lys Asp Pro Gly Thr Asp Met Asp Met Ser Gly Ile Tyr
    275                 280                 285
Ser Ser Lys Ala Asp Trp Gly Ala Gln Phe Arg Ala Pro Ser Thr Leu
290                 295                 300
Gln Ser Phe Gly Gly Asn Gly Gly Gly Asn Gly Leu Val Asn Gly
305                 310                 315                 320
Ala Asn Pro Asn Gly Leu Thr Lys Lys Gln Glu Met Met Val Arg Ser
                325                 330                 335
Ala Ile Lys Tyr Trp Val Glu Arg Lys His Val Val Arg Leu Val
            340                 345                 350
Ala Ala Ile Gly Asp Thr Tyr Gly Ala Ala Leu Leu Leu His Met Leu
        355                 360                 365
Thr Ser Thr Ile Lys Leu Thr Leu Leu Ala Tyr Gln Ala Thr Lys Ile
    370                 375                 380
Asn Gly Val Asn Val Tyr Ala Phe Thr Val Val Gly Tyr Leu Gly Tyr
385                 390                 395                 400
Ala Leu Ala Gln Val Phe His Phe Cys Ile Phe Gly Asn Arg Leu Ile
                405                 410                 415
Glu Glu Ser Ser Ser Val Met Glu Ala Ala Tyr Ser Cys His Trp Tyr
            420                 425                 430
Asp Gly Ser Glu Glu Ala Lys Thr Phe Val Gln Ile Val Cys Gln Gln
        435                 440                 445
Cys Gln Lys Ala Met Ser Ile Ser Gly Ala Lys Phe Phe Thr Val Ser
    450                 455                 460
Leu Asp Leu Phe Ala Ser Val Leu Gly Ala Val Val Thr Tyr Phe Met
465                 470                 475                 480
Val Leu Val Gln Leu Lys
                485

<210> SEQ ID NO 105
<211> LENGTH: 1317
<212> TYPE: DNA
<213> ORGANISM: Drosophila melanogaster DOR44

<400> SEQUENCE: 105
atgaagagca cattcaagga agaaaggatt aaggacgact ccaagcgtcg cgacctgttt      60
gtattcgtga ggcaaaccat gtgtatagcg gccatgtatc ccttcggtta ctacgtgaat     120
ggatctggag tcctggccgt tctggtgcga ttctgtgact tgacctacga gctctttaac     180
tacttcgttt cggtacacat agctggcctg tacatctgca ccatctacat caactatggg     240
caaggcgatt tggacttctt cgtgaactgt tgatacaaa ccattattta tctgtggaca     300
atagcgatga aactctactt tcggaggttc agacctggtt tgttgaatac cattctgtcc     360
aacatcaatg atgagtacga gacacgttcg gctgtgggat tcagtttcgt cacaatggcg     420
ggatcctatc ggatgtccaa gctatggatc aaaacctatg tgtattgctg ctacataggc     480 accatttct ggctggctct tcccattgcc taccgggata ggagtcttcc tcttgcctgc     540
tggtatccct ttgactatac acaacccggt gtctatgagg tagtgttcct tctccaggcg     600
atgggacaga tccaagtggc cgcatccttt gcctcctcca gtggcctgca tatggtgctt     660
```

-continued

```
tgtgtgctga tatcagggca gtacgatgtc ctcttttgca gtctcaagaa tgtattagcc    720
agcagctatg tccttatggg agccaatatg acggaactga atcaattgca ggctgagcaa    780
tctgcggccg atgtcgagcc aggtcagtat gcttactccg tggaggagga gacacctttg    840
caagaacttc taaaagttgg gagctcaatg gacttctcct ccgcattcag gctgtctttt    900
gtgcggtgca ttcagcacca tcgatacata gtggcggcac tgaagaaaat tgagagtttc    960
tacagtccca tatggttcgt gaagattggc gaagtcacct ttcttatgtg cctggtagcc   1020
ttcgtctcca cgaagagcac cgcggccaac tcattcatgc gaatggtctc cttgggccag   1080
tacctgctct tagttctcta cgagctgttc atcatctgct acttcgcgga catcgttttt   1140
cagaacagcc agcggtgcgg tgaagccctc tggcgaagtc cttggcagcg acatttgaag   1200
gatgttcgca gtgattacat gttctttatg ctgaattccc gcaggcagtt ccaacttacg   1260
gccggaaaaa taagcaatct aaacgtggat cgtttcagag gggtgggtat ccttact      1317
```

<210> SEQ ID NO 106
<211> LENGTH: 439
<212> TYPE: PRT
<213> ORGANISM: Drosophila melanogaster DOR44

<400> SEQUENCE: 106

```
Met Lys Ser Thr Phe Lys Glu Glu Arg Ile Lys Asp Asp Ser Lys Arg
  1               5                  10                  15

Arg Asp Leu Phe Val Phe Val Arg Gln Thr Met Cys Ile Ala Ala Met
             20                  25                  30

Tyr Pro Phe Gly Tyr Tyr Val Asn Gly Ser Gly Val Leu Ala Val Leu
         35                  40                  45

Val Arg Phe Cys Asp Leu Thr Tyr Glu Leu Phe Asn Tyr Phe Val Ser
     50                  55                  60

Val His Ile Ala Gly Leu Tyr Ile Cys Thr Ile Tyr Ile Asn Tyr Gly
 65                  70                  75                  80

Gln Gly Asp Leu Asp Phe Phe Val Asn Cys Leu Ile Gln Thr Ile Ile
                 85                  90                  95

Tyr Leu Trp Thr Ile Ala Met Lys Leu Tyr Phe Arg Arg Phe Arg Pro
            100                 105                 110

Gly Leu Leu Asn Thr Ile Leu Ser Asn Ile Asn Asp Glu Tyr Glu Thr
        115                 120                 125

Arg Ser Ala Val Gly Phe Ser Phe Val Thr Met Ala Gly Ser Tyr Arg
    130                 135                 140

Met Ser Lys Leu Trp Ile Lys Thr Tyr Val Tyr Cys Cys Tyr Ile Gly
145                 150                 155                 160

Thr Ile Phe Trp Leu Ala Leu Pro Ile Ala Tyr Arg Asp Arg Ser Leu
                165                 170                 175

Pro Leu Ala Cys Trp Tyr Pro Phe Asp Tyr Thr Gln Pro Gly Val Tyr
            180                 185                 190

Glu Val Val Phe Leu Leu Gln Ala Met Gly Gln Ile Gln Val Ala Ala
        195                 200                 205

Ser Phe Ala Ser Ser Gly Leu His Met Val Leu Cys Val Leu Ile
    210                 215                 220

Ser Gly Gln Tyr Asp Val Leu Phe Cys Ser Leu Lys Asn Val Leu Ala
225                 230                 235                 240

Ser Ser Tyr Val Leu Met Gly Ala Asn Met Thr Glu Leu Asn Gln Leu
                245                 250                 255

Gln Ala Glu Gln Ser Ala Ala Asp Val Glu Pro Gly Gln Tyr Ala Tyr
```

-continued

```
                260                 265                 270
Ser Val Glu Glu Thr Pro Leu Gln Glu Leu Leu Lys Val Gly Ser
    275                 280                 285

Ser Met Asp Phe Ser Ser Ala Phe Arg Leu Ser Phe Val Arg Cys Ile
290                 295                 300

Gln His His Arg Tyr Ile Val Ala Ala Leu Lys Lys Ile Glu Ser Phe
305                 310                 315                 320

Tyr Ser Pro Ile Trp Phe Val Lys Ile Gly Glu Val Thr Phe Leu Met
                325                 330                 335

Cys Leu Val Ala Phe Val Ser Thr Lys Ser Thr Ala Ala Asn Ser Phe
            340                 345                 350

Met Arg Met Val Ser Leu Gly Gln Tyr Leu Leu Leu Val Leu Tyr Glu
    355                 360                 365

Leu Phe Ile Ile Cys Tyr Phe Ala Asp Ile Val Phe Gln Asn Ser Gln
370                 375                 380

Arg Cys Gly Glu Ala Leu Trp Arg Ser Pro Trp Gln Arg His Leu Lys
385                 390                 395                 400

Asp Val Arg Ser Asp Tyr Met Phe Phe Met Leu Asn Ser Arg Arg Gln
                405                 410                 415

Phe Gln Leu Thr Ala Gly Lys Ile Ser Asn Leu Asn Val Asp Arg Phe
            420                 425                 430

Arg Gly Val Gly Ile Leu Thr
        435
```

<210> SEQ ID NO 107
<211> LENGTH: 26
<212> TYPE: PRT
<213> ORGANISM: unidentified - insect odorant receptor motif
<220> FEATURE:
<221> NAME/KEY: VARIANT
<222> LOCATION: (1)..(1)
<223> OTHER INFORMATION: X = F, Y, L, A, T, S or C
<220> FEATURE:
<221> NAME/KEY: VARIANT
<222> LOCATION: (2)..(2)
<223> OTHER INFORMATION: X = P, I, M, V, T, L, Q, S or H
<220> FEATURE:
<221> NAME/KEY: VARIANT
<222> LOCATION: (3)..(3)
<223> OTHER INFORMATION: X = F, Y, I, S, L, C, M or V
<220> FEATURE:
<221> NAME/KEY: VARIANT
<222> LOCATION: (4)..(4)
<223> OTHER INFORMATION: X = C, Y, T, S, L or A
<220> FEATURE:
<221> NAME/KEY: VARIANT
<222> LOCATION: (5)..(5)
<223> OTHER INFORMATION: X = Y, N, F, M, I, L, K, S, H or T
<220> FEATURE:
<221> NAME/KEY: VARIANT
<222> LOCATION: (6)..(25)
<223> OTHER INFORMATION: X = Any

<400> SEQUENCE: 107

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Trp
            20                  25
```

<210> SEQ ID NO 108
<211> LENGTH: 363
<212> TYPE: PRT
<213> ORGANISM: DROSOPHILA MELANOGASTER DOR61

-continued

```
<400> SEQUENCE: 108

Met Gly His Lys Asp Asp Met Asp Ser Thr Asp Ser Thr Ala Leu Ser
1               5                   10                  15

Leu Lys His Ile Ser Ser Leu Ile Phe Val Ile Ser Ala Gln Tyr Pro
            20                  25                  30

Leu Ile Ser Tyr Val Ala Tyr Asn Arg Asn Asp Met Glu Lys Val Thr
        35                  40                  45

Ala Cys Leu Ser Val Val Phe Thr Asn Met Leu Thr Val Ile Lys Ile
    50                  55                  60

Ser Thr Phe Leu Ala Asn Arg Lys Asp Phe Trp Glu Met Ile His Arg
65              70                  75                  80

Phe Arg Lys Met His Glu Gln Cys Lys Tyr Arg Glu Gly Leu Asp Tyr
            85                  90                  95

Val Ala Glu Ala Asn Lys Leu Ala Ser Phe Leu Gly Arg Ala Tyr Cys
        100                 105                 110

Val Ser Cys Gly Leu Thr Gly Leu Tyr Phe Met Leu Gly Pro Ile Val
    115                 120                 125

Lys Ile Gly Val Cys Arg Trp His Gly Thr Thr Cys Asp Lys Glu Leu
130                 135                 140

Pro Met Pro Met Lys Phe Pro Phe Asn Asp Leu Glu Ser Pro Gly Tyr
145                 150                 155                 160

Glu Val Cys Phe Leu Tyr Thr Val Leu Val Thr Val Val Val Val Ala
                165                 170                 175

Tyr Ala Ser Ala Val Asp Gly Leu Phe Ile Ser Phe Ala Ile Asn Leu
            180                 185                 190

Arg Ala His Phe Gln Thr Leu Gln Arg Gln Ile Glu Asn Trp Glu Phe
        195                 200                 205

Pro Ser Ser Glu Pro Asp Thr Gln Ile Arg Leu Lys Ser Ile Val Glu
210                 215                 220

Tyr His Val Leu Leu Leu Ser Leu Ser Arg Lys Leu Arg Ser Ile Tyr
225                 230                 235                 240

Thr Pro Thr Val Met Gly Gln Phe Val Ile Thr Ser Leu Gln Val Gly
                245                 250                 255

Val Ile Ile Tyr Gln Leu Val Thr Asn Met Asp Ser Val Met Asp Leu
            260                 265                 270

Leu Leu Tyr Ala Ser Phe Phe Gly Ser Ile Met Leu Gln Leu Phe Ile
        275                 280                 285

Tyr Cys Tyr Gly Gly Glu Ile Ile Lys Ala Glu Ser Leu Gln Val Asp
    290                 295                 300

Thr Ala Val Arg Leu Ser Asn Trp His Leu Ala Ser Pro Lys Thr Arg
305                 310                 315                 320

Thr Ser Leu Ser Leu Ile Ile Leu Gln Ser Gln Lys Glu Val Leu Ile
                325                 330                 335

Arg Ala Gly Phe Phe Val Ala Ser Leu Ala Asn Phe Pro Tyr Arg Leu
            340                 345                 350

Ile Thr Leu Ile Lys Ser Ile Asp Ser Ile Cys
        355                 360

<210> SEQ ID NO 109
<211> LENGTH: 26
<212> TYPE: PRT
<213> ORGANISM: unidentified - insect odorant receptor motif
<220> FEATURE:
<221> NAME/KEY: VARIANT
<222> LOCATION: (1)..(1)
```

-continued

```
<223> OTHER INFORMATION: X = F, Y OR L
<220> FEATURE:
<221> NAME/KEY: VARIANT
<222> LOCATION: (2)..(2)
<223> OTHER INFORMATION: X = P, I, M, V OR T
<220> FEATURE:
<221> NAME/KEY: VARIANT
<222> LOCATION: (3)..(3)
<223> OTHER INFORMATION: X = F, Y, I, S, L OR C
<220> FEATURE:
<221> NAME/KEY: VARIANT
<222> LOCATION: (4)..(4)
<223> OTHER INFORMATION: X = C, Y OR T
<220> FEATURE:
<221> NAME/KEY: VARIANT
<222> LOCATION: (5)..(5)
<223> OTHER INFORMATION: X = Y, N OR F
<220> FEATURE:
<221> NAME/KEY: VARIANT
<222> LOCATION: (6)..(25)
<223> OTHER INFORMATION: X = ANY

<400> SEQUENCE: 109

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Trp
            20                  25

<210> SEQ ID NO 110
<211> LENGTH: 411
<212> TYPE: PRT
<213> ORGANISM: Drosophila Melanogaster DOR37
<220> FEATURE:
<221> NAME/KEY: UNSURE
<222> LOCATION: (243)..(243)
<223> OTHER INFORMATION: Unknown
<220> FEATURE:
<221> NAME/KEY: UNSURE
<222> LOCATION: (256)..(256)
<223> OTHER INFORMATION: Unknown

<400> SEQUENCE: 110

Lys Val Asp Ser Thr Arg Ala Leu Val Asn His Trp Arg Ile Phe Arg
1               5                   10                  15

Ile Met Gly Ile His Pro Pro Gly Lys Arg Thr Phe Trp Gly Arg His
            20                  25                  30

Tyr Thr Ala Tyr Ser Met Val Trp Asn Val Thr Phe His Ile Cys Ile
        35                  40                  45

Trp Val Ser Phe Ser Val Asn Leu Leu Gln Ser Asn Ser Leu Glu Thr
    50                  55                  60

Phe Cys Glu Ser Leu Cys Val Thr Met Pro His Thr Leu Tyr Met Leu
65                  70                  75                  80

Lys Leu Ile Asn Val Arg Arg Met Arg Gly Gln Met Ile Ser Ser His
                85                  90                  95

Trp Leu Leu Arg Leu Leu Asp Lys Arg Leu Gly Cys Asp Asp Glu Arg
            100                 105                 110

Gln Ile Ile Met Ala Gly Ile Glu Arg Ala Glu Phe Ile Phe Arg Thr
        115                 120                 125

Ile Phe Arg Gly Leu Ala Cys Thr Val Val Leu Gly Ile Ile Tyr Ile
    130                 135                 140

Ser Ala Ser Ser Glu Pro Thr Leu Met Tyr Pro Thr Trp Ile Pro Trp
145                 150                 155                 160

Asn Trp Arg Asp Ser Thr Ser Ala Tyr Leu Ala Thr Ala Met Leu His
                165                 170                 175
```

```
Thr Thr Ala Leu Met Ala Asn Ala Thr Leu Val Leu Asn Leu Ser Ser
            180                 185                 190

Tyr Pro Gly Thr Tyr Leu Ile Leu Val Ser Val His Thr Lys Ala Leu
            195                 200                 205

Ala Leu Arg Val Ser Lys Leu Gly Tyr Gly Ala Pro Leu Pro Ala Val
    210                 215                 220

Arg Met Gln Ala Ile Leu Val Gly Tyr Ile His Asp His Gln Ile Ile
225                 230                 235                 240

Leu Arg Xaa Val Ser Gly Asn Leu Ile Ser Gln Cys Lys Asn Phe Xaa
                245                 250                 255

Ser Ile Ser Gly Val Leu Thr Phe Ile Glu Arg Arg Met Tyr Thr His
            260                 265                 270

Phe Gly Val Pro Asn Ile Phe Ile Val Ile Glu Asp Tyr Tyr Ile Leu
            275                 280                 285

Phe Leu Asn Tyr Ser Leu Phe Lys Ser Leu Glu Arg Ser Leu Ser Met
    290                 295                 300

Thr Cys Phe Leu Gln Phe Phe Ser Thr Ala Cys Ala Gln Cys Thr Ile
305                 310                 315                 320

Cys Tyr Phe Leu Leu Phe Gly Asn Val Gly Ile Met Arg Phe Met Asn
                325                 330                 335

Met Leu Phe Leu Leu Val Ile Leu Thr Thr Glu Thr Leu Leu Leu Cys
            340                 345                 350

Tyr Thr Ala Glu Leu Pro Cys Lys Glu Gly Glu Ser Leu Leu Thr Ala
            355                 360                 365

Val Tyr Ser Cys Asn Trp Leu Ser Gln Ser Val Asn Phe Arg Arg Leu
    370                 375                 380

Leu Leu Leu Met Leu Ala Arg Cys Gln Ile Pro Met Ile Leu Val Ser
385                 390                 395                 400

Gly Val Ile Val Pro Ile Ser Met Lys Thr Phe
                405                 410

<210> SEQ ID NO 111
<211> LENGTH: 26
<212> TYPE: PRT
<213> ORGANISM: unidentified - insect odorant receptor motif
<220> FEATURE:
<221> NAME/KEY: VARIANT
<222> LOCATION: (1)..(1)
<223> OTHER INFORMATION: X = F, Y, L, A or T
<220> FEATURE:
<221> NAME/KEY: VARIANT
<222> LOCATION: (2)..(2)
<223> OTHER INFORMATION: X = P, I, M, V or T
<220> FEATURE:
<221> NAME/KEY: VARIANT
<222> LOCATION: (3)..(3)
<223> OTHER INFORMATION: X = F, Y, I, S, L or C
<220> FEATURE:
<221> NAME/KEY: VARIANT
<222> LOCATION: (4)..(4)
<223> OTHER INFORMATION: X = C, Y or T
<220> FEATURE:
<221> NAME/KEY: VARIANT
<222> LOCATION: (5)..(5)
<223> OTHER INFORMATION: X = Y, N, F, M or I
<220> FEATURE:
<221> NAME/KEY: VARIANT
<222> LOCATION: (6)..(25)
<223> OTHER INFORMATION: X = Any

<400> SEQUENCE: 111

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Trp
            20                  25

<210> SEQ ID NO 112
<211> LENGTH: 26
<212> TYPE: PRT
<213> ORGANISM: unidentified - insect odorant receptor motif
<220> FEATURE:
<221> NAME/KEY: VARIANT
<222> LOCATION: (3)..(3)
<223> OTHER INFORMATION: X = Any
<220> FEATURE:
<221> NAME/KEY: VARIANT
<222> LOCATION: (6)..(25)
<223> OTHER INFORMATION: X = Any

<400> SEQUENCE: 112

Phe Pro Xaa Cys Tyr Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Trp
            20                  25
```